US011026599B2

(12) United States Patent
Barton

(10) Patent No.: US 11,026,599 B2
(45) Date of Patent: Jun. 8, 2021

(54) METHOD FOR ASSESSING FALL RISK BASED ON TRACKING DATA OF A MOVING TARGET

(71) Applicants: University Of Maryland, Baltimore, Baltimore, MD (US); The United States of America as Represented by the Department of Veterans Affairs, Washington, DC (US)

(72) Inventor: Joseph E. Barton, Washington, DC (US)

(73) Assignees: University of Maryland, Baltimore, Baltimore, MD (US); The United States of America as Represented by the Department of Veterans Affairs, Washington, DC (US)

( * ) Notice: Subject to any disclaimer, the term of this patent is extended or adjusted under 35 U.S.C. 154(b) by 487 days.

(21) Appl. No.: 15/753,339

(22) PCT Filed: Aug. 17, 2016

(86) PCT No.: PCT/US2016/047258
§ 371 (c)(1),
(2) Date: May 24, 2018

(87) PCT Pub. No.: WO2017/031152
PCT Pub. Date: Feb. 23, 2017

(65) Prior Publication Data
US 2018/0235518 A1 Aug. 23, 2018

Related U.S. Application Data

(60) Provisional application No. 62/316,278, filed on Mar. 31, 2016, provisional application No. 62/205,894, filed on Aug. 17, 2015.

(51) Int. Cl.
*A61B 5/11* (2006.01)
*A61B 5/00* (2006.01)
(Continued)

(52) U.S. Cl.
CPC .......... *A61B 5/1117* (2013.01); *A61B 5/0024* (2013.01); *A61B 5/1114* (2013.01);
(Continued)

(58) Field of Classification Search
CPC ................ A61B 5/7235; A61B 5/7275; A61B 2562/0219; A61B 5/11–1128;
(Continued)

(56) References Cited

U.S. PATENT DOCUMENTS 8,764,532 B1 * 7/2014 Berme ................... G16H 50/30
463/7
8,845,556 B1 * 9/2014 Schickler .............. A61B 5/1116
600/595

(Continued)

FOREIGN PATENT DOCUMENTS

WO 2010026513 A1 3/2010

OTHER PUBLICATIONS

European Extended Search Report, in application No. 16837719.0, dated Feb. 20, 2019, pp. 1-9.
(Continued)

*Primary Examiner* — David J. McCrosky
*Assistant Examiner* — Chanel J Jhin
(74) *Attorney, Agent, or Firm* — Wolter Van Dyke Davis, PLLC; Eugene J. Molinelli; Cian O'Brien

(57) ABSTRACT

Techniques are provided for assessing a risk of fall based on tracking data of a subject tracking a moving target. Tracking data of a first subject to the moving target is determined based on sensing a body of the first subject that measure a position of one or more body segments at time increments
(Continued)

over a time period. A response of the first subject is characterized based on the tracking data of the first subject. Tracking data of a second subject to the moving target is determined based on sensing a body of the second subject that measure a position of one or more body segments at each time increment over the time period. A risk of fall of the second subject is determined based on the response of the first subject and the response of the second subject.

19 Claims, 45 Drawing Sheets

(51) Int. Cl.
  *G16H 50/30* (2018.01)
  *G16H 40/63* (2018.01)
  *G16H 50/70* (2018.01)
  *G06F 19/00* (2018.01)
(52) U.S. Cl.
  CPC .......... *A61B 5/7235* (2013.01); *A61B 5/7275* (2013.01); *G06F 19/00* (2013.01); *G16H 40/63* (2018.01); *G16H 50/30* (2018.01); *G16H 50/70* (2018.01); *A61B 2562/0219* (2013.01)

(58) Field of Classification Search
  CPC ........ G16H 50/30; G16H 40/63; G16H 50/70; G06F 19/00
  USPC .......................................................... 600/595
  See application file for complete search history.

(56) References Cited

U.S. PATENT DOCUMENTS

| | | |
|---|---|---|
| 9,081,436 B1 | 7/2015 | Berme et al. |
| 2012/0133655 A1* | 5/2012 | Kristjansson ........ A61B 5/1124 345/419 |
| 2014/0330159 A1* | 11/2014 | Costa ................... A61B 5/1124 600/558 |
| 2015/0208975 A1 | 7/2015 | Ghajar |

OTHER PUBLICATIONS

ISA/EPO: Extended European Search Report, European Patent Application No. 16837719.0, dated Feb. 20, 2019, pp. 1-9.

\* cited by examiner

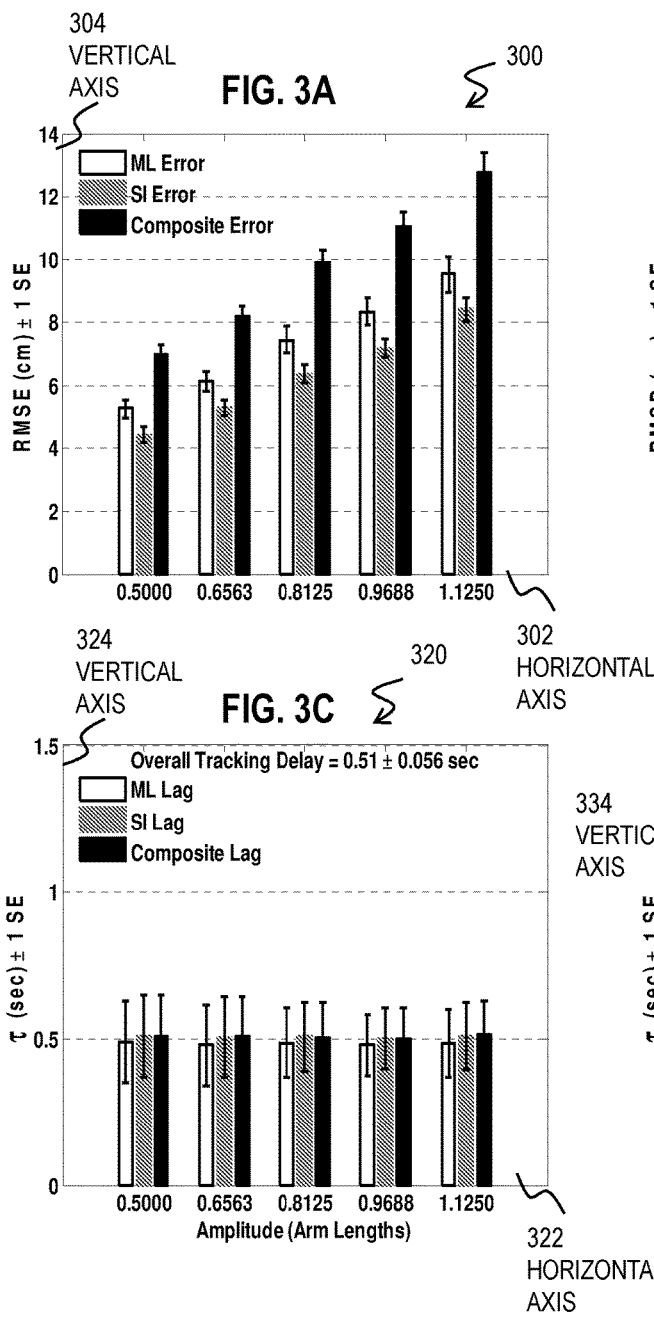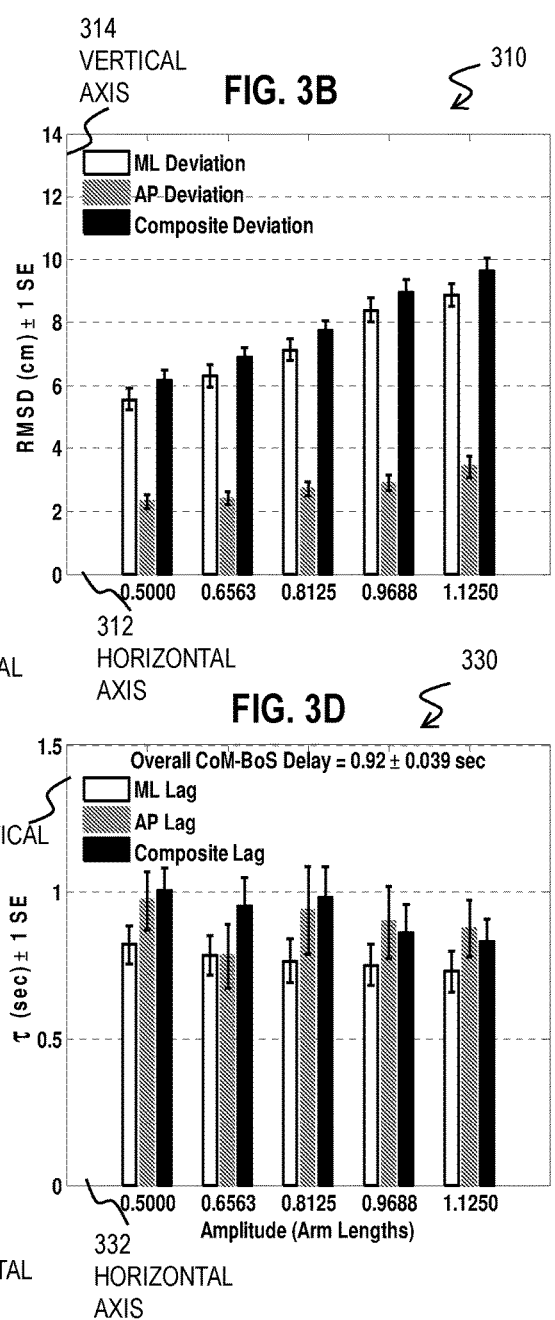

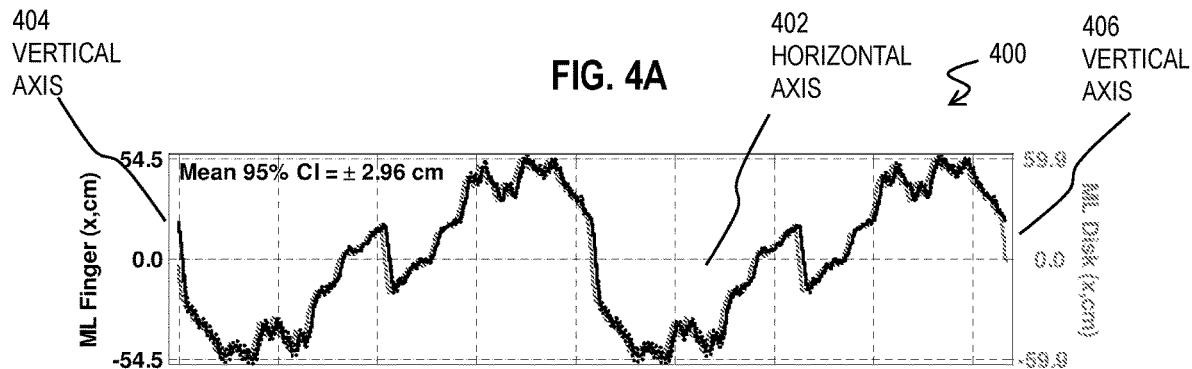
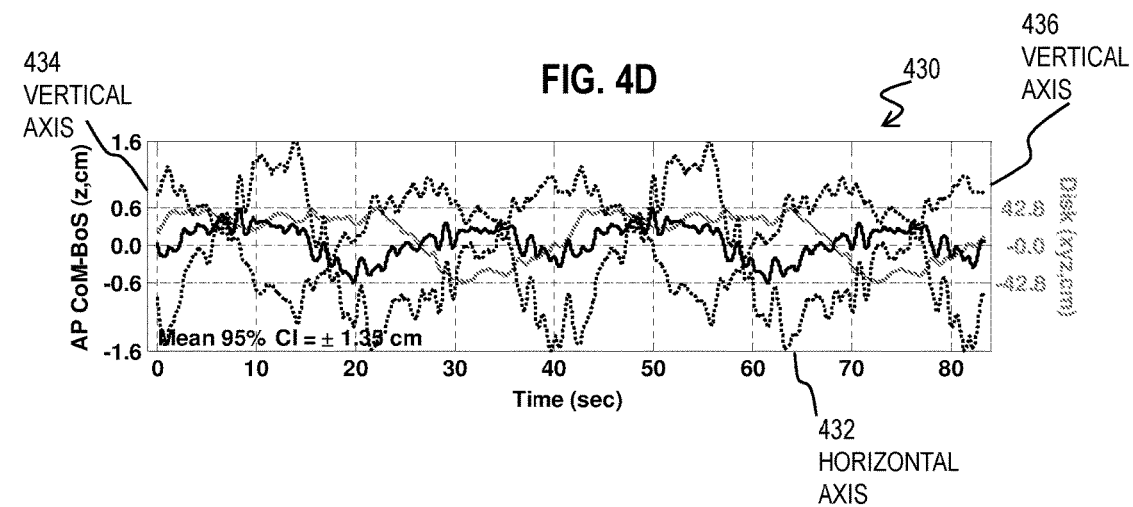

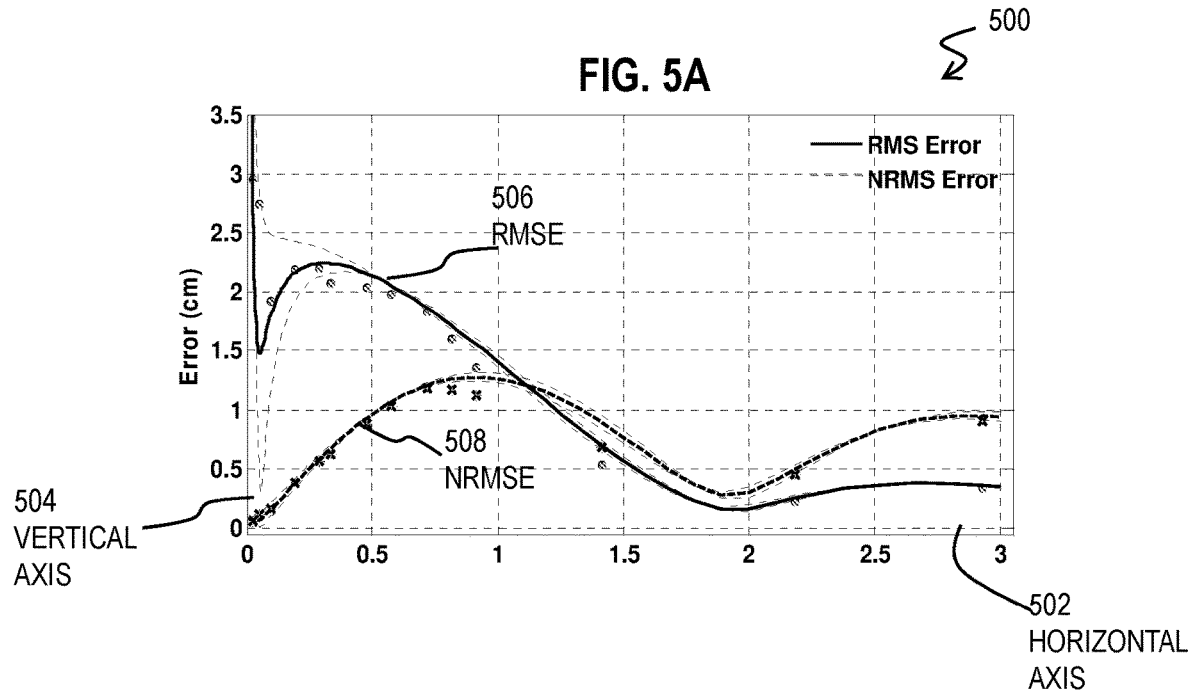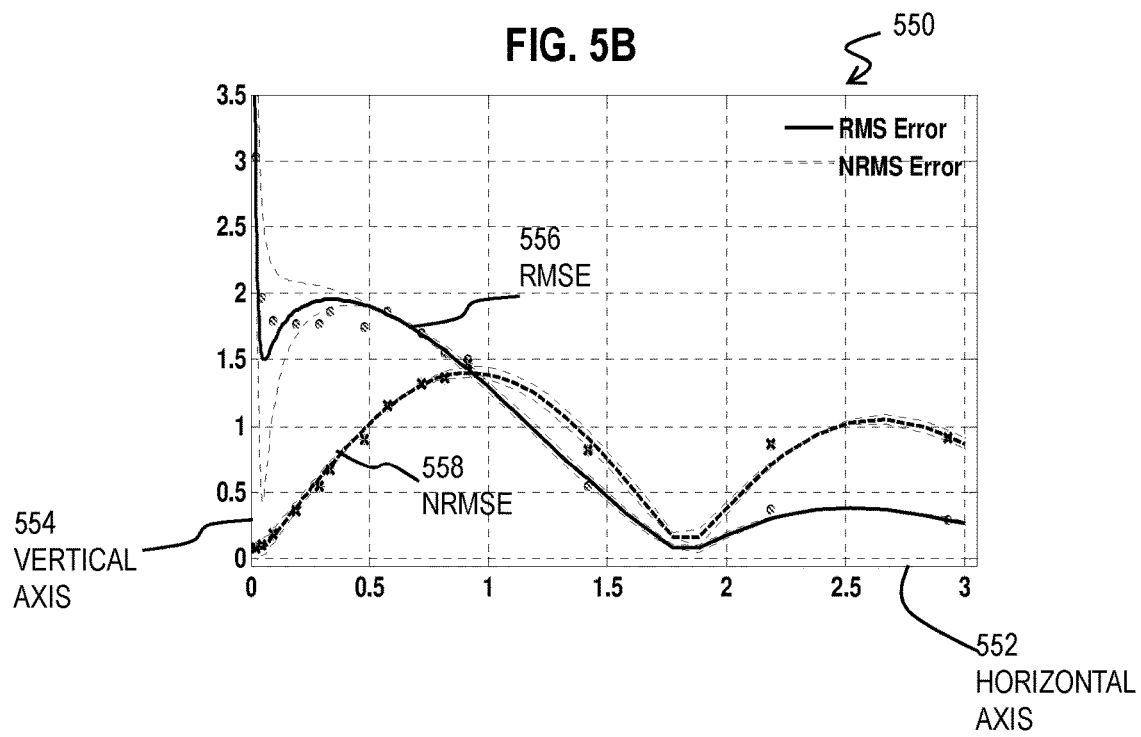

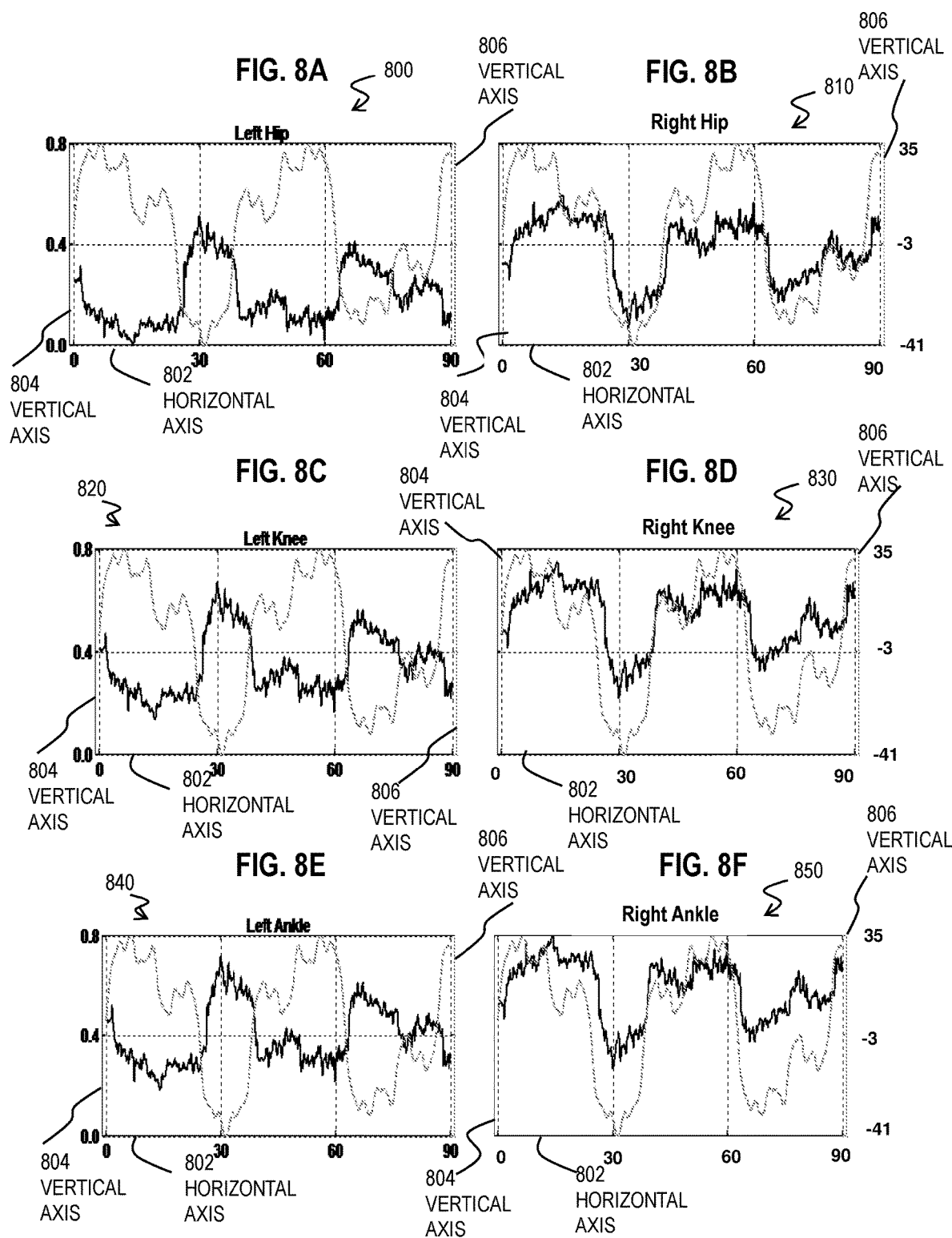

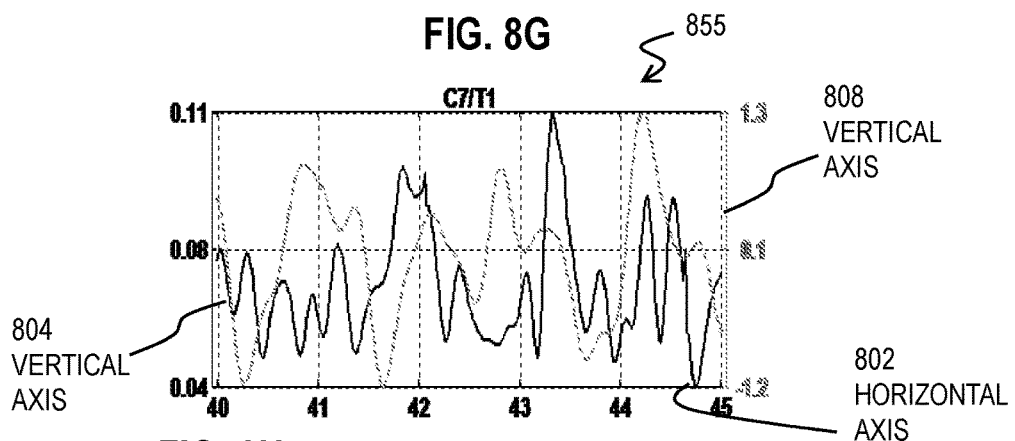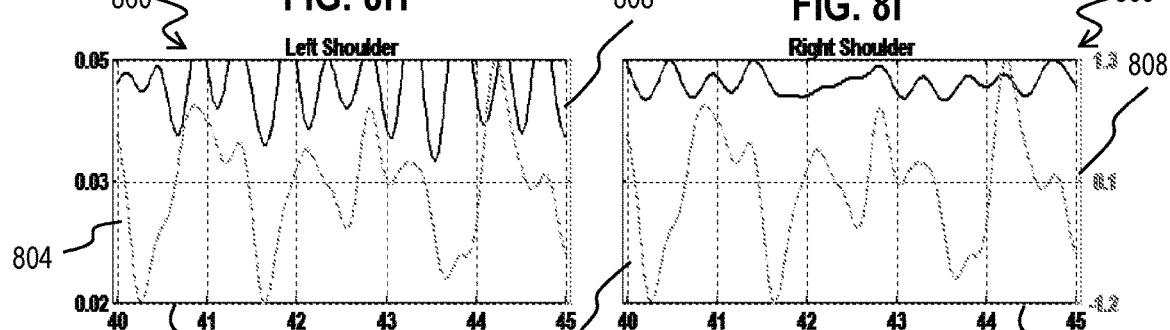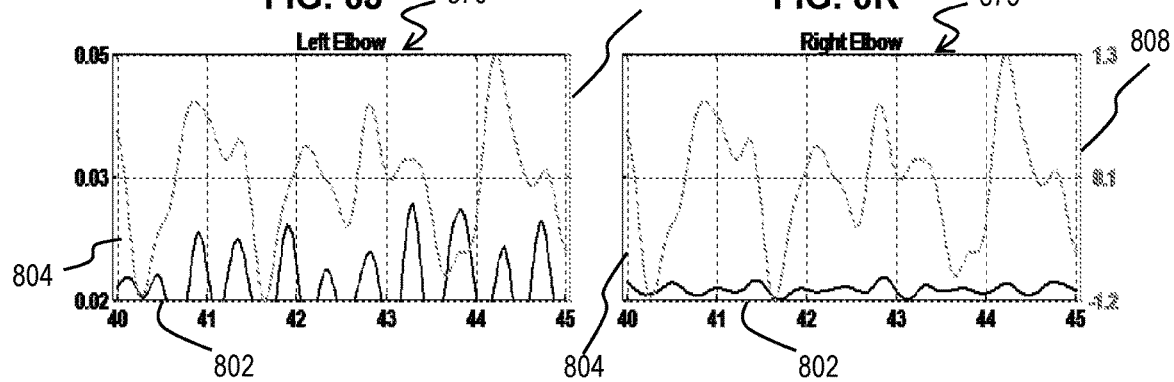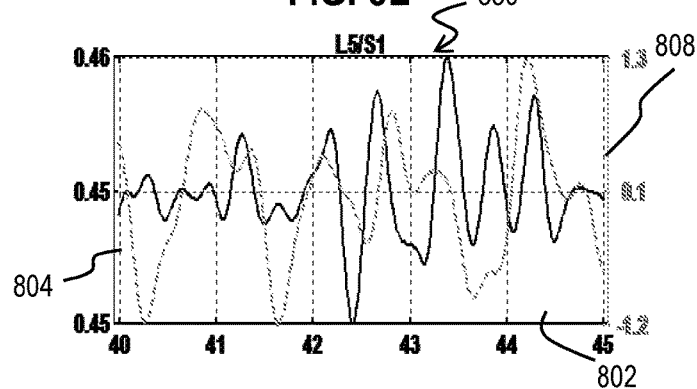

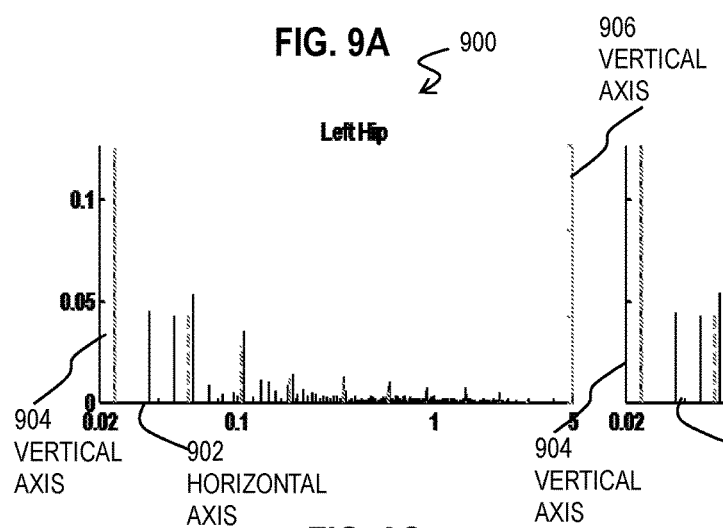
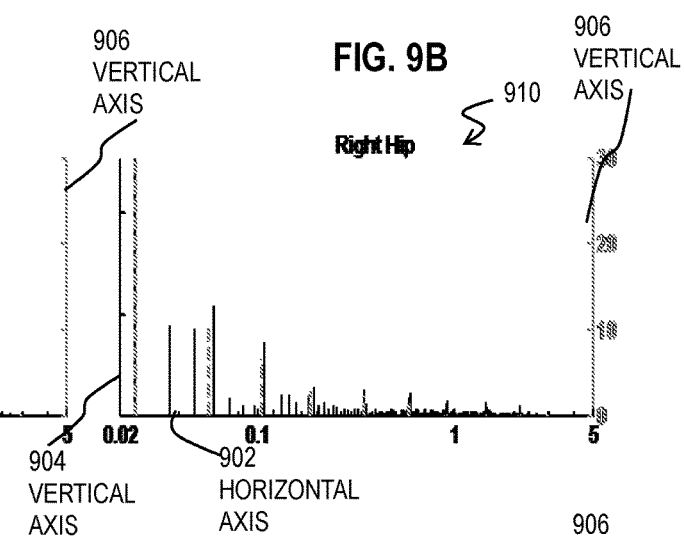
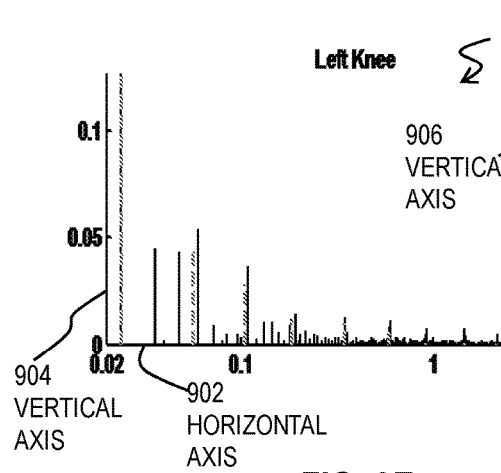
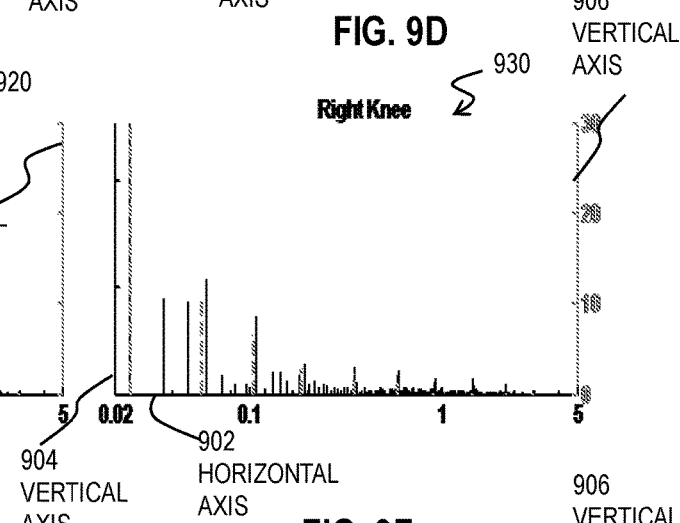
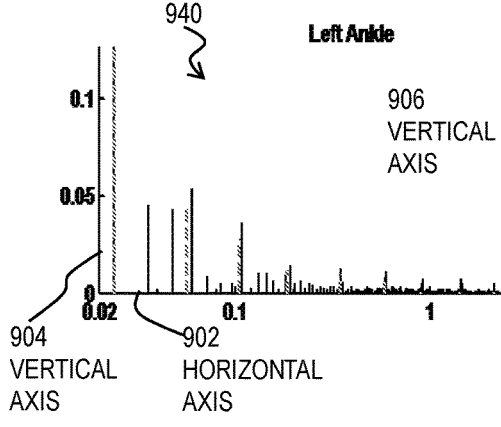
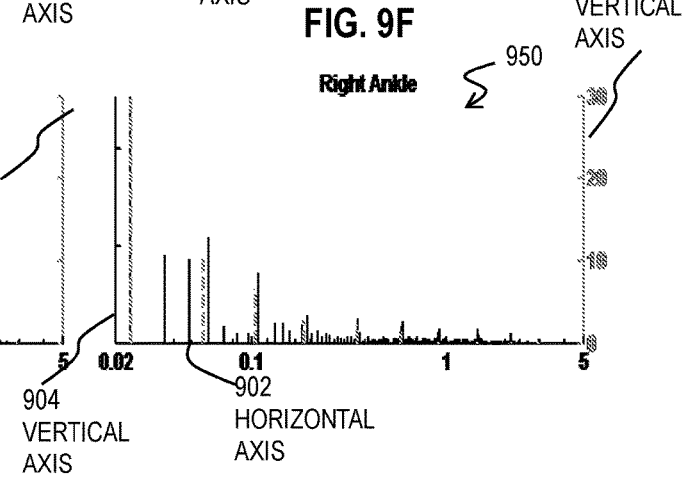

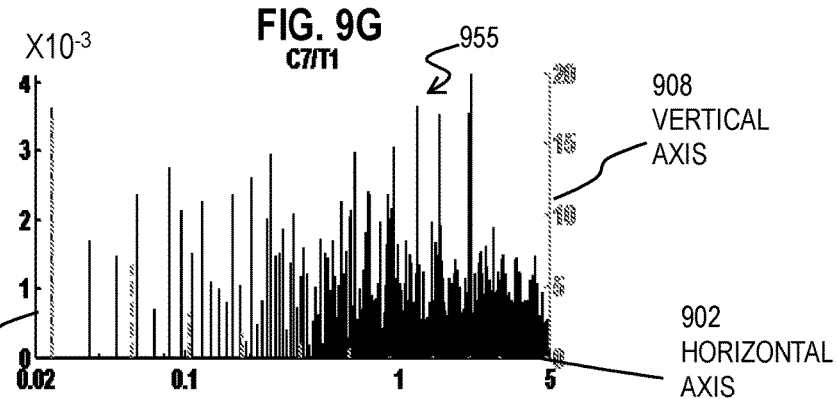
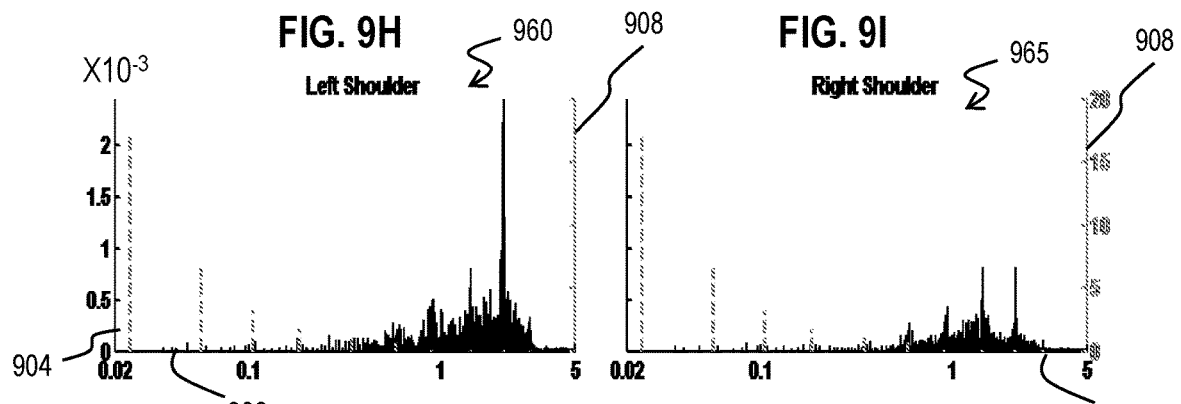
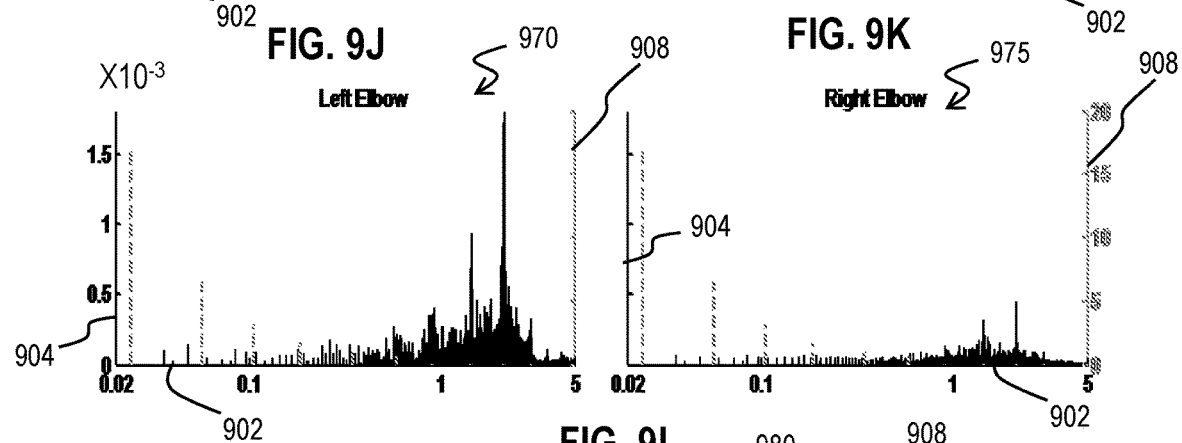
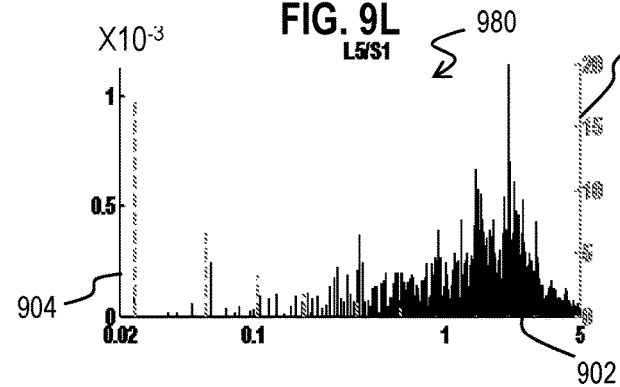

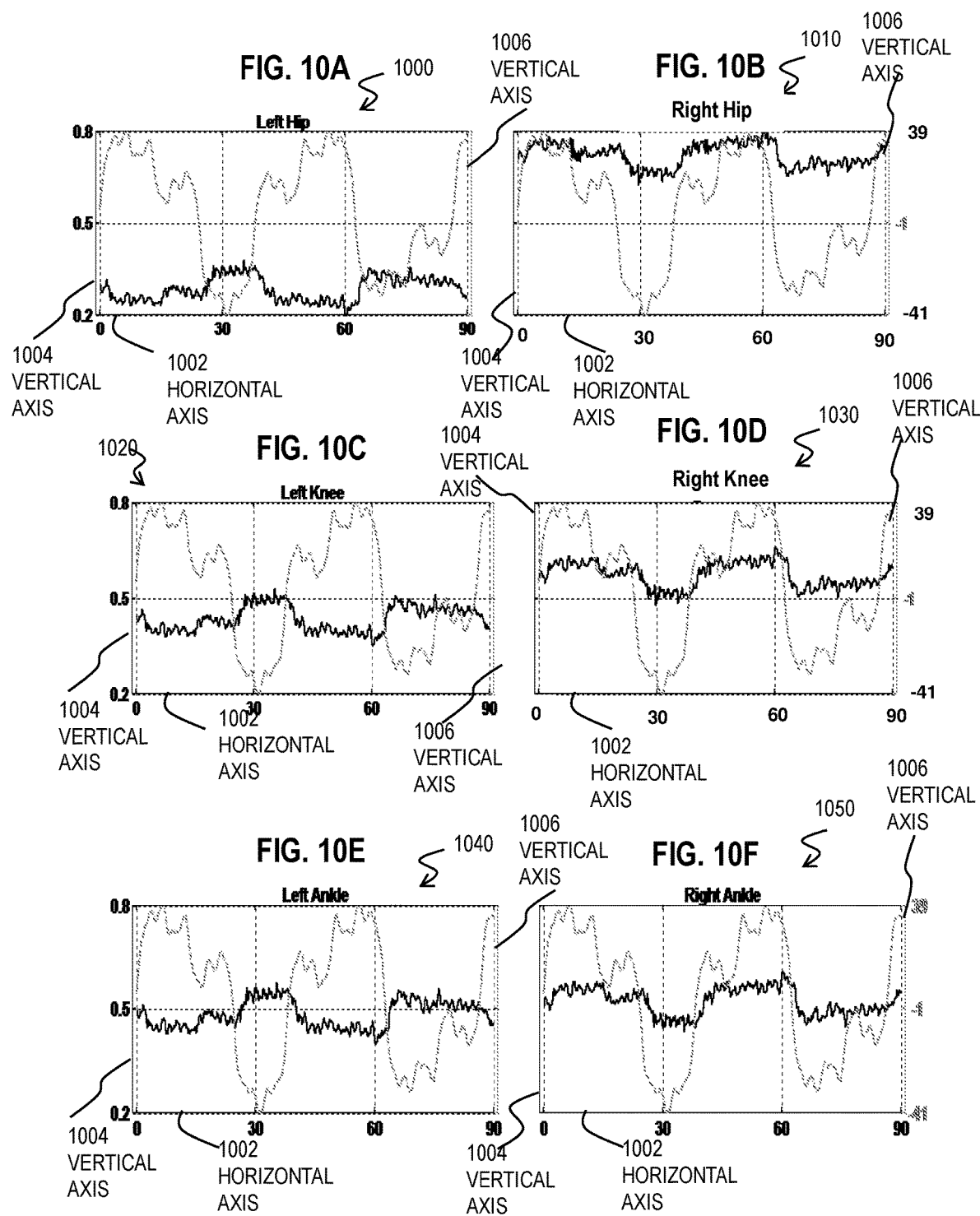

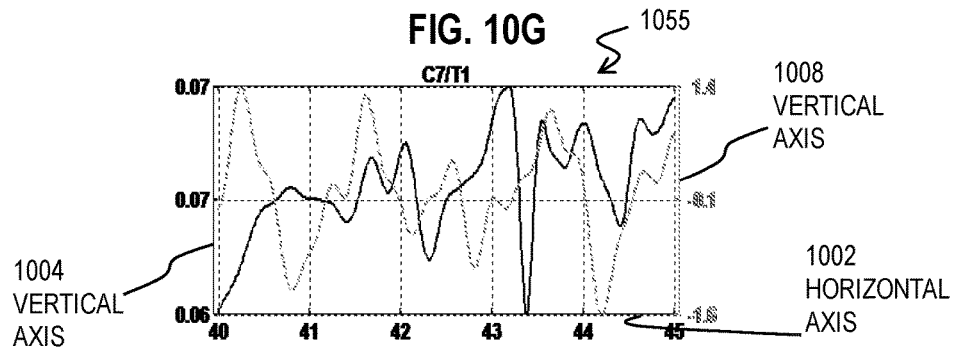
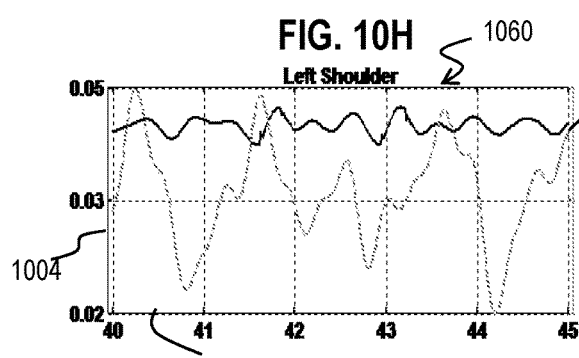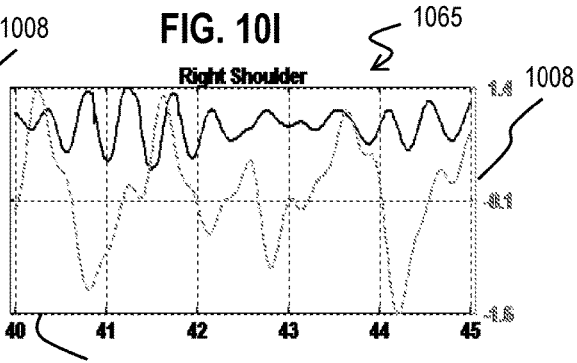
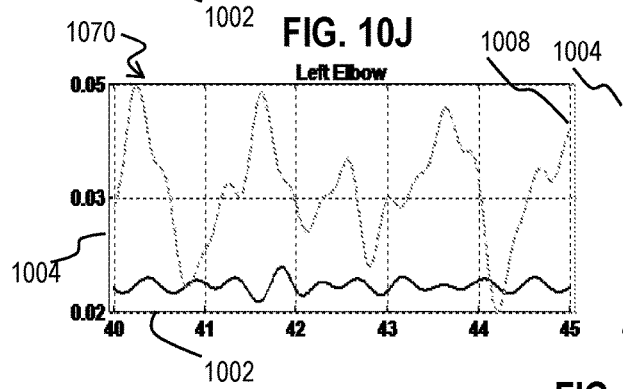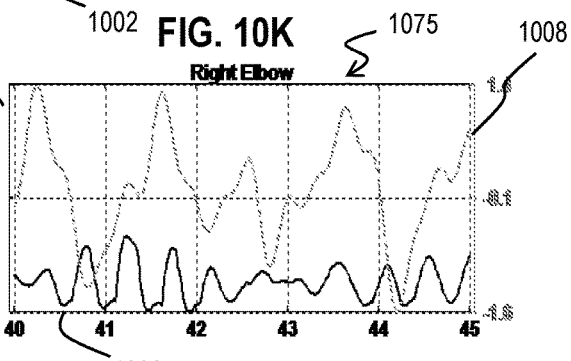
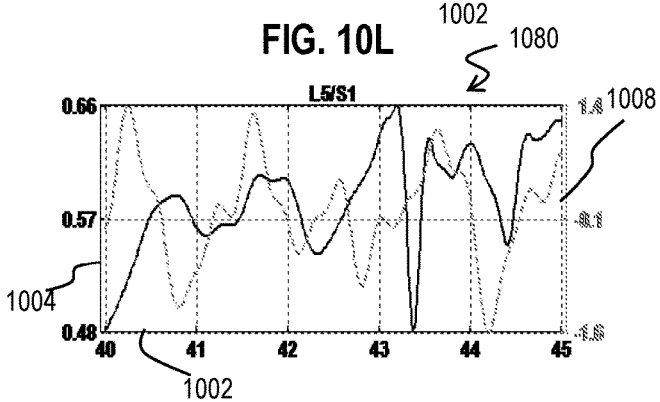

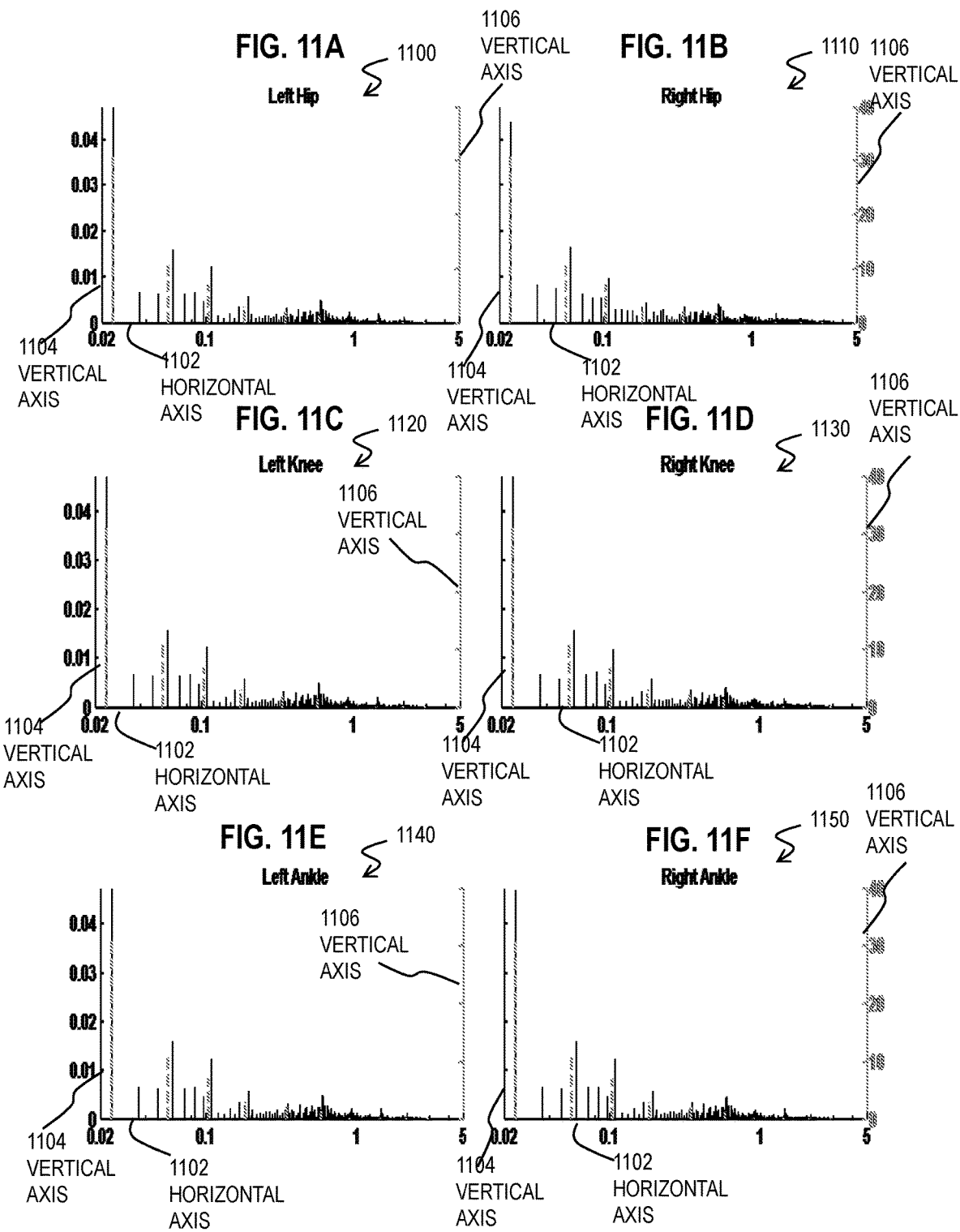

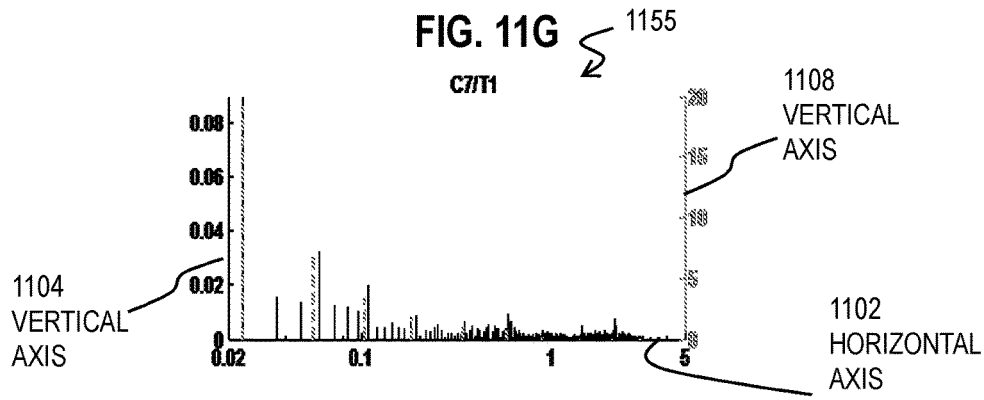
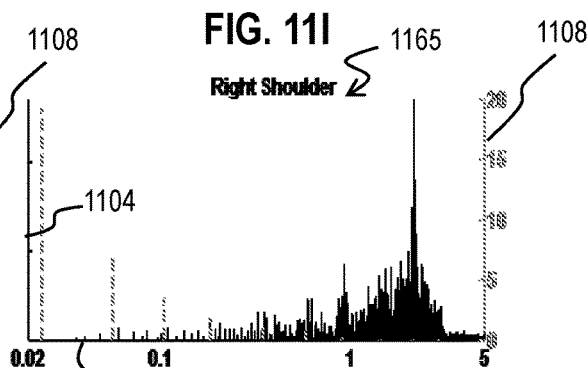
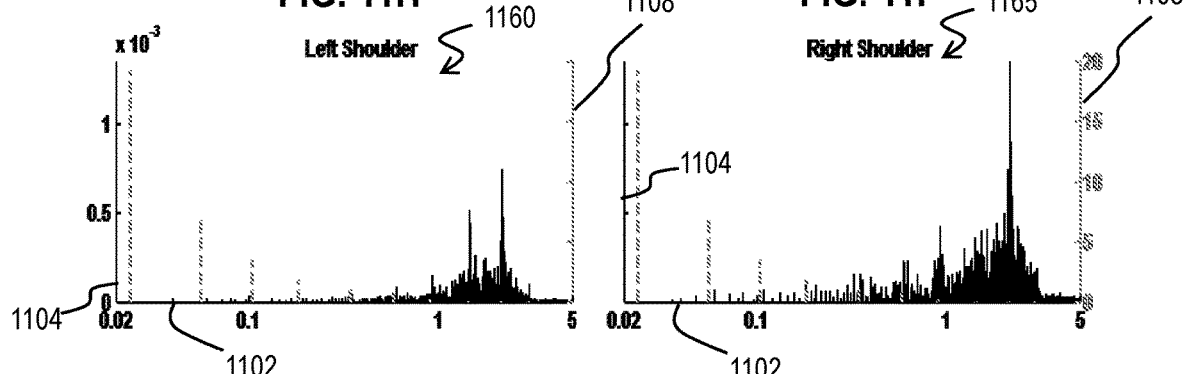
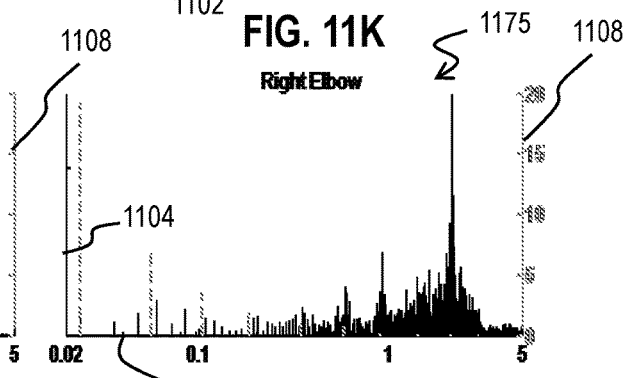
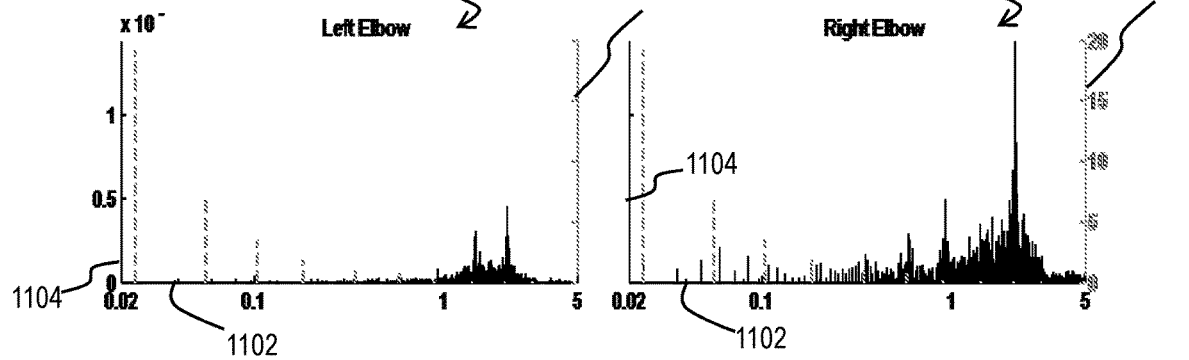
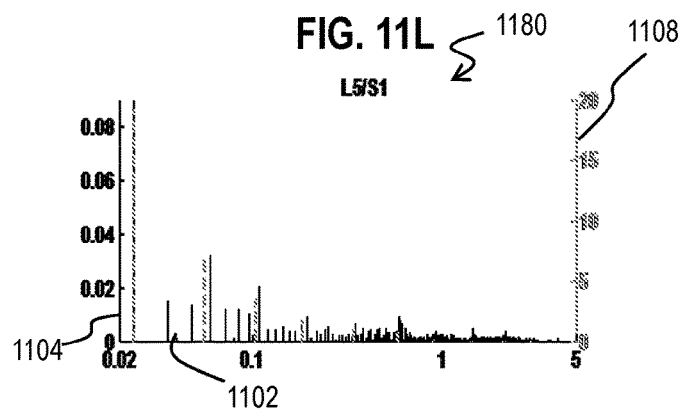

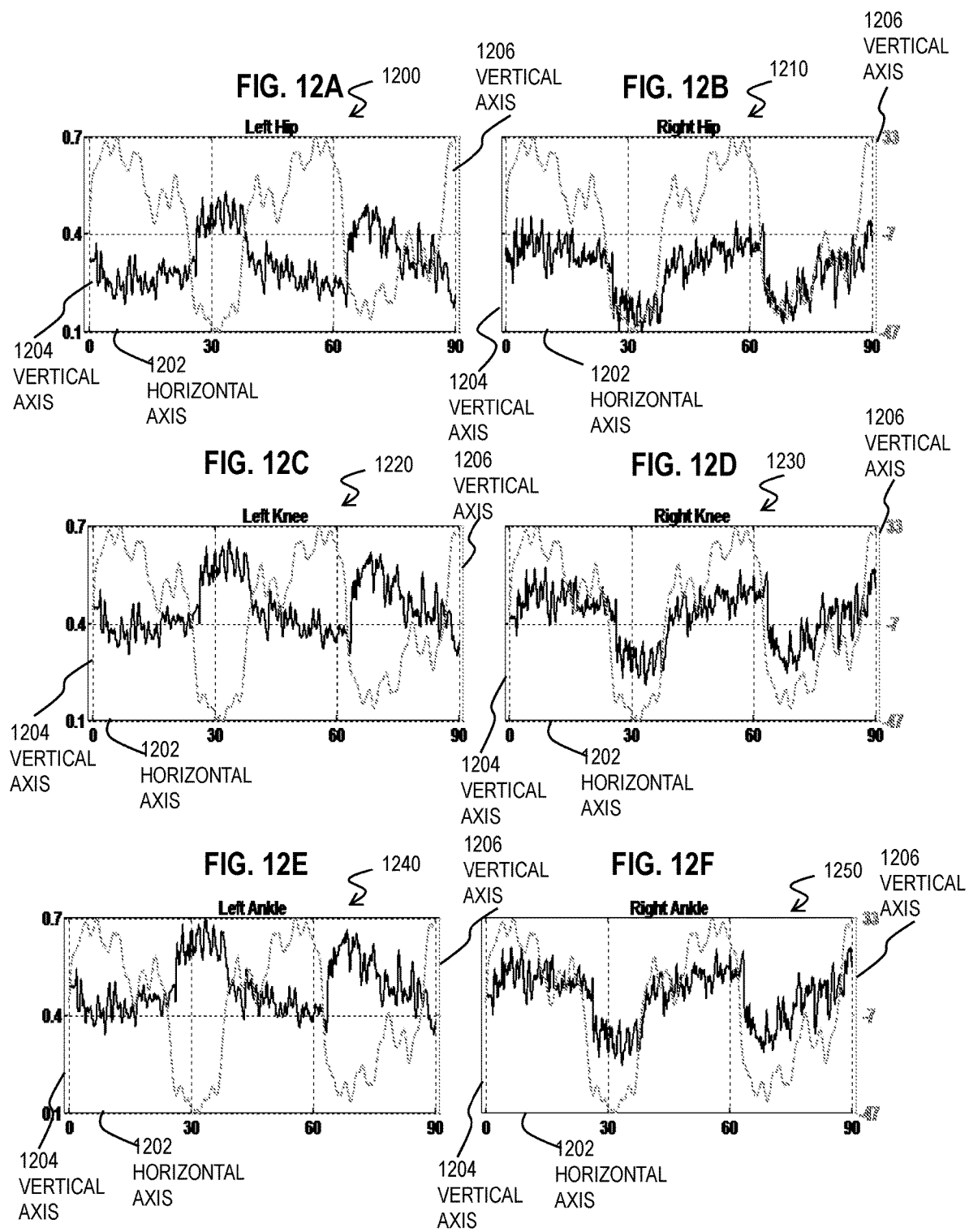

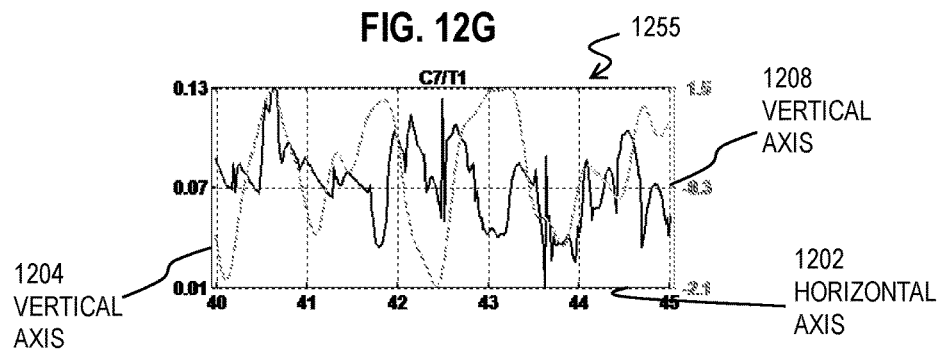
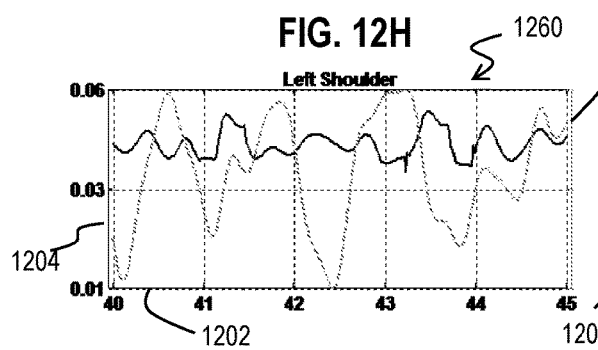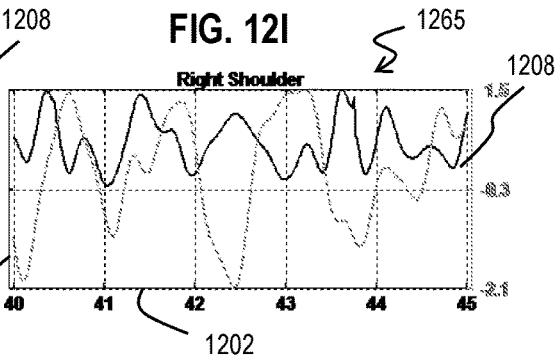
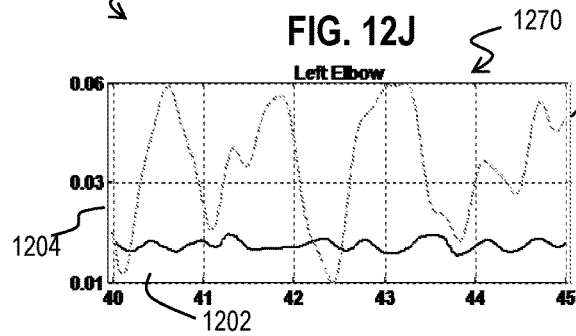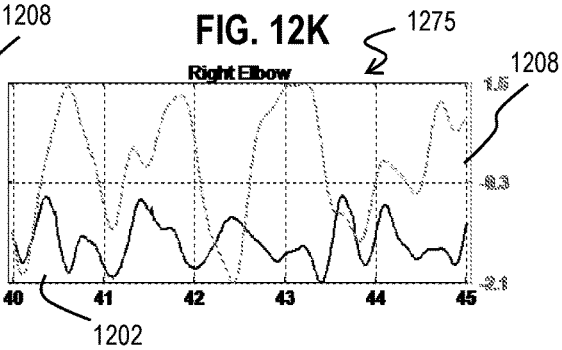
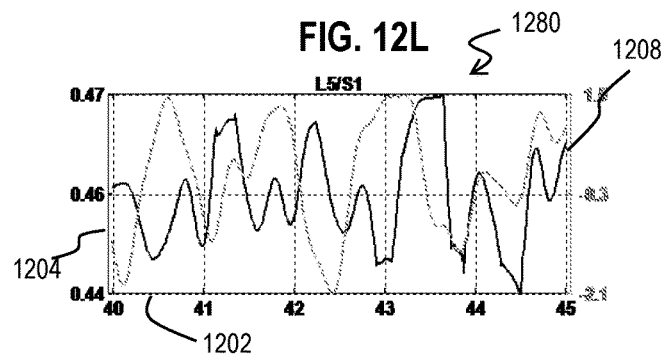

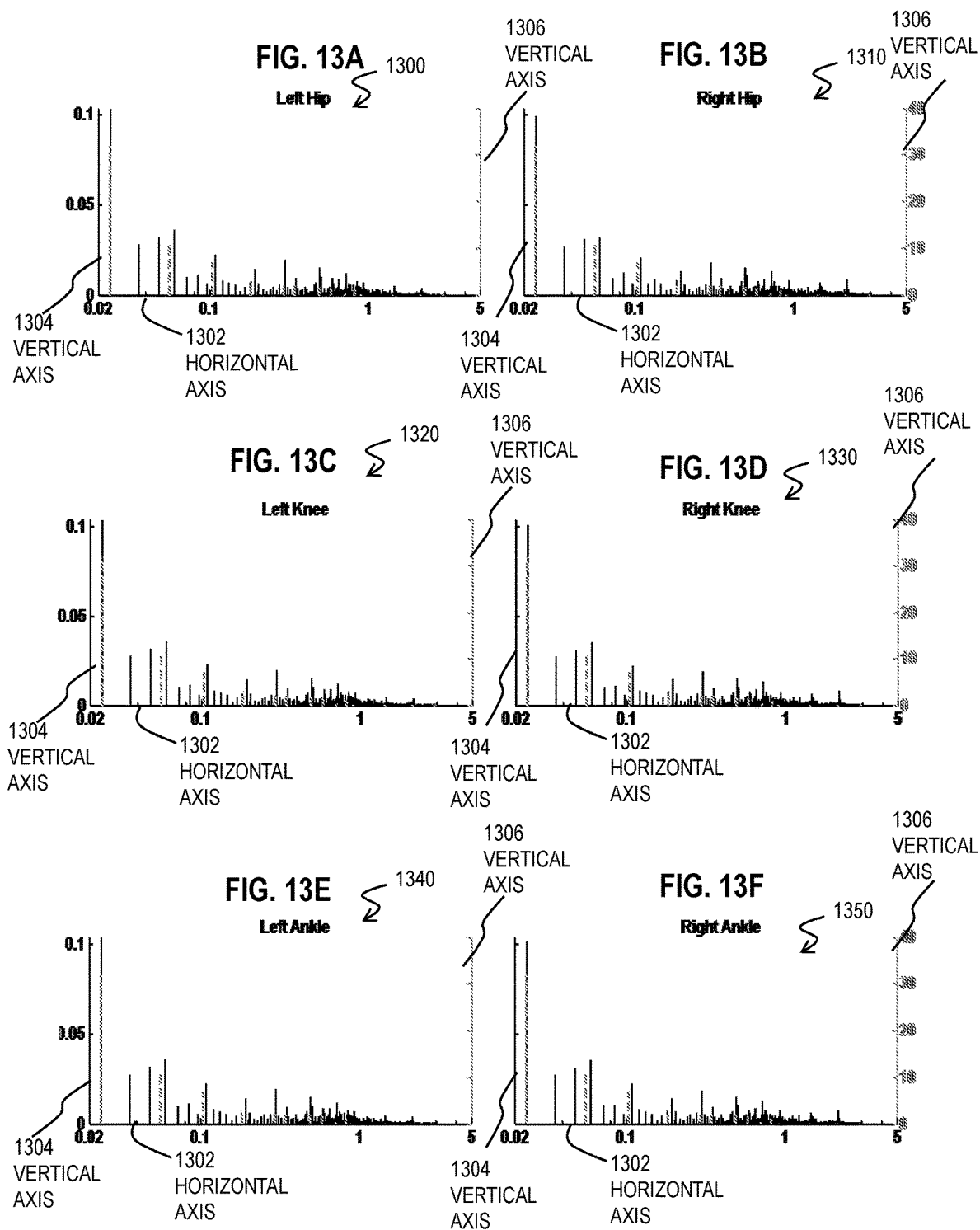

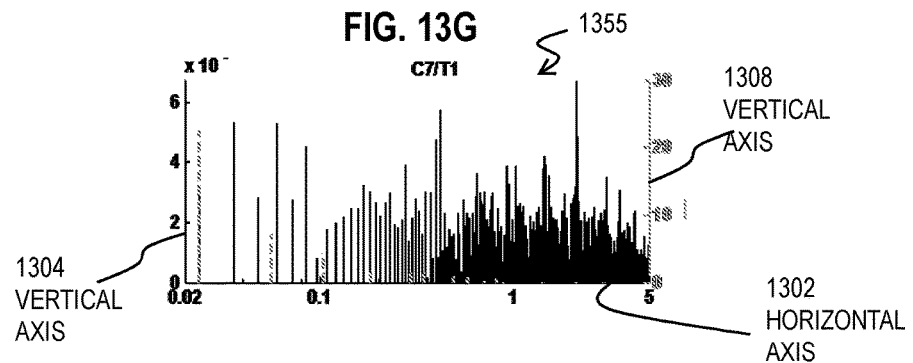
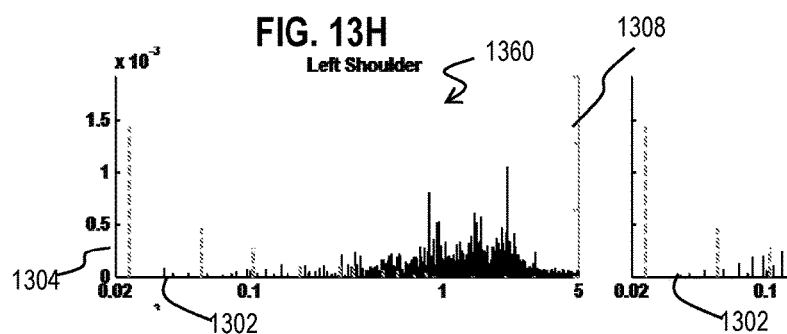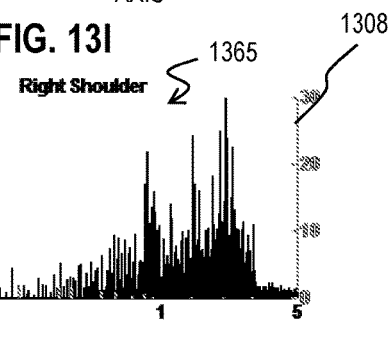
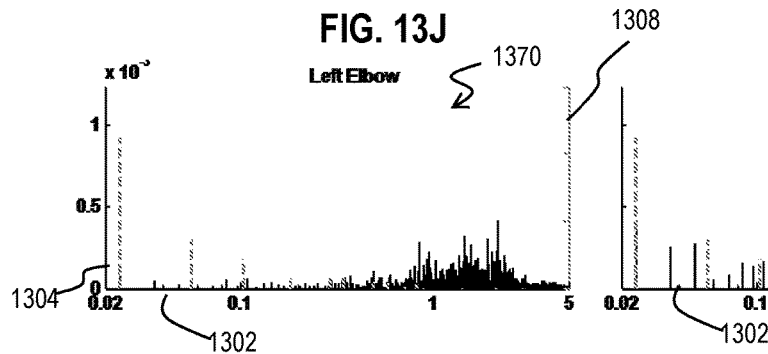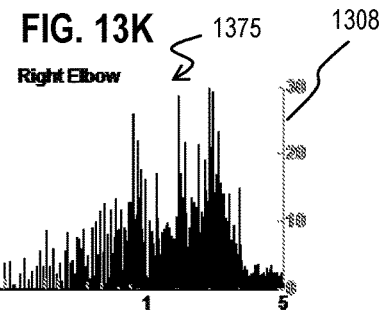
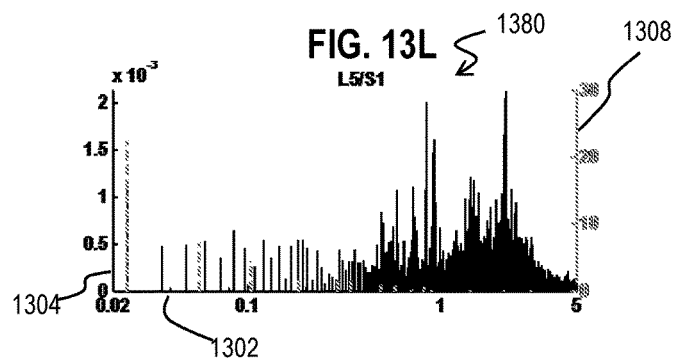

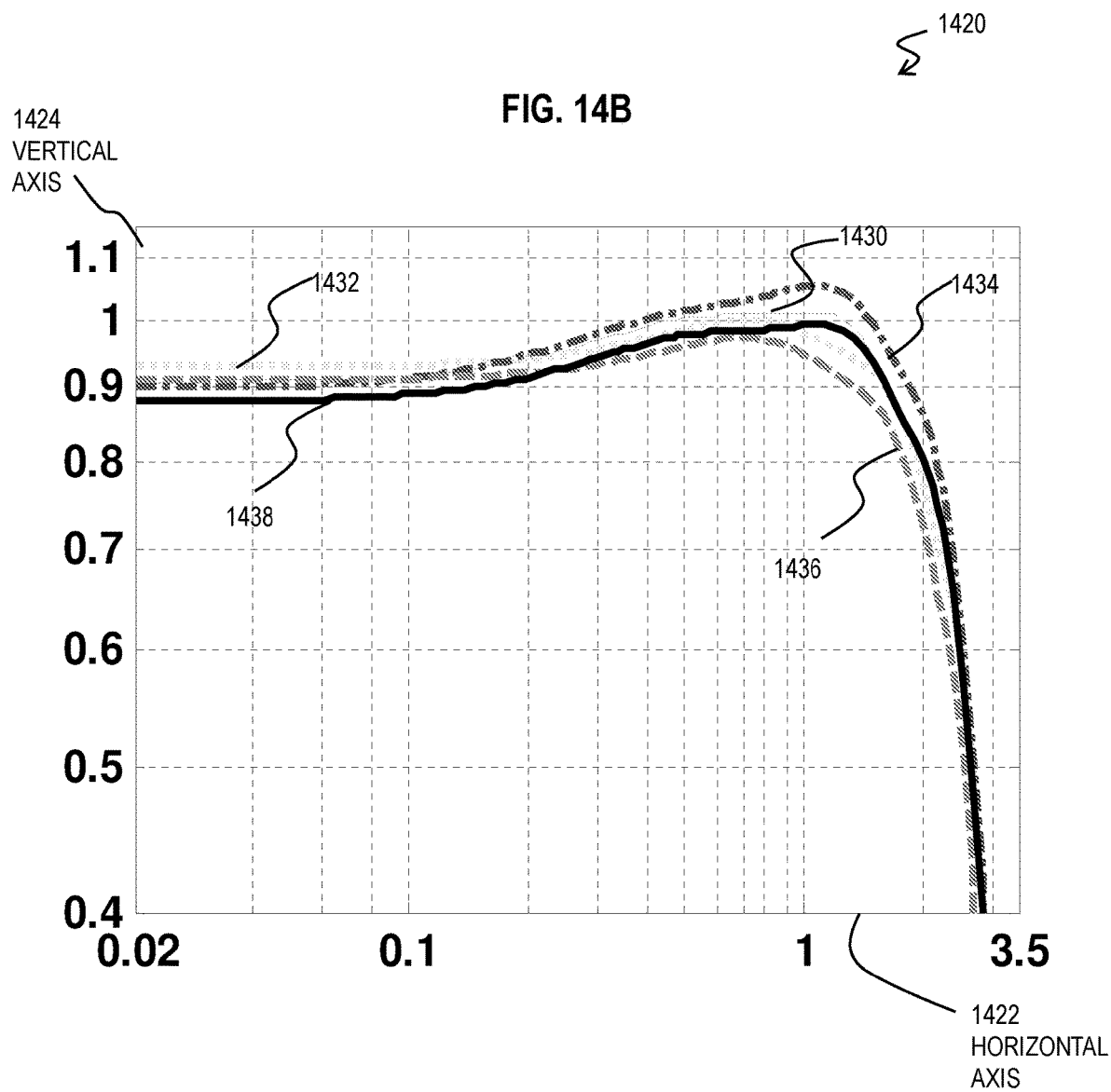

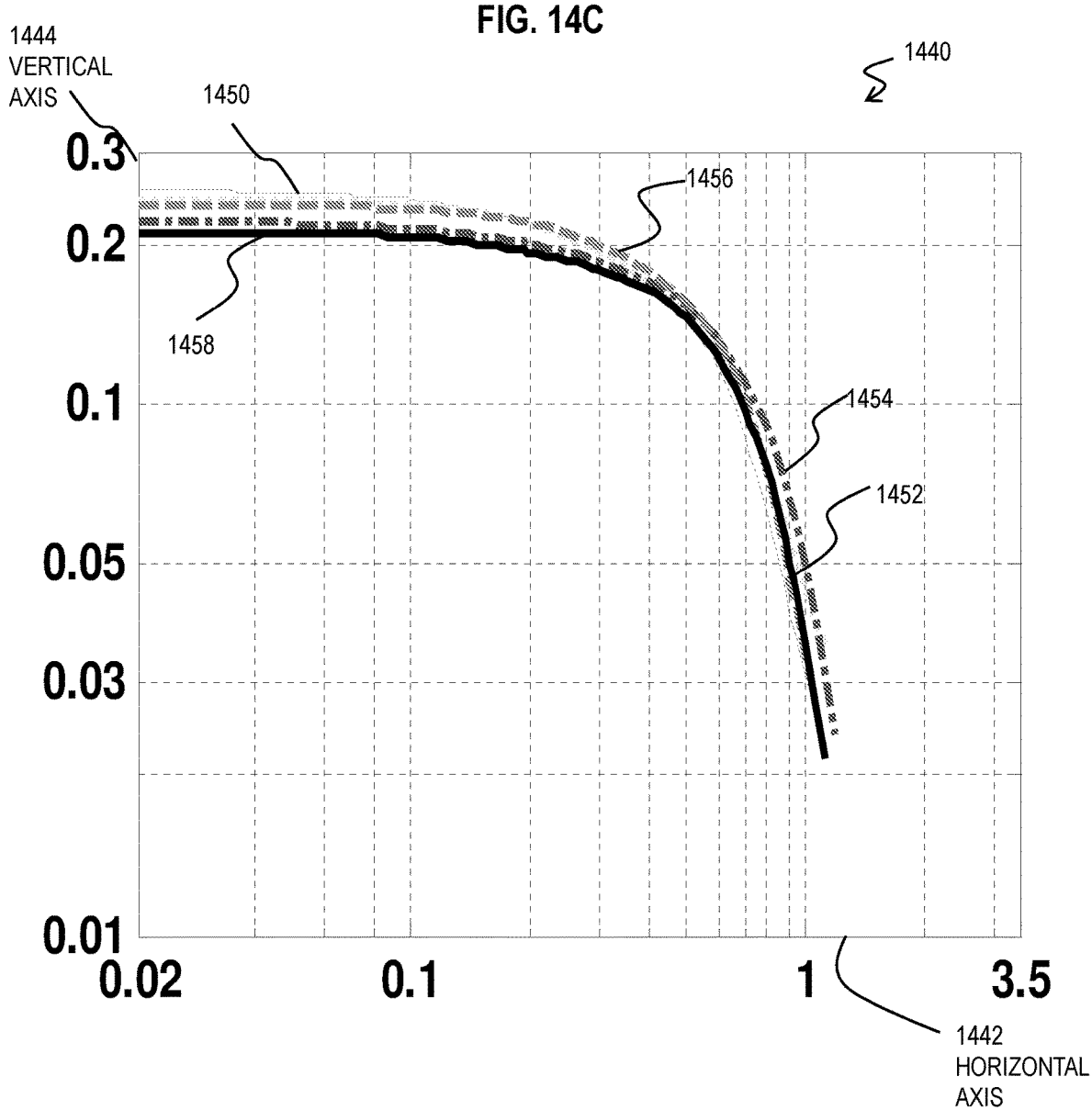

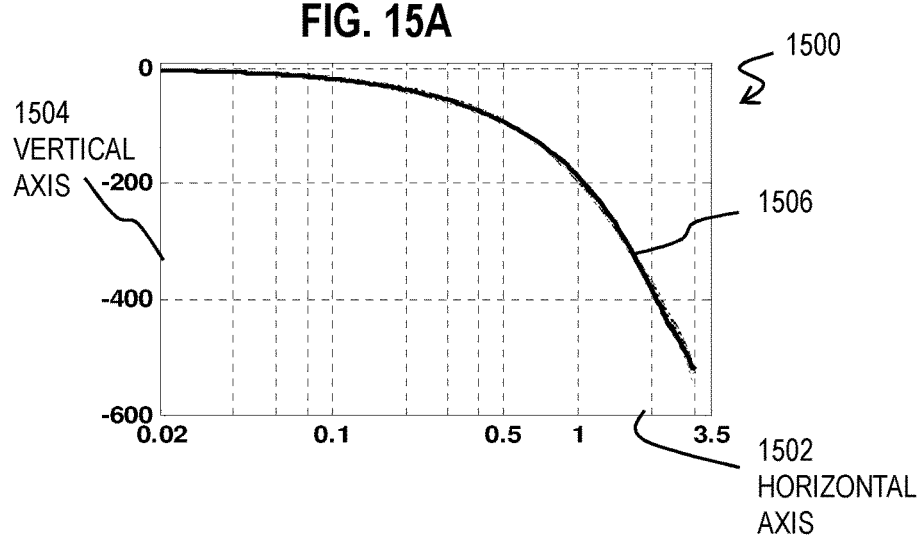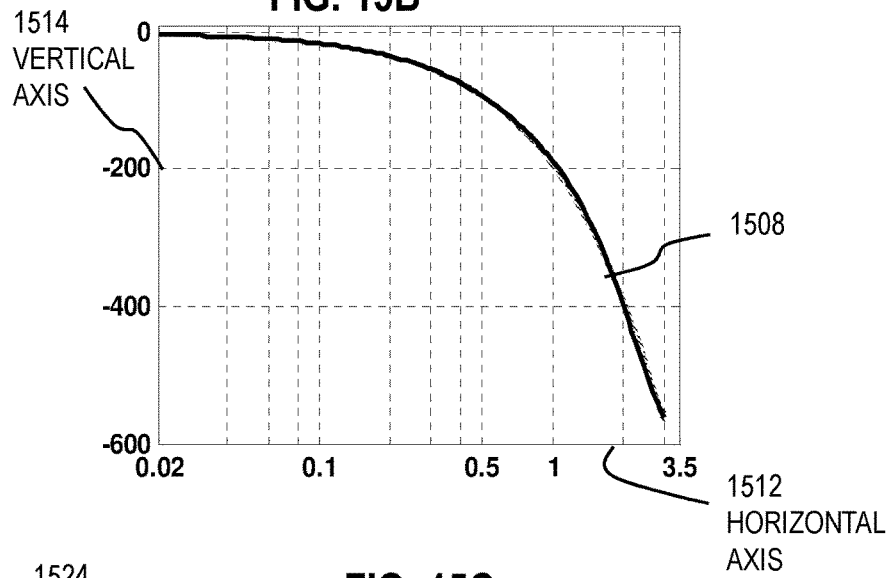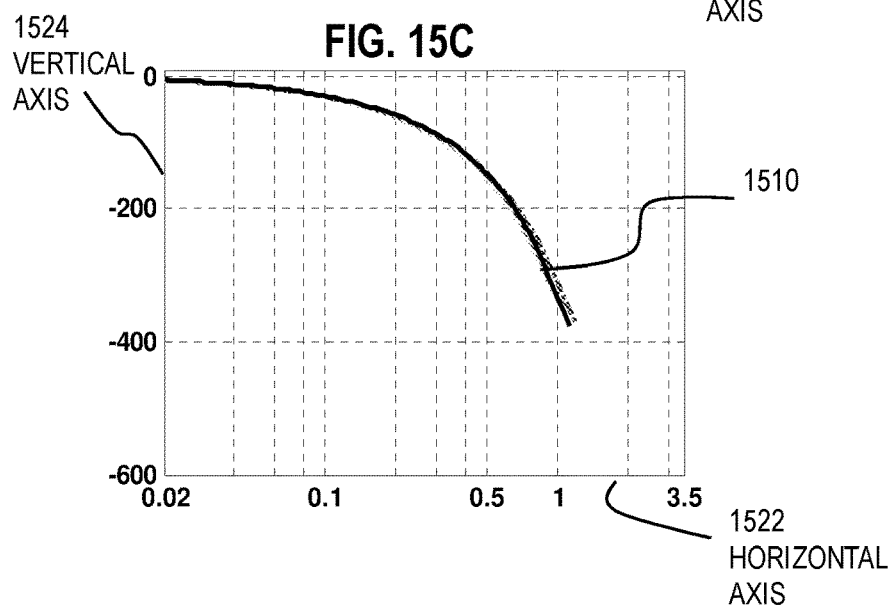

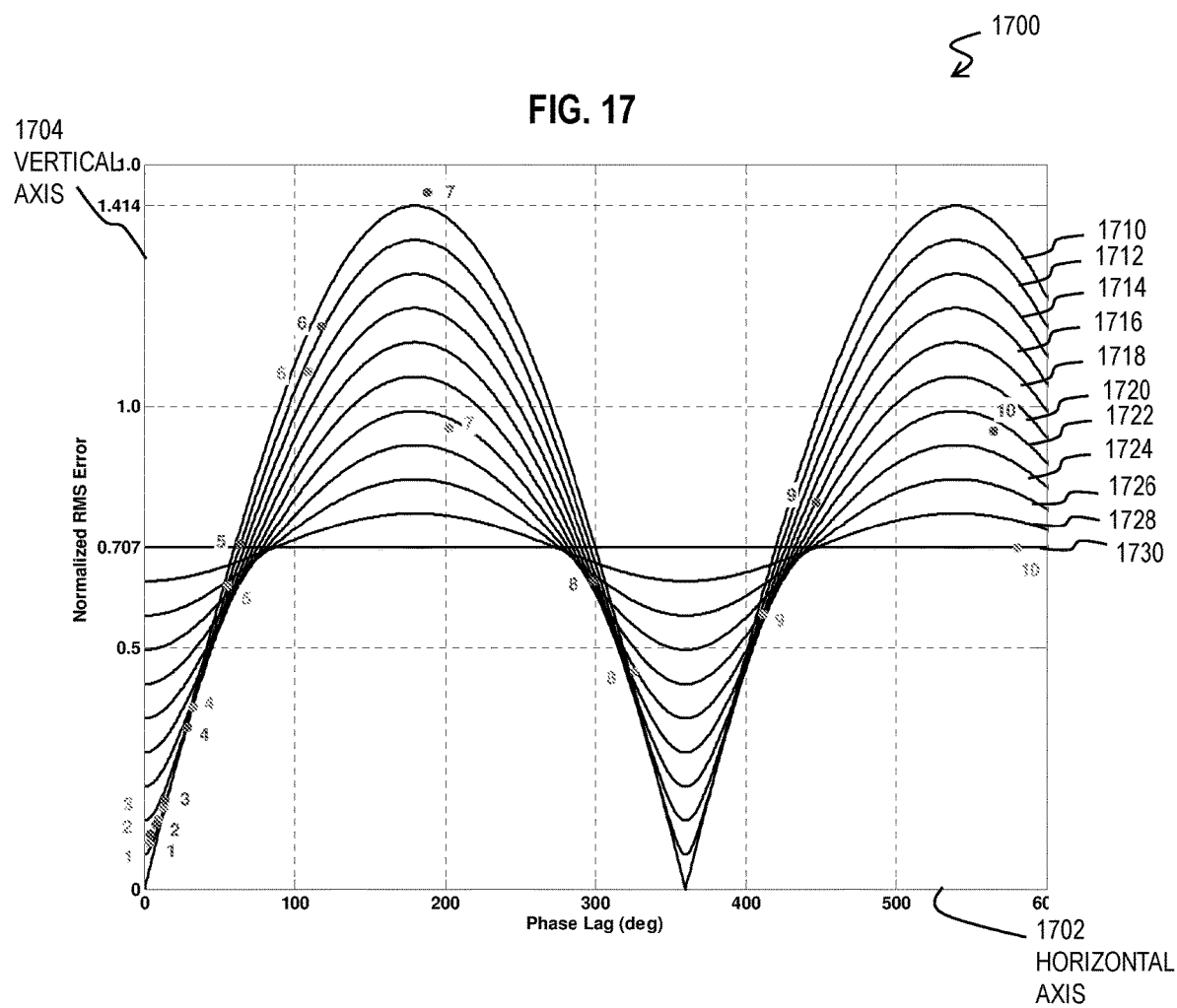

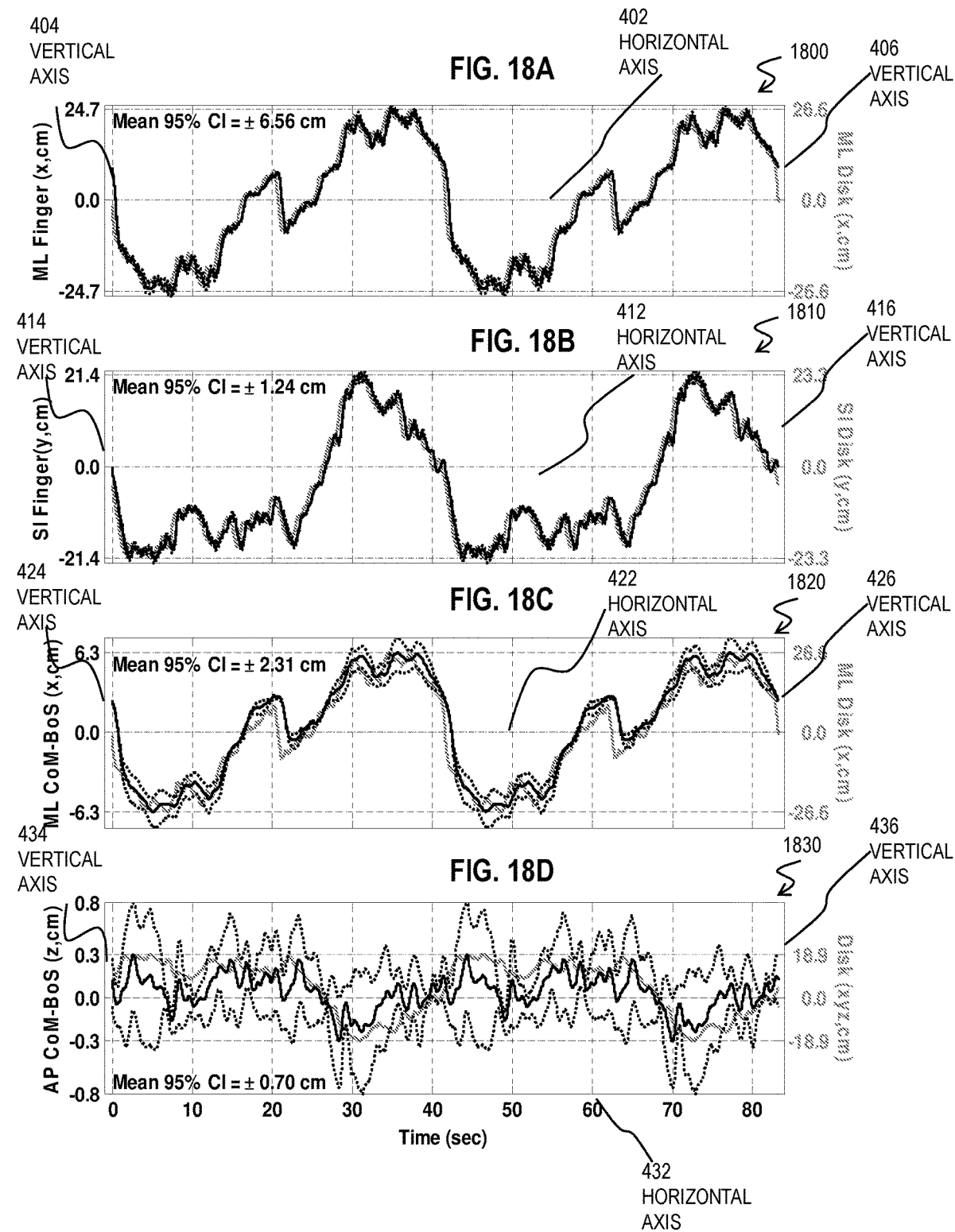

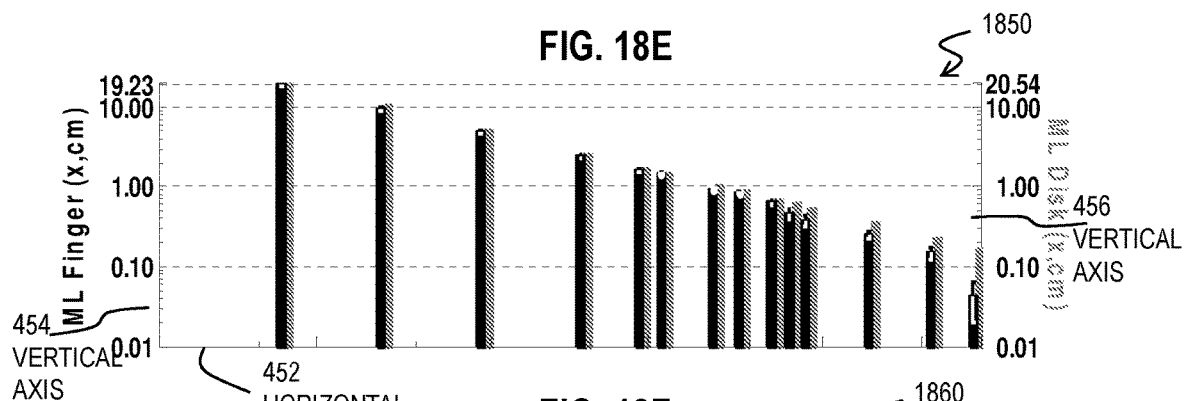
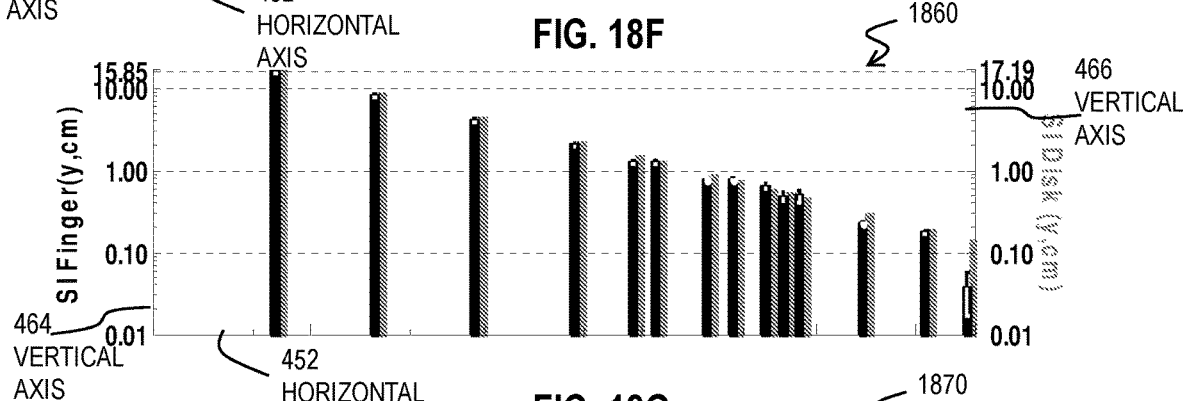
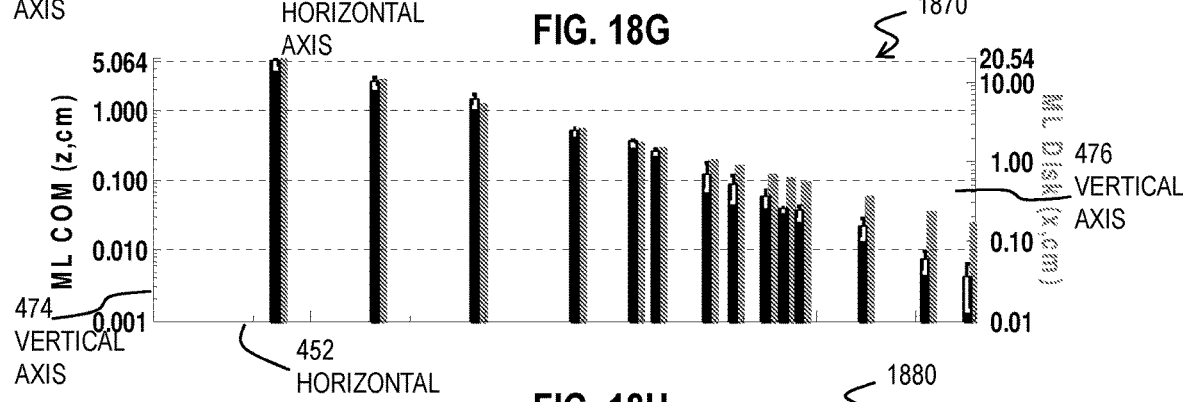
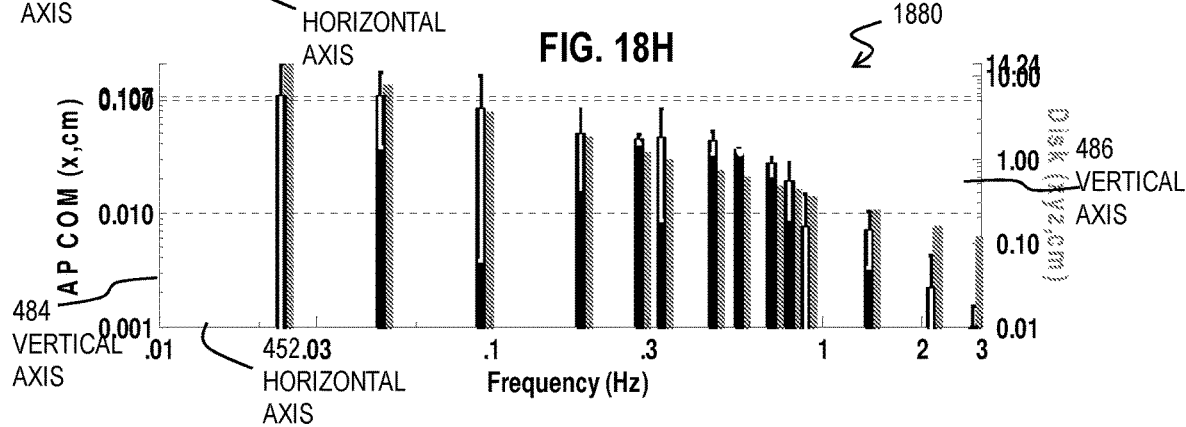

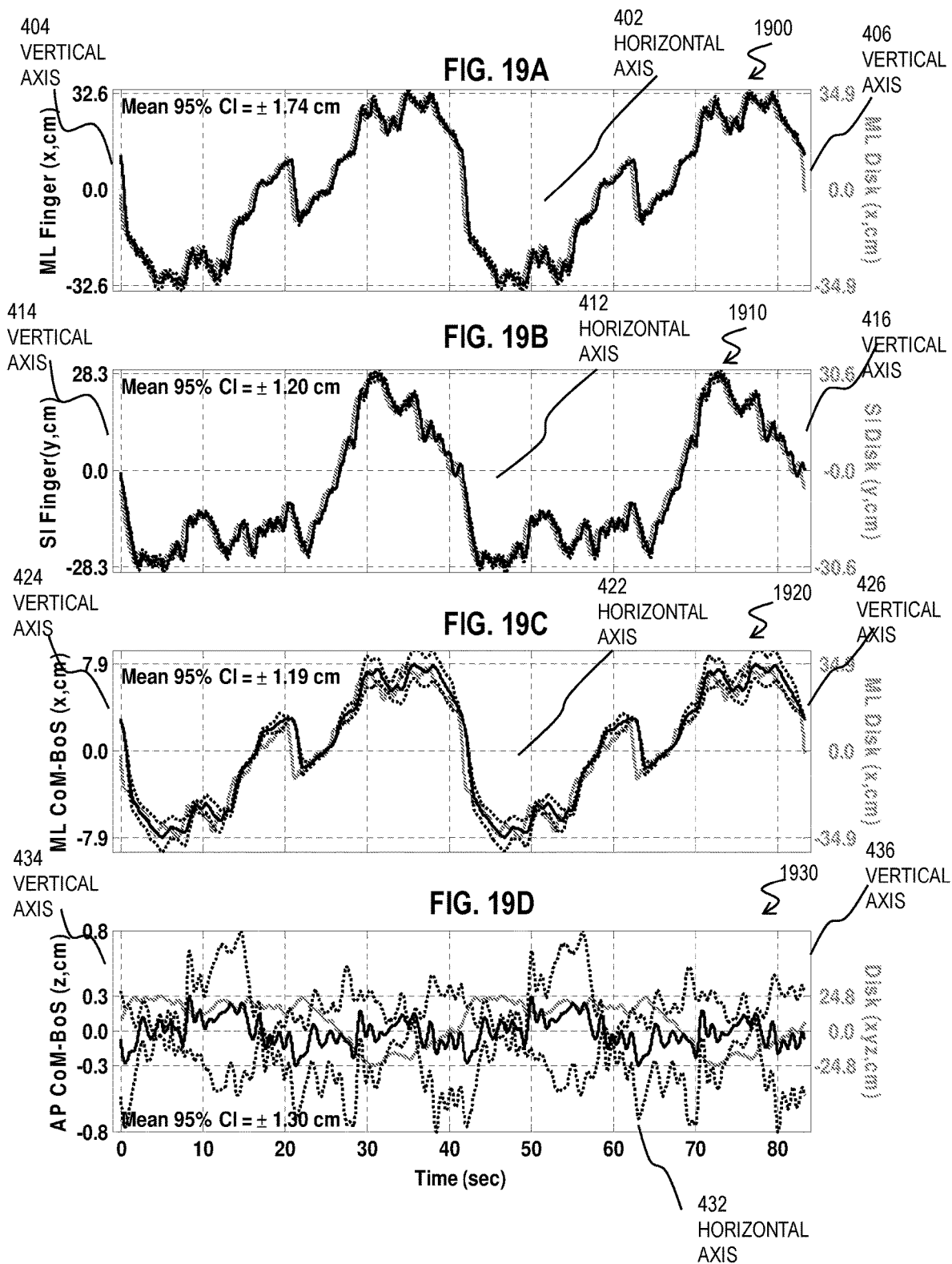

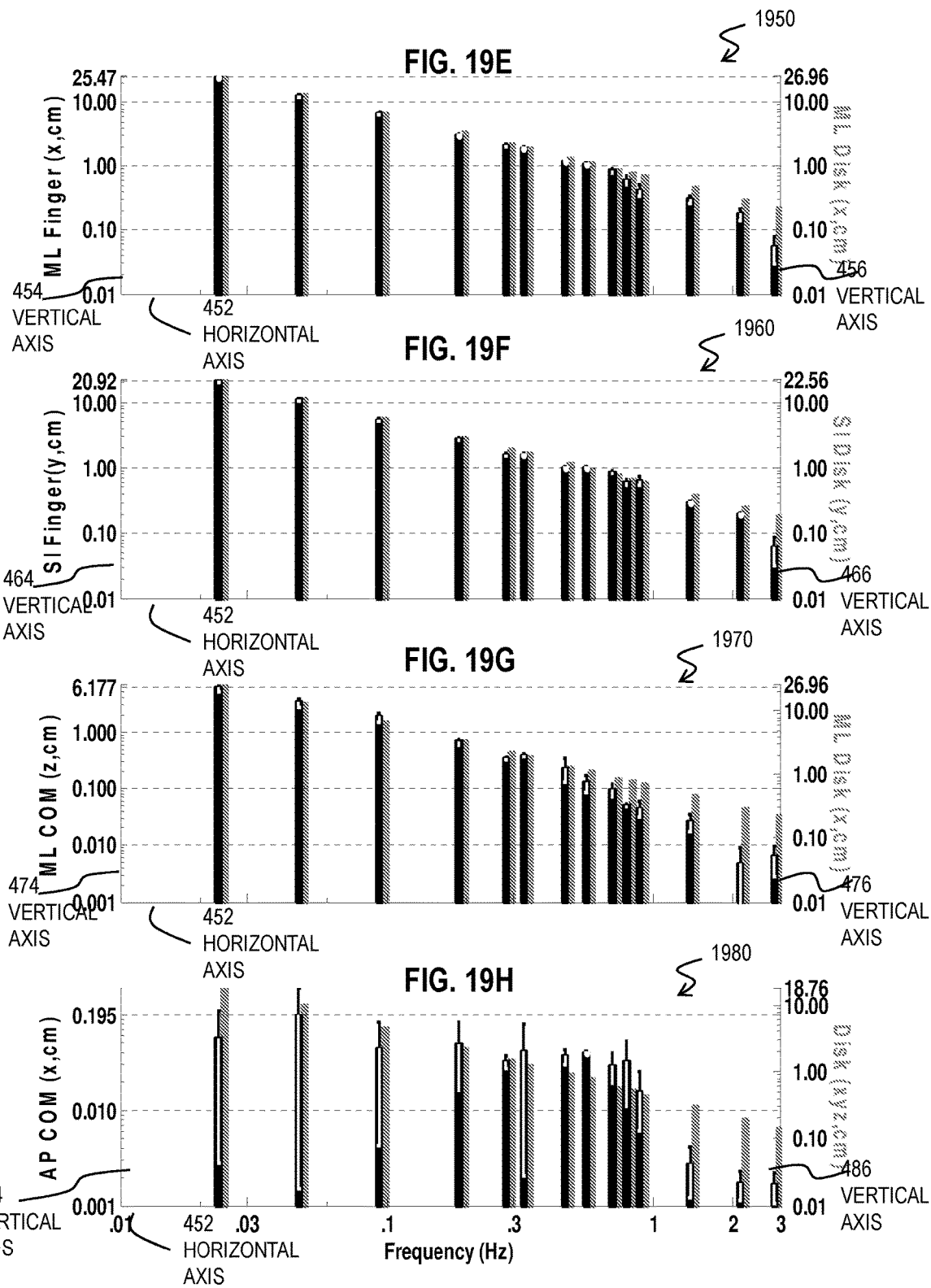

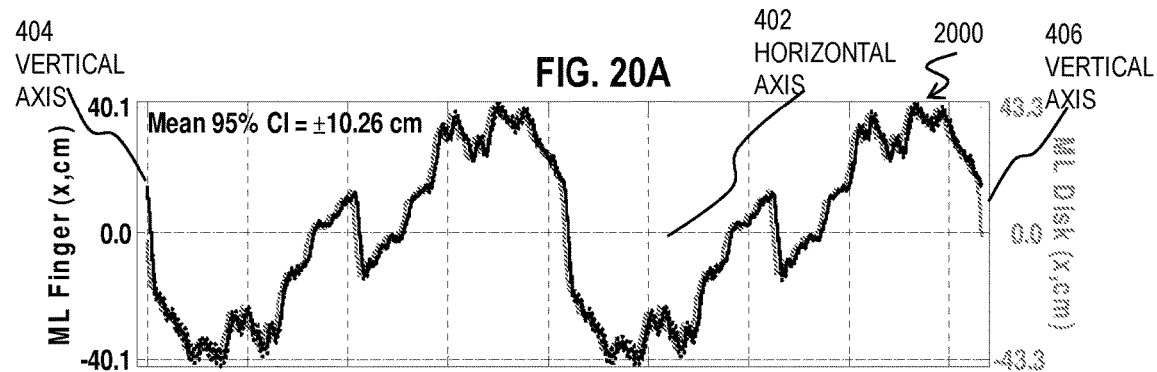
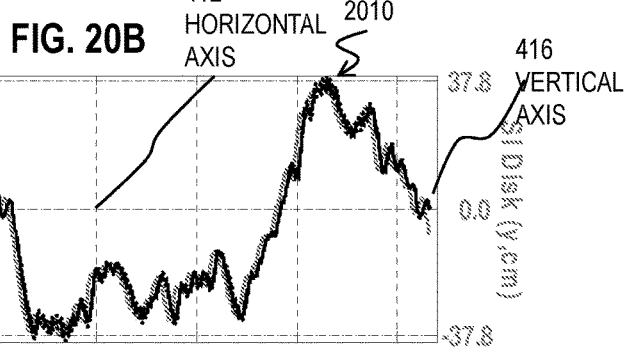
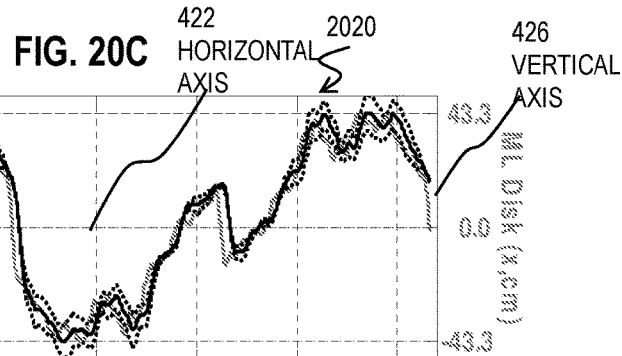
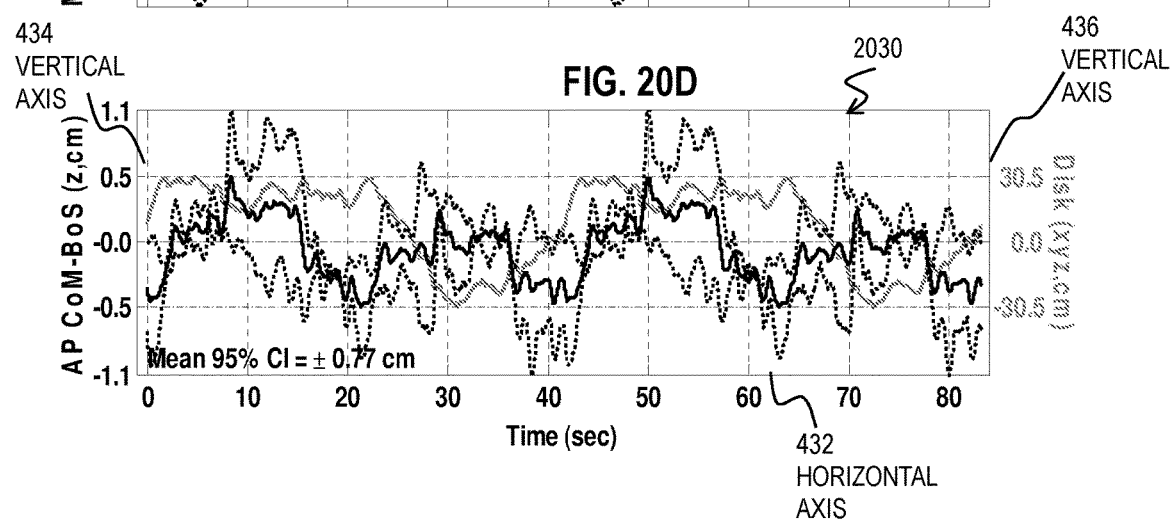

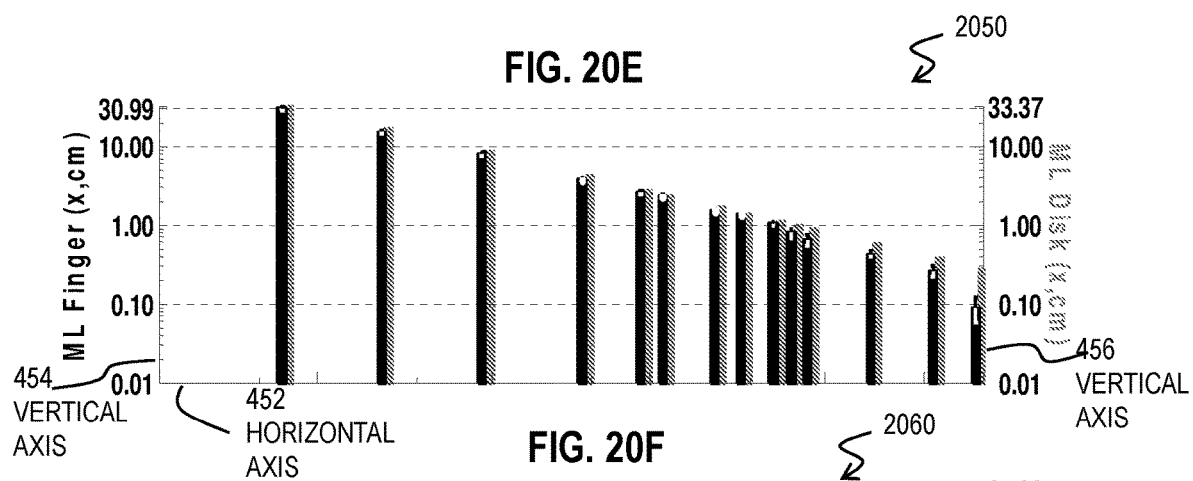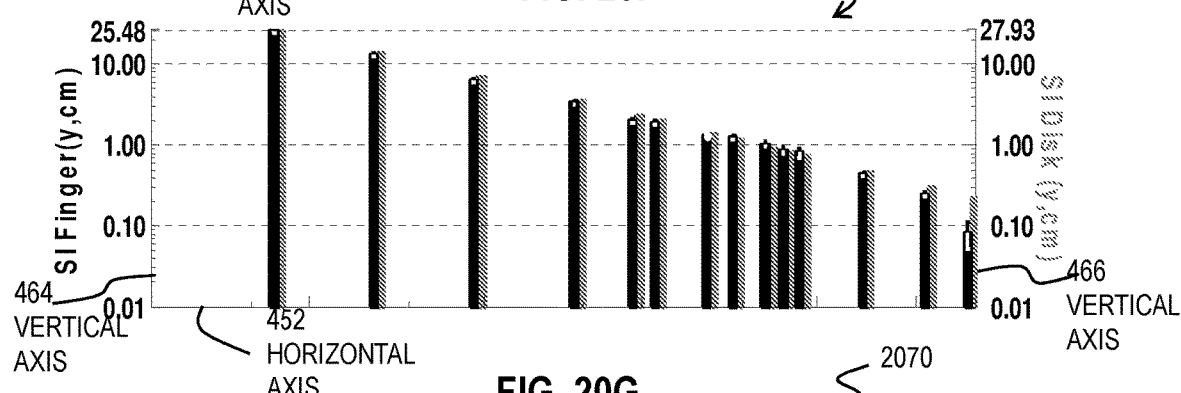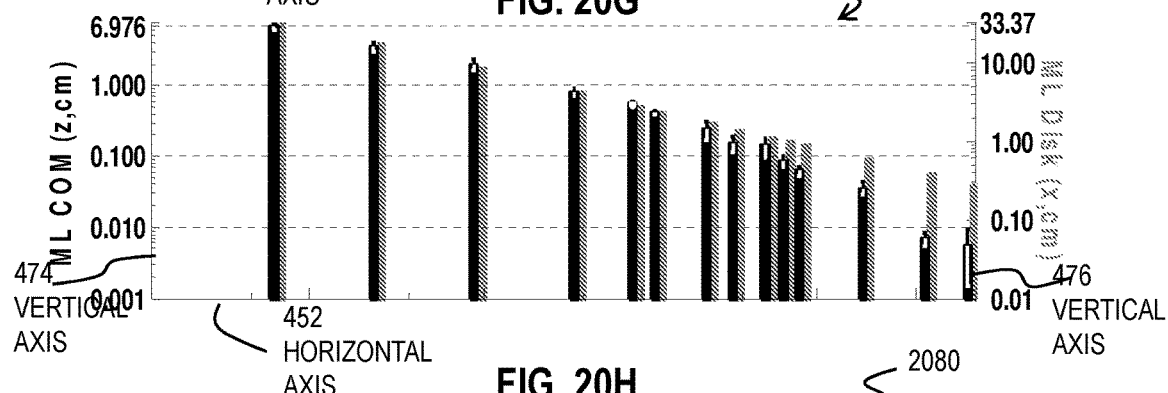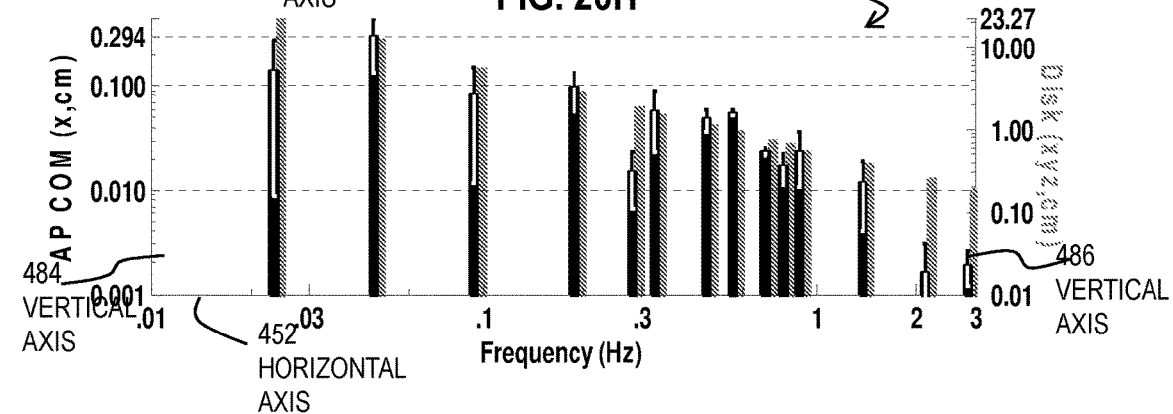

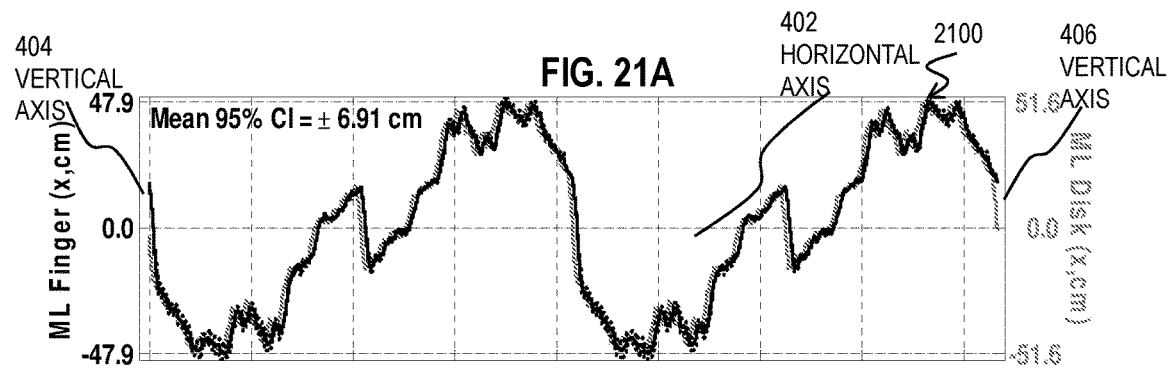
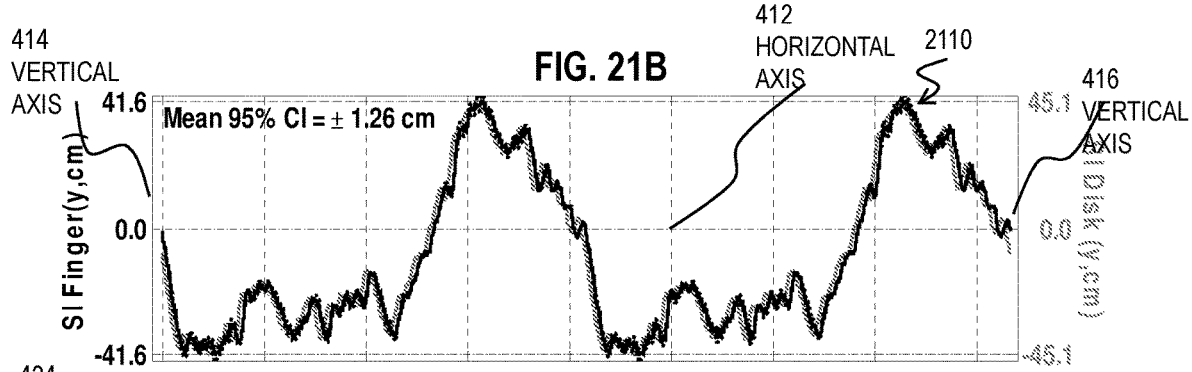
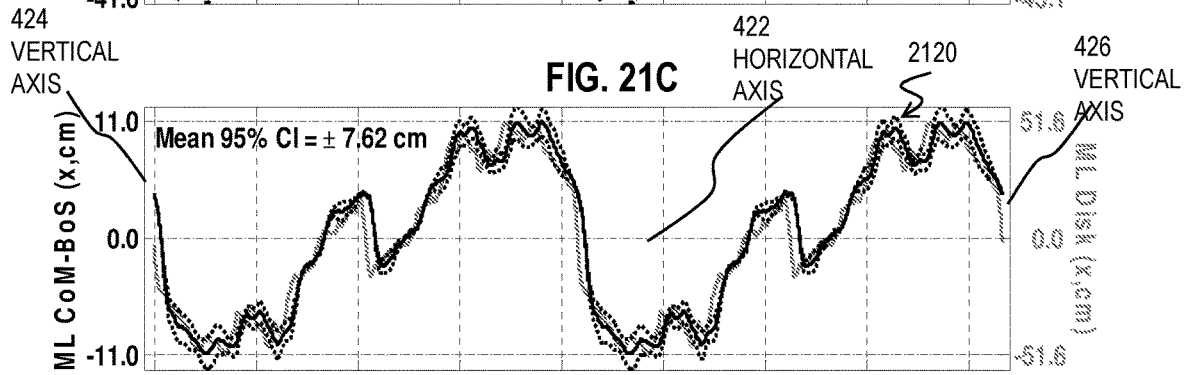
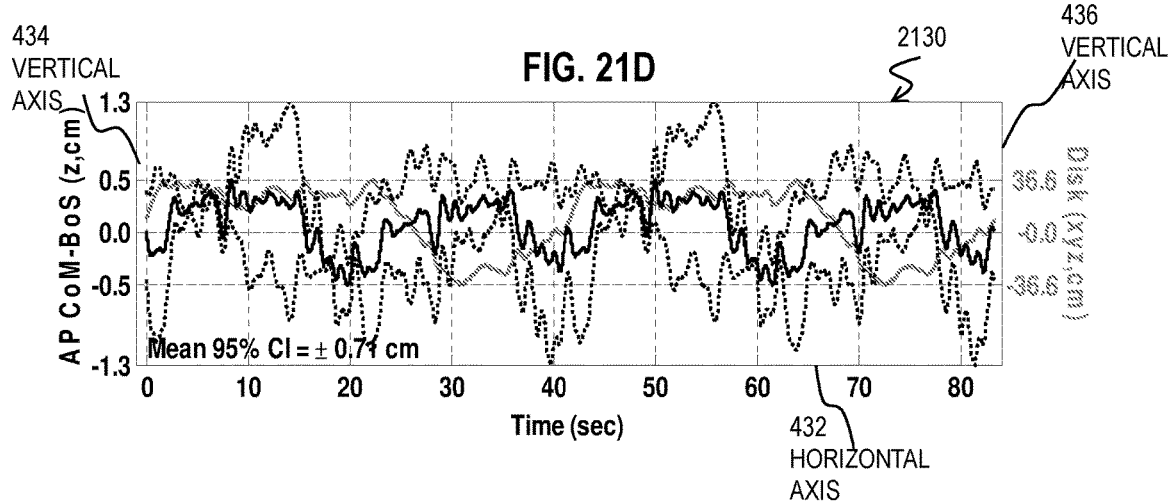

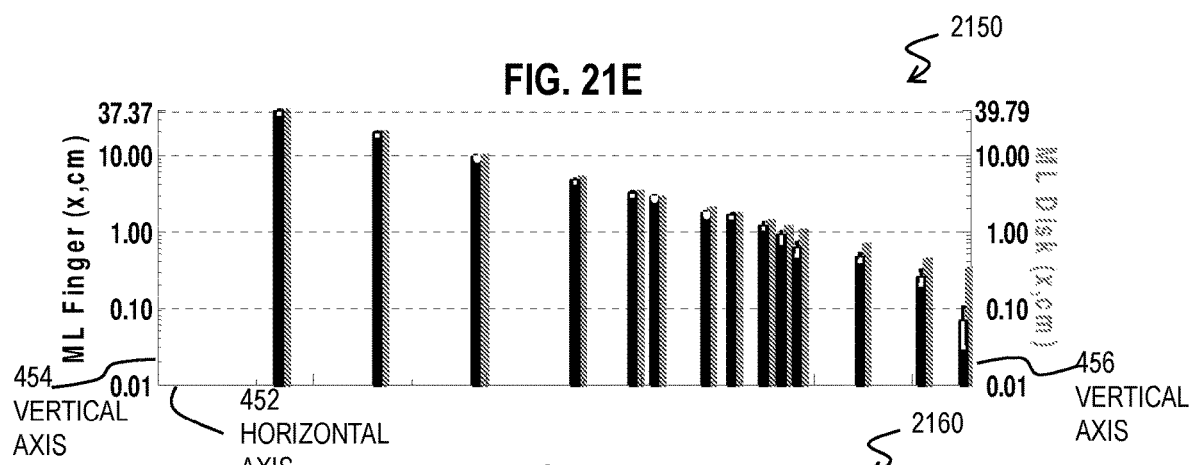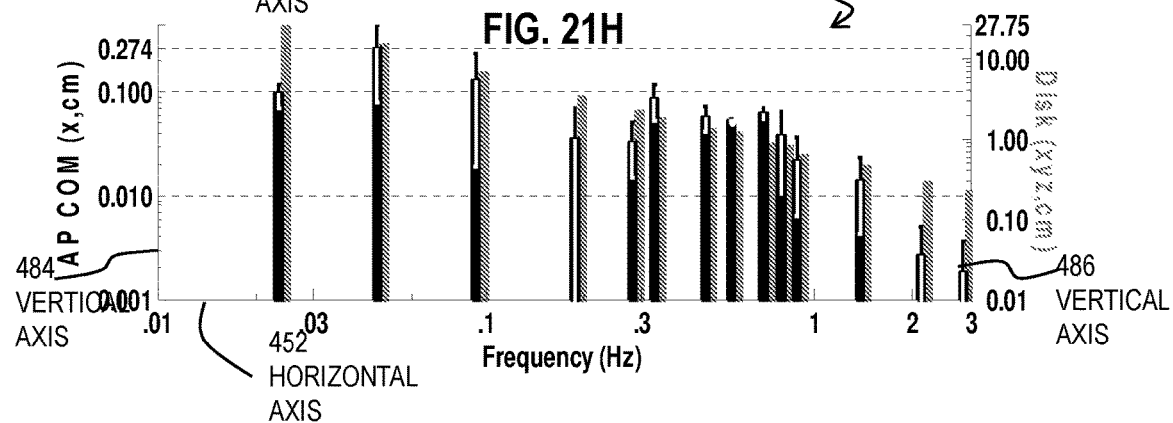

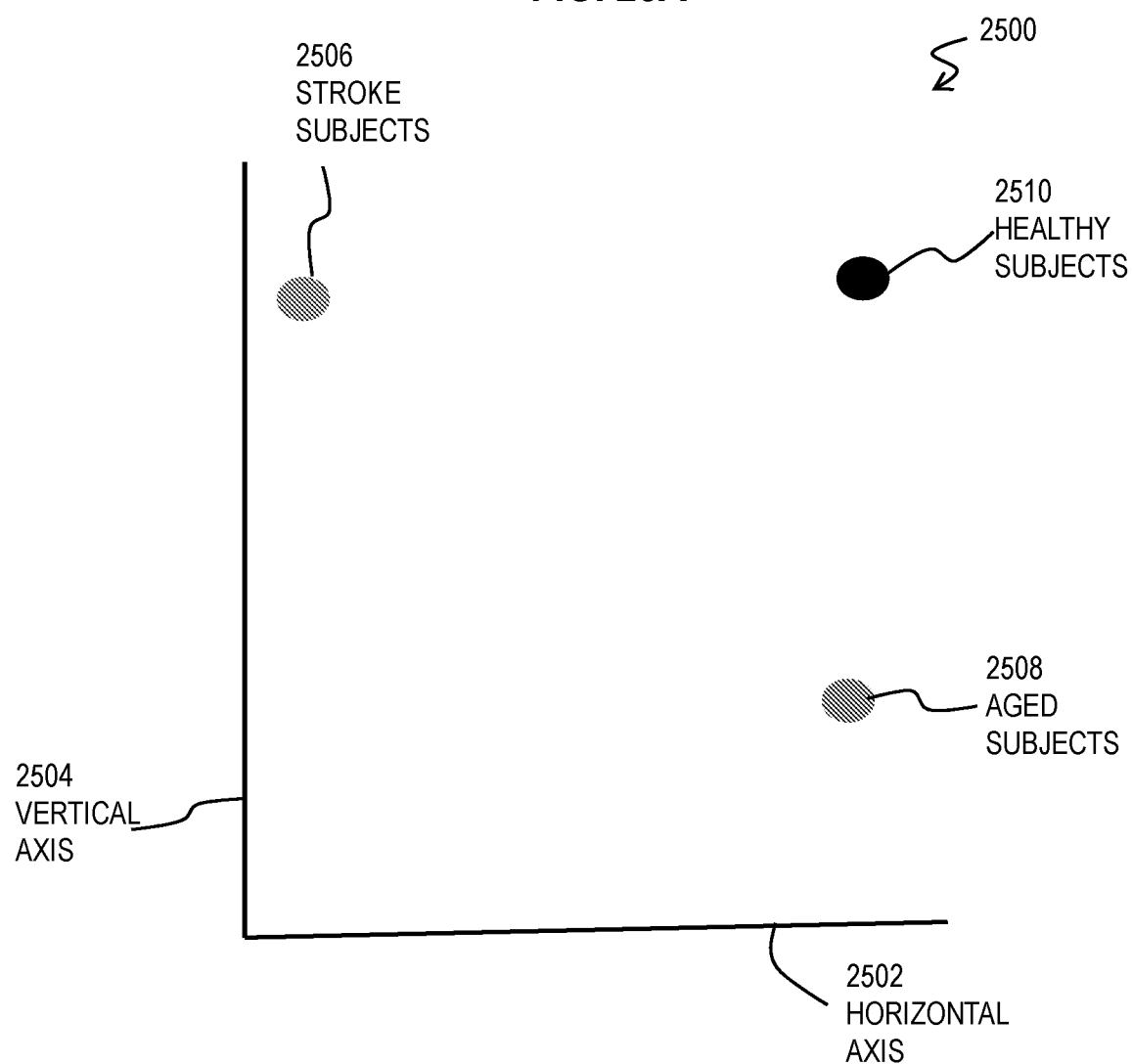

METHOD FOR ASSESSING FALL RISK BASED ON TRACKING DATA OF A MOVING TARGET

CROSS-REFERENCE TO RELATED APPLICATIONS

This application is a 371 national stage application of PCT Application No. PCT/US16/47258, filed Aug. 17, 2016, and claims benefit of U.S. Provisional Appln. 62/205,894, filed Aug. 17, 2015, and U.S. Provisional Appln 62/316,278, filed Mar. 31, 2016, the entire contents of which are hereby incorporated by reference as if fully set forth herein, under 35 U.S.C. § 119(e).

STATEMENT OF GOVERNMENTAL INTEREST

This invention was made with government support under Grant Number AG028747 awarded by the National Institutes of Health. The government has certain rights in the invention.

BACKGROUND

Bipedal standing balance is inherently unstable and requires coordinated interactions between various systems of a subject including sensorimotor and multi-segment musculoskeletal systems. As adults age, their sensorimotor and musculoskeletal systems gradually deteriorate which predisposes some aging adults to an increased risk of fall.

SUMMARY

It is here recognized that conventional methods for assessing fall risk are deficient, since they employ subjectively-determined scales which do not lend themselves to quantitative analysis. Additionally, many conventional methods for assessing fall risk encompass a narrow range of performance and thus exhibit floor and ceiling (switch and saturation) effects for those whose performance falls outside of this range. Additionally, conventional methods for assessing fall risk focus exclusively on balance assessment rather than a combination of tracking and balance assessment. Also, conventional methods for assessing fall risk are limited to balance assessment using involuntary perturbations and do not consider balance assessment based on volitional perturbations.

In a first set of embodiments, a method is provided for assessing a risk of fall based on tracking data of a moving target. The method includes obtaining movement data for the moving target and determining tracking data of a first subject to the moving target including a position of a body segment tracking the moving target and a position of a body center of mass. The method includes characterizing a response of the first subject to the moving target based on the movement data of the moving target and the tracking data of the first subject. The method includes determining tracking data of a second subject to the moving target including a body segment position tracking the moving target and a position of a body center of mass and determining a risk of fall of the second subject based on the response of the first subject and the tracking data of the second subject.

In a second set of embodiments, a method is provided for assessing a risk of fall based on tracking a moving target. The method includes determining tracking data of a first subject to the moving target based on sensors attached to a body of the first subject that measure a position of one or more body segments at incremental time increments over a time period. The method includes characterizing a response of the first subject to the moving target based on the tracking data of the first subject. The method includes determining tracking data of a second subject to the moving target based on sensors attached to a body of the second subject that measure a position of one or more body segments at each time increment over the time period. The method includes determining a risk of fall of the second subject based on the response of the first subject and the tracking data of the second subject.

In other embodiments, a computer-readable medium carrying one or more sequences of instructions is provided, where execution of the one or more sequences of instructions by one or more processors causes the one or more processors to perform one or more steps of the above methods, or an apparatus or system is configured to perfume one or more steps of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 3A is a graph that illustrates an example of root mean square error (RMSE) between a body segment and the moving target in the system of FIG. 1B, according to an embodiment;

FIG. 3B is a graph that illustrates an example of a root mean square deviation (RMSD) between a body center of mass and a center of the base of support of FIG. 1C, according to an embodiment;

FIG. 3C is a graph that illustrates an example of a time delay between a body segment and the moving target in the system of FIG. 1B, according to an embodiment;

FIG. 3D is a graph that illustrates an example of a time delay between a body center of mass and the moving target in the system of FIG. 1B, according to an embodiment;

FIG. 4A is a graph that illustrates an example of a position of a body segment and the moving target in a medial-lateral (ML) direction, according to an embodiment;

FIG. 4B is a graph that illustrates an example of a position of a body segment and the moving target in a superior-inferior (SI) direction, according to an embodiment;

FIG. 4C is a graph that illustrates an example of a position of a body center of mass and the moving target in a medial-lateral (ML) direction, according to an embodiment;

FIG. 4D is a graph that illustrates an example of a position of a body center of mass and the moving target in an anterior-posterior (AP) direction, according to an embodiment;

FIG. 5A is a graph that illustrates an example of a root mean square error (RMSE) and a normalized root mean square error (NRMSE) between a body segment and the moving target in a medial-lateral (ML) direction as a function of target frequency, according to an embodiment;

FIG. 5B is a graph that illustrates an example of a root mean square error (RMSE) and a normalized root mean square error (NRMSE) between a body segment and the moving target in a superior-inferior (SI) direction as a function of target frequency, according to an embodiment;

FIGS. 8A to 8F are graphs that illustrate an example of a normalized force imparted on joints of lower extremity (LE) body segments in a healthy subject and a position of the moving target in a medial-lateral (ML) direction, according to an embodiment;

FIGS. 8G to 8L are graphs that illustrate an example of a normalized force imparted on joints of upper extremity (UE) body segments in a healthy subject and a magnitude of the XYZ position of the moving target, according to an embodiment;

FIGS. 9A to 9F are graphs that illustrate an example of a frequency spectrum of the normalized force imparted on joints of LE body segments in a healthy subject and a frequency spectrum of the moving target in the ML direction, according to an embodiment;

FIG. 9G to 9L are graphs that illustrates an example of a frequency spectrum of the normalized force imparted on joints of the UE body segments in a healthy subject and a frequency spectrum of the magnitude of the position of the moving target, according to an embodiment;

FIGS. 10A to 10F are graphs that illustrate an example of a normalized force imparted on joints of lower extremity (LE) body segments in a second subject and a position of the moving target in a medial-lateral (ML) direction, according to an embodiment;

FIGS. 10G to 10L are graphs that illustrate an example of a normalized force imparted on joints of upper extremity (UE) body segments in a second subject and a magnitude of the XYZ position of the moving target, according to an embodiment;

FIGS. 11A to 11F are graphs that illustrate an example of a frequency spectrum of the normalized force imparted on joints of LE body segments in a second subject and a frequency spectrum of the moving target in the ML direction, according to an embodiment;

FIG. 11G to 11L are graphs that illustrates an example of a frequency spectrum of the normalized force imparted on joints of the UE body segments in a second subject and a frequency spectrum of the magnitude of the position of the moving target, according to an embodiment;

FIGS. 12A to 12F are graphs that illustrate an example of a normalized force imparted on joints of lower extremity (LE) body segments in a second subject after training and a position of the moving target in a medial-lateral (ML) direction, according to an embodiment;

FIGS. 12G to 12L are graphs that illustrate an example of a normalized force imparted on joints of upper extremity (UE) body segments in a second subject after training and a magnitude of the XYZ position of the moving target, according to an embodiment;

FIGS. 13A to 13F are graphs that illustrate an example of a frequency spectrum of the normalized force imparted on joints of LE body segments in a second subject after training and a frequency spectrum of the moving target in the ML direction, according to an embodiment;

FIG. 13G to 13L are graphs that illustrates an example of a frequency spectrum of the normalized force imparted on joints of the UE body segments in a second subject after training and a frequency spectrum of the magnitude of the position of the moving target, according to an embodiment;

FIG. 14B is a graph that illustrates an example of a ratio of an amplitude of the frequency spectrum of the body segment and an amplitude of the frequency spectrum of the moving target in the superior-inferior (SI) direction as a function of target frequency, according to an embodiment;

FIG. 14C is a graph that illustrates an example of a ratio of an amplitude of the frequency spectrum of the body center of mass and an amplitude of the frequency spectrum of the moving target in the medial-lateral (ML) direction as a function of target frequency, according to an embodiment;

FIG. 15A is a graph that illustrates an example of a phase lag of the frequency spectrum of the body segment and the frequency spectrum of the moving target in the medial-lateral (ML) direction as a function of target frequency, according to an embodiment;

FIG. 15B is a graph that illustrates an example of a phase lag of the frequency spectrum of the body segment and the frequency spectrum of the moving target in the superior-inferior (SI) direction as a function of target frequency, according to an embodiment;

FIG. 15C is a graph that illustrates an example of a phase lag of the frequency spectrum of the body center of mass and the frequency spectrum of the moving target in the medial-lateral (ML) direction as a function of target frequency, according to an embodiment;

FIG. 17 is a graph that illustrates an example of a normalized root mean square error (NRMSE) between a body segment and the moving target as a function of phase lag between the frequency spectrum of the body segment and the frequency spectrum of the moving target, according to an embodiment;

FIGS. 18A to 18B are graphs that illustrate an example of a position of a body segment and the moving target, according to an embodiment;

FIGS. 18C to 18D are graphs that illustrate an example of a position of a body center of mass and the moving target, according to an embodiment;

FIGS. 18E to 18F are graphs that illustrate an example of a frequency spectrum of the body segment and a frequency spectrum of the moving target, according to an embodiment;

FIGS. 18G to 18H are graphs that illustrate an example of a frequency spectrum of the body center of mass and a frequency spectrum of the moving target, according to an embodiment;

FIGS. 19A to 19B are graphs that illustrate an example of a position of a body segment and the moving target, according to an embodiment;

FIGS. 19C to 19D are graphs that illustrate an example of a position of a body center of mass and the moving target, according to an embodiment;

FIGS. 19E to 19F are graphs that illustrate an example of a frequency spectrum of the body segment and a frequency spectrum of the moving target, according to an embodiment;

FIGS. 19G to 19H are graphs that illustrate an example of a frequency spectrum of the body center of mass and a frequency spectrum of the moving target, according to an embodiment;

FIGS. 20A to 20B are graphs that illustrate an example of a position of a body segment and the moving target, according to an embodiment;

FIGS. 20C to 20D are graphs that illustrate an example of a position of a body center of mass and the moving target, according to an embodiment;

FIGS. 20E to 20F are graphs that illustrate an example of a frequency spectrum of the body segment and a frequency spectrum of the moving target, according to an embodiment;

FIGS. 20G to 20H are graphs that illustrate an example of a frequency spectrum of the body center of mass and a frequency spectrum of the moving target, according to an embodiment;

FIGS. 21A to 21B are graphs that illustrate an example of a position of a body segment and the moving target, according to an embodiment;

FIGS. 21C to 21D are graphs that illustrate an example of a position of a body center of mass and the moving target, according to an embodiment;

FIGS. 21E to 21F are graphs that illustrate an example of a frequency spectrum of the body segment and a frequency spectrum of the moving target, according to an embodiment;

FIGS. 21G to 21H are graphs that illustrate an example of a frequency spectrum of the body center of mass and a frequency spectrum of the moving target, according to an embodiment;

FIG. 25A is a graph that illustrates an example of a mean force magnitude of a left joint as a function of a mean force magnitude of a right joint over the time period for a plurality of subject groups, according to an embodiment.

DETAILED DESCRIPTION

Figure 1A:
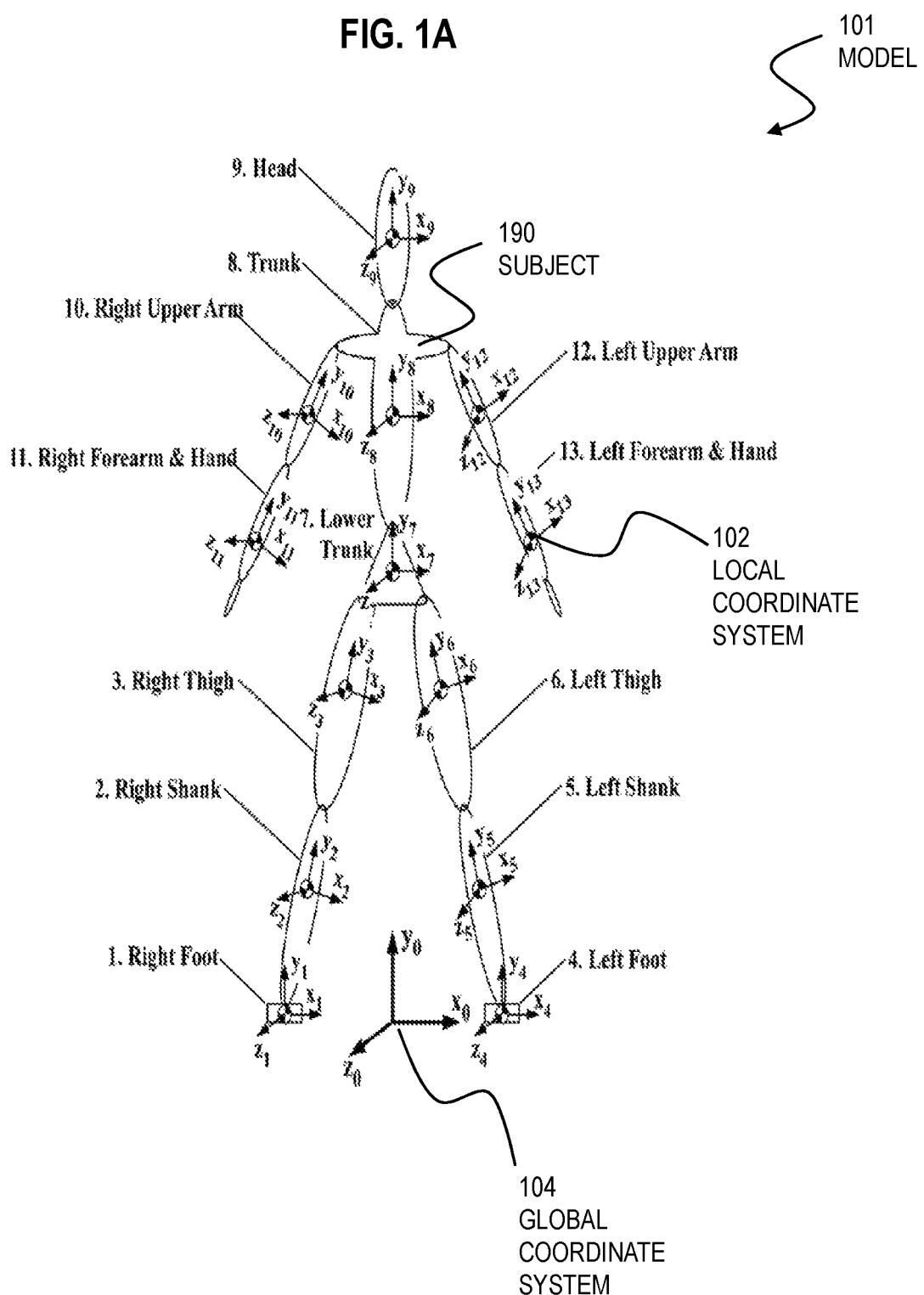
FIG. 1A is a block diagram that illustrates an example of a biomechanical model of a human subject, according to an embodiment.

A method is described for assessing a fall risk based on tracking data of a subject who is tracking a moving target. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of assessing a fall risk of a subject based on tracking data of the subject who is tracking a moving target. However, the invention is not limited to this context. In other embodiments the system is used to determine a robotic assist for a subject in order to achieve better tracking or balance or some combination. In other embodiments, the system is used to assess a fall risk of a subject based on tracking data of the subject to a moving target while the subject is instructed to keep their feet in place during the assessment. In other embodiments, the moving target travels beyond the reach of the subject and the subject is instructed to step, when necessary, to maintain tracking of the moving target. This embodiment allows precise determination of the limits of the subject's standing balance as a function of a reaching direction.

In other embodiments, the tracking data is analyzed in real time as part of an adaptive staircase algorithm to assess the subject's performance. In this embodiment, when the subject demonstrates proficiency in tracking the moving target at a given excursion amplitude, the amplitude is increased, making the tracking more difficult and challenging the subject to perform at the limits of their balance. In other embodiments, the moving target travels in three dimensions and the subject wears virtual reality goggles while tracking the moving target. In other embodiments, the tracking data is measured as the subject walks on a treadmill.

In other embodiments, the tracking data is measured as the subject stands on a low cost and portable force sensitive pad (e.g. Zeno Walkway® System). In other embodiments, the tracking data is measured as the subject stands on low cost and portable foot pressure sensors (e.g. Medilogic® Foot Pressure Measuring System). In other embodiments, the tracking data is measured by low cost and portable three dimensional accelerometers (e.g. Noraxon MyoMotion® Accelerometer System).

In other embodiments, the tracking data is measured by a machine-vision system including charge-coupled device (CCD) cameras. In this embodiment, each CCD camera captures the subject's body motion from a different perspective and identifies each body segment and its respective location and orientation in 3D coordinates throughout the subject movement. In this embodiment, a mass and a location of a center of mass (COM) for each body segment are computed using anthropometric data and combined to give whole-body mass and a center of mass for the body. In other embodiments, the tracking data is measured by a low cost machine-vision system that employs three ASUS Xtion PRO LIVE® motion sensing systems.

1. Overview

FIG. 1A is a block diagram that illustrates an example of a biomechanical model 101 of a human subject 190, according to an embodiment. In an example embodiment, the model 01 includes 13 rigid segments and 12 joints as listed in Table 1 below:

TABLE 1

Biomechanical model segments and joint centers of rotation

| Segment Index | Segment | Joint |
|---|---|---|
| 1. | Right Foot | Right Ankle |
| 2. | Right Shank | Right Knee |
| 3. | Right Thigh | Right Hip |
| 4. | Left Foot | Left Ankle |
| 5. | Left Shank | Left Knee |
| 6. | Left Thigh | Left Hip |
| 7. | Lower Trunk | L5/S1[a] |
| 8. | Trunk | C7/T1[b] |

TABLE 1-continued

Biomechanical model segments and joint centers of rotation

| Segment Index | Segment | Joint |
|---|---|---|
| 9. | Head | |
| 10. | Right Upper Arm | Right Shoulder |
| 11. | Right Forearm & Hand | Right Elbow |
| 12. | Left Upper Arm | Left Shoulder |
| 13. | Left Forearm & Hand | Left Elbow |

However, in other embodiments, a biomechanical model of a subject need not include all of the segments listed in Table 1 and FIG. 1A and can include fewer or more than those depicted in FIG. 1A and listed in Table 1. A local coordinate system 102 $(x_j y_j z_j)$ is assigned to each body segment j ($1 \le j \le 13$ in the illustrated embodiment) with its origin at the segment's center of mass (CoM) and is oriented in the manner indicated in FIG. 1A. With the subject 190 standing in the position shown in FIG. 1A, each local coordinate system 102 $x_j y_j$ plane is parallel to the subject's 190 (and segment's) frontal plane, while the $y_j z_j$ plane is parallel to the segment's sagittal plane. For the feet, which are assumed to remain in contact with the ground, the $y_j$ axis points vertically upward. For the shanks, thighs, trunk, upper arms, forearms, and hands, the $y_j$ axis is directed along a line joining the proximal and distal joint centers of rotation (CoRs), which composes these segments' end points. In an example embodiment, the hands are splinted so there is no motion at the wrist, and the hand therefore is functionally an extension of the forearm. The local coordinate system 102 is fixed with respect to their associated segments and move in the same manner as the segments. A fixed global coordinate system 104 $(x_0 y_0 z_0)$ is located between the two feet approximately in the middle of a base of support (BOS) area between the feet.

Figure 1B:
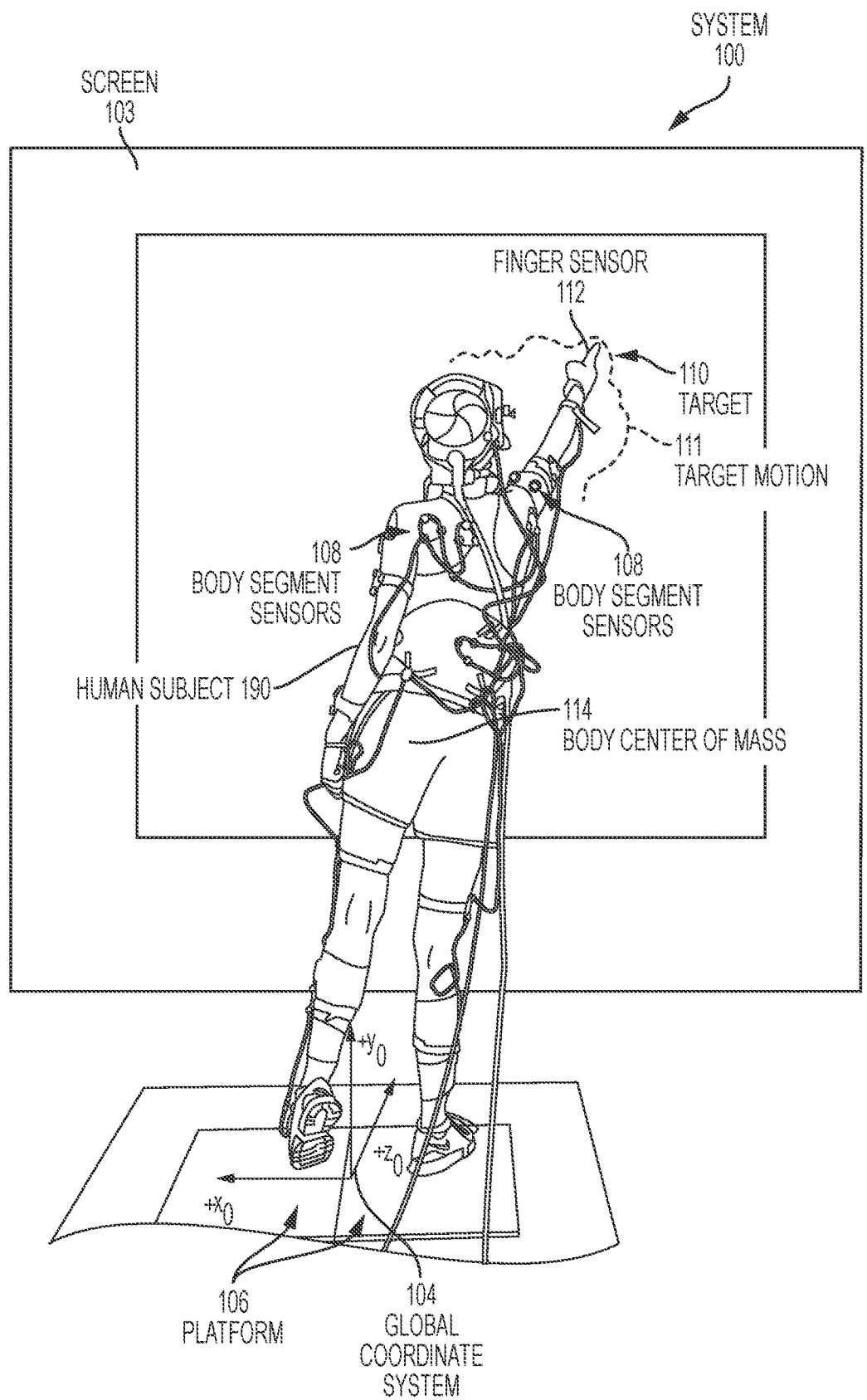
FIG. 1B is a front view that illustrates an example of a system for assessing a fall risk of a subject based on tracking data of the subject and a moving target, according to an embodiment.

FIG. 1B is a front view that illustrates an example of a system 100 for assessing a fall risk of the subject 190 based on tracking data of the subject 190 and a moving target 110, according to an embodiment. Although the subject 190 is depicted for purposes of illustration, the subject is not part of the system 100. A screen 103 is positioned approximately one arm length (AL) in front of the subject 190 and is aligned approximately perpendicular to the anterior-posterior (AP) direction or $z_0$ axis of the global coordinate system 104. A target 110, such as an image of a disk, is projected onto the screen 103 by a projector (not shown) and follows a path that defines target motion 111. In an example embodiment, the screen 103 is a 6'×10' reverse projection screen and the projector is a high resolution digital projector. Although FIG. 1B depicts that the target 110 is an image of an object (e.g., an image of a disk), in an example embodiment the target 110 is a moving object, such as a suspended object operated by servo motors or a drone or some other remotely controlled vehicle. In various embodiments, the target motion is controlled by a controller and the target motion is described by target tracking data that is either used to control the target or sensed as the target moves in response to unknown commands.

A tracking sensor is attached to a body segment of the subject 190, which segment is used to most closely track the target 110. In the example embodiment of FIG. 1B, the tracking sensor is a finger sensor 112 attached to a finger of the subject 190 that the subject 190 uses to track the target 110 as it moves across the screen 103. The tracking sensor (e.g., finger sensor 112) measures the position of the finger in the global coordinate system 104 for each time increment over a time period.

Although the system 100 depicts moving the target 110 along a two-dimensional (2D) screen 103, the invention is not limited to this arrangement and encompasses a system in which a target is moved in three-dimensional (3D) space, such as on a curved screen. The target is an object or an image of an object in various embodiments. In an example embodiment, the target has a limited excursion from the subject, such as one arm length or one step from the subject. In one example embodiment of the 3D system, the subject is not permitted to step during the tracking. In another example embodiment of the 3D system, the subject is permitted to step during the tracking.

A position of the target 110 or target motion 111 is described by a medial-lateral (ML) or X position in the global coordinate system 104 and in a superior-inferior (SI) or Y position in the global coordinate system 104 at time t. In an example embodiment, the position of the target 110 is driven to follow a spatial track defined by a sum of 14 sine functions:

$$X(t) = \sum_{i=1}^{14} \frac{1}{2\pi f_i} \sin(2\pi f_i t),$$

$$Y(t) = \sum_{i=1}^{14} \frac{1}{2\pi f_i} \sin(2\pi f_i t + \phi_i).$$

(1)

where $f_i$ is the frequency of the sine function with index i and $\phi_i$ is a randomly selected phase shift of the $i^{th}$ sine function. As provided in equation 1, the amplitude of the $i^{th}$ sine function is inversely proportional to the magnitude of the frequency $f_i$. In an example embodiment, the randomly selected phase shift $\phi_i$ is applied to the SI component of the target motion 111, to remove any visible correlation between the SI component and the ML component of the target motion 111. In the example embodiment, the frequencies $f_i$ are selected (see Table 2) within a range ($0.05 \leq f_i \leq 3.0$ Hz). In another example embodiment, the frequencies $f_i$ are selected as either multiples of each other (right column, Table 2), resulting in predictable target motion 111 or frequencies $f_i$ not multiples of each other (left column, Table 2), resulting in unpredictable target motion 111. In other embodiments, other frequency components and phases are used.

TABLE 2

Disk motion parameters

| Unpredictable Frequency Set | | | Predictable Frequency Set | | |
|---|---|---|---|---|---|
| $f_i$ (Hz) | Period (sec) | $\phi_i$ (deg) | $f_i$ (Hz) | Period (sec) | $\phi_i$ (deg) |
| 0.024 | 41.67 | 90 | 0.024 | 41.67 | 90 |
| 0.056 | 17.86 | 284 | 0.048 | 20.83 | 76 |
| 0.104 | 9.62 | 76 | 0.096 | 10.42 | 192 |
| 0.184 | 5.43 | 215 | 0.192 | 5.21 | 238 |
| 0.296 | 3.38 | 122 | 0.288 | 3.47 | 99 |
| 0.344 | 2.91 | 99 | 0.336 | 2.98 | 145 |
| 0.488 | 2.05 | 330 | 0.480 | 2.08 | 261 |
| 0.584 | 1.71 | 145 | 0.576 | 1.74 | 30 |
| 0.712 | 1.40 | 261 | 0.720 | 1.39 | 168 |
| 0.824 | 1.21 | 238 | 0.816 | 1.23 | 284 |
| 0.904 | 1.11 | 168 | 0.912 | 1.10 | 215 |
| 1.432 | 0.70 | 192 | 1.416 | 0.71 | 307 |

TABLE 2-continued

Disk motion parameters

| Unpredictable Frequency Set | | | Predictable Frequency Set | | |
|---|---|---|---|---|---|
| $f_i$ (Hz) | Period (sec) | $\phi_i$ (deg) | $f_i$ (Hz) | Period (sec) | $\phi_i$ (deg) |
| 2.104 | 0.48 | 30 | 2.184 | 0.46 | 330 |
| 2.936 | 0.34 | 53 | 2.928 | 0.34 | 122 |

Overall excursion amplitudes: 0.5, 0.6563, 0.8125, .09688, 1.25 arm lengths (ALs)

In an example embodiment, an amplitude of the target motion 111 is determined based on the AL of the subject 190. In an example embodiment, the AL is measured by a sensor (not shown) between a tip of the pointing index finger and the acromion process, with the arm extended in front of the body. An advantage of this arrangement is that the target motion 111 is customized to each subject 190 based on the AL of the subject 190. In an example embodiment, the amplitude of the target motion 111 is based on a plurality of multiples of the AL, such as the multiples listed at the bottom of Table 2. In an example embodiment, for each AL-multiple that is used to determine the amplitude of the target motion 111, the subject 190 tracks the target 110 over two time periods—one time period for the set of unpredictable frequencies (left column, Table 2) and another time period for the set of predictable frequencies (right column, Table 2). An advantage of this approach is that the target moves in a fashion (e.g. the range of amplitudes) that is at or just beyond the ability of a healthy subject to track the target while maintaining balance. In the example embodiment of Table 2, with five AL-multiples to determine the amplitude of the target motion 111, the subject 190 tracks the target 110 over a total of ten time periods (e.g. two time periods for each of the five target motion amplitudes). In an example embodiment, where each time period is approximately 90 seconds, the total time that the subject 190 tracks the target 110 is approximately 15 minutes. An advantage of these durations is that the subject is tested for a wide range of motions without causing exhaustion of a healthy or typical subject. The numerical parameters of target motion 111, including the frequencies $f_i$ and AL-multiples listed in Table 2 are merely examples and the frequencies and AL-multiples used to determine the amplitude of target motion 111 are not limited to those listed in Table 2.

In some embodiments, the system 100 also includes body segment sensors 108 that are attached to each body segment of the subject 190 listed in Table 1. In other embodiments, the body segment sensors 108 are attached to zero or fewer or more body segments than those listed in Table 1. The body segment sensors 108 are located at a position of the CoM of each body segment and measure the position of the CoM of each body segment in the global coordinate system 104, as the subject 190 tracks the target 110. In an example embodiment, the body segment sensors 108 are initially positioned at the CoM of each segment, which is determined based on a location of the CoRs of each body segment which are related to a height of the subject 190, which are both measured by a sensor (not shown). The mass of each body segment is determined, in the example embodiment, based on a weight of the subject 190 that is measured by a platform 106 on which the subject 190 stands. In some embodiments, the platform 106 includes force plates that measure a force and torque applied by the feet of the subject 190 in the global coordinate system 104. In an example embodiment, the force plate is a triaxial force plate such as AMTI Optima series, Advanced Mechanical Technology Inc., Watertown, Mass. For example, in an example embodiment, the height and weight of the subject 190 are used to determine a length and a mass of each body segment, based on gender-specific anthropometric data of the length and mass of each body segment according to an average height and an average weight of human subjects. In an example embodiment, the body segment sensor 108 is a triangular rigid body with infrared emitting diodes (IREDs) positioned at each vertices of the rigid body to form the local coordinate system 102 of each body segment.

A body center of mass 114 of the subject 190 is calculated at each time increment of the time period that the subject 190 tracks the target 110. The body center of mass 114 is a weighted sum of the CoM of each body segment, as measured by the body segment sensors 108 for position of the body segment and the pre-determined mass of the body segment. In an example embodiment, a weighting coefficient of each body segment in the weighted sum is a ratio of the body segment's mass to the total body mass. At each time increment of the time period, the body center of mass 114 is calculated in the global coordinate system 104 and a projection 124 of the body center of mass 114 is determined in the xz plane (the floor plane), as discussed below.

Figure 1C:
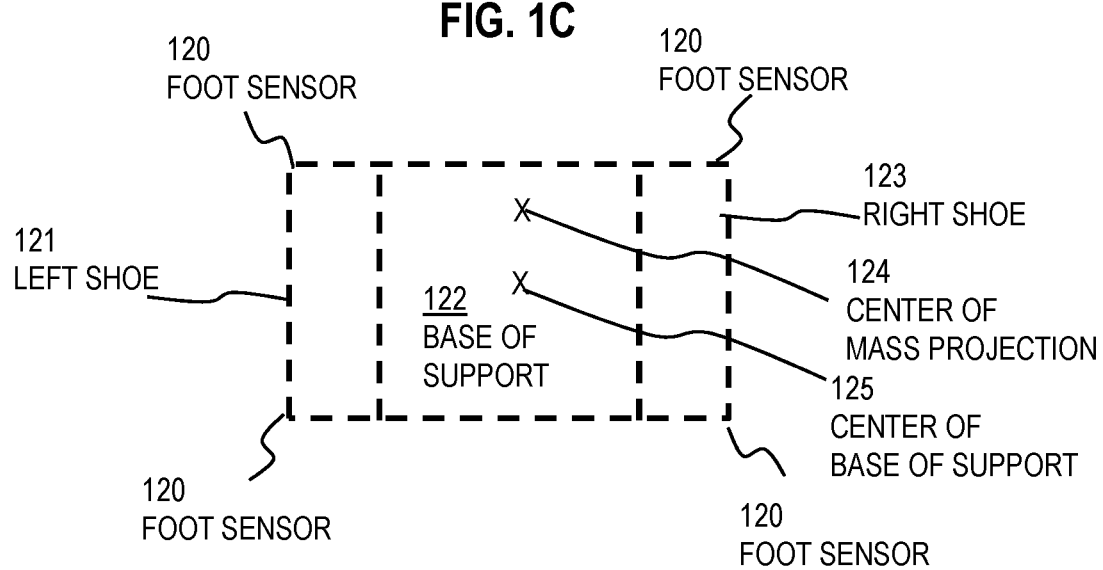
FIG. 1C is a block diagram that illustrates an example of a base of support between the feet of the subject in the system of FIG. 1B, according to an embodiment.

FIG. 1C is a block diagram that illustrates an example of a base of support 122 between the feet of the subject 190 in the system 100 of FIG. 1B, according to an embodiment. Foot sensors 120 are positioned in a left shoe 121 and right shoe 123, to measure a location and an area or a base of support 122 between the left and right feet. In an example embodiment, the foot sensors 120 are positioned in the left and right shoes 121, 123 to measure a location of a fifth metatarsal joint and a lateral outside of a heel of each foot. These four points define vertices of a quadrilateral that defines the base of support 122 and is used to calculate a center 125 of the base of support 122. As previously discussed, the projection 124 of the body center of mass 114 in the xz plane is determined by removing the y component from the body center of mass 114. A deviation between the center 125 of the base of support 122 and the projection 124 of the body center of mass is used to assess the subjects 190 balance as they track the target 110. In an example embodiment, the subject 190 is instructed to move their feet as little as possible, to minimize variation in the base of support 122.

Figure 1D:
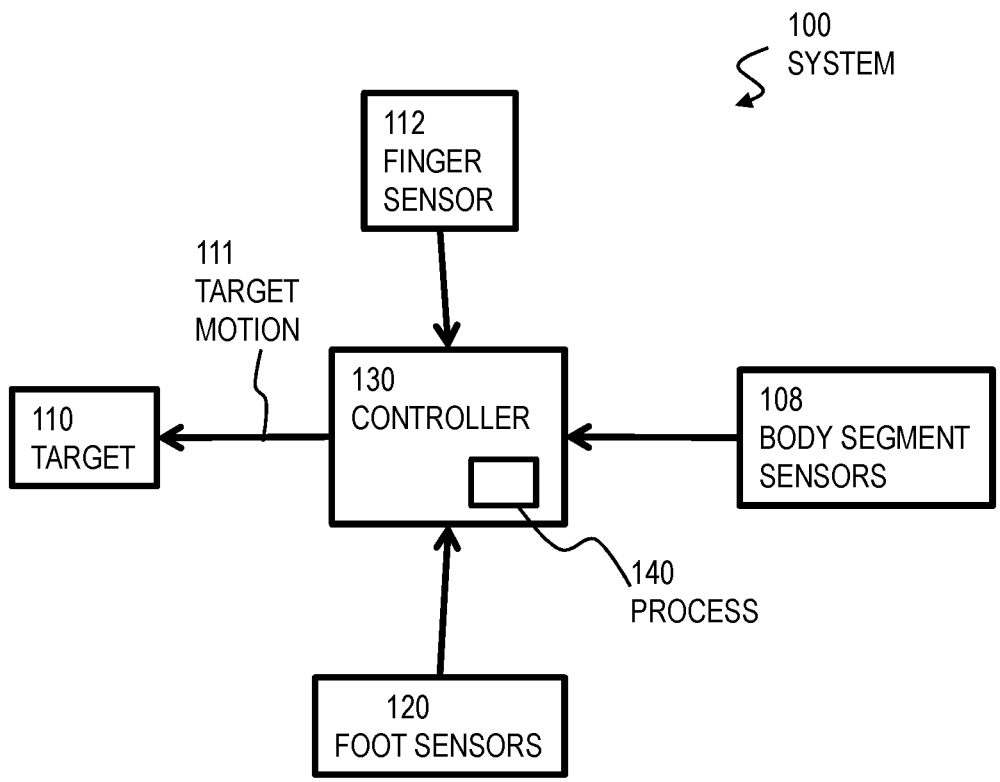
FIG. 1D is a block diagram that illustrates an example of the system of FIG. 1B, according to an embodiment.

FIG. 1D is a block diagram that illustrates an example of the system 100 of FIG. 1B, according to an embodiment. A controller 130 includes a process 140 that determines the target motion 111 in the ML (X) position and in the SI (Y) position and subsequently causes the target 110 to move in accordance with the determined target motion 111. In the example embodiment of FIG. 1B, the process 140 determines the target motion 111 of the image of the disk along the screen 103 and the controller 130 causes the image of the disk to move along the screen 103 in accordance with the target motion 111. In an example embodiment, the controller 130 transmits the target motion 111 data to the projector after which the projector causes the image of the disk to move along the screen 103 based on the target motion 111 data received from the controller 130. The process 140 need not determine the target motion 111 and the controller 130 subsequently cause the target 110 to move in accordance with the target motion 111, provided that the controller 130 receives the target motion 111 data from a secondary source, including either a separate controller for the target or measurements of the target 110, or some combination.

The tracking sensor (e.g. finger sensor 112) transmits the position data of the finger to the controller 130 in the global coordinate system 104, for each time increment over the time period that the subject 190 tracks the target 110. In an example embodiment, the finger sensor 112 transmits ML (X) position data of the finger and SI (Y) position data of the finger to the controller 130, for each time increment over the time period that the subject 190 tracks the target 110. In an example embodiment, the process 140 compares the position data of the finger to the position data of the target 110 at each time increment over the time period. Although FIG. 1D depicts a finger sensor 112, the system 100 is not limited to the finger sensor 112 and encompasses any tracking sensor that detects a position of the body segment that is tracking the target 110. In the example embodiment, the time increment is selected in a range from about 0.3 to 20 milliseconds (msec).

The body segment sensors 108 transmit the CoM of each body segment to the controller 130 in the global coordinate system 104, for each time increment over the time period. In an example embodiment, the body segment sensors 108 transmit ML (X) position data and AP (Z) position data of the CoM of each body segment to the controller 130 for each time increment over the time period. The process 140 measures a location of the body center of mass 114 at each time increment based on a weighted sum of the CoM of each body segment. In the example embodiment, the process 140 measures the location of the body center of mass 114 in the ML (X) direction and in the AP (Z) direction, based on a weighted sum of the CoM of each body segment in the ML (X) direction and in the AP (Z) direction. Additionally, the process 140 determines the projection 124 of the body center of mass 114 at each time increment over the time period, by eliminating the y component of the body center of mass 114.

Figure 22:
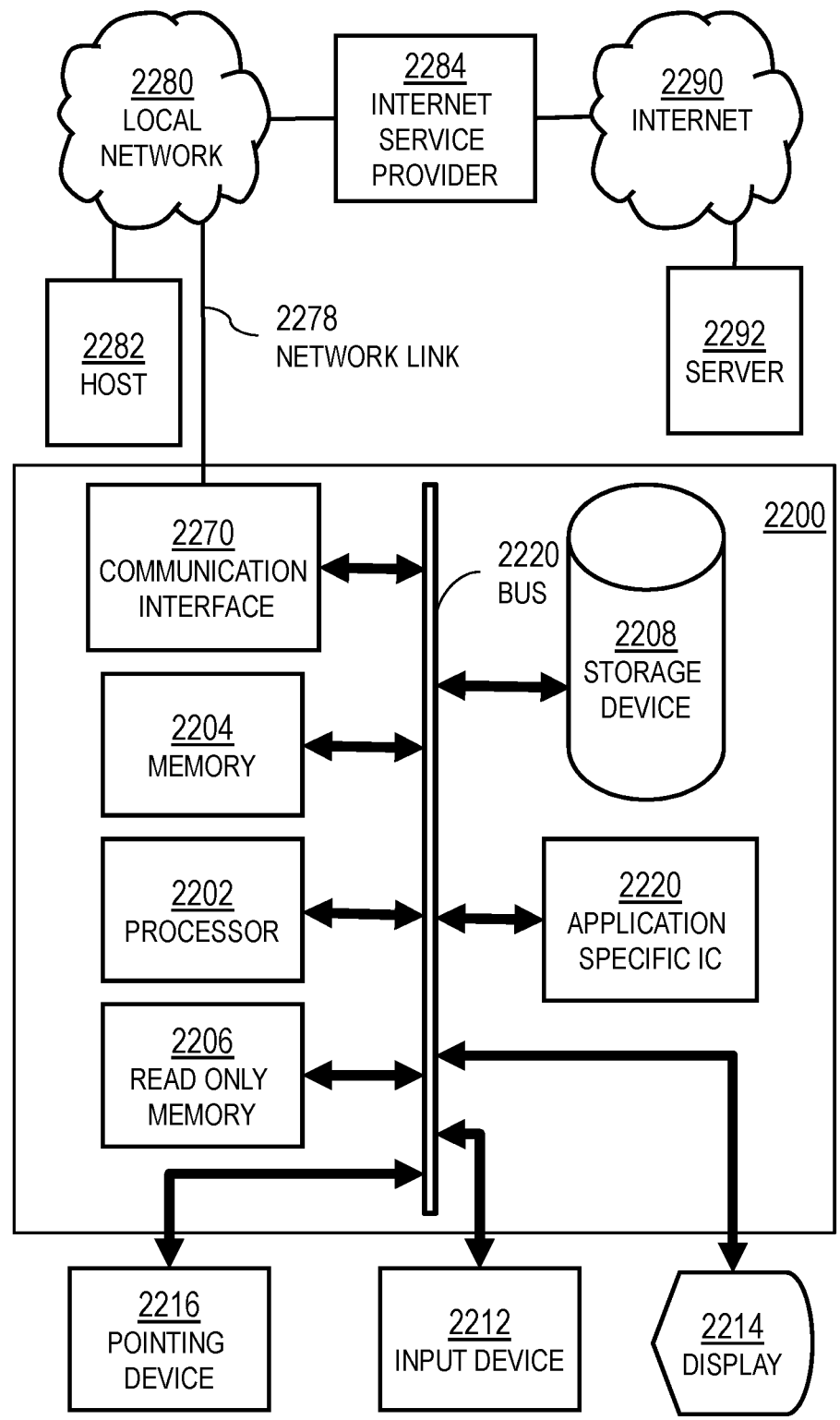
FIG. 22 is a block diagram that illustrates a computer system upon which an embodiment of the invention may be implemented.
Figure 23:
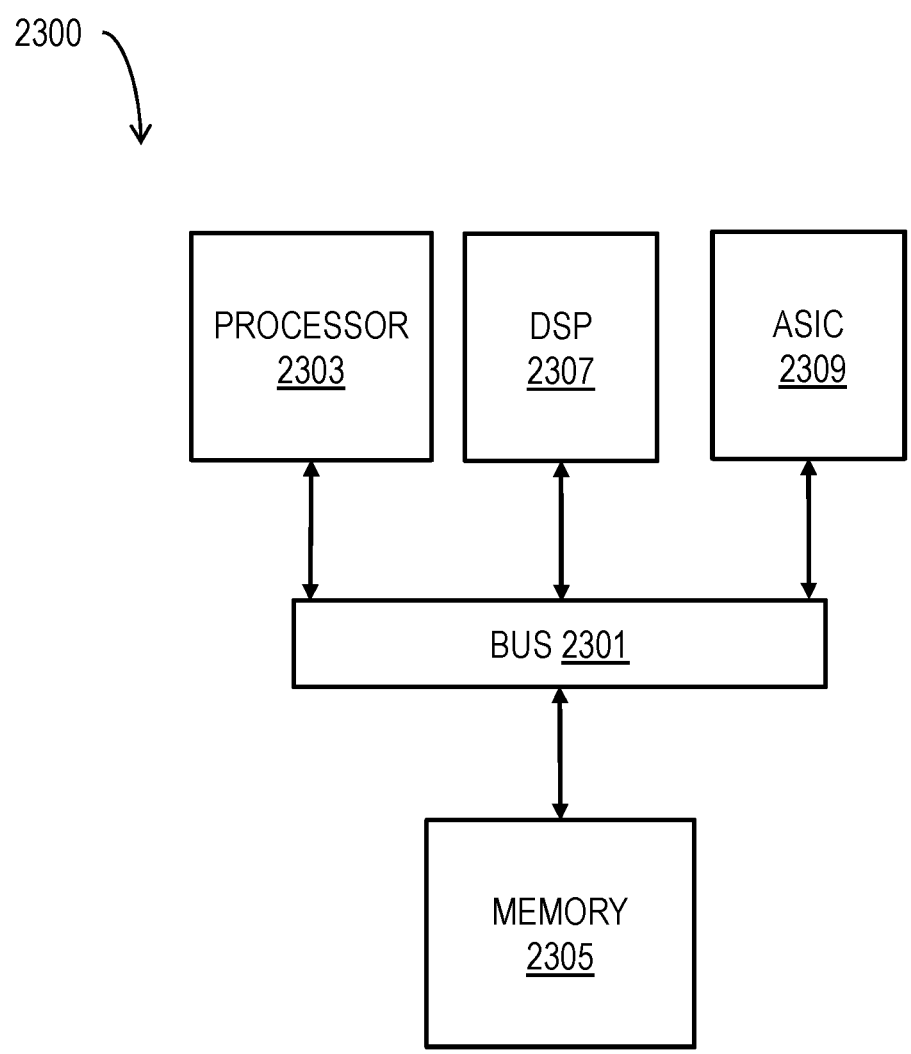
FIG. 23 is a block diagram that illustrates a chip set upon which an embodiment of the invention may be implemented.

The foot sensors 120 transmit data to the controller 130 indicating the boundaries of the base of support 122 at each time increment over the time period. The process 140 determines the area of the base of support 122 and the center 125 of the base of support 122 at each time increment over the time period, based on this data from the foot sensors 120. The process 140 compares the projection 124 of the body center of mass 114 and the center 125 of the base of support 122 at each time increment over the time period. In an example embodiment, the process 140 computes a deviation between the projection 124 of the body center of mass and the center 125 of the base of support 122 at each time increment, such as a deviation in one or more of the ML (X) or AP (Z) directions, for example. In various embodiments, the controller 130 and process 140 comprise one or more general purpose computer systems, as depicted in FIG. 22 or one or more chip sets as depicted in FIG. 23, and instructions to cause the computer or chip set to perform one or more steps of the method 200 described below with reference to FIG. 2.

Although processes, equipment, and data structures are depicted in FIGS. 1A to 1D as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

Figure 2:
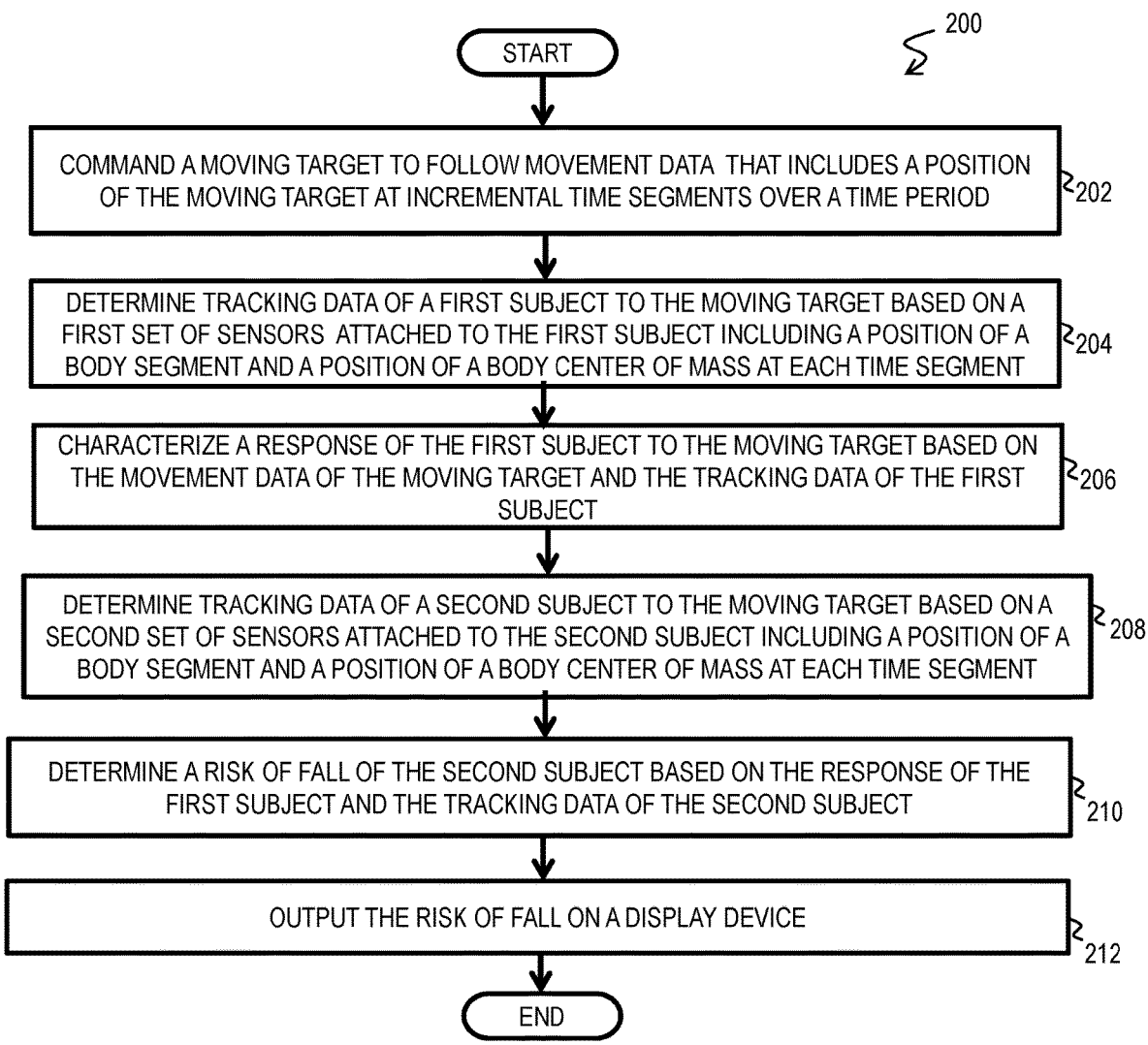
FIG. 2 is a flow diagram that illustrates an example of a method for assessing a fall risk based on tracking data of a moving target, according to an embodiment.

FIG. 2 is a flow diagram that illustrates an example of a method 200 for assessing a fall risk based on tracking data of the moving target 110, according to an embodiment. Although steps are depicted in FIG. 2 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 202, the moving target 110 is commanded to follow movement data that includes the target motion 111 which indicates a position of the moving target 110 at each time increment over the time period. In an example embodiment, in step 202, the process 140 determines the target motion 111 in the ML (X) position and the SI (Y) position, e.g., using the 14 sine waves of Equation 1, described above, and subsequently the controller 130 causes the target 110 to move in accordance with the determined target motion 111 across the screen 103. In step 202, the process 140 determines one or more parameters of the target motion 111. In an example embodiment, the process 140 determines an amplitude of the target motion 111, based on one or more multiples of the AL of the subject 190. In another example embodiment, the process 140 determines a frequency spectrum of the target motion 111, based on whether the target motion 111 is unpredictable (left side, Table 2) or predictable (right side, Table 2). In some embodiments, the commands come from a different source, and, in step 202, a sensor measures the movement of the target so a processor can determine the tracking data that describes the motion of the target based on the sensor data.

In step 204, tracking data of a first subject 190 to the moving target 110 is determined based on the body segment sensors 108 and tracking sensor (e.g., finger sensor 112) attached to the first subject 190. During step 204, the body segment sensors 108 transmit the CoM of each body segment to the controller 130 in the global coordinate system 104, for each time increment over the time period. In an example embodiment, the body segment sensors 108 transmit ML (X) position data and AP (Z) position data of the CoM of each body segment to the controller 130 for each time increment over the time period. Additionally, during step 204, the tracking sensor (e.g., finger sensor 112) transmits the position data of the tracking segment to the controller 130 in the global coordinate system 104, for each time increment over the time period that the subject 190 tracks the target 110. In an example embodiment, the tracking sensor (e.g., finger sensor 112) transmits ML (X) position data of the finger and SI (Y) position data of the finger to the controller 130, for each time increment over the time period that the subject 190 tracks the target 110.

In step 206, a response is characterized of the first subject 190 to the moving target 110. In step 206, the process 140 characterizes the response of the first subject 190 based on the movement data of the moving target 110 from step 202 and the tracking data of the first subject 190 to the moving target 110 from step 204.

In an example embodiment, in step 206, the response is characterized by comparing the position of the finger of the first subject 190 tracking the moving target 110 and the position of the moving target 110. In an example embodiment, the process 140 computes a Root Mean Square Error (RMSE) between the position of the finger of the first subject 190 and the position of the moving target 110 in the ML (X) and SI (Y) directions. $RMSE_x$ is defined as the RMSE between the position of the finger of the first subject 190 and the position of the moving target 110 in the ML (X) direction and is expressed as:

$$RMSE_x = \sqrt{\frac{\sum_{i=1}^{n_x} [x_d(i) - x_f(i)]^2}{n_x}}, \quad (2)$$

where $x_d(i)$ is the X component of the target 110 at sampling instant i; $x_f(i)$ is the X component of the finger of the first subject 190 at sampling instant i; and $n_x$ is the number of data points associated with the X direction. $RMSE_y$ is defined as the RMSE between the position of the finger of the first subject 190 and the position of the moving target 110 in the SI (Y) direction and is defined similarly as $RMSE_x$ in equation 2. A composite error $RMSE_{xy}$ is defined as the RMSE between the position of the finger of the first subject 190 and the position of the moving target 110 in both the ML (X) and SI (Y) directions and is expressed as:

$$RMSE_{xy} = \sqrt{\frac{\sum_{i=1}^{n_x} [x_d(i) - x_f(i)]^2}{n_x} + \frac{\sum_{i=1}^{n_y} [y_d(i) - y_f(i)]^2}{n_y}} \quad (3)$$

where $y_d(i)$ is the Y component of the target 110 at sampling instant i; $y_f(i)$ is the Y component of the finger of the first subject 190 at sampling instant i; and $n_y$ is the number of data points associated with the Y direction.

FIG. 3A is a graph 300 that illustrates an example of RMSE between a body segment and the moving target 110 in the system 100 of FIG. 1B, according to an embodiment. The horizontal axis 302 is the amplitude of the moving target 110, in units of multiples of AL. The vertical axis 304 is the RMSE in units of centimeters (cm). The graph 300 depicts the $RMSE_x$ in the ML direction (white), the $RMSE_y$ in the SI direction (grey) and the $RMSE_{xy}$ in both the ML and SI directions (black). As depicted in the graph 300, the magnitude of the $RMSE_x$, $RMSE_y$ and $RMSE_{xy}$ rises with increasing amplitude of the moving target 110. Additionally, as depicted in the graph 300, the magnitude of $RMSE_y$ in the SI direction is less than the magnitude of the $RMSE_x$ in the ML direction for the same moving target 110 amplitude.

In an example embodiment, in step 206, the response is characterized by comparing the position of the projection 124 of the body center of mass and the center 125 of the base of support 122. In an example embodiment, the process 140 computes a Root Mean Square Deviation (RMSD) between the projection 124 of the body center of mass and the center 125 of the base of support 122 in the ML (X) and AP (Z) directions. $RMSD_x$ is defined as the RMSD between the position of the projection 124 of the body center of mass and the position of the center 125 of the base of support 122 in the ML (X) direction. $RMSD_z$ is defined as the RMSD between the position of the projection 124 of the body center of mass and the center 125 of the base of support 122 in the AP (Z) direction and is defined similarly as $RMSD_x$. A composite deviation $RMSD_{xz}$ is defined as the RMSD between the position of the projection 124 of the body center of mass and the position of the center 125 of the base of support 122 in both the ML (X) and AP (Z) directions. In one example embodiment, the $RMSD_x$ and $RMSD_{xz}$ are expressed as:

$$RMSD_x = \sqrt{\frac{\sum_{i=1}^{n_x} [x_{BoS}(i) - x_{CoM}(i)]^2}{n_x}} \quad (4)$$

$$RMSD_{xz} = \sqrt{\frac{\sum_{i=1}^{n_x} [x_{BoS}(i) - x_{CoM}(i)]^2}{n_x} + \frac{\sum_{i=1}^{n_z} [z_{BoS}(i) - z_{CoM}(i)]^2}{n_z}}$$

where $x_{BoS}(i)$ is the X component of the center 125 at sampling instant i; $x_{CoM}(i)$ is the X component of the projection 124 at sampling instant i; $z_{BoS}(i)$ is the Z component of the center 125 at sampling instant i; $z_{CoM}(i)$ is the Z component of the projection 124 at sampling instant i; $n_x$ is the number of data points associated with the X direction; and $n_z$ is the number of data points associated with the Z direction. In an example embodiment, the composite deviation $RMSD_{xz}$ computed in equation 4 can range from zero to values corresponding to a boundary of the base of support 122, which may indicate a risk of fall.

FIG. 3B is a graph 310 that illustrates an example of a RMSD between the projection 124 of the body center of mass and the center 125 of the base of support of FIG. 1C, according to an embodiment. The horizontal axis 312 is the amplitude of the moving target 110, in units of multiples of AL. The vertical axis 314 is the RMSD in units of centimeters (cm). The graph 310 depicts the $RMSD_x$ in the ML direction (white), the $RMSD_z$ in the AP direction (grey) and the $RMSD_{xz}$ in both the ML and AP directions (black). As depicted in the graph 310, the magnitude of the $RMSD_x$, $RMSD_z$ and $RMSD_{xz}$ rises with increasing amplitude of the moving target 110. Additionally, as depicted in the graph 310, the magnitude of $RMSD_z$ in AP direction is less than the magnitude of the $RMSD_x$ in the ML direction for the same moving target 110 amplitude.

In an example embodiment, in step 206, the response is characterized by measuring a time delay τ between the position of the finger of the first subject 190 tracking the moving target 110 and the position of the moving target 110. In an example embodiment, the time delay τ between the position of the finger of the first subject 190 tracking the moving target 110 and the position of the moving target 110 is measured in the ML (X) and SI (Y) directions. FIG. 3C is a graph 320 that illustrates an example of a time delay τ between the finger and the moving target 110 in the system 100 of FIG. 1B, according to an embodiment. The horizontal axis 322 is the amplitude of the moving target 110, in units of multiples of AL. The vertical axis 324 is the time delay τ in units of seconds (secs). The graph 320 depicts the time delay in the ML direction (white), the time delay in the SI direction (grey) and the time delay in both the ML and SI directions (black). As depicted in the graph 320, the magnitude of the time delay in the ML direction, SI direction and in both the ML and SI directions is relatively constant for a given amplitude of the moving target 110. Additionally, as depicted in the graph 320, the magnitude of the time delay in the ML direction, the SI direction and in both the ML and SI directions are relatively constant over a range of amplitudes of the moving target 110. In an example embodiment, for a group of 32 young healthy subjects 190, an average time delay in the ML and SI directions across all amplitudes of the moving target 110 is approximately 0.51±0.056 seconds.

In an example embodiment, in step 206, the response is characterized by measuring a time delay τ between the position of the projection 124 of the body center of mass and the position of the moving target 110. In an example embodiment, the time delay τ between the position of the projection 124 and the position of the moving target 110 is measured in the ML (X) and AP (Z) directions. FIG. 3D is a graph 330 that illustrates an example of a time delay τ between the projection 124 and the moving target 110 in the system 100 of FIG. 1B, according to an embodiment. The horizontal axis 332 is the amplitude of the moving target 110, in units of multiples of AL. The vertical axis 334 is the time delay τ in units of seconds (secs). The graph 330 depicts the time delay in the ML direction (white), the time delay in the AP direction (grey) and the time delay in both the ML and AP directions (black). As depicted in the graph 330, the magnitude of the time delay in the ML direction, AP direction and in both the ML and AP directions is relatively constant for a given amplitude of the moving target 110. Additionally, as depicted in the graph 330, the magnitude of the time delay in the ML direction, the AP direction and in both the ML and AP directions are relatively constant over a range of amplitudes of the moving target 110. In an example embodiment, for a group of 32 young healthy subjects 190, an average time delay in the ML and AP directions across all amplitudes of the moving target 110 is approximately 0.92±0.039 seconds.

In an example embodiment, in step 206, the response is characterized by comparing a frequency spectrum of the moving target 110 with a frequency spectrum of the position of the finger of the first subject 190 tracking the moving target 110. In an example embodiment, in step 202, the frequency spectrum of the target motion 111 is determined and includes discrete frequencies $f_i$ for each sine function of index i expressed in equation 1. The frequency spectrum of the position of the finger of the first subject 190 is obtained by performing a Fourier Transform of the position of the finger of the first subject 190 at each time increment over the time period. FIG. 4A is a graph 400 that illustrates an example of a position of the finger and the moving target in the ML (X) direction, according to an embodiment. The horizontal axis 402 is time in units of second (sec). The left vertical axis 404 is the ML position of the finger in units of centimeters (cm) and the right vertical axis 406 is the ML position of the target 110 in units of centimeter (cm). The graph 400 depicts the ML position of the finger (black plot), the ML position of the target 110 (grey plot) and a 95% confidence interval range of the ML position of the finger (dotted lines) for a group of young healthy subjects 190. In an example embodiment, the 95% confidence interval range is ±2.96 cm of the ML positions of the finger depicted in graph 400. FIG. 4B is a graph 410 that illustrates an example of a position of the finger and the moving target in the SI (Y) direction, according to an embodiment. The horizontal axis 412 is time in units of second (sec). The left vertical axis 414 is the SI position of the finger in units of centimeters (cm) and the right vertical axis 416 is the SI position of the target 110 in units of centimeter (cm). The graph 410 depicts the SI position of the finger (black plot), the SI position of the target 110 (grey plot) and a 95% confidence interval range of the SI position of the finger (dotted lines) for a group of young healthy subjects 190. In an example embodiment, the 95% confidence interval range is ±1.39 cm of the SI positions of the finger depicted in graph 410.

Figure 4E:
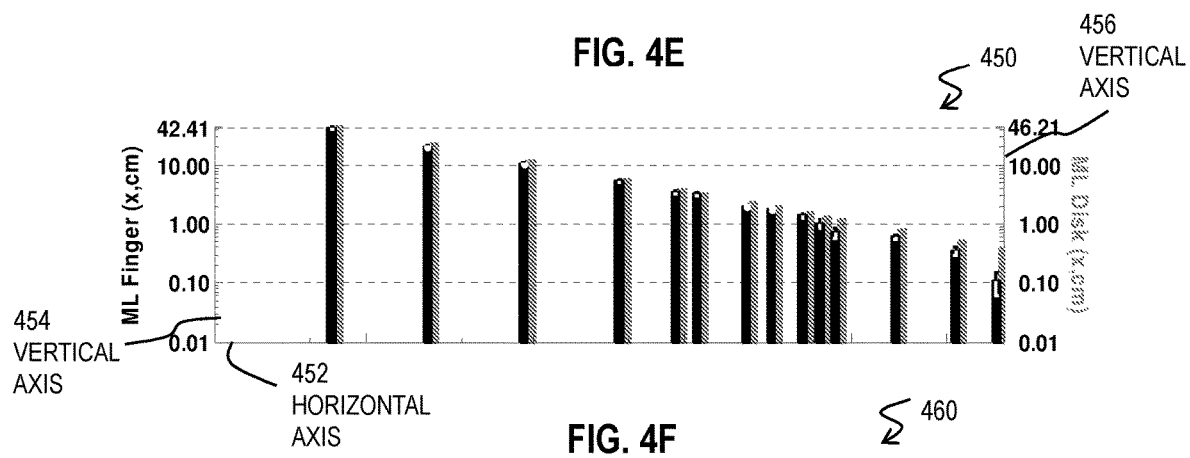
FIG. 4E is a graph that illustrates an example of a frequency spectrum of the body segment and a frequency spectrum of the moving target in the medial-lateral (ML) direction, according to an embodiment.

FIG. 4E is a graph 450 that illustrates an example of a frequency spectrum of the finger and a frequency spectrum of the moving target in the ML direction, according to an embodiment. The horizontal axis 452 is frequency in units of Hertz (Hz), the left vertical axis 454 is an amplitude of the frequency spectrum of the finger in the ML direction in units of centimeters (cm) and the right vertical axis 456 is an amplitude of the frequency spectrum of the moving target in the ML direction in units of centimeters (cm). In an example embodiment, the frequency spectrum of the finger in the ML direction is obtained by performing a Fourier transform of the position of the finger in the ML direction in graph 400 of FIG. 4A, where the values of the frequency spectrum are set to zero for all frequencies except the discrete frequencies $f_i$ of the moving target 110. The graph 450 depicts the amplitude of the frequency spectrum of the finger in the ML direction (black) and the amplitude of the frequency spectrum of the moving target in the ML direction (grey) for each discrete frequency $f_i$ of the moving target 110 expressed in equation 1. In an example embodiment, during step 206, the controller 130 automatically determines a ratio of the amplitude of the frequency spectrum of the finger to the amplitude of the frequency spectrum of the moving target in the ML direction for each discrete frequency $f_i$. In the example embodiment, the ratio is calculated for each multiple of the AL that is used to determine the amplitude of motion of the moving target 110. In an example embodiment, where a group of young healthy subject 190 track the moving target 110, the ratio is at least 0.9 for the six lowest frequencies $f_i$ of the moving target 110.

Figure 4F:
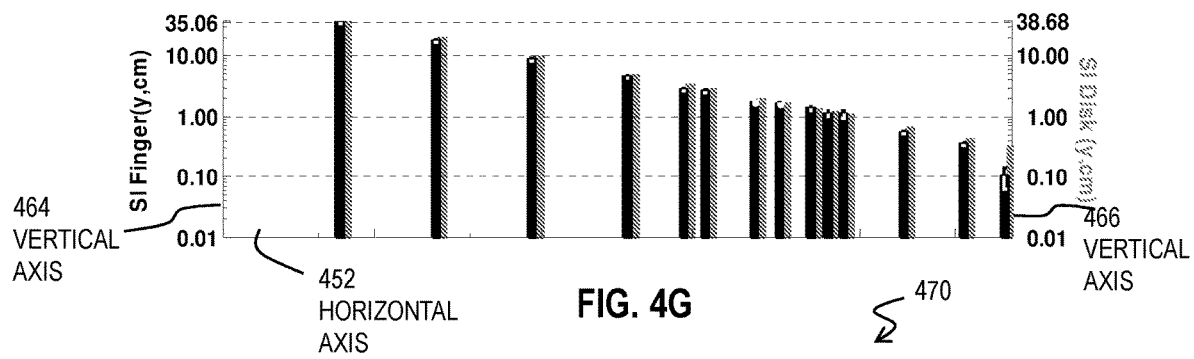
FIG. 4F is a graph that illustrates an example of a frequency spectrum of the body segment and a frequency spectrum of the moving target in a superior-inferior (SI) direction, according to an embodiment.

FIG. 4F is a graph 460 that illustrates an example of a frequency spectrum of the finger and a frequency spectrum of the moving target in the SI direction, according to an embodiment. The horizontal axis 452 is frequency in units of Hertz (Hz), the left vertical axis 464 is an amplitude of the frequency spectrum of the finger in the SI direction in units of centimeters (cm) and the right vertical axis 466 is an amplitude of the frequency spectrum of the moving target in the SI direction in units of centimeters (cm). In an example embodiment, the frequency spectrum of the finger in the SI direction is obtained by performing a Fourier transform of the position of the finger in the SI direction in the graph 410 of FIG. 4A, where the values of the frequency spectrum are set to zero for all frequencies except the discrete frequencies $f_i$ of the moving target 110. The graph 460 depicts the amplitude of the frequency spectrum of the finger in the SI direction (black) and the amplitude of the frequency spectrum of the moving target in the SI direction (grey) for each discrete frequency fi of the moving target 110 expressed in equation 1. In an example embodiment, during step 206, the controller 130 automatically determines a ratio of the amplitude of the frequency spectrum of the finger to the amplitude of the frequency spectrum of the moving target in the SI direction for each discrete frequency $f_i$. In the example embodiment, the ratio is calculated for each multiple of the AL that is used to determine the amplitude of motion of the moving target 110. In an example embodiment, where a group of young healthy subject 190 track the moving target 110, the ratio is at least 0.9 for the six lowest frequencies $f_i$ of the moving target 110.

In an example embodiment, in step 206, the response is characterized by comparing a frequency spectrum of the moving target 110 with a frequency spectrum of the projection 124 of the body center of mass. In an example embodiment, in step 202, the frequency spectrum of the target motion 110 is determined and includes discrete frequencies $f_i$ for each sine function of index i expressed in equation 1. The frequency spectrum of the position of the projection 124 of the body center of mass is obtained by performing a Fourier Transform of the position of the projection 124 of the body center of mass at each time increment over the time period. FIG. 4C is a graph 420 that illustrates an example of a position of the projection 124 of the body center of mass in the ML (X) direction, according to an embodiment. The horizontal axis 422 is time in units of second (sec). The left vertical axis 424 is the ML position of the projection 124 in units of centimeters (cm) and the right vertical axis 426 is the ML position of the target 110 in units of centimeter (cm). The graph 420 depicts the ML position of the projection 124 (black plot), the ML position of the target 110 (grey plot) and a 95% confidence interval range of the ML position of the projection 124 (dotted lines) for a group of young healthy subjects 190. In an example embodiment, the 95% confi-dence interval range is ±1.49 cm of the ML positions of the projection 124 depicted in graph 420. FIG. 4D is a graph 430 that illustrates an example of a position of the projection 124 in the AP (Z) direction, according to an embodiment. The horizontal axis 432 is time in units of second (sec). The left vertical axis 434 is the AP position of the projection 124 in units of centimeters (cm) and the right vertical axis 436 is a magnitude of the XYZ position of the target 110 in units of centimeter (cm). The graph 430 depicts the AP position of the projection 124 (black plot), the XYZ position of the target 110 (grey plot) and a 95% confidence interval range of the AP position of the projection 124 (dotted lines) for a group of young healthy subjects 190. In an example embodiment, the 95% confidence interval range is ±1.35 cm of the AP positions of the projection 124 depicted in graph 430.

Figure 4G:
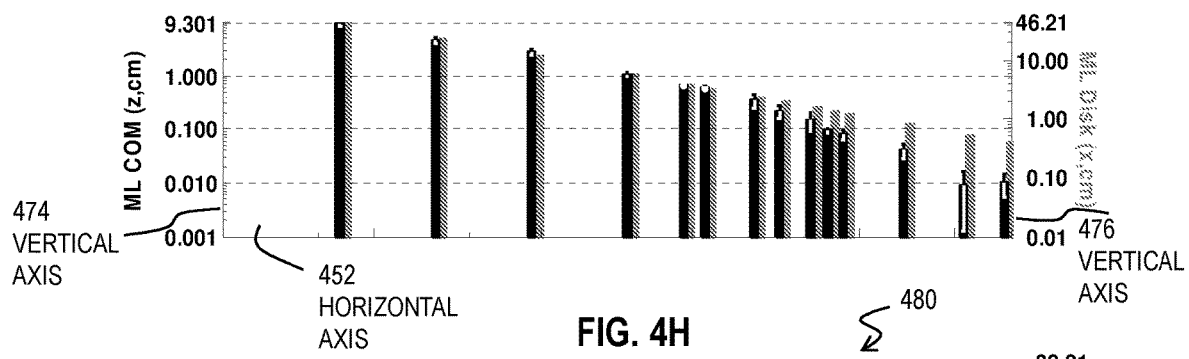
FIG. 4G is a graph that illustrates an example of a frequency spectrum of the body center of mass and a frequency spectrum of the moving target in a medial-lateral (ML) direction, according to an embodiment.

FIG. 4G is a graph 470 that illustrates an example of a frequency spectrum of the projection 124 and a frequency spectrum of the moving target in the ML direction, according to an embodiment. The horizontal axis 452 is frequency in units of Hertz (Hz), the left vertical axis 474 is an amplitude of the frequency spectrum of the projection 124 in the ML direction in units of centimeters (cm) and the right vertical axis 476 is an amplitude of the frequency spectrum of the moving target in the ML direction in units of centimeters (cm). In an example embodiment, the frequency spectrum of the projection 124 in the ML direction is obtained by performing a Fourier transform of the position of the projection 124 in the ML direction in graph 420 of FIG. 4C, where the values of the frequency spectrum are set to zero for all frequencies except the discrete frequencies $f_i$ of the moving target 110. The graph 470 depicts the amplitude of the frequency spectrum of the projection 124 in the ML direction (black) and the amplitude of the frequency spectrum of the moving target in the ML direction (grey) for each discrete frequency $f_i$ of the moving target 110 expressed in equation 1. In an example embodiment, during step 206, the controller 130 automatically determines a ratio of the amplitude of the frequency spectrum of the projection 124 to the amplitude of the frequency spectrum of the moving target in the ML direction for each discrete frequency $f_i$. In the example embodiment, the ratio is calculated for each multiple of the AL that is used to determine the amplitude of motion of the moving target 110. In an example embodiment, where a group of young healthy subject 190 track the moving target 110, the ratio is at least 0.2 for the six lowest frequencies $f_i$ of the moving target 110.

Figure 4H:
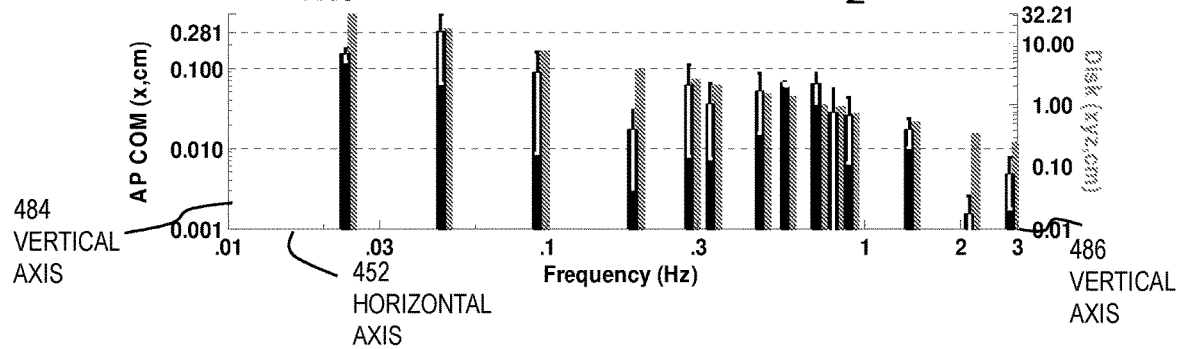
FIG. 4H is a graph that illustrates an example of a frequency spectrum of the body center of mass and a frequency spectrum of the moving target in an anterior-posterior (AP) direction, according to an embodiment.

FIG. 4H is a graph 480 that illustrates an example of a frequency spectrum of the projection 124 and a frequency spectrum of the moving target in the AP direction, according to an embodiment. The horizontal axis 452 is frequency in units of Hertz (Hz), the left vertical axis 484 is an amplitude of the frequency spectrum of the projection 124 in the AP direction in units of centimeters (cm) and the right vertical axis 486 is an amplitude of the frequency spectrum of the moving target in the XYZ direction in units of centimeters (cm). In an example embodiment, the frequency spectrum of the projection 124 in the AP direction is obtained by performing a Fourier transform of the position of the projection 124 in the AP direction in the graph 430 of FIG. 4D, where the values of the frequency spectrum are set to zero for all frequencies except the discrete frequencies $f_i$ of the moving target 110. The graph 480 depicts the amplitude of the frequency spectrum of the projection 124 in the AP direction (black) and the amplitude of the frequency spectrum of the moving target in the XYZ direction (grey) for each discrete frequency $f_i$ of the moving target 110 expressed in equation 1. In an example embodiment, during step 206, the controller 130 automatically determines a ratio of the amplitude of the frequency spectrum of the projection 124 to the amplitude of the frequency spectrum of the moving target in the AP direction for each discrete frequency $f_i$. In the example embodiment, the ratio is calculated for each multiple of the AL that is used to determine the amplitude of motion of the moving target 110.

In an example embodiment, in step 206, an $RMSE_i$ is determined that is a RMSE between the position of the moving target 110 and the position of the finger, as a function of each discrete frequency $f_i$ of the moving target 110. Additionally, in an example embodiment, a normalized $RMSE_i$ ($NRMSE_i$) is determined, which is a ratio of the $RMSE_i$ to the amplitude of the frequency spectrum of the moving target 110 for the discrete frequency $f_i$. In an example embodiment, the $RMSE_i$ and the $NRMSE_i$ are determined by:

$$RMSE(f_i) = a_i \sqrt{\frac{1 + g_i^2 - 2g_i \cos \chi_i}{2}}, \quad (5)$$

$$NRMSE(f_i) = \frac{RMSE(f_i)}{a_i} = \sqrt{\frac{1 + g_i^2 - 2g_i \cos \chi_i}{2}},$$

where g is the ratio of the amplitude of the frequency spectrum of the finger to the amplitude of the frequency spectrum of the moving target for each discrete frequency $f_i$; $\chi_i$ is a phase lag between the discrete frequency $f_i$ component of the frequency spectrum of the finger and the discrete frequency $f_i$ component of the frequency spectrum of the moving target; and $a_i$ is the amplitude of the frequency spectrum of the moving target 110 for the discrete frequency $f_i$. FIG. 5A is a graph 500 that illustrates an example of the $RMSE_i$ 506 and the $NRMSE_i$ 508 between the finger and the moving target 110 in the ML direction, as a function of target frequency, according to an embodiment. The horizontal axis 502 is target frequency $f_i$ in units of hertz (Hz) and the vertical axis 504 is ML error in units of centimeters (cm). FIG. 5B is a graph 550 that illustrates an example of the $RMSE_i$ 556 and the $NRMSE_i$ 558 between the finger and the moving target 110 in the SI direction as a function of target frequency, according to an embodiment. The horizontal axis 552 is target frequency $f_i$ in units of hertz (Hz) and the vertical axis 554 is SI error in units of centimeters (cm). As depicted in graphs 500, 550, the $RMSE_i$ generally decreases for target frequencies <1 Hz, whereas the $NRMSE_i$ generally increases for target frequencies <1 Hz.

In step 208, tracking data of a second subject is determined using the system 100 in the same manner as the tracking data of the first subject 190 was obtained in step 204. In an example embodiment, the body segment sensors 108 and the tracking sensor (e.g. finger sensor 112) are placed on the second subject to determine the tracking data of the subject in response to the movement of the target 110.

In step 210, a risk of fall is determined of the second subject, based on the response of the first subject determined in step 206 and the tracking data of the second subject determined in step 208. In an example embodiment, the risk of fall is determined using any statistical method known to one skilled in the art to assess a significance of a deviation between the tracking data of the second subject and the response of the first subject. In one example embodiment, where tracking data of a group of first subjects 190 is obtained in step 204, the response of the group of first subjects 190 is characterized in step 206. In this example embodiment, in step 210 any statistical method, such as 95% confidence interval of the group response of the first subjects 190 is used to assess a deviation between the tracking data of the second subject and the response of the first subjects 190. If a deviation between the tracking data of the second subject and the response of the first subjects 190 is outside of the 95% confidence interval range, the tracking data of the second subject is significantly different than the group response of the first subjects 190. If the group of first subjects 190 are a group of young healthy subjects and the tracking data of the second subject is significantly different than the group response, a positive risk of fall is determined. However, the invention is not limited to the first subject or the second subject being characterized in a specific group, such as the first subject being a young healthy subject and the second subject being an at-risk subject. In one example embodiment, the first subject is an at-risk subject and the response of the first subject determined in step 206 is used to assess if the second subject is also at-risk, based on whether the tracking data of the second subject is statistically similar to the response of the first subject 190. In an example embodiment, the fall risk is determined based on one or more discrete categories, such as high or low. In an example embodiment, the fall risk is determined based on a continuous measure of fall risk. In an example embodiment, the continuous measure of fall risk is determined based on at least one of the RMSE and RMSD. In an example embodiment, the continuous measure of fall risk is determined based on the composite $RMSE_{xy}$ from equation 4 and the composite $RMSD_{xz}$ from equation 5.

In some embodiments, in step 210, a relationship is determined between the risk of fall of the second subject and a quantity derived from one or more measures of the response of the first subject from step 206. In some embodiments, the relationship is determined between the risk of fall of the second subject and a quantity derived from a plurality of responses of a respective plurality of groups of first subjects from step 206. In an example embodiment, the group of first subjects includes one or more of a group of young healthy subjects, a group of aged subjects and a group of stroke subjects.

Figure 24A:
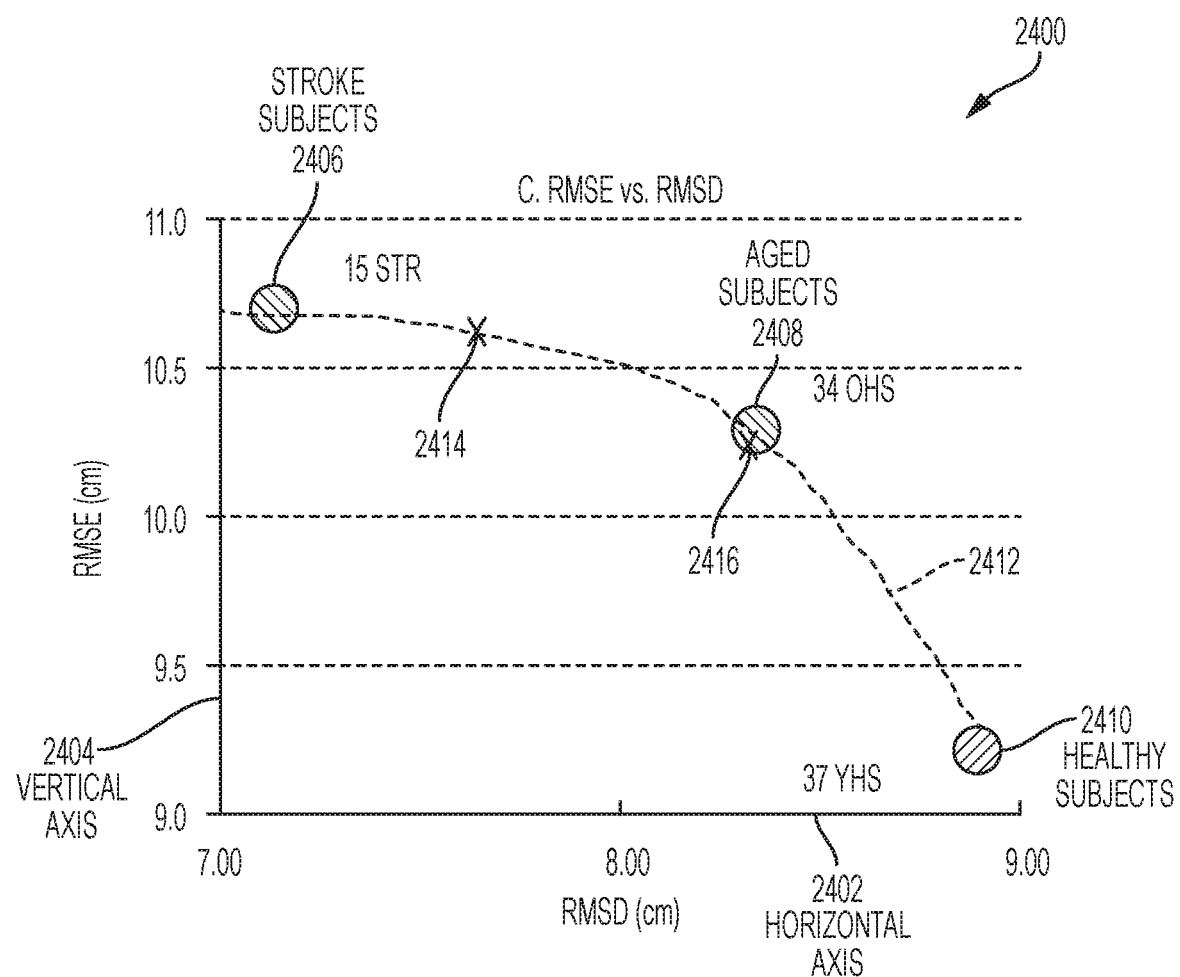
FIG. 24A is a graph that illustrates an example of a root mean square error (RMSE) as a function of root mean square deviation (RMSD) for a plurality of subject groups, according to an embodiment.

For example, in one embodiment, in step 210, a relationship is determined between the risk of fall of the second subject and a quantity based on the RMSE and RMSD of a plurality of groups of first subjects from step 206. FIG. 24A is a graph 2400 that illustrates an example of a root mean square error (RMSE) as a function of root mean square deviation (RMSD) for a plurality of subject groups, according to an embodiment. The horizontal axis 2402 is RMSD in units of centimeters (cm). The vertical axis 2404 is RMSE in units of centimeters (cm). For each group of first subjects, a data cluster of the RMSE and RMSD of the response in step 206 is plotted on the graph 2400. A first cluster 2406 of RMSE and RMSD for a group of stroke subjects, a second cluster 2408 of RMSE and RMSD for a group of aged subjects and a third cluster 2410 of RMSE and RMSD for a group of young healthy subjects is shown on the graph 2400. These clusters 2406, 2408, 2410 demonstrate an inverse relationship between the RMSE and RMSD for the plurality of groups of subjects.

In an embodiment, the risk of fall of the second subject is determined by associating the tracking data of the second subject with the response of one of the groups of first subjects. In the example embodiment, the risk of fall of the second subject is determined by associating the RMSE and RMSD for the second subject with the RMSE and RMSD for one of the groups of first subjects. In an example embodiment, where the RMSE and RMSD 2416 of the second subject corresponds to the second cluster 2408 of RMSE and RMSD of the group of aged subjects, the risk of fall of the second subject is assigned the same risk of fall as the group of aged subjects.

In some embodiments, the risk of fall of each group of subjects is quantified, using an absolute measure (e.g. a percentage) that depends on a comparison with control groups of known fall risk, e.g., based on pre measurement or post measurement logs of fall events. In some of these embodiments, the risk of fall of each group is quantified, by determining whether each subject of the group experienced a fall after the response was measured in step 206. In some embodiments, the determination of whether the subject fell is performed at one or more time lengths after the response was measured in step 206. In one example embodiment, each subject is contacted (e.g. telephone) to determine whether they experienced a fall. The risk of fall of each group is then quantified, based on the fall data obtained from the subjects of the group. The fall risk can be quantified in any way, such as the number of falls per week averaged over the group during the period of logging such events. In an example embodiment, where the group of aged subjects has thirty-four subjects over ten weeks and 100 falls were experienced, the quantified risk of fall is 29% per week. In these embodiments, the second subject with the RMSE and RMSD 2416 is assigned the quantified fall risk of the group of aged subjects (e.g. 29%), since the RMSE and RMSD 2416 of the second subject corresponds to the second cluster 2408 of RMSE and RMSD of the group of aged subjects.

In other embodiments, the quantified risk of fall for each group of subjects is used to generate a best fit curve 2412. In an example embodiment, the best fit curve 2412 is a least square curve determined from the RMSD and RMSE of each data cluster 2406, 2408, 2410 as well as the calculated quantified risk (e.g. from the fall data) associated with each data cluster 2406, 2408, 2410. In an example embodiment, the best fit curve 2412 provides an estimate of the quantified risk of fall of a second subject, based on an input of the RMSE and RMSD 2414 of a second subject. Even though the RMSE and RMSD 2414 of a second subject does not correspond with any of the clusters 2406, 2408, 2410 of the groups of first subjects, the best fit curve 2412 provides an estimate of the quantified risk of fall of the second subject.

In an example embodiment, the risk of fall of each group of subjects is a comparative fall risk and provides a relative risk of fall of the group as compared with the risk of fall of another group. In these embodiments, the comparative risk of fall of each group is determined, based on the quantified risk of fall of each group. A group with a higher quantified risk of fall has a greater comparative risk of fall than a group with a lower quantified risk of fall. In these embodiments, the second subject with the RMSE and RMSD 2416 is assigned a comparative risk of fall that is lower than a risk of fall of a stroke subject yet higher than the risk of fall of a young healthy subject, since the RMSE and RMSD 2416 of the second subject corresponds to the second cluster 2408 of RMSE and RMSD of the group of aged subjects.

Figure 24B:
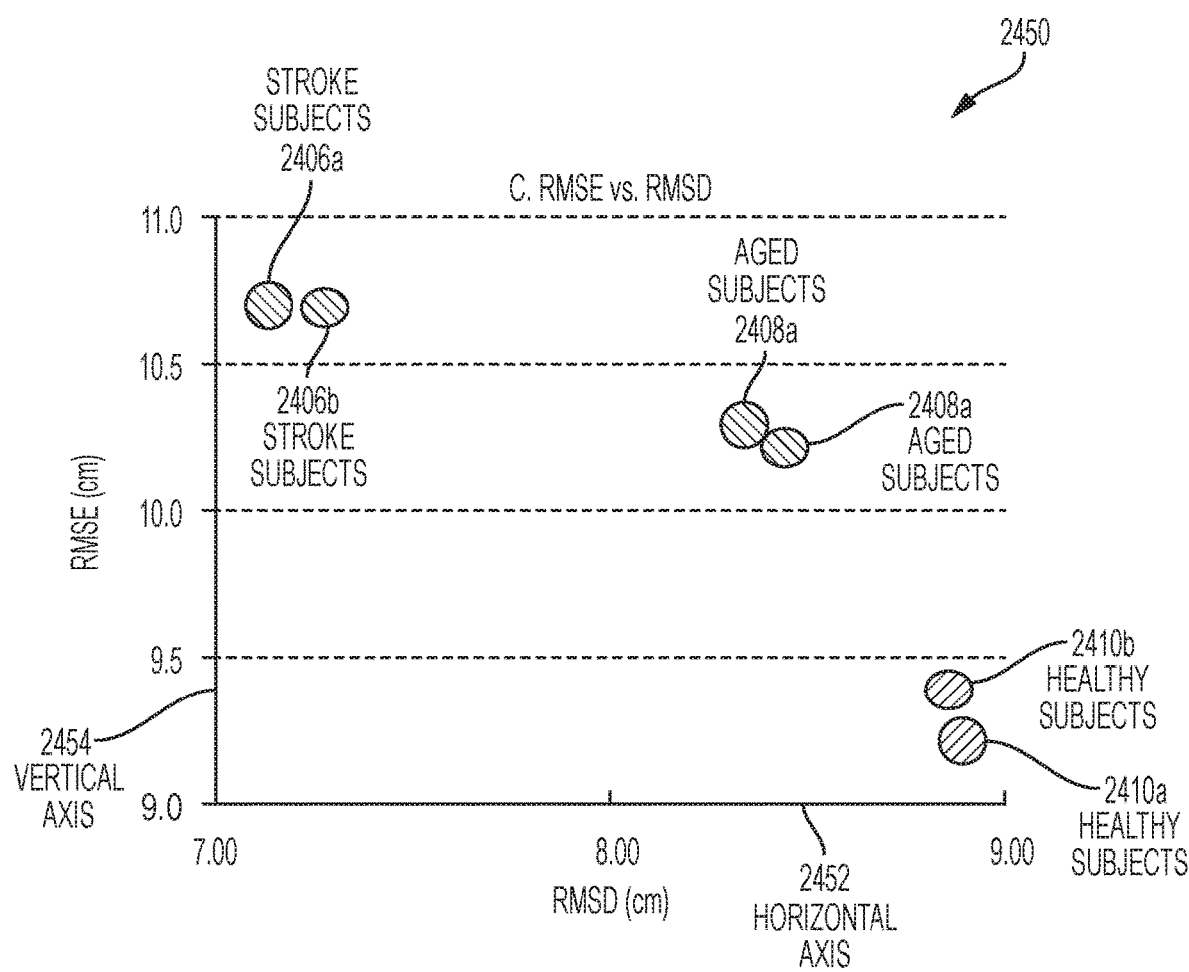
FIG. 24B is a graph that illustrates an example of a root mean square error (RMSE) as a function of root mean square deviation (RMSD) for a plurality of subject groups, according to an embodiment.

In other embodiments, in step 206, a response is determined from a plurality of groups where each group has a large number of subjects, e.g. larger than the groups depicted in FIG. 24A. FIG. 24B is a graph 2450 that illustrates an example of a root mean square error (RMSE) as a function of root mean square deviation (RMSD) for a plurality of subject groups, according to an embodiment. The horizontal axis 2452 is RMSD in units of centimeters (cm). The vertical axis 2454 is RMSE in units of centimeters (cm). In some embodiments, where the group of healthy subjects includes a larger number of subjects, the data cluster 2410 divided into a plurality of distinct data clusters 2410*a*, 2410*b*. In an example embodiment, the RMSE and/or RMSD of the data clusters 2410*a*, 2410*b* overlap. In an example embodiment, the data clusters 2410*a*, 2410*b* represent distinct subgroups of healthy subjects, based on data of a large number of healthy subjects. In an example embodiment, data cluster 2410*a* represents a lower age range of the young healthy subjects whereas data cluster 2410*b* represents an upper age range of the young healthy subjects. Similarly, where the group of aged subjects includes a larger number of subjects, the data cluster 2408 is divided into a plurality of data clusters 2408*a*, 2408*b* and where the group of stroke subjects include a large number of subjects, the data cluster 2406 is divided into a plurality of data clusters 2406*a*, 2406*b*. In some embodiments, the quantified risk of each group is determined by subsequently obtaining fall data from each subject of the group, in the same manner as previously discussed. Additionally, the quantified risk of each group is used to generate a best fit curve that is used to estimate a risk of fall of a second subject, in the same manner as previously discussed. The data clusters of FIGS. 24A and 24B are merely one example of data clusters for the plurality of groups of first subjects and different data clusters would result based on different fall data and/or different groups of subjects.

In some embodiments, in step 210, a relationship is determined between the risk of fall of the second subject and one or more measures of the response of the first subject from step 206, using a similar approach as discussed above with respect to the RMSE and RMSD measures of the response. In an example embodiment, a mean magnitude of a normalized left joint force (e.g. left hip) and a mean magnitude of a normalized right joint force (e.g. right hip) is determined over the time period for the plurality of subject groups. FIG. 25A is a graph 2500 that illustrates an example of a mean force magnitude of a left joint as a function of a mean force magnitude of a right joint over the time period for a plurality of subject groups, according to an embodiment. The horizontal axis 2502 is the mean magnitude of the normalized left joint force (unitless). The vertical axis 2504 is the mean magnitude of the normalized right joint force (unitless). In an example embodiment, the mean magnitude of the left and right normalized joint forces over the time period are within a range of each other (FIGS. 8A and 8B) in a healthy subject, due to a relative symmetric distribution of force between the left and right joints over the time period. In an example embodiment, the mean magnitude of the left and right normalized joint forces over the time period are not within a range of each other (FIGS. 11A and 11B) in an aged subject, due to a relative asymmetric distribution of force between the left and right joints over the time period. A first data cluster 2506 of a group of stroke subjects indicates that the mean magnitude of the right joint force is far greater than the mean magnitude of the left joint force. A second data cluster 2508 of a group of aged subjects indicates that the mean magnitude of the left joint force is greater than the mean magnitude of the right joint force. A third data cluster 2510 of a group of young healthy subjects indicates that the mean magnitude of the left joint force is approximately equal or at least within a range of, the mean magnitude of the right joint force. In an example embodiment, the data clusters 2506, 2508, 2510 are used to quantify fall risk and determine a risk of fall of a second subject, in a similar manner as discussed above with regard to the data clusters of FIGS. 24A and 24B.

Figure 25B:
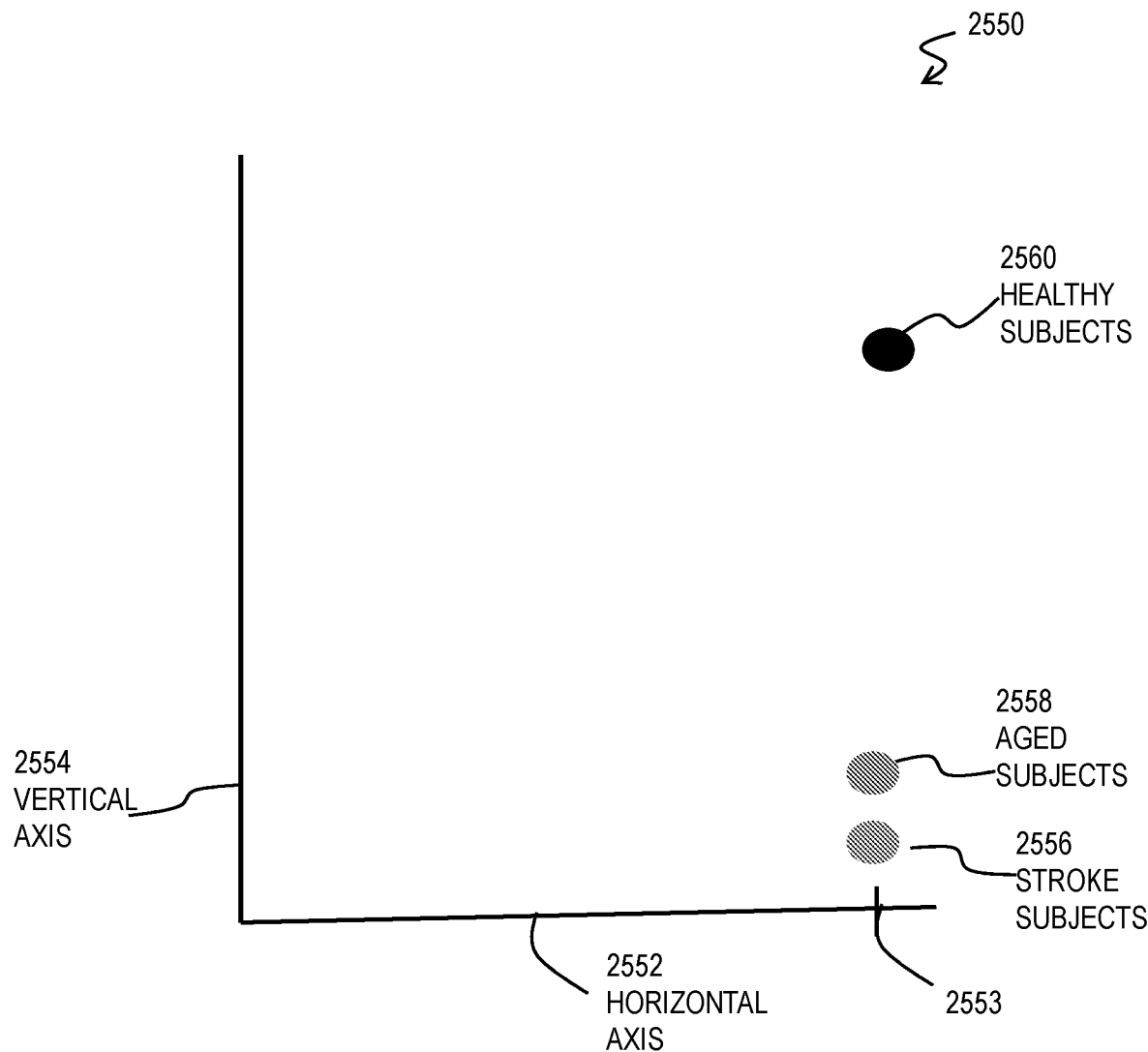
FIG. 25B is a graph that illustrates an example of an amplitude of the frequency spectrum of the normalized force of a UE body segment joint as a function of the frequency spectrum of the moving target for a plurality of subject groups, according to an embodiment.

In an example embodiment, the amplitude of the frequency spectrum of the normalized force of a UE body segment (e.g. L5/S1) for one or more discrete frequencies (e.g. high discrete frequency >1 Hz) is determined for the plurality of subject groups. FIG. 25B is a graph 2550 that illustrates an example of an amplitude of the frequency spectrum of the normalized force of a UE body segment joint (e.g. L5/S1) as a function of the frequency spectrum of the moving target for a plurality of subject groups, according to an embodiment. The horizontal axis 2552 is frequency in units of Hertz (Hz). The vertical axis 2554 is the amplitude of the frequency spectrum of the normalized joint of a UE body segment (unit less). In an example embodiment, the graph 2550 depicts the amplitude of the frequency spectrum for a high discrete frequency 2553 (e.g. >1 Hz). In an example embodiment, the amplitude of the frequency spectrum of the normalized joint of a UE body segment (e.g. L5/S1) is relatively large for a high discrete frequency 2553 (FIG. 9L for frequencies >1 Hz) in a healthy subject. In an example embodiment, the amplitude of the frequency spectrum of the normalized joint of a UE body segment (e.g. L5/S1) is relatively small for a high discrete frequency 2553 (FIG. 11L for frequencies >1 Hz) in an aged subject. A first data cluster 2556 of a group of stroke subjects indicates that the amplitude of the frequency spectrum at the high discrete frequency 2553 is very low. A second data cluster 2558 of a group of aged subjects indicates that the amplitude of the frequency spectrum at the high discrete frequency 2553 is low, although greater than the amplitude of the first data cluster 2556. A third data cluster 2560 of a group of young healthy subjects indicates that the amplitude of the frequency spectrum at the high discrete frequency 2553 is relatively large. In an example embodiment, the data clusters 2556, 2558, 2560 are used to quantify fall risk and determine a risk of fall of a second subject, in a similar manner as discussed above with regard to the data clusters of FIGS. 24A and 24B. A graph that is similar to the graph 2550 can be generated using the frequency spectrums of the normalized force of any joint of the UE body segments and LE body segments, at one or more discrete frequencies, in order to generate data clusters between the plurality of groups of first subjects. The data clusters of FIGS. 25A and 25B are merely one example of data clusters for the plurality of groups of first subjects and different data clusters would result based on different fall data and/or different groups of subjects.

In some embodiments, the clusters are not defined over just two dimensions at a time, as in FIG. 24A through FIG. 25B, but in multidimensional space. Then the combination of two or more parameters most likely to distinguish the clusters can be determined objectively.

In step 212, the risk of fall or a result based on the risk of fall is output on a display device. In an example embodiment, the display device outputs the risk of fall and/or a recommended treatment plan based on the risk of fall.

Additionally, in some embodiments, one or more additional steps is performed, such as providing treatment to the second subject, based on the risk of fall. For example, in some embodiments, the risk of fall is used to affect the movement provided by an external or internal robotic apparatus, such as a boot or ankle-bot. For example, if the risk of fall is low or negligible, the robotic apparatus does not engage or assist the subject; but, if the risk is greater than negligible, the response of the robotic apparatus increases with the amount of risk determined.

2. Example Embodiments

Figure 6:
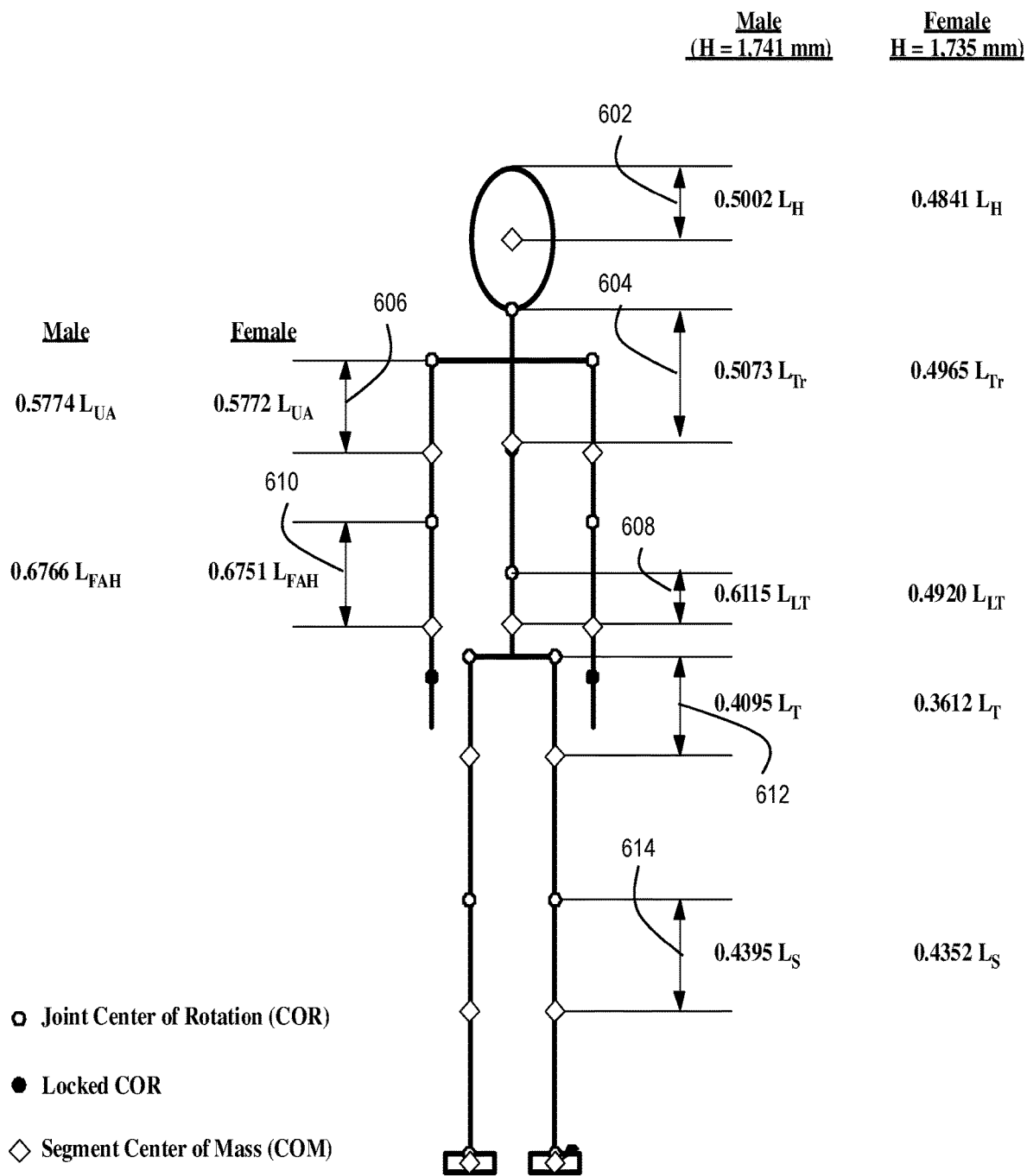
FIG. 6 is a block diagram that illustrates an example of a length between the center of mass (CoM) and joint center of rotation (CoR) in each segment of the biomechanical model of FIG. 1A, according to an embodiment.

FIG. 6 is a block diagram that illustrates an example of a length between the center of mass (CoM) and joint center of rotation (CoR) in each segment of the biomechanical model of FIG. 1A, according to an embodiment. The length between the CoM and CoR is expressed as a ratio of the length of the respective body segment. In an example embodiment, a length 602 between a top of the head segment and the CoM of the head segment is approximately 0.502 (male) or 0.4841 (female) times the length $L_H$ of the head segment. In an example embodiment, a length 604 between a CoR and the CoM of the trunk segment is approximately 0.50703 (male) or 0.4965 (female) times the length $L_{Tr}$ of the trunk segment. In an example embodiment, a length 606 between a CoR and the CoM of the upper arm segment is approximately 0.5774 (male) or 0.5772 (female) times the length $L_{UA}$ of the upper arm segment. In an example embodiment, a length 608 between a CoR and the CoM of the lower trunk segment is approximately 0.6115 (male) or 0.4920 (female) times the length $L_{LT}$ of the lower trunk segment. In an example embodiment, a length 610 between a CoR and the CoM of the forearm segment is approximately 0.6766 (male) or 0.6751 (female) times the length $L_{FAH}$ of the forearm segment. In an example embodiment, a length 612 between a CoR and the CoM of the thigh segment is approximately 0.4095 (male) or 0.3612 (female) times the length $L_T$ of the thigh segment. In an example embodiment, a length 614 between a COR and the CoM of the shank segment is approximately 0.4395 (male) or 0.4352 (female) times the length $L_S$ of the shank segment. Table 3 below provides an example embodiment of a mass of each body segment ($M_{seg}$), expressed as a ratio of a mass (M) of a human subject and a length ($L_{seg}$) of each body segment, expressed as a ratio of a height (H) of a human subject, including respective ratios for male and female subjects. Additionally, Table 3 below provides an example embodiment of a length between the CoM and CoR ($y_{com}$) expressed as a ratio of the length ($L_{seg}$) of each body segment for male and female subjects. Additionally, Table 3 provides an example embodiment of a radius of gyration about the x-axis ($\rho_{xx}$), a radius of gyration about the y-axis ($\rho_{yy}$) and a radius of gyration about the z-axis ($\rho_{zz}$), each expressed as a ratio of the length ($L_{seg}$) of each body segment for male and female subjects.

TABLE 3

| | | Men | | | | | |
|---|---|---|---|---|---|---|---|
| Body Segment | End Points | $M_{seg}$ (kg) | $L_{seg}$ (mm) | $y_{CoM}$ (mm)[1] | $\rho_{xx}$ (mm) | $\rho_{yy}$ (mm) | $\rho_{zz}$ (mm) |
| 1. Head (Hd) | Vertex Cervicale | 0.0694 M | 0.1395 H | 0.5002 $L_{Hd}$ | 0.303 $L_{Hd}$ | 0.261 $L_{Hd}$ | 0.315 $L_{Hd}$ |
| 2. Upper Trunk (UTr) | Cervicale Xyphion | 0.1596 M | 0.1391 H | 0.5066 $L_{UTr}$ | 0.505 $L_{UTr}$ | 0.465 $L_{UTr}$ | 0.320 $L_{UTr}$ |
| 3. Middle Trunk (MTr) | Xyphion Omphalion | 0.1633 M | 0.1238 H | 0.4502 $L_{MTr}$ | 0.482 $L_{MTr}$ | 0.468 $L_{MTr}$ | 0.383 $L_{MTr}$ |
| 4. Lower Trunk (LTr) | Omphalion Hip Jnt Ctr | 0.1117 M | 0.0084 H | 0.6115 $L_{LTr}$ | 0.615 $L_{LTr}$ | 0.587 $L_{LTr}$ | 0.551 $L_{LTr}$ |

TABLE 3-continued

| | | | | | | | |
|---|---|---|---|---|---|---|---|
| 5. Thigh (T) | Hip Jnt Ctr Knee Jnt Ctr | 0.1416 M | 0.2425 H | 0.4095 $L_T$ | 0.329 $L_T$ | 0.149 $L_T$ | 0.329 $L_T$ |
| 6. Shank (S) | Knee Jnt Ctr Ankel Jnt Ctr | 0.0433 M | 0.2529 H | 0.4395 $L_S$ | 0.251 $L_S$ | 0.102 $L_S$ | 0.246 $L_S$ |
| 7. Foot (Ft) | Ankel Jnt Ctr Ground | 0.0137 M | | | 0.257 $L_F$ | 0.124 $L_F$ | 0.245 $L_F$ |
| 8. Upper Arm (UA) | Shldr Jnt Ctr Elbow Jnt Ctr | 0.0271 M | 0.1618 H | 0.5772 $L_{UA}$ | 0.285 $L_{UA}$ | 0.158 $L_{UA}$ | 0.269 $L_{UA}$ |
| 9. Forearm (FA) | Elbow Jnt Ctr Wrst Jnt Ctr | 0.0162 M | 0.1545 H | 0.4574 $L_{FA}$ | 0.276 $L_{FA}$ | 0.121 $L_{FA}$ | 0.265 $L_{FA}$ |
| 10. Hand (Hnd) | Wrst Jnt Ctr $3^{rd}$ Metacarpale | 0.0061 M | 0.0495 H | 0.7900 $L_{Hnd}$ | 0.628 $L_{Hnd}$ | 0.401 $L_{Hnd}$ | 0.513 $L_{Hnd}$ |
| 11. Trunk (Tr) | Cervicale Omphalion | 0.3229 M | 0.2628 H | 0.5073 $L_{Tr}$ | 0.248 $L_{Tr}$ | 0.332 $L_{Tr}$ | 0.175 $L_{Tr}$ |
| 12. Forearm/ Hand (FAHnd) | Elbow Jnt Ctr $3^{rd}$ Metacarpale | 0.0223 M | 0.2040 H | 0.5112 $L_{FAHnd}$ | 0.195 $L_{FAHnd}$ | 0.097 $L_{FAHnd}$ | 0.183 $L_{FAHnd}$ |

| | | Women | | | | | |
|---|---|---|---|---|---|---|---|
| Body Segment | End Points | $M_{seg}$ (kg) | $L_{seg}$ (mm) | $y_{CoM}$ (mm)[1] | $\rho_{xx}$ (mm) | $\rho_{yy}$ (mm) | $\rho_{zz}$ (mm) |
| 1. Head (Hd) | Vertex Cervicale | 0.0668 M | 0.1405 H | 0.4841 $L_{Hd}$ | 0.271 $L_{Hd}$ | 0.261 $L_{Hd}$ | 0.295 $L_{Hd}$ |
| 2. Upper Trunk (UTr) | Cervicale Xyphion | 0.1545 M | 0.1314 H | 0.5050 $L_{UTr}$ | 0.466 $L_{UTr}$ | 0.449 $L_{UTr}$ | 0.314 $L_{UTr}$ |
| 3. Middle Trunk (MTr) | Xyphion Omphalion | 0.1465 M | 0.1183 H | 0.4512 $L_{MTr}$ | 0.433 $L_{MTr}$ | 0.415 $L_{MTr}$ | 0.354 $L_{MTr}$ |
| 4. Lower Trunk (LTr) | Omphalion Hip Jnt Ctr | 0.1247 M | 0.1046 H | 0.4920 $L_{LTr}$ | 0.433 $L_{LTr}$ | 0.444 $L_{LTr}$ | 0.402 $L_{LTr}$ |
| 5. Thigh (T) | Hip Jnt Ctr Knee Jnt Ctr | 0.1478 M | 0.2124 H | 0.3612 $L_T$ | 0.369 $L_T$ | 0.162 $L_T$ | 0.364 $L_T$ |
| 6. Shank (S) | Knee Jnt Ctr Ankel Jnt Ctr | 0.0481 M | 0.2528 H | 0.4352 $L_S$ | 0.267 $L_S$ | 0.092 $L_S$ | 0.263 $L_S$ |
| 7. Foot (Ft) | Ankel Jnt Ctr Ground | 0.0129 M | | | 0.299 $L_F$ | 0.139 $L_F$ | 0.279 $L_F$ |
| 8. Upper Arm (UA) | Shldr Jnt Ctr Elbow Jnt Ctr | 0.0255 M | 0.1586 H | 0.5754 $L_{UA}$ | 0.278 $L_{UA}$ | 0.148 $L_{UA}$ | 0.260 $L_{UA}$ |
| 9. Forearm (FA) | Elbow Jnt Ctr Wrst Jnt Ctr | 0.0138 M | 0.1523 H | 0.4559 $L_{FA}$ | 0.261 $L_{FA}$ | 0.094 $L_{FA}$ | 0.257 $L_{FA}$ |
| 10. Hand (Hnd) | Wrst Jnt Ctr $3^{rd}$ Metacarpale | 0.0056 M | 0.0045 H | 0.7474 $L_{Hnd}$ | 0.531 $L_{Hnd}$ | 0.335 $L_{Hnd}$ | 0.454 $L_{Hnd}$ |
| 11. Trunk (Tr) | Cervicale Omphalion | 0.3010 M | 0.2497 H | 0.4966 $L_{Tr}$ | 0.227 $L_{Tr}$ | 0.322 $L_{Tr}$ | 0.246 $L_{Tr}$ |
| 12. Forearm/ Hand (FAHnd) | Elbow Jnt Ctr $3^{rd}$ Metacarpale | 0.0194 M | 0.1973 H | 0.5225 $L_{FAHnd}$ | 0.182 $L_{FAHnd}$ | 0.278 $L_{FAHnd}$ | 0.176 $L_{FAHnd}$ |

However, in other embodiments, the lengths and masses of each body segment are not limited to the ratios expressed in Table 3, and are assigned a length and mass using any convention that is known to one skilled in the art. In some embodiments, the lengths and masses of each body segment are selected within a range of ±10% of the ratios expressed in Table 3. Additionally, in other embodiments, the distances between the CoM and CoR of each body segment are not limited to the ratios expressed in Table 3, and are assigned a length and mass using any convention that is known to one skilled in the art.

Figure 7A:
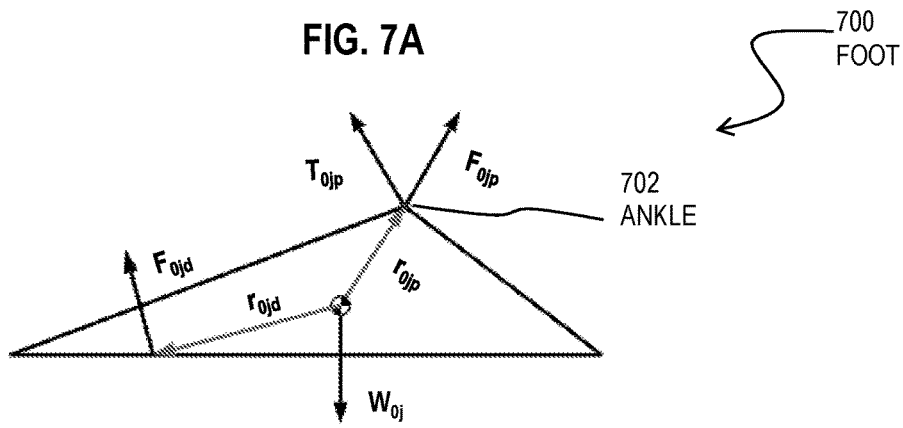
FIGS. 7A to 7G are block diagrams that illustrate forces and torques imparted at the CoM and CoR of each segment of the biomechanical model of FIG. 1A, according to an embodiment.
Figure 7B:
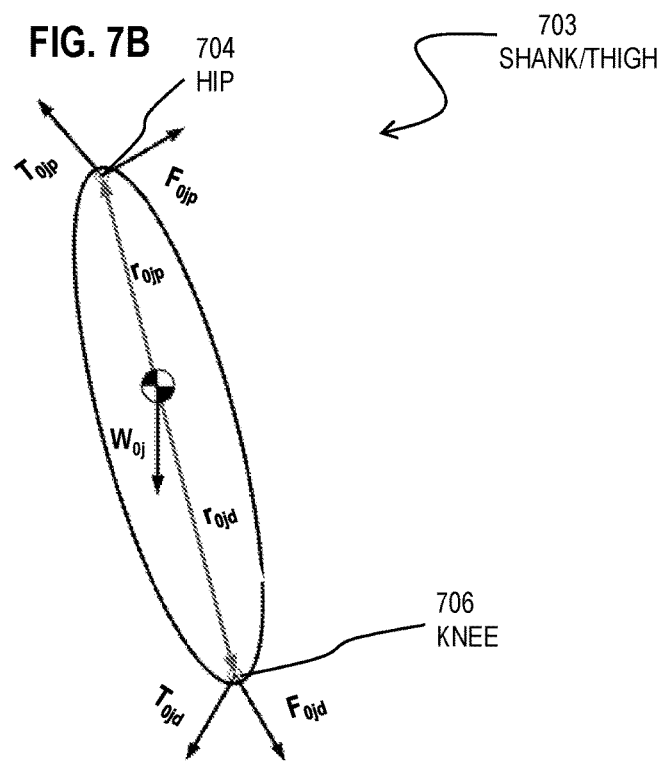
Figure 7C:
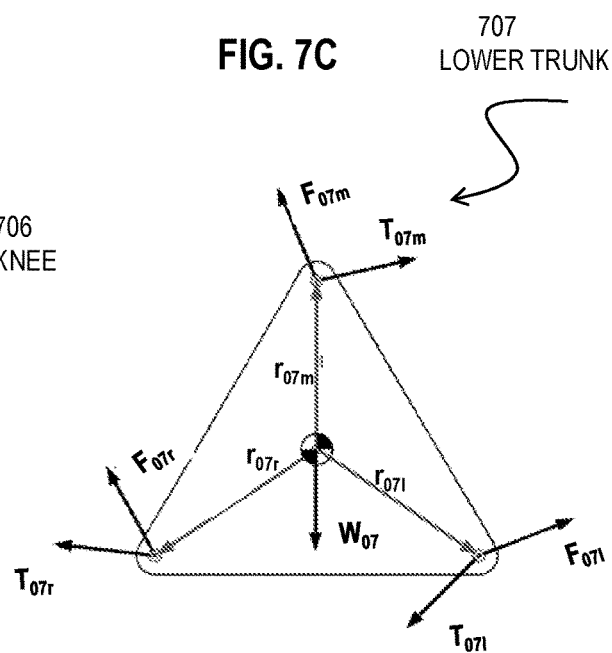
Figure 7D:
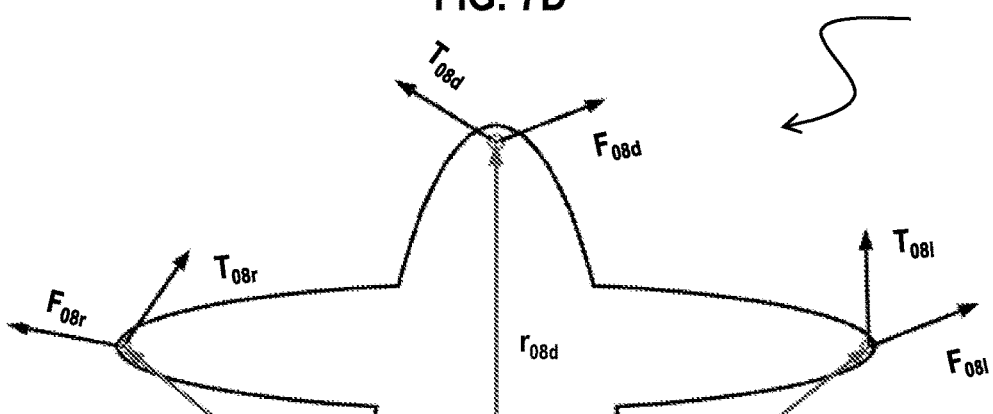
Figure 7E:
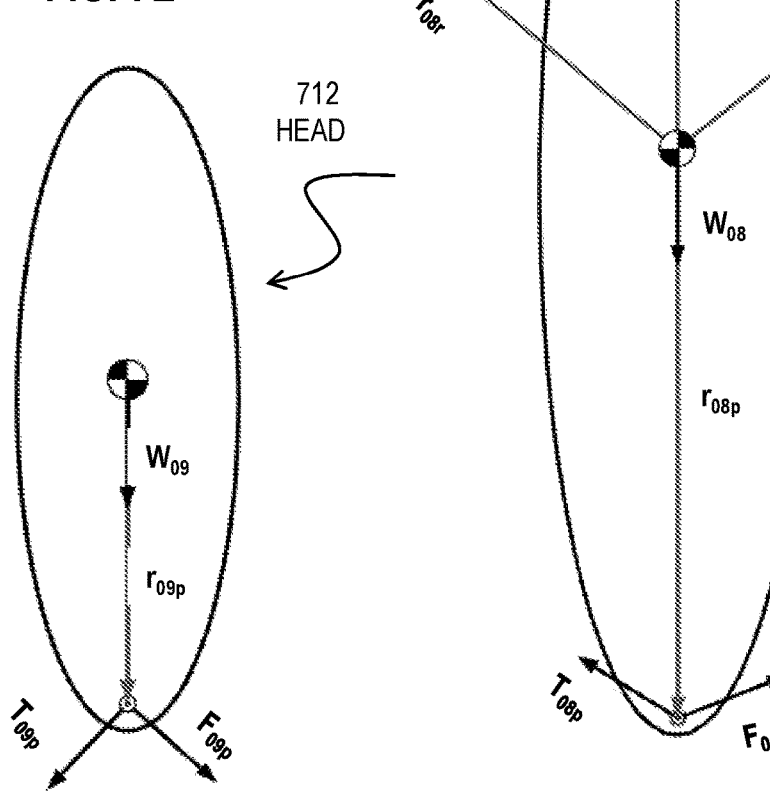
Figure 7F:
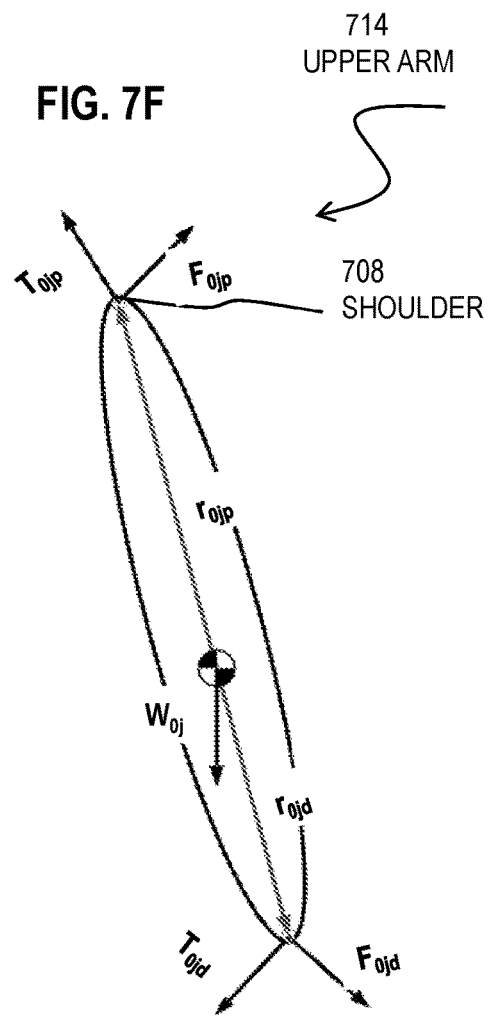
Figure 7G:
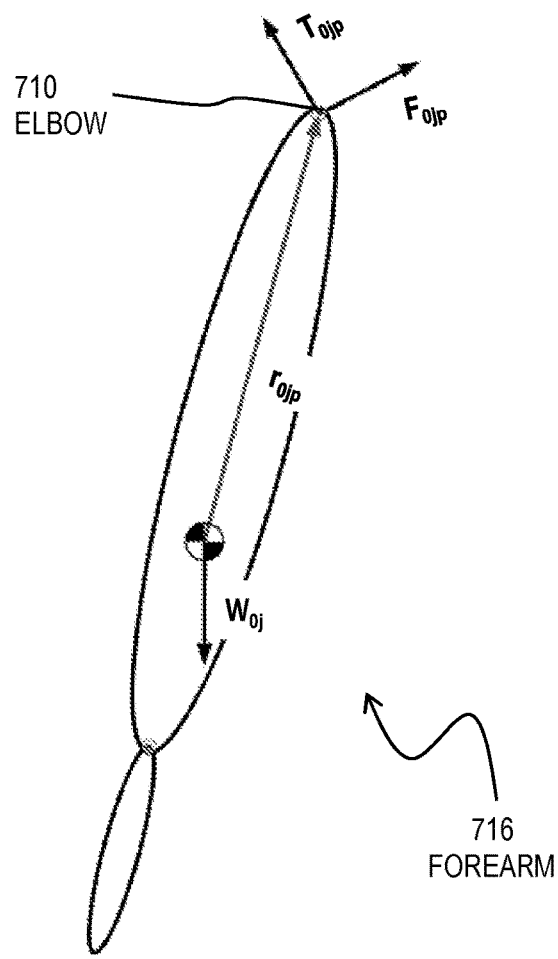

FIGS. 7A to 7G are block diagrams that illustrate forces and torques imparted at the CoM and CoR of each segment of the biomechanical model of FIG. 1A, according to an embodiment. For each block diagram, the force at each body segment CoR is represented by $F_{ojk}$, the torque at each body segment CoR is represented by $T_{ojk}$, the body segment weight at each CoM is represented by $W_{oj}$ and the position vector from the CoM to each body segment CoR is represented by $r_{ojk}$, where o is the index of the global coordinate system 104 that each vector is measured with respect to; j is an index of the segment (see Table 1) and k is an index of the CoR of the segment (p, d, r, l, m, etc). FIG. 7A is a block diagram that illustrates forces and torques imparted at the ankle 702 CoR of the left and right foot 700 body segments (e.g. j=1, 4), according to an embodiment. In some embodiments, the joint forces $F_{ojd}$ imposed on a distal CoR (e.g. ball joint) of the foot 700 are ground reaction forces that are measured by the force plates in the platform 106 at each time increment of the time period. FIG. 7B is a block diagram that illustrates forces and torques imparted at the hip 704 CoR and knee 706 CoR of the left and right shank/thigh 703 body segments (e.g. j=2, 3, 5, 6), according to an embodiment. FIG. 7C is a block diagram that illustrates forces and torques imparted at the CoR of the lower trunk 707 body segment (e.g. j=7), according to an embodiment. FIG. 7D is a block diagram that illustrates forces and torques imparted at the CoR of the mid/upper trunk 710 body segment (e.g. j=8), according to an embodiment. FIG. 7E is a block diagram that illustrates forces and torques imparted at the CoR of the head 712 body segment (e.g. j=9), according to an embodiment. FIG. 7F is a block diagram that illustrates forces and torques imparted at the shoulder 708 CoR of the left and right upper arm 714 body segments (e.g. j=10, 12), according to an embodiment. FIG. 7G is a block diagram that illustrates forces and torques imparted at the elbow 710 CoR of the left and right forearm 716 body segments (e.g. j=11, 13), according to an embodiment.

In some embodiments, one or more joint forces $F_{ojk}$ at each time increment are determined using the positions of the CoM and CoR of each body segment from the tracking data of step 204, as well as the estimated length of the body segment and estimated mass of the body segment. Any method appreciated by one skilled in the art is used to determine the joint forces $F_{ojk}$ at each time increment using the position data of the CoM and CoR of each body segment, the estimated length of the body segment and the estimated mass of the body segment. In an example embodiment, the joint force $F_{ojk}$ is determined by initially determining a net force $F_{ojc}$ (e.g. vector sum of the joint forces $F_{ojk}$ and weight $W_{oj}$) at each body segment, based on the position of the CoM and CoR from the tracking data of step 204, as well as the estimated length and estimated mass of the body segment. The joint forces $F_{ojk}$ are then determined by subtracting the weight $W_{oj}$ from the net force $F_{ojc}$.

In some embodiments, a vector sum of the forces at each body segment in FIGS. 7A-7G is represented by:

$$F_{01p} + F_{01d} + W_{01} = F_{01c} = m_1 \cdot a_{01c}$$

$$F_{02p} + F_{02d} + W_{02} = F_{02c} = m_2 \cdot a_{02c}$$

$$F_{03p} + F_{03d} + W_{03} = F_{03c} = m_3 \cdot a_{03c}$$

$$F_{04p} + F_{04d} + W_{04} = F_{04c} = m_4 \cdot a_{04c}$$

$$F_{05p} + F_{05d} + W_{05} = F_{05c} = m_5 \cdot a_{05c}$$

$$F_{06p} + F_{06d} + W_{06} = F_{06c} = m_6 \cdot a_{06c}$$

$$F_{07r} + F_{07m} + F_{07l} + W_{07} = F_{07c} = m_7 \cdot a_{07c}$$

$$F_{08p} + F_{08d} + F_{08r} + F_{08l} + W_{08} = F_{08c} = m_8 \cdot a_{08c}$$

$$F_{09p} + W_{09} = F_{09c} = m_9 \cdot a_{09c}$$

$$F_{10p} + F_{10d} + W_{10} = F_{10c} = m_{10} \cdot a_{10c}$$

$$F_{11p} + W_{11} = F_{11c} = m_{11} \cdot a_{11c}$$

$$F_{12p} + F_{12d} + W_{12} = F_{12c} = m_{12} \cdot a_{12c}$$

$$F_{13p} + W_{13} = F_{13c} = m_{13} \cdot a_{13c} \tag{6}$$

where $F_{ojc}$ is the net force on the body segment CoM of index j, $a_{ojc}$ is the net acceleration of the body segment CoM of index j and $m_j$ is the mass of the body segment of index j. The net force and net acceleration are measured with respect to the global coordinate system 104. Additionally, in some embodiments, the vector sum of the net torques at each body segment in FIGS. 7A to 7G is represented by:

$$\tag{7}$$

$$r_{01p} \times F_{01p} + r_{01d} \times F_{01d} + T_{01d} = T_{01c} = [I_{01c}] \cdot \alpha_{01c} + \omega_{01c} \times [I_{01c}] \cdot \omega_{01c},$$

$$r_{02p} \times F_{02p} + r_{02d} \times F_{02d} + T_{02p} + T_{02d} =$$

$$T_{02c} = [I_{02c}] \cdot \alpha_{02c} + \omega_{02c} \times [I_{02c}] \cdot \omega_{02c},$$

$$r_{03p} \times F_{03p} + r_{03d} \times F_{03d} + T_{03p} + T_{03d} =$$

$$T_{03c} = [I_{03c}] \cdot \alpha_{03c} + \omega_{03c} \times [I_{03c}] \cdot \omega_{03c},$$

$$r_{04p} \times F_{04p} + r_{04d} \times F_{04d} + T_{04d} = T_{04c} = [I_{04c}] \cdot \alpha_{04c} + \omega_{04c} \times [I_{04c}] \cdot \omega_{04c},$$

$$r_{05p} \times F_{05p} + r_{05d} \times F_{05d} + T_{05p} + T_{05d} =$$

$$T_{05c} = [I_{05c}] \cdot \alpha_{05c} + \omega_{05c} \times [I_{05c}] \cdot \omega_{05c},$$

$$r_{06p} \times F_{06p} + r_{06d} \times F_{06d} + T_{06d} + T_{06d} =$$

$$T_{06c} = [I_{06c}] \cdot \alpha_{06c} + \omega_{06c} \times [I_{06c}] \cdot \omega_{06c},$$

$$r_{07r} \times F_{07r} + r_{07m} \times F_{07m} + r_{07l} \times F_{07l} + T_{07r} + T_{07m} + T_{07l} =$$

$$T_{07c} = [I_{07c}] \cdot \alpha_{07c} + \omega_{07c} \times [I_{07c}] \cdot \omega_{07c},$$

$$r_{08p} \times F_{08p} + r_{08d} \times F_{08d} + r_{08r} \times F_{08r} + r_{08l} + F_{08l} + T_{08p} +$$

$$T_{08d} + T_{08r} + T_{08l} = T_{08c} = [I_{07c}] \cdot \alpha_{07c} + \omega_{07c} \times [I_{07c}] \cdot \omega_{07c},$$

$$r_{09p} \times F_{09p} + T_{09p} = T_{09c} = [I_{09c}] \cdot \alpha_{09c} + \omega_{09c} \times [I_{09c}] \cdot \omega_{09c},$$

$$r_{010p} \times F_{010p} + r_{010d} \times F_{010d} + T_{010p} + T_{010d} =$$

$$T_{010c} = [I_{010c}] \cdot \alpha_{010c} + \omega_{010c} \times [I_{010c}] \cdot \omega_{010c},$$

$$r_{011p} \times F_{011p} + T_{011p} = T_{011c} = [I_{011c}] \cdot \alpha_{011c} + \omega_{011c} \times [I_{011c}] \cdot \omega_{011c},$$

$$r_{012p} \times F_{012p} + r_{012d} \times F_{012d} + T_{012p} + T_{012d} =$$

$$T_{012c} = [I_{012c}] \cdot \alpha_{012c} + \omega_{012c} \times [I_{012c}] \cdot \omega_{012c},$$

$$r_{013p} \times F_{013p} + T_{013p} = T_{013c} = [I_{013c}] \cdot \alpha_{013c} + \omega_{013c} \times [I_{013c}] \cdot \omega_{013c}.$$

where $T_{ojc}$ is the net torque imparted about the body segment of index j, $\alpha_{ojc}$ is the net angular acceleration of the body segment CoM of index j and $I_{ojc}$ is the moment of inertia of the body segment of index j. The net torque and net angular acceleration are measured with respect to the global coordinate system 104. Since forces and torques at adjoining body segment joints are equal and opposite:

$$\tag{8}$$

| | | | |
|---|---|---|---|
| $F_{01p} + F_{02d} = 0$ | $F_{07m} + F_{08p} = 0$ | $T_{01p} + T_{02d} = 0$ | $T_{07m} + T_{08p} = 0$ |
| $F_{02p} + F_{03d} = 0$ | $F_{08d} + F_{09p} = 0$ | $T_{02p} + T_{03d} = 0$ | $T_{08d} + T_{09p} = 0$ |
| $F_{03p} + F_{07r} = 0$ | $F_{08r} + F_{010p} = 0$ | $T_{03p} + T_{07r} = 0$ | $T_{08r} + T_{010p} = 0$ |
| $F_{04p} + F_{05d} = 0$ | $F_{08l} + F_{012p} = 0$ | $T_{04p} + T_{05d} = 0$ | $T_{08l} + T_{012p} = 0$ |
| $F_{05p} + F_{06d} = 0$ | $F_{010d} + F_{011p} = 0$ | $T_{05p} + T_{06d} = 0$ | $T_{010d} + T_{011p} = 0$ |
| $F_{06p} + F_{07l} = 0$ | $F_{012d} + F_{013p} = 0$ | $T_{06p} + T_{07l} = 0$ | $T_{012d} + T_{013p} = 0$ |

In an example embodiment, forces and torques pertaining to a non-pointing elbow are not considered in equation 8. In this example embodiment, for right-handed subjects the equations in 8 including $F_{013p}$ and $T_{013p}$ (e.g. joint forces and joint torques of the left-elbow) are not considered and for left-handed subjects, the equations in 8 including $F_{011p}$ and $T_{011p}$ (e.g. joint forces and joint torques of the right-elbow) are not considered.

In some embodiments, during step 206, one or more net forces $F_{ojc}$ and net torques $T_{ojc}$ at the body segment CoM are determined at each time increment over the time period. The weight $W_{oj}$ of each body segment is estimated, based on the estimated body segment mass that is based on a ratio of the body mass M of the subject. As shown in FIG. 7A, the joint forces $F_{ojd}$ of the left and right foot (j=1, 4) are ground reaction forces imposed on the foot. In some embodiments, these ground reaction forces are measured by the force plates in the platform 106 at each time increment over the time period. Moving known terms to the right side of equation 6 yields:

$$F_{01p} = F_{01c} - F_{01d} - W_{01}$$

$$F_{02p} + F_{02d} = F_{02c} - W_{02}$$

$$F_{03p} + F_{03d} = F_{03c} - W_{03}$$

$$F_{04p} = F_{04c} - F_{04d} - W_{04}$$

$$F_{05p} + F_{05d} = F_{05c} - W_{05}$$

$$F_{06p} + F_{06d} = F_{06c} - W_{06}$$

$$F_{07r} + F_{07m} + F_{07l} = F_{07c} - W_{07}$$

$$F_{08p} + F_{08d} + F_{08r} + F_{08l} = F_{08c} - W_{08}$$

$$F_{09p} = F_{09c} - W_{09}$$

$$F_{10p} + F_{10d} = F_{10c} - W_{10}$$

$$F_{11p} = F_{11c} - W_{11}$$

$$F_{12p} + F_{12d} = F_{12c} - W_{12}$$

$$F_{13p} = F_{13c} - W_{13} \quad (9)$$

Additionally, moving known terms to the right side of equation 7 yields:

$$r_{01p} \cdot F_{01p} + T_{01p} = T_{01c} - r_{01d} \cdot F_{01d} - T_{01d}, \quad (10)$$

$$r_{02p} \cdot F_{02p} + r_{02d} \cdot F_{02d} + T_{02p} + T_{02d} = T_{02c},$$

$$r_{03p} \cdot F_{03p} + r_{03d} \cdot F_{03d} + T_{03p} + T_{03d} = T_{03c},$$

$$r_{04p} \cdot F_{04p} + T_{04p} = T_{04c} - r_{04d} \cdot F_{04d} - T_{04d},$$

$$r_{05p} \cdot F_{05p} + r_{05d} \cdot F_{05d} + T_{05p} + T_{05d} = T_{05c},$$

$$r_{06p} \cdot F_{06p} + r_{06d} \cdot F_{06d} + T_{06p} + T_{06d} = T_{06c},$$

$$r_{07r} \cdot F_{07r} + r_{07m} \cdot F_{07m} + r_{07l} \cdot F_{07l} + T_{07r} + T_{07m} + T_{07l} = T_{07c},$$

$$r_{08p} \cdot F_{08p} + r_{08d} \cdot F_{08d} + r_{08r} \cdot F_{08r} +$$

$$r_{08l} \cdot F_{08l} + T_{08p} + T_{08d} + T_{08r} + T_{08l} = T_{08c},$$

$$r_{09p} \cdot F_{09p} + T_{09p} = T_{09c},$$

$$r_{010p} \cdot F_{010p} + r_{010d} \cdot F_{010d} + T_{010p} + T_{010d} = T_{010c},$$

$$r_{011p} \cdot F_{011p} + T_{011p} = T_{011c},$$

$$r_{012p} \cdot F_{012p} + r_{012d} \cdot F_{012d} + T_{012p} + T_{012d} = T_{012c},$$

$$r_{013p} \cdot F_{013p} + T_{013p} = T_{013c}.$$

where the joint torques $T_{Ojd}$ of the left and right foot (j=1, 4) are ground reaction torques imposed on the foot and measured by the force plates in the platform 106 at each time increment over the time period;
and where $r_{Ojk}$ is a 3×3 skew-symmetric matrix of a position vector [x, y, z] from the CoM to each body segment CoR in the global coordinate system 104 as defined by:

$$\underline{r_{ojk}} = \begin{bmatrix} 0 & -z & y \\ z & 0 & -x \\ -y & x & 0 \end{bmatrix} \quad (11)$$

As shown in FIG. 7A, the position vectors $r_{Ojd}$ for the left and right foot (j=1, 4) from the CoM to the distal CoR (e.g. ball joint) are determined at each time increment, based on the position data of the CoM and CoR from step 204. After determining one or more net forces $F_{ojc}$ and net torques $T_{ojc}$ at the body segment CoM at each time increment, equations 9 and 10 are used to determine one or more joint forces $F_{ojk}$ on the left side of equations 9 and 10 at each time increment over the time period.

In some embodiments, during step 206, one or more net forces $F_{ojc}$ and net torques $T_{ojc}$ at the body segment CoM are determined at each time increment over the time period. In these embodiments, a velocity and acceleration of the CoM of the body segment at each time increment is initially determined based on the tracking data from step 204. In some embodiments, the velocity and acceleration includes one or more of a linear velocity, a linear acceleration, an angular velocity and an angular acceleration. In some embodiments, a direction cosine matrix $R_{ij}$ between the ($x_o$, $y_o$, $z_o$) axes of the global coordinate system 104 and the respective ($x_j$, $y_j$, $z_j$) axes of the local coordinate system 102 for each body segment, is defined as:

$$R_{ij} = \begin{bmatrix} r_{11} & r_{12} & r_{13} \\ r_{21} & r_{22} & r_{23} \\ r_{31} & r_{32} & r_{33} \end{bmatrix} = \begin{bmatrix} \cos(x_j, x_o) & \cos(x_j, y_o) & \cos(x_j, z_o) \\ \cos(y_j, x_o) & \cos(y_j, y_o) & \cos(y_j, z_o) \\ \cos(z_j, x_o) & \cos(z_j, y_o) & \cos(z_j, z_o) \end{bmatrix} \quad (12)$$

where (a, b) is defined as an angle between the a and b axes. The position of the CoM and CoR of each body segment from the tracking data of step 204 provides the respective ($x_j$, $y_j$, $z_j$) axes for each body segment, at each time increment. The axes ($x_o$, $y_o$, $z_o$) axes of the global coordinate system 104 are fixed and known. Based on the known axes ($x_j$, $y_j$, $z_j$) and ($x_o$, $y_o$, $z_o$) at each time increment from the tracking data of step 204, the matrix values of equation 12 are determined at each time increment.

Additionally, in some embodiments, the direction cosine matrix $R_{ij}$ of equation 12 is expressed as:

$$R_{ij} = \begin{bmatrix} r_{11} & r_{12} & r_{13} \\ r_{21} & r_{22} & r_{23} \\ r_{31} & r_{32} & r_{33} \end{bmatrix} = \quad (13)$$

$$\begin{bmatrix} \cos\phi\cos\theta & \sin\phi\cos\theta & -\sin\theta \\ -\sin\phi\cos\psi + \cos\phi\sin\theta\sin\psi & \cos\phi\cos\psi + \sin\phi\sin\theta\sin\psi & \cos\theta\sin\psi \\ \sin\phi\sin\psi + \cos\phi\sin\theta\cos\psi & -\cos\phi\sin\psi + \sin\phi\sin\theta\cos\psi & \cos\theta\cos\psi \end{bmatrix}.$$

where ($\psi$, $\theta$, $\phi$) are Euler angles used to define the local coordinate system 102 based on the global coordinate system 104. Using the Euler angles ($\psi$, $\theta$, $\phi$), the local coordinate system 102 is determined by initially rotating the global coordinate system 104 by the angle $\phi$ in a counter-clockwise (ccw) direction about the $z_o$ axis (in the $x_o y_o$ plane), subsequently rotated by the angle $\theta$ in the ccw direction about the rotated $y_o$ axis and subsequently rotated by the angle $\psi$ in the ccw direction about the twice-rotated $x_o$ axis. In some embodiments, the Euler angles ($\psi$, $\theta$, $\phi$) for each body segment coordinate system 102 are determined, based on the position of the CoM (e.g. origin of the local coordinate system 102) of each body segment provided by the sensors 108. In other embodiments, equations 12 and 13 are used to solve for the Euler angles, in terms of elements of the direction cosine matrix $R_{ij}$:

$$\theta = \tan_2^{-1}\left(\frac{-r_{13}}{+\sqrt{1-r_{13}^2}}\right), \quad \phi = \tan_2^{-1}\left(\frac{r_{12}}{r_{11}}\right), \quad \psi = \tan_2^{-1}\left(\frac{r_{23}}{r_{33}}\right), \quad (14)$$

In some embodiments, where the matrix values $r_{11}$ and $r_{12}$ in equation 12 are both zero, equation 14 is simplified to:

$$\theta = \pm\frac{\pi}{2} \quad \phi + \psi = \tan_2^{-1}\left(\frac{-r_{32}}{-r_{22}}\right) \tag{15}$$

where $\tan_2^{-1}$ is the two-argument arc-tangent function. In an example embodiment, equation 15 is used to solve for $\psi$ by setting $\phi$ to zero degrees.

In some embodiments, the Euler angles defined in equation 14 or 15 are solved by substituting the determined matrix values of equation 12 into equation 14 or 15. The Euler angles are solved for each time increment over the time period, resulting in time-based functions $\psi(t)$, $\theta(t)$, $\phi(t)$ for each Euler angle.

In some embodiments, a first time derivative $[\dot{\phi}, \dot{\theta}, \dot{\psi}]$ and second time derivative $[\ddot{\psi}, \ddot{\theta}, \ddot{\phi}]$ of each Euler angle are obtained using stencil equations:

$$\frac{dx}{dt} \approx \frac{x_{t-2} - 8x_{t-1} + 8x_{t+1} - x_{t+2}}{12\Delta t}, \tag{16}$$
$$\frac{d^2x}{dt^2} \approx \frac{-x_{t-2} + 16x_{t-1} - 30x_t + 16x_{t+1} - x_{t+2}}{12\Delta t^2}.$$

where x is a placeholder function; dx/dt is a first time derivative of the function; $d^2x/dt^2$ is a second time derivative of the function; $\Delta t$ is a length of the time increment over the time period; $x_t$ is a value of the function x at time increment t over the time period; $x_{t-2}$ is a value of the function x at the time increment t−2; $x_{t-1}$ is a value of the function x at the time increment t−1; $x_{t+1}$ is a value of the function x at the time increment t+1; $x_{t+2}$ is a value of the function x at the time increment t+2. In an example embodiment, the tracking data of step 204 is measured at 60 Hz and thus the time increment is 1/60 seconds (sec). In an example embodiment, the stencil equations 16 are used to compute the first time derivative and second time derivative at each time increment over the time period.

In some embodiments, the first time derivative $[\dot{\phi}, \dot{\theta}, \dot{\psi}]$ and second time derivative $[\ddot{\psi}, \ddot{\theta}, \ddot{\phi}]$ of each Euler angle are generated by substituting each Euler angle time-based function for the placeholder function x in the stencil equations 16. In an example embodiment, the first and second time derivatives of the Euler angles are determined at each time increment over the time period. In other embodiments, the first time derivative $[\dot{\phi}, \dot{\theta}, \dot{\psi}]$ and second time derivative $[\ddot{\psi}, \ddot{\theta}, \ddot{\phi}]$ of the Euler angle time-based functions are generated using any method appreciated by one of ordinary skill in the art.

In some embodiments, the position of each body segment CoM is represented by point $P_{ij}$ [$P_x$, $P_y$, $P_z$] in the global coordinate system 104, where the values of $P_x$, $P_y$, and $P_z$ at each time increment are determined from the tracking data of step 204. In some embodiments, a linear velocity or first time derivative [$v_x$, $v_y$, $v_z$] and linear acceleration or second time derivative [$a_x$, $a_y$, $a_z$] of the position of each body segment CoM is obtained by substituting each of the time-based functions $P_x$, $P_y$ and $P_z$ into the placeholder function x in the stencil equations 16.

An angular velocity [$\omega_x$, $\omega_y$, $\omega_z$] of the body segment CoM with respect to the global coordinate axis 104 is provided by:

$$\begin{bmatrix} \omega_{x_i} \\ \omega_{y_i} \\ \omega_{z_i} \end{bmatrix} = \begin{bmatrix} -\sin\theta & 0 & 1 \\ \cos\theta\sin\psi & \cos\psi & 0 \\ \cos\theta\cos\psi & -\sin\psi & 0 \end{bmatrix} \begin{bmatrix} \dot{\phi} \\ \dot{\theta} \\ \dot{\psi} \end{bmatrix}, \tag{17}$$

where $\phi$, $\theta$ and $\psi$ are the Euler angles defined above in equation 14 or 15 and $\dot{\phi}$, $\dot{\theta}$ and $\dot{\psi}$ is the first time derivative of the Euler angles determined from equations 14-16. Additionally, an angular acceleration [$\alpha_x$, $\alpha_y$, $\alpha_z$] of the body segment CoM with respect to the global coordinate axis 104 is determined by:

$$\begin{bmatrix} (\alpha_{ij})_{x_i} \\ (\alpha_{ij})_{y_i} \\ (\alpha_{ij})_{z_i} \end{bmatrix} = \begin{bmatrix} (\dot{\omega}_{ij})_{x_i} \\ (\dot{\omega}_{ij})_{y_i} \\ (\dot{\omega}_{ij})_{z_i} \end{bmatrix} = \tag{18}$$

$$\begin{bmatrix} -\ddot{\phi}\sin\theta - \dot{\phi}\dot{\theta}\cos\theta + \ddot{\psi} \\ \ddot{\phi}\cos\theta\sin\psi + \ddot{\theta}\cos\psi - \dot{\phi}\dot{\theta}\sin\theta\sin\psi + \dot{\phi}\dot{\psi}\cos\theta\cos\psi - \dot{\theta}\dot{\psi}\sin\psi \\ \ddot{\phi}\cos\theta\cos\psi - \ddot{\theta}\sin\psi - \dot{\phi}\dot{\theta}\sin\theta\cos\psi - \dot{\phi}\dot{\psi}\cos\theta\sin\psi - \dot{\theta}\dot{\psi}\cos\psi \end{bmatrix}.$$

where $\dot{\phi}$, $\dot{\theta}$ and $\dot{\psi}$ is the first time derivative of the Euler angles determined from equations 14-16; $\ddot{\psi}$, $\ddot{\theta}$, and $\ddot{\phi}$ is the second time derivative of the Euler angles determined from equations 14-16 and $\dot{\omega}_x$, $\dot{\omega}_y$, and $\dot{\omega}_z$ are the respective time rates of change of the angular velocity components $\omega_x$, $\omega_y$, $\omega_z$.

Where the body segment CoM is represented by point $P_{ij}$ [$P_x$, $P_y$, $P_z$] in the global coordinate system 104, then the velocity of the body segment CoM in the global coordinate system 104 can be expressed as:

$$\dot{P}_{ij} = W_{ij} P_{ij}, \tag{19}$$

where $\dot{P}_{ij}$ is the velocity of point $P_{ij}$ in the global coordinate system 104 and $W_{ij}$ is a velocity matrix defined as:

$$W_{ij} = \begin{bmatrix} 0 & -\omega_z & \omega_y & v_x \\ \omega_z & 0 & -\omega_x & v_y \\ -\omega_y & \omega_x & 0 & v_z \\ 0 & 0 & 0 & 0 \end{bmatrix} = \begin{bmatrix} \omega_{ij} & v_{ij} \\ 0\ 0\ 0 & 0 \end{bmatrix}, \tag{20}$$

where $\omega_x$, $\omega_y$, and $\omega_z$ are the angular velocity values from equation 17; $v_x$, $v_y$, $v_z$ are linear velocity values of the CoM determined from equation 16; and $\omega_{ij}$ is a 3×3 skew-symmetric matrix of the angular velocity [$\omega_x$, $\omega_y$, $\omega_z$]. Generally, a 3×3 skew-symmetric matrix of any vector S [$s_1$, $s_2$, $s_3$] is defined as:

$$S = \begin{bmatrix} 0 & -s_3 & s_2 \\ s_3 & 0 & -s_1 \\ -s_2 & s_1 & 0 \end{bmatrix}. \tag{21}$$

The acceleration of the body segment CoM in the global coordinate system 104 is obtained by differentiating equation 19 to obtain:

$$\ddot{P}_{ij} = \dot{W}_{ij} P_{ij} + W_{ij} \dot{P}_{ij}, \tag{22}$$

-continued $$= \dot{W}_{ij}P_{ij} + W_{ij}W_{ij}P_{ij},$$

$$= (\dot{W}_{ij} + W_{ij}^2)P_{ij},$$

$$= H_{ij}P_{ij}.$$

where $\dot{W}_{ij}$ is the time rate of change of the velocity matrix in equation 20 and $H_{ij}$ is an acceleration matrix including linear and angular accelerations of the CoM of the $j^{th}$ body segment, defined as:

$$H_{ij} = \dot{W}_{ij} + W_{ij}^2 \qquad (23)$$

$$= \begin{bmatrix} 0 & -\dot{\omega}_z & \dot{\omega}_y & \dot{v}_x \\ \dot{\omega}_z & 0 & -\dot{\omega}_x & \dot{v}_y \\ -\dot{\omega}_y & \dot{\omega}_x & 0 & \dot{v}_z \\ 0 & 0 & 0 & 0 \end{bmatrix} + \begin{bmatrix} 0 & -\omega_z & \omega_y & v_x \\ \omega_z & 0 & -\omega_x & v_y \\ -\omega_y & \omega_x & 0 & v_z \\ 0 & 0 & 0 & 0 \end{bmatrix}^2,$$

$$= \begin{bmatrix} -\omega_y^2-\omega_z^2 & \omega_x\omega_y-\dot{\omega}_z & \omega_x\omega_z+\dot{\omega}_y & \omega_y v_z - \omega_z v_y + a_x \\ \omega_x\omega_y+\dot{\omega}_z & -\omega_x^2-\omega_z^2 & \omega_y\omega_z-\dot{\omega}_x & -\omega_x v_z + \omega_z v_x + a_y \\ \omega_x\omega_z-\dot{\omega}_y & \omega_y\omega_z+\dot{\omega}_x & -\omega_x^2-\omega_y^2 & \omega_x v_y - \omega_y v_x + a_z \\ 0 & 0 & 0 & 0 \end{bmatrix};$$

$$= \begin{bmatrix} \dot{\omega}+\omega^2 & a_o+\omega v_o \\ \hline 0 \ 0 \ 0 & 0 \end{bmatrix},$$

where $[a_x, a_y, a_z]$ are components of the linear acceleration of the CoM determined from equation 16, $\dot{\omega}$ is a skew-symmetric matrix of the time rate of change of the angular velocity; $\omega$ is a skew-symmetric matrix of the angular velocity; $a_o$ is the linear acceleration $[a_x, a_y, a_z]$ of the CoM in the global coordinate system 104 determined from equation 16 and $v_o$ is the linear velocity $[v_x, v_y, v_z]$ of the CoM in the global coordinate system 104 determined from equation 16.

An action matrix $\Phi$ is defined as:

$$\Phi = FP^T - PF^T = \qquad (24)$$

$$\begin{bmatrix} fp^T - pf^T & f_x \\ & f_y \\ & f_z \\ \hline -f_x \ -f_y \ -f_z & 0 \end{bmatrix} = \begin{bmatrix} 0 & -t_z & t_y & f_x \\ t_z & 0 & -t_x & f_y \\ -t_y & t_x & 0 & f_z \\ \hline -f_x & -f_y & -f_z & 0 \end{bmatrix}.$$

where f is the net force $F_{ojc}$ vector $[f_x, f_y, f_z]$, p is the position vector $[p_x, p_y, p_z]$ of the body segment CoM in the global coordinate system 104; F is $[f_x, f_y, f_z, 0]$, P is $[p_x, p_y, p_z, 1]$ and $[t_x, t_y, t_z]$ is the net torque $T_{ojc}$ vector. Using Newton's second law (e.g. F=ma) and equation 22, F=mHP, which is substituted into equation 24 to yield:

$$\Phi = mHPP^T - PmPP^T H^T,$$

$$= HJ - JH^T, \qquad (25)$$

where J is a Pseudo-Inertial matrix that is defined as:

$$J = mPP^T = \begin{bmatrix} J_{xx} & J_{xy} & J_{xz} & m\,x_{CG} \\ J_{yx} & J_{yy} & J_{yz} & m\,y_{CG} \\ J_{zx} & J_{zy} & J_{zz} & m\,z_{CG} \\ \hline m\,x_{CG} & m\,y_{CG} & m\,z_{CG} & m \end{bmatrix} = \begin{bmatrix} J & \\ \hline & m \end{bmatrix}. \qquad (26)$$

where $J_{xx}$ is the pseudo moment of inertia about the $x_o$ axis; $J_{yy}$ is the pseudo moment of inertia about the $y_o$ axis; $J_{zz}$ is the pseudo moment of inertia about the $z_o$ axis; $J_{xy}$ is the pseudo product of inertia about the $x_o y_o$ axes; $J_{xz}$ is the pseudo product of inertia about the $x_o z_o$ axes; $J_{yx}$ is the pseudo product of inertia about the $y_o x_o$ axes; $J_{yz}$ is the pseudo product of inertia about the $y_o z_o$ axes; $J_{zx}$ is the pseudo product of inertia about the $z_o x_o$ axes; $J_{zy}$ is the pseudo product of inertia about the $z_o y_o$ axes; m is the mass of the body segment; $x_{cg}$ is an x-component of the body segment CoM in the global coordinate system 104; $y_{cg}$ is a y-component of the body segment CoM in the global coordinate system 104; and $z_{cg}$ is a z-component of the body segment CoM in the global coordinate system 104. The elements of matrix in equation 26 are given by:

$$J = \begin{bmatrix} J_{xx} & J_{xy} & J_{xz} \\ J_{yx} & J_{yy} & J_{yz} \\ J_{zx} & J_{zy} & J_{zz} \end{bmatrix} \qquad (27)$$

$$= \begin{bmatrix} \int x^2 dm & \int xy dm & \int xz dm \\ \int xy dm & \int y^2 dm & \int yz dm \\ \int xz dm & \int yz dm & \int z^2 dm \end{bmatrix},$$

$$= \begin{bmatrix} \dfrac{-I_{xx}+I_{yy}+I_{zz}}{2} & I_{xy} & I_{xz} \\ I_{xy} & \dfrac{I_{xx}-I_{yy}+I_{zz}}{2} & I_{yz} \\ I_{xz} & I_{yz} & \dfrac{I_{xx}+I_{yy}-I_{zz}}{2} \end{bmatrix},$$

where $I_{xx}$ is the moment of inertia about the $x_o$ axis; $I_{yy}$ is the moment of inertia about the $y_o$ axis; $I_{zz}$ is the moment of inertia about the $z_o$ axis; $I_{xy}$ is the product of inertia about the $x_o y_o$ axes; $I_{xz}$ is the product of inertia about the $x_o z_o$ axes; and $I_{yz}$ is the product of inertia about the $y_o z_o$ axes.

In these embodiments, since the elements of the acceleration matrix in equation 23 are known from the tracking data in step 204 and since the elements of the Inertial matrix in equation 26 are known, the action matrix $\Phi$ of equation 25 is solved. After solving for the action matrix $\Phi$ in equation 25, the net force $F_{ojc}$ $[f_x, f_y, f_z]$ and net torque $T_{ojc}$ $[t_x, t_y, t_z]$ values are extracted from the action matrix $\Phi$ using equation 24.

After determining the net force $F_{ojc}$ and net torque $T_{ojc}$ at each time increment, equations 9 and 10 are used to determine one or more joint forces $F_{ojk}$ (on the left side of equations 9 and 10) at each time increment over the time period. In some embodiments, the net force $F_{ojc}$ and net torque $T_{ojc}$ at each body segment CoM is determined at each time increment, after which equations 9 and 10 are used to determine each body segment joint force $F_{ojk}$ at each time increment. In some embodiments, the process 140 incorporates at least equations 9, 10, 23, 24, 25, 26. During step 206, the process 140 determines the body segment joint force $F_{ojk}$ at each time increment, based on the tracking data from step 204. In other embodiments, the process 140 incorporates equations other than equations 9, 10, 23, 24, 25, 26, in order to determine the body segment joint force $F_{ojk}$ at each time increment, based on the tracking data from step 204. In an example embodiment, the process 140 initially determines the net force $F_{ojc}$ at each time increment, based on the tracking data from step 204, the estimated length of the body segment from Table 3 and the estimated mass of the body segment from Table 3. In this example embodiment, the process 140 then subsequently determines the body segment joint force $F_{ojk}$ based on a difference between the net force $F_{ojc}$ and the weight $W_{oj}$ of the body segment.

In an example embodiment, in step 206, the response is characterized by comparing a frequency spectrum of the moving target 110 with a frequency spectrum of one or more joint forces $F_{ojk}$ of a healthy subject tracking the moving target 110. In an example embodiment, in step 202, the frequency spectrum of the target motion 111 is determined and includes discrete frequencies $f_i$ for each sine function of index i expressed in equation 1. The frequency spectrum of the joint force $F_{ojk}$ of the first subject 190 is obtained by performing a Fourier Transform of the joint force $F_{ojk}$ of the first subject 190 at each time increment over the time period. FIGS. 8A to 8F are graphs that illustrate an example of a normalized force imparted on joints of lower extremity (LE) body segments in a healthy subject and a position of the moving target 110 in the ML direction, according to an embodiment. For each graph, the horizontal axis 802 is time in units of second (sec). The left vertical axis 804 is normalized force defined as a ratio of the joint force $F_{ojk}$ to the subject body weight (unit less) and the right vertical axis 806 is the ML position of the target 110 in units of centimeters (cm). The graph 800 of FIG. 8A depicts the normalized joint force of the left hip (black plot) and the ML position of the target 110 (grey plot). The graph 810 of FIG. 8B depicts the normalized joint force of the right hip (black plot) and the ML position of the target 110 (grey plot). The graph 820 of FIG. 8C depicts the normalized joint force of the left knee (black plot) and the ML position of the target 110 (grey plot). The graph 830 of FIG. 8D depicts the normalized joint force of the right knee (black plot) and the ML position of the target 110 (grey plot). The graph 840 of FIG. 8E depicts the normalized joint force of the left ankle (black plot) and the ML position of the target 110 (grey plot). The graph 850 of FIG. 8F depicts the normalized joint force of the right ankle (black plot) and the ML position of the target 110 (grey plot).

FIGS. 9A to 9F are graphs that illustrate an example of a frequency spectrum of the normalized force imparted on joints of LE body segments in a healthy subject and a frequency spectrum of the moving target in the ML direction, according to an embodiment. For each graph, the horizontal axis 902 is frequency in units of Hertz (Hz), the left vertical axis 904 is an amplitude of the frequency spectrum of the normalized joint force (unit less) and the right vertical axis 906 is an amplitude of the frequency spectrum of the moving target in the ML direction in units of centimeters (cm). In an example embodiment, the frequency spectrums of the normalized joint forces in the graphs of FIGS. 9A-9F are obtained by performing a Fourier transform of the normalized joint forces in the respective graphs of FIGS. 8A to 8F. The graph 900 of FIG. 9A depicts the amplitude of the frequency spectrum of the normalized joint force of the left hip (black) and the amplitude of the frequency spectrum of the moving target in the ML direction (grey) for each discrete frequency $f_i$ of the moving target 110 expressed in equation 1. The graph 910 of FIG. 9B depicts the amplitude of the frequency spectrum of the normalized joint force of the right hip (black) and the amplitude of the frequency spectrum of the moving target in the ML direction (grey) for each discrete frequency $f_i$. The graph 920 of FIG. 9C depicts the amplitude of the frequency spectrum of the normalized joint force of the left knee (black) and the amplitude of the frequency spectrum of the moving target in the ML direction (grey) for each discrete frequency $f_i$. The graph 930 of FIG. 9D depicts the amplitude of the frequency spectrum of the normalized joint force of the right knee (black) and the amplitude of the frequency spectrum of the moving target in the ML direction (grey) for each discrete frequency $f_i$. The graph 940 of FIG. 9E depicts the amplitude of the frequency spectrum of the normalized joint force of the left ankle (black) and the amplitude of the frequency spectrum of the moving target in the ML direction (grey) for each discrete frequency $f_i$. The graph 950 of FIG. 9F depicts the amplitude of the frequency spectrum of the normalized joint force of the right ankle (black) and the amplitude of the frequency spectrum of the moving target in the ML direction (grey) for each discrete frequency $f_i$.

In an example embodiment, during step 206, for each joint of the LE body segments in the healthy subject, the process 140 automatically determines a bandwidth of the joint corresponding to a range of the frequency spectrum of the moving target within the frequency spectrum of the normalized joint force. During step 206, the process 140 determines that each joint of the LE body segments has a low frequency bandwidth and responds to low frequency components of the moving target (e.g. low discrete frequencies $f_i$ in Table 2).

FIGS. 8G to 8L are graphs that illustrate an example of a normalized force imparted on joints of upper extremity (UE) body segments in a healthy subject and a magnitude of the XYZ position of the moving target 110, according to an embodiment. For each graph, the horizontal axis 802 is time in units of second (sec). The left vertical axis 804 is normalized force defined as a ratio of joint force $F_{ojk}$ to the subject body weight (unit less) and the right vertical axis 808 is the magnitude of the XYZ position of the moving target 110 in units of centimeters (cm). The graph 855 of FIG. 8G depicts the normalized joint force of the C7/T1 joint (black plot) and the magnitude of the XYZ position of the target 110 (grey plot). The graph 860 of FIG. 8H depicts the normalized joint force of the left shoulder (black plot) and the magnitude of the XYZ position of the target 110 (grey plot). The graph 865 of FIG. 8I depicts the normalized joint force of the right shoulder (black plot) and the magnitude of the XYZ position of the target 110 (grey plot). The graph 870 of FIG. 8J depicts the normalized joint force of the left elbow (black plot) and the magnitude of the XYZ position of the target 110 (grey plot). The graph 875 of FIG. 8K depicts the normalized joint force of the right elbow (black plot) and the magnitude of the XYZ position of the target 110 (grey plot). The graph 880 of FIG. 8L depicts the normalized joint force of the L5/S1 joint (black plot) and the magnitude of the XYZ position of the target 110 (grey plot).

FIG. 9G to 9L are graphs that illustrate an example of a frequency spectrum of the normalized force imparted on joints of the UE body segments in a healthy subject and a frequency spectrum of the magnitude of the position of the moving target, according to an embodiment. For each graph, the horizontal axis 902 is frequency in units of Hertz (Hz), the left vertical axis 904 is an amplitude of the frequency spectrum of the normalized joint force (unit less) and the right vertical axis 908 is an amplitude of the frequency spectrum of the magnitude of the position of the moving target in units of centimeters (cm). In an example embodiment, the frequency spectrums of the normalized joint forces in the graphs of FIGS. 9G to 9L are obtained by performing a Fourier transform of the normalized joint forces in the respective graphs of FIGS. 8G to 8L. The graph 955 of FIG. 9G depicts the amplitude of the frequency spectrum of the normalized joint force of the C7/T1 joint (black) and the amplitude of the frequency spectrum of the magnitude of the position of the moving target (grey) for each discrete frequency $f_i$ of the moving target 110 expressed in equation 1. The graph 960 of FIG. 9H depicts the amplitude of the frequency spectrum of the normalized joint force of the left shoulder (black) and the amplitude of the frequency spectrum of the magnitude of the position of the moving target (grey) for each discrete frequency $f_i$. The graph 965 of FIG. 9I depicts the amplitude of the frequency spectrum of the normalized joint force of the right shoulder (black) and the amplitude of the frequency spectrum of the magnitude of the position of the moving target (grey) for each discrete frequency $f_i$. The graph 970 of FIG. 9J depicts the amplitude of the frequency spectrum of the normalized joint force of the left elbow and the amplitude of the frequency spectrum of the magnitude of the position of the moving target (grey) for each discrete frequency $f_i$. The graph 975 of FIG. 9K depicts the amplitude of the frequency spectrum of the normalized joint force of the right elbow (black) and the amplitude of the frequency spectrum of the magnitude of the position of the moving target (grey) for each discrete frequency $f_i$. The graph 980 of FIG. 9L depicts the amplitude of the frequency spectrum of the normalized joint force of the L5/S1 joint (black) and the amplitude of the frequency spectrum of the magnitude of the position of the moving target (grey) for each discrete frequency $f_i$.

In an example embodiment, during step 206, for each joint of the UE body segments, the process 140 automatically determines a bandwidth of the joint corresponding to a range of the frequency spectrum of the moving target within the frequency spectrum of the normalized joint force. During step 206, the process 140 determines that the shoulder joints, elbow joints and L5/S1 joints of the UE have a high frequency bandwidth and respond to high frequency components of the moving target (e.g. high discrete frequencies $f_i$ in Table 2). Additionally, during step 206, the process 140 determines that the C7/T1 joint has a broad frequency bandwidth and responds to frequency components throughout the frequency spectrum of the moving target 110.

In an example embodiment, during step 206, the process 140 determines that joints of the LE body segments primarily respond to low frequency components of the moving target 110 whereas joints of the UE body segments primarily respond to middle and high frequency components of the moving target 110. In an example embodiment, the process 140 determines that joints of the LE body segments operate as an integrated lower frequency platform unit while joints of the UE body segments operate as a second higher frequency reaching unit. In an example embodiment, the process 140 determines that the L5/S1 joint responds to middle and high frequency components of the moving target 110, as the L5/S1 joint bends and turns the trunk to bring the pointing arm and hand into proximity with the moving target 110 center. In another example embodiment, the process 140 determines that the C7/T1 joint responds throughout the frequency range of the moving target 110, as the joint turns the head to follow the moving target 110. In another example embodiment, the process 140 determines that the pointing shoulder and elbow (e.g. left shoulder and knee, see FIGS. 9H, 9J) respond to high frequency components of the moving target 110, in order to continuously bring the pointing finger into contact with the moving target 110.

In some embodiments, in step 210, after tracking data of a second subject is determined, a response of the second subject is characterized by comparing a frequency spectrum of the moving target 110 with a frequency spectrum of one or more joint forces $F_{ojk}$ of the second subject tracking the moving target 110. In some embodiments, in step 210, the response of the second subject is characterized in a similar manner as the response of the first subject was characterized in step 206. In these embodiments, in step 210, the response of the second subject is then compared with the response of the first subject from step 206.

FIGS. 10A to 10F are graphs that illustrate an example of a normalized force imparted on joints of lower extremity (LE) body segments in the second subject and a position of the moving target 110 in the ML direction, according to an embodiment. For each graph, the horizontal axis 1002 is time in units of second (sec). The left vertical axis 1004 is normalized force defined as a ratio of joint force $F_{ojk}$ to the subject body weight (unit less) and the right vertical axis 1006 is the ML position of the target 110 in units of centimeters (cm). The graph 1000 of FIG. 10A depicts the normalized joint force of the left hip (black plot) and the ML position of the target 110 (grey plot). The graph 1010 of FIG. 10B depicts the normalized joint force of the right hip (black plot) and the ML position of the target 110 (grey plot). The graph 1020 of FIG. 10C depicts the normalized joint force of the left knee (black plot) and the ML position of the target 110 (grey plot). The graph 1030 of FIG. 10D depicts the normalized joint force of the right knee (black plot) and the ML position of the target 110 (grey plot). The graph 1040 of FIG. 10E depicts the normalized joint force of the left ankle (black plot) and the ML position of the target 110 (grey plot). The graph 1050 of FIG. 10F depicts the normalized joint force of the right ankle (black plot) and the ML position of the target 110 (grey plot).

FIGS. 11A to 11F are graphs that illustrate an example of a frequency spectrum of the normalized force imparted on joints of LE body segments in the second subject and a frequency spectrum of the moving target in the ML direction, according to an embodiment. For each graph, the horizontal axis 1102 is frequency in units of Hertz (Hz), the left vertical axis 1104 is an amplitude of the frequency spectrum of the normalized joint force (unit less) and the right vertical axis 1106 is an amplitude of the frequency spectrum of the moving target in the ML direction in units of centimeters (cm). In an example embodiment, the frequency spectrums of the normalized joint forces in the graphs of FIGS. 11A to 11F are obtained by performing a Fourier transform of the normalized joint forces in the respective graphs of FIGS. 10A to 10F. The graph 1100 of FIG. 11A depicts the amplitude of the frequency spectrum of the normalized joint force of the left hip (black) and the amplitude of the frequency spectrum of the moving target in the ML direction (grey) for each discrete frequency $f_i$ of the moving target 110 expressed in equation 1. The graph 1110 of FIG. 11B depicts the amplitude of the frequency spectrum of the normalized joint force of the right hip (black) and the amplitude of the frequency spectrum of the moving target in the ML direction (grey) for each discrete frequency $f_i$. The graph 1120 of FIG. 11C depicts the amplitude of the frequency spectrum of the normalized joint force of the left knee (black) and the amplitude of the frequency spectrum of the moving target in the ML direction (grey) for each discrete frequency $f_i$. The graph 1130 of FIG. 11D depicts the amplitude of the frequency spectrum of the normalized joint force of the right knee (black) and the amplitude of the frequency spectrum of the moving target in the ML direction (grey) for each discrete frequency $f_i$. The graph 1140 of FIG. 11E depicts the amplitude of the frequency spectrum of the normalized joint force of the left ankle (black) and the amplitude of the frequency spectrum of the moving target in the ML direction (grey) for each discrete frequency $f_i$. The graph 1150 of FIG. 11F depicts the amplitude of the frequency spectrum of the normalized joint force of the right ankle (black) and the amplitude of the frequency spectrum of the moving target in the ML direction (grey) for each discrete frequency $f_i$.

FIGS. 10G to 10L are graphs that illustrate an example of a normalized force imparted on joints of upper extremity (UE) body segments in the second subject and a magnitude of the XYZ position of the moving target 110, according to an embodiment. For each graph, the horizontal axis 1002 is time in units of second (sec). The left vertical axis 1004 is normalized force defined as a ratio of joint force $F_{ojk}$ to the subject body weight (unit less) and the right vertical axis 1008 is the magnitude of the XYZ position of the moving target 110 in units of centimeters (cm). The graph 1055 of FIG. 10G depicts the normalized joint force of the C7/T1 joint (black plot) and the magnitude of the XYZ position of the target 110 (grey plot). The graph 1060 of FIG. 10H depicts the normalized joint force of the left shoulder (black plot) and the magnitude of the XYZ position of the target 110 (grey plot). The graph 1065 of FIG. 10I depicts the normalized joint force of the right shoulder (black plot) and the magnitude of the XYZ position of the target 110 (grey plot). The graph 1070 of FIG. 10J depicts the normalized joint force of the left elbow (black plot) and the magnitude of the XYZ position of the target 110 (grey plot). The graph 1075 of FIG. 10K depicts the normalized joint force of the right elbow (black plot) and the magnitude of the XYZ position of the target 110 (grey plot). The graph 1080 of FIG. 10L depicts the normalized joint force of the L5/S1 joint (black plot) and the magnitude of the XYZ position of the target 110 (grey plot).

FIG. 11G to 11L are graphs that illustrate an example of a frequency spectrum of the normalized force imparted on joints of the UE body segments in the second subject and a frequency spectrum of the magnitude of the position of the moving target, according to an embodiment. For each graph, the horizontal axis 1102 is frequency in units of Hertz (Hz), the left vertical axis 1104 is an amplitude of the frequency spectrum of the normalized joint force (unit less) and the right vertical axis 1108 is an amplitude of the frequency spectrum of the magnitude of the position of the moving target in units of centimeters (cm). In an example embodiment, the frequency spectrums of the normalized joint forces in the graphs of FIGS. 11G to 11L are obtained by performing a Fourier transform of the normalized joint forces in the respective graphs of FIGS. 10G to 10L. The graph 1155 of FIG. 11G depicts the amplitude of the frequency spectrum of the normalized joint force of the C7/T1 joint (black) and the amplitude of the frequency spectrum of the magnitude of the position of the moving target (grey) for each discrete frequency $f_i$ of the moving target 110 expressed in equation 1. The graph 1160 of FIG. 11H depicts the amplitude of the frequency spectrum of the normalized joint force of the left shoulder (black) and the amplitude of the frequency spectrum of the magnitude of the position of the moving target (grey) for each discrete frequency $f_i$. The graph 1165 of FIG. 11I depicts the amplitude of the frequency spectrum of the normalized joint force of the right shoulder (black) and the amplitude of the frequency spectrum of the magnitude of the position of the moving target (grey) for each discrete frequency $f_i$. The graph 1170 of FIG. 11J depicts the amplitude of the frequency spectrum of the normalized joint force of the left elbow (black) and the amplitude of the frequency spectrum of the magnitude of the position of the moving target (grey) for each discrete frequency $f_i$. The graph 1175 of FIG. 11K depicts the amplitude of the frequency spectrum of the normalized joint force of the right elbow (black) and the amplitude of the frequency spectrum of the magnitude of the position of the moving target (grey) for each discrete frequency $f_i$. The graph 1180 of FIG. 11L depicts the amplitude of the frequency spectrum of the normalized joint force of the L5/S1 joint (black) and the amplitude of the frequency spectrum of the magnitude of the position of the moving target (grey) for each discrete frequency $f_i$.

In an example embodiment, during step 210, for each joint of the LE body segments in the second subject, the process 140 automatically determines a bandwidth of the joint corresponding to a range of the frequency spectrum of the moving target within the frequency spectrum of the normalized joint force. During step 210, the process 140 compares the bandwidth of each joint of the LE body segments of the second subject to the bandwidth of each joint of the LE body segments in the healthy subject from step 206. In some embodiments, in step 210, the process 140 determines a positive fall risk for the second subject, based on the comparison of the bandwidths of each joint of the LE body segments of the second subject and the healthy subject.

In an example embodiment, during step 210, for each joint of the UE body segments in the second subject, the process 140 automatically determines a bandwidth of the joint corresponding to a range of the frequency spectrum of the moving target within the frequency spectrum of the normalized joint force. During step 210, the process 140 compares the bandwidth of each joint of the UE body segments of the second subject to the bandwidth of each joint of the UE body segments in the healthy subject from step 206. In some embodiments, in step 210, the process 140 determines a positive fall risk for the second subject, based on the comparison of the bandwidths of each joint of the UE body segments of the second subject and the healthy subject.

In other embodiments, in step 206, an accuracy of the calculated magnitudes of the body segment joint forces $F_{ojk}$ using equations 9, 10, 23, 24, 25 and 26 is verified. To verify the accuracy of the calculated magnitudes of the body segment joint forces $F_{ojk}$, a mean of the joint force magnitude over the time period is compared to a weight of one or more body segments supported by the joint. In an example embodiment, as depicted in FIG. 1A, the right shoulder joint supports the weight of the right upper arm (j=10) and right forearm/hand segments (j=11). Table 4 below provides an example embodiment of the calculated mean

TABLE 4

Mean resultant joint forces vs. weight of body segments supported

| Joint | Mean Computed Joint Force (N) | Supported Segment Weight (N) |
|---|---|---|
| Left & Right Ankle | 588.97 | 589.82 |
| Left & Right Knee | 530.95 | 531.57 |
| Left & Right Hip | 353.00 | 352.59 |
| L5/S1 | 274.97 | 277.08 |
| C7/T1 | 47.11 | 51.13 |
| Right Shoulder | 27.26 | 27.18 |

TABLE 4-continued

Mean resultant joint forces vs. weight of body segments supported

| Joint | Mean Computed Joint Force (N) | Supported Segment Weight (N) |
|---|---|---|
| Right Elbow | 11.82 | 11.75 |
| Left Shoulder | 27.31 | 27.19 |
| Left Elbow | 11.96 | 11.75 | joint force in step 206 (e.g. using equations 9, 10, 23, 24, 25 and 26) and weight of supported body segments, for each joint. In some embodiments, during step 206, the calculated mean joint force and weight of supported body segments are approximately equal or within ±5% of each other. In some embodiments, in step 206, the process 140 verifies the accuracy of the calculated magnitudes of the body segment forces (e.g. using equations 9, 10, 23, 24, 25 and 26), based on the calculated mean joint force being within 5% of the weight of the supported body segments.

In other embodiments, in step 206, a magnitude of the joint force $F_{ojk}$ of a body segment on a left side of the body is compared to a magnitude of the joint force $F_{ojk}$ of the body segment on a right side of the body. In some embodiments, the magnitude of the joint force $F_{ojk}$ is a mean of the magnitude of the joint force computed over the time period. In an example embodiment, in step 206, the magnitude of the joint force of the left hip (FIG. 8A) is compared to the magnitude of the joint force of the right hip (FIG. 8B) over the time period. In an example embodiment, in step 206, the magnitude of the joint force of the left knee (FIG. 8C) is compared to the magnitude of the joint force of the right knee (FIG. 8D) over the time period. In an example embodiment, in step 206, the magnitude of the joint force of the left ankle (FIG. 8E) is compared to the magnitude of the right ankle (FIG. 8F) over the time period. In an example embodiment, in step 206, the response of a healthy subject is characterized, based on the comparison of the magnitude of the joint force of the body segment on the left side of the body with the magnitude of the joint force of the body segment on the right side of the body.

In other embodiments, in step 206, a frequency spectrum of the joint force $F_{ojk}$ of a first joint is compared with the frequency spectrum of the joint force $F_{ojk}$ of a second joint. In an example embodiment, in step 206, the frequency spectrum of the joint force $F_{ojk}$ of the C7/T1 joint (e.g. FIG. 9G) is compared with the frequency spectrum of the joint force $F_{ojk}$ of the L5/S1 joint (e.g. FIG. 9L). In the example embodiment, the frequency spectrum of the C7/T1 joint is wider than the frequency spectrum of the L5/S1 joint and/or amplitude of the frequency spectrum of the C7/T1 is larger than the amplitude of the frequency spectrum of the L5/S1 joint, at low frequencies (e.g. less than 0.5 Hz). In some embodiments, during step 210, the process 140 determines a positive fall risk based on the comparison of the frequency spectrum of the joint force of the first joint (e.g. FIG. 11G) with the frequency spectrum of the joint force of the second joint (e.g. FIG. 11L).

In some embodiments, in step 212, a recommended treatment plan is output on the display device, based on the determined fall risk in step 210. In an example embodiment, the recommended treatment plan is a training program for the second subject that includes tracking the moving target 110 a minimum number of times over a treatment time period. In an example embodiment, the training program includes the treatment time period, a time rate for the subject to track the moving target 110 over the treatment time period and/or a duration of each tracking session of the moving target 110. However, the training program is not limited to these parameters and can include the minimum number of tracking sessions and duration of each tracking session or any training program parameters appreciated by one skilled in the art to improve the balance of the second subject. In an example embodiment, the treatment time period is eight weeks long, the time rate to track the moving target 110 is twice per week, the minimum number of tracking sessions is sixteen and the duration of each tracking session is 60 minutes. However, in other embodiments, the duration of each tracking session is the time period of the moving target 111 or multiples of the time period of the moving target 111. In another example embodiment, the duration of each tracking session includes a first time period to track the moving target 110, a second time period to track the moving target 110 with a recess time period in between the first and second time period. However, the parameters of the training program are not limited to these values. In some embodiments, one or more parameters of the training program are determined based on the risk of fall from step 210.

In some embodiments, the recommended treatment plan includes repeating steps 208 and 210 after performing the training program, to assess whether the risk of fall of the second subject has improved. In some embodiments, after the second iteration of steps 208 and 210, step 212 is repeated to output an updated risk of fall of the second subject on the display device, after the second subject has completed the training program. In an example embodiment, when step 212 is repeated, a second training program is outputted on the display device. In this example embodiment, after performing the second treatment program, steps 208 and 210 are repeated, to assess whether the risk of fall of the second subject has improved after performing the second training program, as compared to the risk of fall of the second subject after performing the first training program. In some embodiments, this process is continuously repeated to improve the risk of fall of the second subject or until the risk of fall improves to an acceptable level.

In some embodiments, in a second iteration of step 208, tracking data of the second subject is determined after the second subject performs the recommended treatment plan from step 212. In these embodiments, in a second iteration of step 210, a response of the second subject after performing the treatment plan is characterized by comparing a frequency spectrum of the moving target 110 with a frequency spectrum of one or more joint forces $F_{ojk}$ of the second subject tracking the moving target 110. In these embodiments, the response of the second subject after performing the treatment plan is then compared with the response of the first subject from step 206. In other embodiments, the response of the second subject after performing the treatment plan (e.g. second iteration of step 210) is compared with the response of the second subject prior to performing the treatment plan (e.g. first iteration of step 210).

FIGS. 12A to 12F are graphs that illustrate an example of a normalized force imparted on joints of lower extremity (LE) body segments in the second subject after performing the treatment plan and a position of the moving target 110 in the ML direction, according to an embodiment. For each graph, the horizontal axis 1202 is time in units of second (sec). The left vertical axis 1204 is normalized force defined as a ratio of joint force $F_{ojk}$ to the subject body weight (unit less) and the right vertical axis 1206 is the ML position of the target 110 in units of centimeters (cm). The graph 1200 of FIG. 12A depicts the normalized joint force of the left hip (black plot) and the ML position of the target 110 (grey plot). The graph 1210 of FIG. 12B depicts the normalized joint force of the right hip (black plot) and the ML position of the target 110 (grey plot). The graph 1220 of FIG. 12C depicts the normalized joint force of the left knee (black plot) and the ML position of the target 110 (grey plot). The graph 1230 of FIG. 12D depicts the normalized joint force of the right knee (black plot) and the ML position of the target 110 (grey plot). The graph 1240 of FIG. 12E depicts the normalized joint force of the left ankle (black plot) and the ML position of the target 110 (grey plot). The graph 1250 of FIG. 12F depicts the normalized joint force of the right ankle (black plot) and the ML position of the target 110 (grey plot).

FIGS. 13A to 13F are graphs that illustrate an example of a frequency spectrum of the normalized force imparted on joints of LE body segments in the second subject after performing the treatment plan and a frequency spectrum of the moving target in the ML direction, according to an embodiment. For each graph, the horizontal axis 1302 is frequency in units of Hertz (Hz), the left vertical axis 1304 is an amplitude of the frequency spectrum of the normalized joint force (unit less) and the right vertical axis 1306 is an amplitude of the frequency spectrum of the moving target in the ML direction in units of centimeters (cm). In an example embodiment, the frequency spectrums of the normalized joint forces in the graphs of FIGS. 13A to 13F are obtained by performing a Fourier transform of the normalized joint forces in the respective graphs of FIGS. 12A to 12F. The graph 1300 of FIG. 13A depicts the amplitude of the frequency spectrum of the normalized joint force of the left hip (black) and the amplitude of the frequency spectrum of the moving target in the ML direction (grey) for each discrete frequency $f_i$ of the moving target 110 expressed in equation 1. The graph 1310 of FIG. 13B depicts the amplitude of the frequency spectrum of the normalized joint force of the right hip (black) and the amplitude of the frequency spectrum of the moving target in the ML direction (grey) for each discrete frequency $f_i$. The graph 1320 of FIG. 13C depicts the amplitude of the frequency spectrum of the normalized joint force of the left knee (black) and the amplitude of the frequency spectrum of the moving target in the ML direction (grey) for each discrete frequency $f_i$. The graph 1330 of FIG. 13D depicts the amplitude of the frequency spectrum of the normalized joint force of the right knee (black) and the amplitude of the frequency spectrum of the moving target in the ML direction (grey) for each discrete frequency $f_i$. The graph 1340 of FIG. 13E depicts the amplitude of the frequency spectrum of the normalized joint force of the left ankle (black) and the amplitude of the frequency spectrum of the moving target in the ML direction (grey) for each discrete frequency $f_i$. The graph 1350 of FIG. 13F depicts the amplitude of the frequency spectrum of the normalized joint force of the right ankle (black) and the amplitude of the frequency spectrum of the moving target in the ML direction (grey) for each discrete frequency $f_i$.

FIGS. 12G to 12L are graphs that illustrate an example of a normalized force imparted on joints of upper extremity (UE) body segments in the second subject after performing the treatment plan and a magnitude of the XYZ position of the moving target 110, according to an embodiment. For each graph, the horizontal axis 1202 is time in units of second (sec). The left vertical axis 1204 is normalized force defined as a ratio of joint force $F_{ojk}$ to the subject body weight (unit less) and the right vertical axis 1208 is the magnitude of the XYZ position of the moving target 110 in units of centimeters (cm). The graph 1255 of FIG. 12G depicts the normalized joint force of the C7/T1 joint (black plot) and the magnitude of the XYZ position of the target 110 (grey plot). The graph 1260 of FIG. 12H depicts the normalized joint force of the left shoulder (black plot) and the magnitude of the XYZ position of the target 110 (grey plot). The graph 1265 of FIG. 12I depicts the normalized joint force of the right shoulder (black plot) and the magnitude of the XYZ position of the target 110 (grey plot). The graph 1270 of FIG. 12J depicts the normalized joint force of the left elbow (black plot) and the magnitude of the XYZ position of the target 110 (grey plot). The graph 1275 of FIG. 12K depicts the normalized joint force of the right elbow (black plot) and the magnitude of the XYZ position of the target 110 (grey plot). The graph 1280 of FIG. 12L depicts the normalized joint force of the L5/S1 joint (black plot) and the magnitude of the XYZ position of the target 110 (grey plot).

FIG. 13G to 13L are graphs that illustrates an example of a frequency spectrum of the normalized force imparted on joints of the UE body segments in the second subject after performing the treatment plan and a frequency spectrum of the magnitude of the position of the moving target, according to an embodiment. For each graph, the horizontal axis 1302 is frequency in units of Hertz (Hz), the left vertical axis 1304 is an amplitude of the frequency spectrum of the normalized joint force (unit less) and the right vertical axis 1308 is an amplitude of the frequency spectrum of the magnitude of the position of the moving target in units of centimeters (cm). In an example embodiment, the frequency spectrums of the normalized joint forces in the graphs of FIGS. 13G to 13L are obtained by performing a Fourier transform of the normalized joint forces in the respective graphs of FIGS. 12G to 12L. The graph 1355 of FIG. 13G depicts the amplitude of the frequency spectrum of the normalized joint force of the C7/T1 joint (black) and the amplitude of the frequency spectrum of the magnitude of the position of the moving target (grey) for each discrete frequency $f_i$ of the moving target 110 expressed in equation 1. The graph 1360 of FIG. 13H depicts the amplitude of the frequency spectrum of the normalized joint force of the left shoulder (black) and the amplitude of the frequency spectrum of the magnitude of the position of the moving target (grey) for each discrete frequency $f_i$. The graph 1365 of FIG. 13I depicts the amplitude of the frequency spectrum of the normalized joint force of the right shoulder (black) and the amplitude of the frequency spectrum of the magnitude of the position of the moving target (grey) for each discrete frequency $f_i$. The graph 1370 of FIG. 13J depicts the amplitude of the frequency spectrum of the normalized joint force of the left elbow and the amplitude of the frequency spectrum of the magnitude of the position of the moving target (grey) for each discrete frequency $f_i$. The graph 1375 of FIG. 13K depicts the amplitude of the frequency spectrum of the normalized joint force of the right elbow (black) and the amplitude of the frequency spectrum of the magnitude of the position of the moving target (grey) for each discrete frequency $f_i$. The graph 1380 of FIG. 13L depicts the amplitude of the frequency spectrum of the normalized joint force of the L5/S1 joint (black) and the amplitude of the frequency spectrum of the magnitude of the position of the moving target (grey) for each discrete frequency $f_i$.

In an example embodiment, during the second iteration of step 210, for each joint of the LE body segments, the process 140 determines the bandwidth of the joint corresponding to the range of the frequency spectrum of the moving target within the frequency spectrum of the normalized joint force. During the second iteration of step 210, the process 140 determines that the bandwidth of each joint of the LE body segments of the second subject after performing the treatment plan has improved (relative to the first iteration of step 210). In an example embodiment, during the second iteration of step 210, the process 140 determines that the bandwidth of each joint in the second subject after performing the treatment plan is closer to the bandwidth of each joint in the healthy subject from step 206, as compared to the bandwidth of each joint in the second subject prior to performing the treatment plan.

In an example embodiment, during the second iteration of step 210, for each joint of the UE body segments, the process 140 automatically determines the bandwidth of the joint corresponding to the range of the frequency spectrum of the moving target within the frequency spectrum of the normalized joint force. During the second iteration of step 210, the process 140 determines that the bandwidth of one or more joints of the UE body segments in the second subject has improved, as compared to the first iteration of step 210. In an example embodiment, the process 140 determines that the bandwidth of the C7/T1 and L5/S1 joints are closer to the bandwidths of the C7/T1 and L5/S1 joints in the healthy subject from step 206, as compared to the bandwidth of these joints in the second subject prior to performing the treatment plan.

In other embodiments, during the second iteration of step 210, the process 140 compares the frequency spectrum of the joint force $F_{ojk}$ of the C7/T1 joint (e.g. FIG. 13G) to the frequency spectrum of the L5/S1 joint (FIG. 13L), as was determined in the first iteration of step 210 (FIGS. 11G and 11L). In an example embodiment, during the second iteration of step 210, the process 140 determines whether the joint frequency spectrums (FIGS. 13G, 13L) from the second iteration of step 210 are less similar than the joint frequency spectrums (FIGS. 11G, 11L) from the first iteration of step 210.

In other embodiments, during the second iteration of step 210, the process 140 determines that the risk of fall has reduced, based on a comparison of the magnitude of the joint force of the left body segment (e.g. left hip, left knee, left ankle) with the magnitude of the joint force of the right body segment (e.g. right hip, right knee, right ankle).

In some embodiments, in step 202, the target 110 is projected onto the screen 103 by the projector at one or more calibration points, whose locations are known in a coordinate system of the projector. A sensor connected to the controller 130, such as a digital stylus, is used to record the locations of the calibration points in the global coordinate system 104. Using the recorded locations of the calibration points in the global coordinate system 104, a function is derived to map the target 110 location from the coordinate system of the projector to the global coordinate system 104, as appreciated by one skilled in the art. This function is stored in the process 140 and is used to convert the target 110 location in the coordinate system of the projector to the global coordinate system 104, for purposes of commanding the target 110 to follow the target motion 110 and for determining the position of the target 110 in the global coordinate system 104, for purposes of calculating the RMSE in equations 2 and 3.

In some embodiments, in step 206, the response of a group of first subjects 190 is characterized. In some embodiments, the ratio of the amplitude of the frequency spectrum of the finger to the amplitude of the frequency spectrum of the moving target for each discrete frequency $f_i$ is determined for each first subject 190. In other embodiments, the ratio of the amplitude of the frequency spectrum of the projection 124 to the amplitude of the frequency spectrum of the moving target for each discrete frequency $f_i$ is determined for each first subject 190. In some embodiments, the computed ratios of the first subjects 190 are averaged, frequency by frequency, to determine a group ratio for each discrete frequency $f_i$. In some embodiments, the group ratio for each discrete frequency $f_i$ is determined for each multiple of AL that is used to determine the amplitude of motion of the moving target 110. In some embodiments, during step 208, the tracking data of the second subject is compared to the response of the group of first subjects 190. In an example embodiment, in step 208, the ratios of the amplitude of the frequency spectrum of the finger to the amplitude of the frequency spectrum of the moving target for the second subject is compared with the group ratios for the group of first subjects 190 from step 206.

In some embodiments, in step 206, a group-representative trajectory of the finger (e.g. in SI and ML directions) and a group-representative trajectory of the projection 124 is determined for a group of first subjects 190, using the group ratios for each discrete frequency $f_i$. In these embodiments, a representative target 110 trajectory is first determined, using an average AL of the group of first subjects 190. In an example embodiment, the average AL of the group of first subjects 190 is 76.5 centimeters (cm). A Fourier transform is then taken of the representative target 110 trajectory to obtain the amplitude of the frequency spectrum of the representative target 110 trajectory at each discrete frequency $f_i$. In an example embodiment, the amplitudes of the frequency spectrum of the representative target 110 trajectory are then multiplied by the group ratio of the finger (e.g. in SI or ML direction) for each discrete frequency $f_i$, to obtain a group-representative frequency spectrum of the finger (e.g. in SI or ML direction). In an example embodiment, the amplitudes of the frequency spectrum of the representative target 110 trajectory are then multiplied by the group ratio of the projection 124 (e.g. in AP or ML direction) for each discrete frequency $f_i$, to obtain a group-representative frequency spectrum of the projection 124 (e.g. in AP or ML direction). In an example embodiment, the group-representative trajectory of the finger or projection 124 is then obtained by taking an inverse Fourier transform of the group-representative frequency spectrums of the finger or projection 124.

In some embodiments, in step 206, the response of the first subject 190 is characterized, by determining a ratio of the trajectory of the position of the finger or the frequency spectrum of the position of the projection 124 that includes the discrete frequencies $f_i$ of the moving target 110. In these embodiments, after obtaining the frequency spectrum of the position of the finger or projection 124, and setting the amplitude of the frequency spectrum to zero for all frequencies other than the discrete frequencies $f_i$ of the moving target 110, an inverse Fourier transform of the frequency spectrum is performed to obtain a revised position of the finger or projection 124 whose frequency spectrum only includes discrete frequencies $f_i$. This revised position of the finger or projection 124 is then compared to the initial position of the finger or projection 124 (e.g. prior to filtering out frequencies other than the discrete frequencies $f_i$). In an example embodiment, in step 206, this ratio is expressed as a percentage (% Fit) that is calculated by:

$$\% \text{ Fit} = \left(1 - \frac{\sum_i (r_i - \hat{r}_i)}{\sum_i (r_i - \bar{r})}\right) \times 100. \quad (28)$$

where i is an index over the time period; $r_i$ is the initial position of the finger or projection 124 at the time increment of index i; $\hat{r}_i$ is the revised position of the finger or projection 124 at the time increment of index i; and $\bar{r}$ is a mean of the initial position over the time period. In an example embodiment, equation 28 provides a percentage of the trajectory of the position of the finger or projection 124 over the time period that includes discrete frequencies $f_i$ of the moving target 110. In an example embodiment, in step 206, for the position of the finger in the ML direction, the % Fit using equation 28 is approximately 93%. In an example embodiment, in step 206, for the position of the finger in the SI direction, the % Fit using equation 28 is approximately 94%. In an example embodiment, in step 206, for the position of the projection 124 in the ML direction, the % Fit using equation 28 is approximately 78%. In an example embodiment, in step 206, for the position of the projection 124 in the AP direction, the % Fit using equation 28 is approximately 36%. Since the % Fit for the position of the finger in the ML and SI directions is nearly 100%, the trajectory of the finger in the ML and SI directions almost exclusively includes the discrete frequencies $f_i$ of the moving target 110.

Figure 5C:
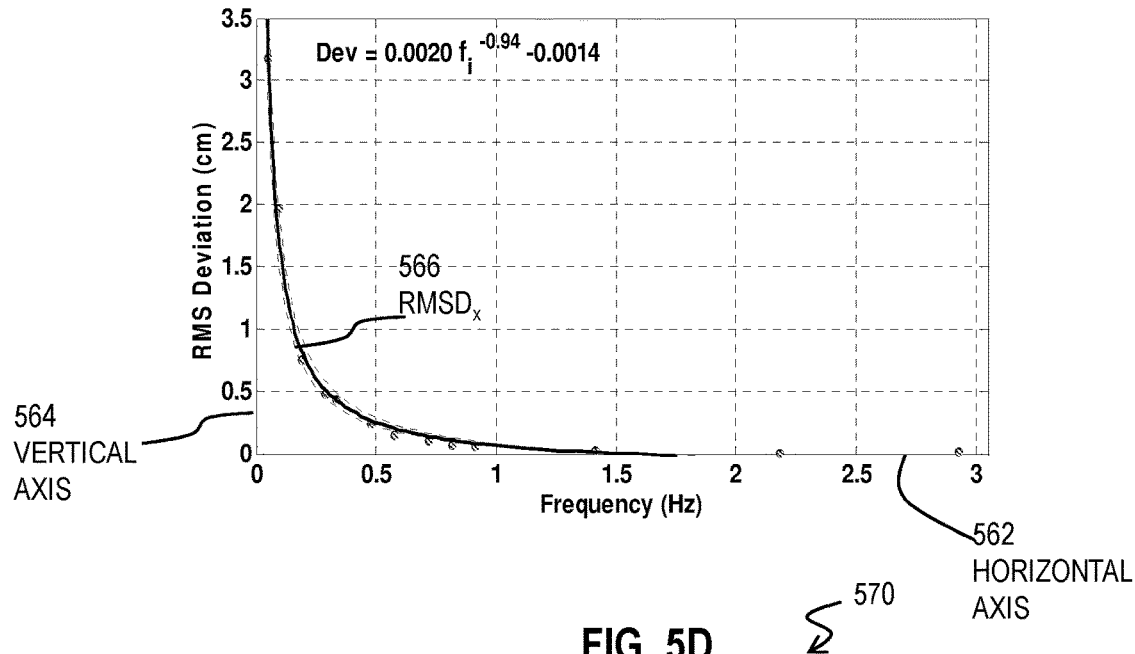
FIG. 5C is a graph that illustrates an example of a root mean square deviation (RMSD) between a body center of mass and a center of a base of support in a medial-lateral (ML) direction as a function of target frequency, according to an embodiment.
Figure 5D:
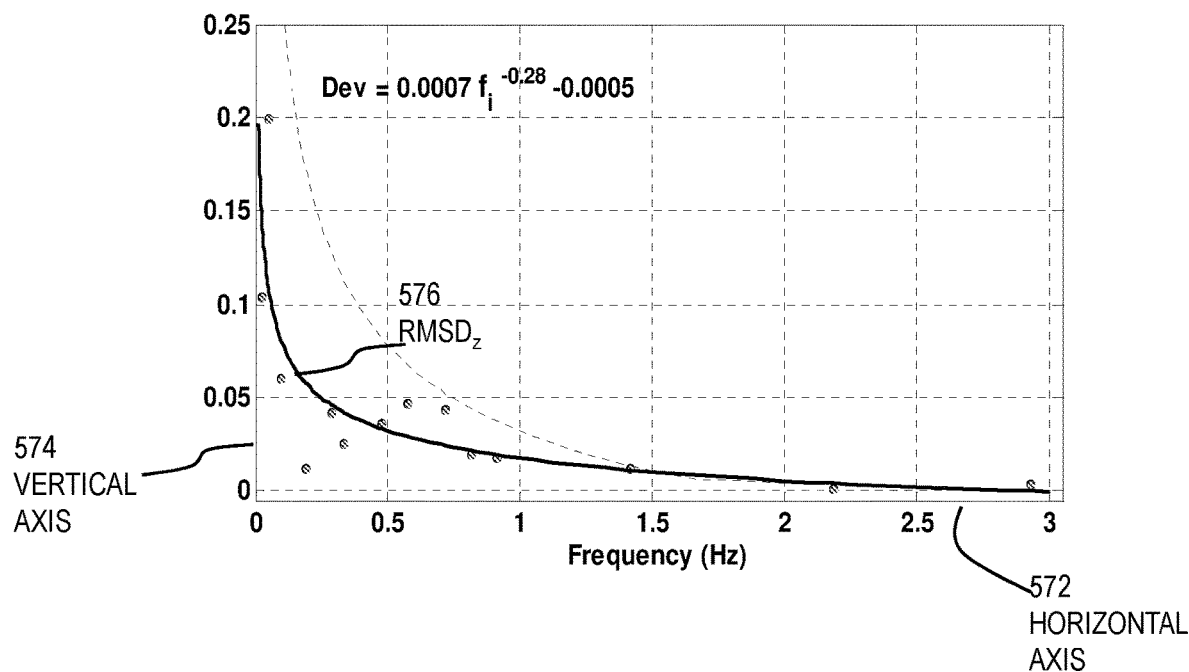
FIG. 5D is a graph that illustrates an example of a root mean square deviation (RMSD) between a body center of mass and a center of a base of support in an anterior-posterior (AP) direction as a function of target frequency, according to an embodiment.

In some embodiments, in step 206, the ratio of the amplitude of the frequency spectrum of the projection 124 to the amplitude of the frequency spectrum of the moving target for each discrete frequency $f_i$ is determined. Based on the ratio at each discrete frequency $f_i$, an X component of the projection 124 ($X_{COM}$) and Z component of the projection 124 ($Z_{COM}$) are determined, for each discrete frequency $f_i$ component of the frequency spectrum. In an example embodiment, an inverse Fourier transform is performed of the frequency spectrum of the projection 124 in the ML direction at only the discrete frequency $f_i$, to determine the X component of the projection 124 based on the discrete frequency $f_i$ component of the frequency spectrum. In an example embodiment, an inverse Fourier transform is performed of the frequency spectrum of the projection 124 in the AP direction at only the discrete frequency $f_i$, to determine the Z component of the projection 124 based on the discrete frequency $f_i$. In these embodiments, the $RMSD_x$ and $RMSD_z$ are determined for each discrete frequency $f_i$, using equation 4. FIG. 5C is a graph 560 that illustrates an example of $RMSD_x$ 566 between the projection 124 and the center 125 of the base of support 122 in a medial-lateral (ML) direction as a function of target frequency, according to an embodiment. The horizontal axis 562 is frequency in units of Hertz (Hz). The vertical axis 564 is deviation in units of centimeters (cm). FIG. 5D is a graph 570 that illustrates an example of $RMSD_z$ 576 between the projection 124 and the center 125 of the base of support 122 in an anterior-posterior (AP) direction as a function of target frequency, according to an embodiment. The horizontal axis 572 is frequency in units of Hertz (Hz). The vertical axis 574 is deviation in units of centimeters (cm). In an example embodiment, the $RMSD_x$ 566 and $RMSD_z$ 576 decrease approximately according to a fitted curve $k_1 * f_i^{k_2} + k_3$, where $k_i$ are fitted constants. In an example embodiment, for the $RMSD_x$ 566, a fitted curve is based on $k_1=0.0020$, $k_2=-0.94$ and $k_3=-0.0014$. In an example embodiment, for the RMSDz 576, a fitted curve is based on $k_1=0.0007$, $k_2=-0.28$ and $k_3=-0.0005$.

Figure 14A:
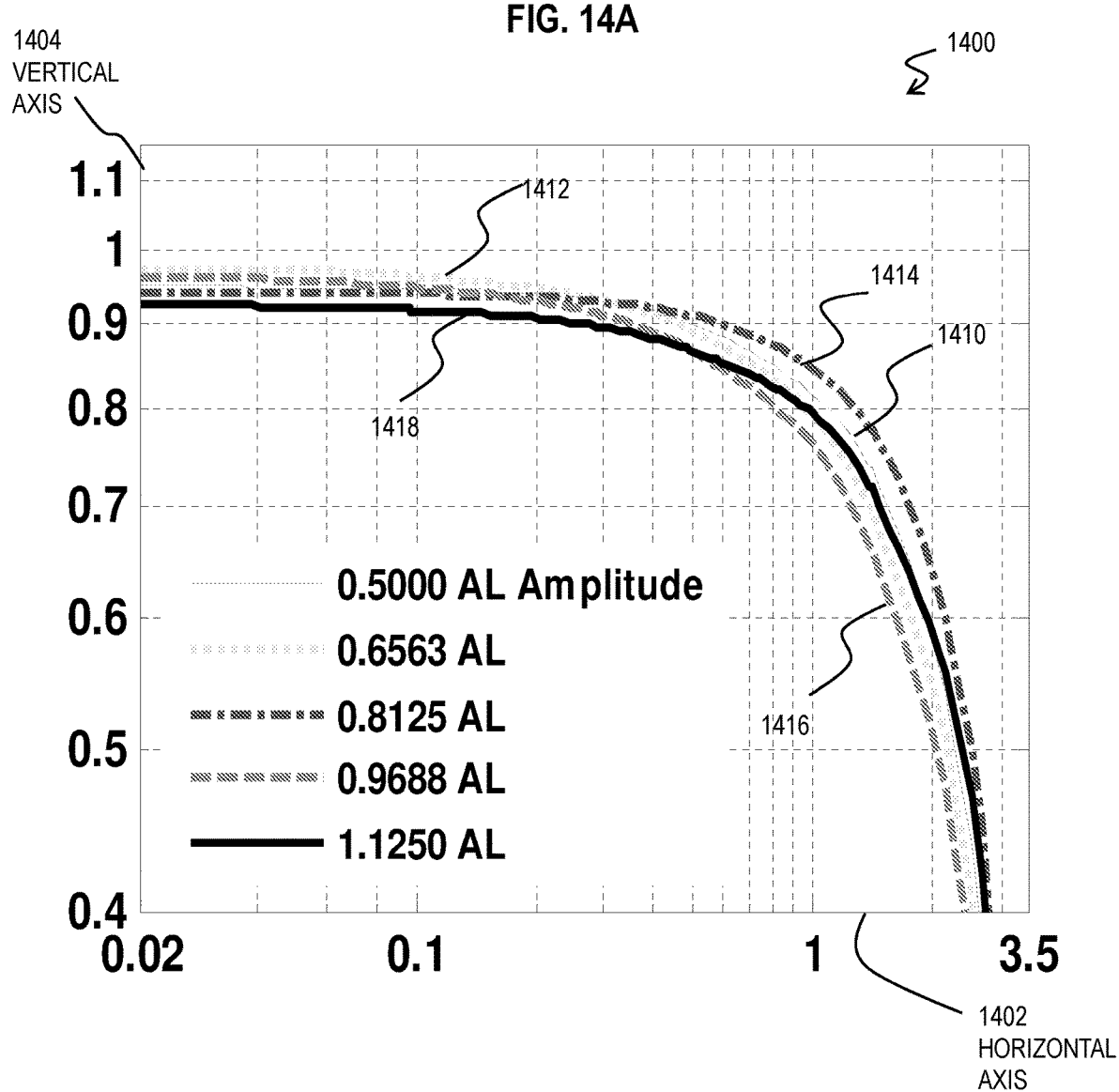
FIG. 14A is a graph that illustrates an example of a ratio of an amplitude of the frequency spectrum of the body segment and an amplitude of the frequency spectrum of the moving target in the medial-lateral (ML) direction as a function of target frequency, according to an embodiment.

FIG. 14A is a graph 1400 that illustrates an example of a ratio of an amplitude of the frequency spectrum of the body segment and an amplitude of the frequency spectrum of the moving target in the medial-lateral (ML) direction as a function of target frequency, according to an embodiment. The horizontal axis 1402 is frequency in units of Hertz (Hz). The vertical axis 1404 is the ratio and has no units. The computed ratio is shown for each amplitude of motion of the moving target 110, based on a multiple of the AL. In an example embodiment, the ratio 1410 is shown for the amplitude of motion of the moving target based on 0.5000 AL. In an example embodiment, the ratio 1412 is shown for the amplitude of motion of the moving target based on 0.6563 AL. In an example embodiment, the ratio 1414 is shown for the amplitude of motion of the moving target based on 0.8125 AL. In an example embodiment, the ratio 1416 is shown for the amplitude of motion of the moving target based on 0.9688 AL. In an example embodiment, the ratio 1418 is shown for the amplitude of motion of the moving target based on 1.125 AL.

FIG. 14B is a graph 1420 that illustrates an example of a ratio of an amplitude of the frequency spectrum of the body segment and an amplitude of the frequency spectrum of the moving target in the SI direction as a function of target frequency, according to an embodiment. The horizontal axis 1422 is frequency in units of Hertz (Hz). The vertical axis 1424 is the ratio and has no units. The computed ratio is shown for each amplitude of motion of the moving target 110, based on a multiple of the AL. In an example embodiment, the ratio 1430 is shown for the amplitude of motion of the moving target based on 0.5000 AL. In an example embodiment, the ratio 1432 is shown for the amplitude of motion of the moving target based on 0.6563 AL. In an example embodiment, the ratio 1434 is shown for the amplitude of motion of the moving target based on 0.8125 AL. In an example embodiment, the ratio 1436 is shown for the amplitude of motion of the moving target based on 0.9688 AL. In an example embodiment, the ratio 1438 is shown for the amplitude of motion of the moving target based on 1.125 AL.

FIG. 14C is a graph that illustrates an example of a ratio of an amplitude of the frequency spectrum of the body center of mass and an amplitude of the frequency spectrum of the moving target in the medial-lateral (ML) direction as a function of target frequency, according to an embodiment. The horizontal axis 1442 is frequency in units of Hertz (Hz). The vertical axis 1444 is the ratio and has no units. The computed ratio is shown for each amplitude of motion of the moving target 110, based on a multiple of the AL. In an example embodiment, the ratio 1450 is shown for the amplitude of motion of the moving target based on 0.5000 AL. In an example embodiment, the ratio 1452 is shown for the amplitude of motion of the moving target based on 0.6563 AL. In an example embodiment, the ratio 1454 is shown for the amplitude of motion of the moving target based on 0.8125 AL. In an example embodiment, the ratio 1456 is shown for the amplitude of motion of the moving target based on 0.9688 AL. In an example embodiment, the ratio 1458 is shown for the amplitude of motion of the moving target based on 1.125 AL. In an example embodiment, the ratios for the frequency spectrum of the body segment in the ML direction (FIG. 14A), the ratios for the frequency spectrum of the body segment in the SI direction (FIG. 14B) and the ratios for the frequency spectrum of the body center of mass in the ML direction (FIG. 14C) are relatively constant for each amplitude of motion of the moving target 110. In this example embodiment, in step 206, the response is characterized based on a linear relationship between the ratios and the amplitude of motion of the moving target 110. In other embodiments, in step 206, the response is characterized based on the tracking body segment (e.g. finger) tracking the moving target 110 closely with ratios of approximately 0.9 for the lowest four discrete target frequencies fi. In other embodiments, in step 206, the response is characterized based on the ratio for the body segment in the ML direction (FIG. 14A) decreasing from 0.9 to 0.8 at a target frequency of 1 Hz, whereas the ratio for the body segment in the SI direction (FIG. 14B) increases from 0.9 to 1 at the target frequency of 1 Hz.

In some embodiments, in step 206, the response of a group of first subjects 190 is characterized. In some embodiments, a phase lag $\chi_1$ (see equation 5) is determined between the discrete frequency $f_i$ component of the frequency spectrum of the finger and the discrete frequency $f_i$ component of the frequency spectrum of the moving target. In other embodiments, a phase lag $\chi_i$ (see equation 5) is determined between the discrete frequency $f_i$ component of the frequency spectrum of the projection 124 and the discrete frequency $f_i$ component of the frequency spectrum of the moving target. In some embodiments, the phase lag $\chi_i$ for the group of first subjects 190 is determined by averaging the individual phase lags $\chi_i$ for each first subject 190. In some embodiments, the phase lag $\chi_i$ for each discrete frequency $f_i$ is determined for each multiple of AL that is used to determine the amplitude of motion of the moving target 110.

FIG. 15A is a graph that illustrates an example of a phase lag $\chi_i$ of the frequency spectrum of the body segment and the frequency spectrum of the moving target in the medial-lateral (ML) direction as a function of target frequency, according to an embodiment. The horizontal axis 1502 is frequency in units of Hertz (Hz). The vertical axis 1504 is phase lag in units of degrees (deg). The phase lag 1506 is shown for each amplitude of motion of the moving target 110, based on a multiple of the AL. FIG. 15B is a graph that illustrates an example of a phase lag $\chi_i$ of the frequency spectrum of the body segment and the frequency spectrum of the moving target in the superior-inferior (SI) direction as a function of target frequency, according to an embodiment. The horizontal axis 1512 is frequency in units of Hertz (Hz). The vertical axis 1514 is phase lag in units of degrees (deg). The phase lag 1508 is shown for each amplitude of motion of the moving target 110, based on a multiple of the AL. FIG. 15C is a graph that illustrates an example of a phase lag $\chi_i$ of the frequency spectrum of the body center of mass and the frequency spectrum of the moving target in the medial-lateral (ML) direction as a function of target frequency, according to an embodiment. The horizontal axis 1522 is frequency in units of Hertz (Hz). The vertical axis 1524 is phase lag in units of degrees (deg). The phase lag 1510 is shown for each amplitude of motion of the moving target 110, based on a multiple of the AL.

In an example embodiment, the phase lag $\chi_i$ for the frequency spectrum of the body segment in the ML direction (FIG. 15A), the phase lag $\chi_i$ for the frequency spectrum of the body segment in the SI direction (FIG. 15B) and the phase lag $\chi_i$ for the frequency spectrum of the body center of mass in the ML (FIG. 15C) direction are relatively constant for each amplitude of motion of the moving target 110. In this example embodiment, in step 206, the response is characterized based on a linear relationship between the phase lag $\chi_i$ and the amplitude of motion of the moving target 110. In other embodiments, in step 206, the response is characterized based on the tracking body segment (e.g. finger) tracking the moving target 110 closely with phase lag $\chi_i$ of less than 32 degrees for the lowest four discrete target frequencies fi. In other embodiments, in step 206, the response is characterized based on the phase lag $\chi_i$ for the body segment (e.g. finger) increasing to 50 degrees at the fifth target frequency.

Figure 16:
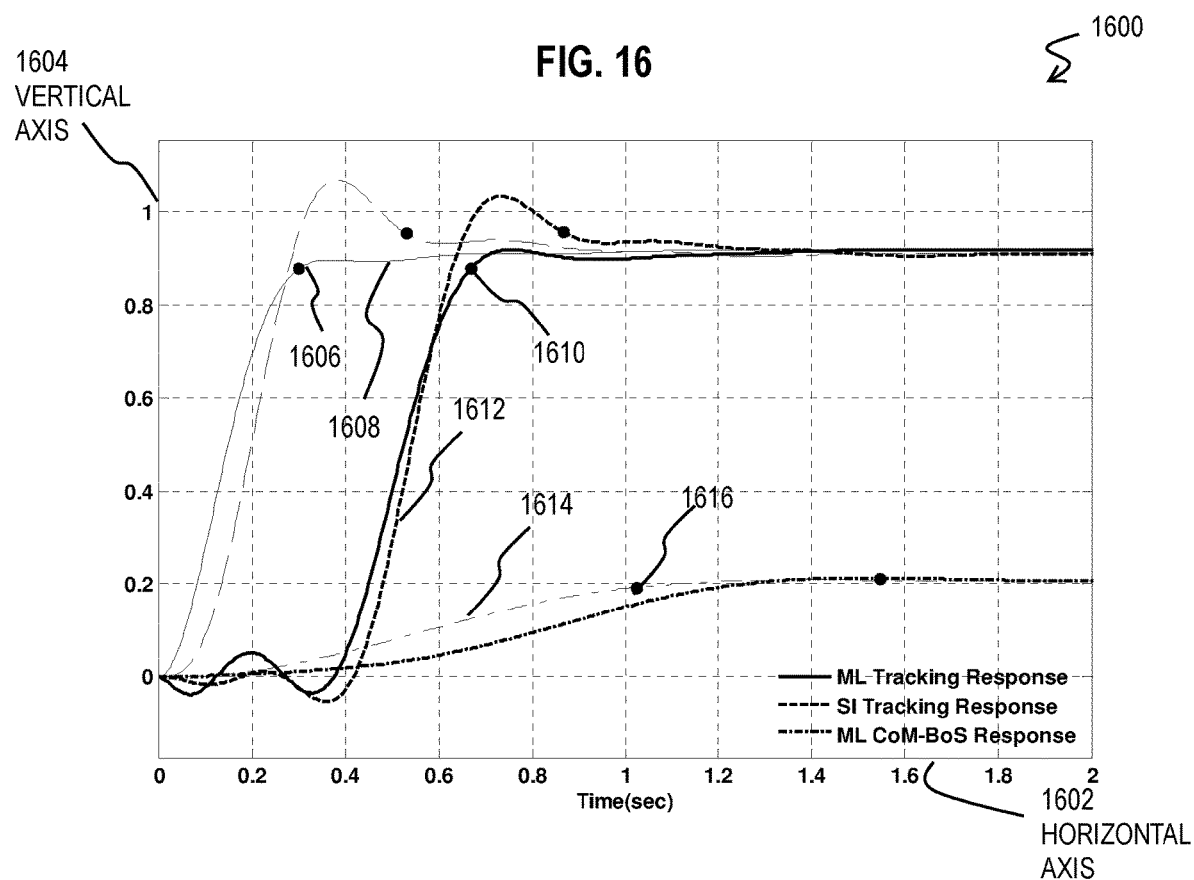
FIG. 16 is a graph that illustrates an example of a step response of the body segment and the body center of mass based on moving the target, according to an embodiment.

In some embodiments, in step 206, a step response is determined of the position of the body segment or the position of the body center of mass based on moving the target 110 a respective distance in each of the SI and ML directions. In some embodiments, the step response is a unit step response determined by causing the target 110 to move the respective distance in each of the SI and ML directions at an initial time t=0 and subsequently determining the position of the body segment or position of the body center mass after t=0. In an example embodiment, the moving target 110 moves a respective distance in each of the ML and SI directions at t=0 and stays fixed at those respective distances in each of the ML and SI direction after t=0. FIG. 16 is a graph 1600 that illustrates an example of a unit step response of the body segment and the body center of mass based moving the target a distance, according to an embodiment. In an example embodiment, the respective distance that the moving target is moved in each of the SI and ML directions is based on 1.125 AL. The horizontal axis 1602 is time in units of seconds (sec). The vertical axis 1604 is the response in units of the respective distance that the target 110 is moved. The response 1608 of the body segment (e.g. finger) in the ML direction reaches a steady state value in a range of 0.30-0.66 seconds and reaches a point 1606 within 5% of its final steady state value at approximately 0.30 seconds. The response 1612 of the body segment (e.g. finger) in the SI direction reaches a steady state value in a range of 0.54-0.89 seconds and reaches a point 1610 within 5% of its final steady state value at approximately 0.70 seconds. The response 1614 of the body center of mass in the ML direction reaches a steady state value in a range of 1.02-1.54 seconds and reaches a point 1616 within 5% of its final steady state value at approximately 1.0 seconds. In step 206, the response of first subject is characterized, by establishing that ML motion of the body center of mass exhibits the most heavily damped response (e.g. longest time to reach the steady state value), followed by ML motion of the body segment (e.g. finger) and that SI Motion of the body segment (e.g. finger) exhibits the least damping.

In some embodiments, in step 206, the $NRMSE_i$ is determined using equation 5 and is based on the ratio (g) of the amplitude of the frequency spectrum of the finger to the amplitude of the frequency spectrum of the moving target and the phase lag (y) between the discrete frequency fi component of the frequency spectrum of the finger and the discrete frequency fi component of the frequency spectrum of the moving target. FIG. 17 is a graph 1700 that illustrates an example of a normalized root mean square error (NRMSE) between a body segment and the moving target as a function of phase lag of the frequency spectrum of the body segment and the frequency spectrum of the moving target, according to an embodiment. The horizontal axis 1702 is phase lag is units of degrees (deg). The vertical axis 1704 is NRMSE and has no units. The NRMSE is shown for different ratios (g) of the amplitude of the frequency spectrum of the finger to the amplitude of the frequency spectrum of the moving target. The NRMSE 1710 versus phase lag $(\chi_i)$ is shown for a gain of 1.0. The NRMSE 1712 versus phase lag $(\chi_i)$ is shown for a gain of 0.9. The NRMSE 1714 versus phase lag $(\chi_i)$ is shown for a gain of 0.8. The NRMSE 1716 versus phase lag $(\chi_i)$ is shown for a gain of 0.7. The NRMSE 1718 versus phase lag $(\chi_i)$ is shown for a gain of 0.6. The NRMSE 1720 versus phase lag $(\chi_i)$ is shown for a gain of 0.5. The NRMSE 1722 versus phase lag $(\chi_i)$ is shown for a gain of 0.4. The NRMSE 1724 versus phase lag $(\chi_i)$ is shown for a gain of 0.3. The NRMSE 1726 versus phase lag $(\chi_i)$ is shown for a gain of 0.2. The NRMSE 1728 versus phase lag ($\chi_i$) is shown for a gain of 0.1. The NRMSE 1730 versus phase lag ($\chi_i$) is shown for a gain of 0.

The NRMSE reaches a maximum value ($\sqrt{2}$) when the phase lag ($\chi_i$) is 180 degrees±360 degrees (e.g. numerator in equation 5 is maximum value among all phase lag values). This is consistent with the discrete frequency $f_i$ component of the frequency spectrum of the finger being completely out of phase with the discrete frequency fi component of the frequency spectrum of the moving target. The NRMSE reaches a minimum value (0) when the phase lag ($\chi_i$) is 0 degrees±360 degrees (e.g. numerator in equation 5 is minimum value among all phase lag values). This is consistent with the discrete frequency $f_i$ component of the frequency spectrum of the finger being completely in phase with the discrete frequency $f_i$ component of the frequency spectrum of the moving target. Additionally, an increased ratio (g) of the NRMSE simultaneously reduces minimum values of the NRMSE and increases maximum values of the NRMSE, as compared to NRMSE with other ratio values.

In an example embodiment, the graphs 400, 410, 420, 430 of FIGS. 4A to 4D depict position trajectories of the tracking body segment (e.g. finger), the body center of mass and the moving target 110, where the amplitude of motion of the moving target 110 is based on 1.1250 AL. In an example embodiment, the graphs 450, 460, 470, 480 of FIGS. 4E to 4H depict frequency spectrums of the tracking body segment position, the center of mass position and the moving target 110 position, where the amplitude of motion of the moving target 110 is based on 1.1250 AL. Table 5 below provides amplitudes of the frequency spectrums of FIGS. 4E to 4H for each discrete frequency component fi of the moving target 110, where the amplitude of motion of the moving target 110 is based on 1.1250 AL. In an example embodiment, in step 206, the ratio of the amplitude of the frequency spectrum of the tracking body segment to the amplitude of the frequency spectrum of the moving target and the ratio of the amplitude of the frequency spectrum of the body center of mass to the amplitude of the frequency spectrum of the moving target are computed using the amplitude values in Table 5.

TABLE 5

| | Frequency (Hz) | Disk Amplitude (cm) | | | Tracking Finger Amplitude (cm) | |
|---|---|---|---|---|---|---|
| i | f (i) | ML (x) | SI (y) | xyz | ML (x) | SI (y) |
| 1 | 0.024 | $4.62 \times 10^{+1}$ | $3.87 \times 10^{+1}$ | $3.22 \times 10^{+1}$ | $4.24 \times 10^{+1} \pm 2.08 \times 10^{+0}$ | $3.51 \times 10^{+1} \pm 1.58 \times 10^{+0}$ |
| 2 | 0.048 | $2.31 \times 10^{+1}$ | $1.93 \times 10^{+1}$ | $1.78 \times 10^{+1}$ | $2.11 \times 10^{+1} \pm 1.03 \times 10^{+0}$ | $1.80 \times 10^{+1} \pm 8.71 \times 10^{-1}$ |
| 3 | 0.096 | $1.16 \times 10^{+1}$ | $9.67 \times 10^{+0}$ | $7.37 \times 10^{+0}$ | $1.08 \times 10^{+1} \pm 5.42 \times 10^{-1}$ | $8.74 \times 10^{+0} \pm 4.40 \times 10^{-1}$ |
| 4 | 0.192 | $5.78 \times 10^{+0}$ | $4.83 \times 10^{+0}$ | $3.71 \times 10^{+0}$ | $5.25 \times 10^{+0} \pm 2.31 \times 10^{-1}$ | $4.44 \times 10^{+0} \pm 2.16 \times 10^{-1}$ |
| 5 | 0.288 | $3.85 \times 10^{+0}$ | $3.22 \times 10^{+0}$ | $2.53 \times 10^{+0}$ | $3.48 \times 10^{+0} \pm 1.92 \times 10^{-1}$ | $2.72 \times 10^{+0} \pm 1.43 \times 10^{-1}$ |
| 6 | 0.336 | $3.30 \times 10^{+0}$ | $2.76 \times 10^{+0}$ | $2.00 \times 10^{+0}$ | $3.21 \times 10^{+0} \pm 1.18 \times 10^{-1}$ | $2.56 \times 10^{+0} \pm 9.97 \times 10^{-2}$ |
| 7 | 0.480 | $2.31 \times 10^{+0}$ | $1.93 \times 10^{+0}$ | $1.51 \times 10^{+0}$ | $1.97 \times 10^{+0} \pm 2.60 \times 10^{-2}$ | $1.70 \times 10^{+0} \pm 1.20 \times 10^{-2}$ |
| 8 | 0.576 | $1.93 \times 10^{+0}$ | $1.61 \times 10^{+0}$ | $1.32 \times 10^{+0}$ | $1.76 \times 10^{+0} \pm 2.56 \times 10^{-2}$ | $1.62 \times 10^{+0} \pm 5.02 \times 10^{-2}$ |
| 9 | 0.720 | $1.54 \times 10^{+0}$ | $1.29 \times 10^{+0}$ | $9.50 \times 10^{-1}$ | $1.38 \times 10^{+0} \pm 1.15 \times 10^{-1}$ | $1.36 \times 10^{+0} \pm 1.15 \times 10^{-1}$ |
| 10 | 0.816 | $1.36 \times 10^{+0}$ | $1.14 \times 10^{+0}$ | $9.20 \times 10^{-1}$ | $1.02 \times 10^{+0} \pm 1.51 \times 10^{-1}$ | $1.12 \times 10^{+0} \pm 1.35 \times 10^{-1}$ |
| 11 | 0.912 | $1.22 \times 10^{+0}$ | $1.02 \times 10^{+0}$ | $6.99 \times 10^{-1}$ | $7.08 \times 10^{-1} \pm 1.26 \times 10^{-1}$ | $1.11 \times 10^{+0} \pm 1.52 \times 10^{-1}$ |
| 12 | 1.416 | $7.83 \times 10^{-1}$ | $6.56 \times 10^{-1}$ | $5.08 \times 10^{-1}$ | $6.00 \times 10^{-1} \pm 4.91 \times 10^{-2}$ | $5.39 \times 10^{-1} \pm 2.11 \times 10^{-2}$ |
| 13 | 2.184 | $5.08 \times 10^{-1}$ | $4.25 \times 10^{-1}$ | $3.25 \times 10^{-1}$ | $3.47 \times 10^{-1} \pm 5.59 \times 10^{-2}$ | $3.47 \times 10^{-1} \pm 7.24 \times 10^{-3}$ |
| 14 | 2.928 | $3.79 \times 10^{-1}$ | $3.17 \times 10^{-1}$ | $2.47 \times 10^{-1}$ | $1.08 \times 10^{-1} \pm 4.60 \times 10^{-2}$ | $1.03 \times 10^{-1} \pm 3.99 \times 10^{-2}$ |

| | Frequency (Hz) | CoM-BoS Amplitude (cm) | |
|---|---|---|---|
| i | f (i) | ML (x) | AP (z) |
| 1 | 0.024 | $9.30 \times 10^{+0} \pm 1.05 \times 10^{+0}$ | $1.47 \times 10^{-1} \pm 2.77 \times 10^{-2}$ |
| 2 | 0.048 | $4.49 \times 10^{+0} \pm 5.48 \times 10^{-1}$ | $2.81 \times 10^{-1} \pm 2.16 \times 10^{-1}$ |
| 3 | 0.096 | $2.78 \times 10^{+0} \pm 3.86 \times 10^{-1}$ | $8.51 \times 10^{-2} \pm 7.63 \times 10^{-2}$ |
| 4 | 0.192 | $1.07 \times 10^{+0} \pm 9.52 \times 10^{-2}$ | $1.66 \times 10^{-2} \pm 1.35 \times 10^{-2}$ |
| 5 | 0.288 | $6.81 \times 10^{-1} \pm 1.35 \times 10^{-2}$ | $5.96 \times 10^{-2} \pm 5.16 \times 10^{-2}$ |
| 6 | 0.336 | $6.17 \times 10^{-1} \pm 8.06 \times 10^{-3}$ | $3.57 \times 10^{-2} \pm 2.83 \times 10^{-2}$ |
| 7 | 0.480 | $3.44 \times 10^{-1} \pm 1.08 \times 10^{-1}$ | $5.07 \times 10^{-2} \pm 3.55 \times 10^{-2}$ |
| 8 | 0.576 | $2.10 \times 10^{-1} \pm 5.63 \times 10^{-2}$ | $6.59 \times 10^{-2} \pm 5.19 \times 10^{-4}$ |
| 9 | 0.720 | $1.46 \times 10^{-1} \pm 5.33 \times 10^{-2}$ | $6.18 \times 10^{-2} \pm 2.58 \times 10^{-2}$ |
| 10 | 0.816 | $9.44 \times 10^{-2} \pm 7.83 \times 10^{-3}$ | $2.74 \times 10^{-2} \pm 2.72 \times 10^{-2}$ |
| 11 | 0.912 | $7.84 \times 10^{-2} \pm 1.78 \times 10^{-2}$ | $2.48 \times 10^{-2} \pm 1.83 \times 10^{-2}$ |
| 12 | 1.416 | $4.00 \times 10^{-2} \pm 1.13 \times 10^{-2}$ | $1.67 \times 10^{-2} \pm 6.61 \times 10^{-3}$ |
| 13 | 2.184 | $8.92 \times 10^{-3} \pm 7.65 \times 10^{-3}$ | $1.47 \times 10^{-3} \pm 1.10 \times 10^{-3}$ |
| 14 | 2.928 | $9.90 \times 10^{-3} \pm 4.68 \times 10^{-3}$ | $4.76 \times 10^{-3} \pm 3.02 \times 10^{-3}$ |

FIGS. 18A to 18B includes graphs 1800, 1810 that illustrate an example of a position of the body segment and the moving target, according to an embodiment. FIGS. 18C to 18D includes graphs 1820, 1830 that illustrate an example of a position of a body center of mass and the moving target, according to an embodiment. The graphs 1800, 1810, 1820, 1830 of FIGS. 18A to 18D are similar to the graphs 400, 410, 420, 430 of FIGS. 4A to 4D except the amplitude of motion of the moving target 110 is based on 0.5000 AL. The graph 1800 depicts the ML position of the finger (black plot), the ML position of the target 110 (grey plot) and a 95% confidence interval range of the ML position of the finger (dotted lines) for a group of young healthy subjects 190. In an example embodiment, the 95% confidence interval range is ±6.56 cm of the ML positions of the finger depicted in graph 1800. The graph 1810 depicts the SI position of the finger (black plot), the SI position of the target 110 (grey plot) and a 95% confidence interval range of the SI position of the finger (dotted lines) for a group of young healthy subjects 190. In an example embodiment, the 95% confidence interval range is ±1.24 cm of the SI positions of the finger depicted in graph 1810. The graph 1820 depicts the ML position of the projection 124 (black plot), the ML position of the target 110 (grey plot) and a 95% confidence interval range of the ML position of the projection 124 (dotted lines) for a group of young healthy subjects 190. In an example embodiment, the 95% confidence interval range is ±2.31 cm of the ML positions of the projection 124 depicted in graph 1820. The graph 1830 depicts the AP position of the projection 124 (black plot), the XYZ position of the target 110 (grey plot) and a 95% confidence interval range of the AP position of the projection 124 (dotted lines) for a group of young healthy subjects 190. In an example embodiment, the 95% confidence interval range is ±0.70 cm of the AP positions of the projection 124 depicted in graph 1830.

FIGS. 18E to 18F includes graphs 1850, 1860 that illustrate an example of a frequency spectrum of the body segment and a frequency spectrum of the moving target, according to an embodiment. FIGS. 18G to 18H includes graphs 1870, 1880 that illustrate an example of a frequency spectrum of the body center of mass and a frequency spectrum of the moving target, according to an embodiment. The graphs 1850, 1860, 1870, 1880 of FIGS. 18E to 18H are similar to the graphs 450, 460, 470, 480 of FIGS. 4E to 4H except the amplitude of motion of the moving target 110 is based on 0.5000 AL. The graph 1850 depicts the amplitude of the frequency spectrum of the finger in the ML direction (black) and the amplitude of the frequency spectrum of the moving target in the ML direction (grey) for each discrete frequency $f_i$ of the moving target 110 expressed in equation 1. The graph 1860 depicts the amplitude of the frequency spectrum of the finger in the SI direction (black) and the amplitude of the frequency spectrum of the moving target in the SI direction (grey) for each discrete frequency $f_i$ of the moving target 110 expressed in equation 1. The graph 1870 depicts the amplitude of the frequency spectrum of the projection 124 in the ML direction (black) and the amplitude of the frequency spectrum of the moving target in the ML direction (grey) for each discrete frequency $f_i$ of the moving target 110 expressed in equation 1. The graph 1880 depicts the amplitude of the frequency spectrum of the projection 124 in the AP direction (black) and the amplitude of the frequency spectrum of the moving target in the XYZ direction (grey) for each discrete frequency $f_i$ of the moving target 110 expressed in equation 1.

In an example embodiment, the graphs 1850, 1860, 1870, 1880 of FIGS. 18E to 18H depict frequency spectrums of the tracking body segment position, the center of mass position and the moving target 110 position, where the amplitude of motion of the moving target 110 is based on 0.5000 AL. Table 6 below provides amplitudes of the frequency spectrums of FIGS. 18E to 18H for each discrete frequency component $f_i$ of the moving target 110, where the amplitude of motion of the moving target 110 is based on 0.5000 AL. In an example embodiment, in step 206, the ratio of the amplitude of the frequency spectrum of the tracking body segment to the amplitude of the frequency spectrum of the moving target and the ratio of the amplitude of the frequency spectrum of the body center of mass to the amplitude of the frequency spectrum of the moving target are computed using the amplitude values in Table 6.

TABLE 6

| Frequency (Hz) | | Disk Amplitude (cm) | | | Tracking Finger Amplitude (cm) | |
|---|---|---|---|---|---|---|
| i | f (i) | ML (x) | SI (y) | xyz | ML (x) | SI (y) |
| 1 | 0.024 | $2.05 \times 10^{+1}$ | $1.72 \times 10^{+1}$ | $1.42 \times 10^{+1}$ | $1.92 \times 10^{+1} \pm 8.71 \times 10^{-1}$ | $1.58 \times 10^{+1} \pm 6.52 \times 10^{-1}$ |
| 2 | 0.048 | $1.03 \times 10^{+1}$ | $8.60 \times 10^{+0}$ | $7.48 \times 10^{+0}$ | $9.45 \times 10^{+0} \pm 4.55 \times 10^{-1}$ | $8.11 \times 10^{+0} \pm 3.44 \times 10^{-1}$ |
| 3 | 0.096 | $5.13 \times 10^{+0}$ | $4.30 \times 10^{+0}$ | $3.42 \times 10^{+0}$ | $4.91 \times 10^{+0} \pm 2.24 \times 10^{-1}$ | $3.98 \times 10^{+0} \pm 1.75 \times 10^{-1}$ |
| 4 | 0.192 | $2.57 \times 10^{+0}$ | $2.15 \times 10^{+0}$ | $1.73 \times 10^{+0}$ | $2.38 \times 10^{+0} \pm 1.00 \times 10^{-1}$ | $2.08 \times 10^{+0} \pm 9.52 \times 10^{-2}$ |
| 5 | 0.288 | $1.71 \times 10^{+0}$ | $1.43 \times 10^{+0}$ | $1.16 \times 10^{+0}$ | $1.58 \times 10^{+0} \pm 8.83 \times 10^{-2}$ | $1.24 \times 10^{+0} \pm 7.49 \times 10^{-2}$ |
| 6 | 0.336 | $1.47 \times 10^{+0}$ | $1.23 \times 10^{+0}$ | $9.57 \times 10^{-1}$ | $1.48 \times 10^{+0} \pm 5.25 \times 10^{-2}$ | $1.22 \times 10^{+0} \pm 4.71 \times 10^{-2}$ |
| 7 | 0.480 | $1.03 \times 10^{+0}$ | $8.60 \times 10^{-1}$ | $6.94 \times 10^{-1}$ | $9.03 \times 10^{-1} \pm 4.05 \times 10^{-3}$ | $7.76 \times 10^{-1} \pm 4.88 \times 10^{-3}$ |
| 8 | 0.576 | $8.56 \times 10^{-1}$ | $7.16 \times 10^{-1}$ | $5.91 \times 10^{-1}$ | $8.50 \times 10^{-1} \pm 1.11 \times 10^{-2}$ | $7.68 \times 10^{-1} \pm 2.00 \times 10^{-2}$ |
| 9 | 0.720 | $6.85 \times 10^{-1}$ | $5.73 \times 10^{-1}$ | $4.54 \times 10^{-1}$ | $6.42 \times 10^{-1} \pm 4.54 \times 10^{-2}$ | $6.32 \times 10^{-1} \pm 4.66 \times 10^{-2}$ |
| 10 | 0.816 | $6.04 \times 10^{-1}$ | $5.06 \times 10^{-1}$ | $4.10 \times 10^{-1}$ | $4.47 \times 10^{-1} \pm 6.69 \times 10^{-2}$ | $4.73 \times 10^{-1} \pm 5.79 \times 10^{-2}$ |
| 11 | 0.912 | $5.40 \times 10^{-1}$ | $4.52 \times 10^{-1}$ | $3.44 \times 10^{-1}$ | $3.79 \times 10^{-1} \pm 5.94 \times 10^{-2}$ | $4.88 \times 10^{-1} \pm 7.56 \times 10^{-2}$ |
| 12 | 1.416 | $3.48 \times 10^{-1}$ | $2.91 \times 10^{-1}$ | $2.33 \times 10^{-1}$ | $2.50 \times 10^{-1} \pm 2.17 \times 10^{-2}$ | $2.29 \times 10^{-1} \pm 6.58 \times 10^{-3}$ |
| 13 | 2.184 | $2.26 \times 10^{-1}$ | $1.89 \times 10^{-1}$ | $1.51 \times 10^{-1}$ | $1.47 \times 10^{-1} \pm 2.35 \times 10^{-2}$ | $1.72 \times 10^{-1} \pm 6.93 \times 10^{-4}$ |
| 14 | 2.928 | $1.68 \times 10^{-1}$ | $1.41 \times 10^{-1}$ | $1.12 \times 10^{-1}$ | $4.21 \times 10^{-2} \pm 2.21 \times 10^{-2}$ | $3.70 \times 10^{-2} \pm 2.06 \times 10^{-2}$ |

| Frequency (Hz) | | CoM-BoS Amplitude (cm) | |
|---|---|---|---|
| i | f (i) | ML (x) | AP (z) |
| 1 | 0.024 | $5.06 \times 10^{+0} \pm 8.72 \times 10^{-1}$ | $1.06 \times 10^{-1} \pm 1.06 \times 10^{-1}$ |
| 2 | 0.048 | $2.58 \times 10^{+0} \pm 4.73 \times 10^{-1}$ | $1.07 \times 10^{-1} \pm 6.85 \times 10^{-2}$ |
| 3 | 0.096 | $1.42 \times 10^{+0} \pm 2.58 \times 10^{-1}$ | $8.39 \times 10^{-2} \pm 8.01 \times 10^{-2}$ |
| 4 | 0.192 | $5.21 \times 10^{-1} \pm 7.15 \times 10^{-2}$ | $4.90 \times 10^{-2} \pm 3.27 \times 10^{-2}$ |
| 5 | 0.288 | $3.55 \times 10^{-1} \pm 3.01 \times 10^{-2}$ | $4.42 \times 10^{-2} \pm 3.56 \times 10^{-3}$ |
| 6 | 0.336 | $2.60 \times 10^{-1} \pm 2.25 \times 10^{-2}$ | $4.52 \times 10^{-2} \pm 3.66 \times 10^{-2}$ |
| 7 | 0.480 | $1.25 \times 10^{-1} \pm 5.26 \times 10^{-2}$ | $4.26 \times 10^{-2} \pm 9.68 \times 10^{-3}$ |
| 8 | 0.576 | $8.50 \times 10^{-2} \pm 3.70 \times 10^{-2}$ | $3.56 \times 10^{-2} \pm 6.93 \times 10^{-4}$ |
| 9 | 0.720 | $5.72 \times 10^{-2} \pm 1.42 \times 10^{-2}$ | $2.64 \times 10^{-2} \pm 4.72 \times 10^{-3}$ |
| 10 | 0.816 | $3.90 \times 10^{-2} \pm 2.83 \times 10^{-3}$ | $1.84 \times 10^{-2} \pm 9.58 \times 10^{-3}$ |
| 11 | 0.912 | $3.54 \times 10^{-2} \pm 8.28 \times 10^{-3}$ | $7.44 \times 10^{-3} \pm 6.95 \times 10^{-3}$ |
| 12 | 1.416 | $2.14 \times 10^{-2} \pm 7.05 \times 10^{-3}$ | $6.81 \times 10^{-3} \pm 3.51 \times 10^{-3}$ |
| 13 | 2.184 | $7.40 \times 10^{-3} \pm 2.57 \times 10^{-3}$ | $2.16 \times 10^{-3} \pm 2.05 \times 10^{-3}$ |
| 14 | 2.928 | $4.00 \times 10^{-3} \pm 2.60 \times 10^{-3}$ | $8.08 \times 10^{-4} \pm 7.08 \times 10^{-4}$ |

FIGS. 19A to 19B includes graphs 1900, 1910 that illustrate an example of a position of the body segment and the moving target, according to an embodiment. FIGS. 19C to 19D includes graphs 1920, 1930 that illustrate an example of a position of a body center of mass and the moving target, according to an embodiment. The graphs 1900, 1910, 1920, 1930 of FIGS. 19A to 19D are similar to the graphs 400, 410, 420, 430 of FIGS. 4A to 4D except the amplitude of motion of the moving target 110 is based on 0.6563 AL. The graph 1900 depicts the ML position of the finger (black plot), the ML position of the target 110 (grey plot) and a 95% confidence interval range of the ML position of the finger (dotted lines) for a group of young healthy subjects 190. In an example embodiment, the 95% confidence interval range is ±1.74 cm of the ML positions of the finger depicted in graph 1900. The graph 1910 depicts the SI position of the finger (black plot), the SI position of the target 110 (grey plot) and a 95% confidence interval range of the SI position of the finger (dotted lines) for a group of young healthy subjects 190. In an example embodiment, the 95% confidence interval range is ±1.20 cm of the SI positions of the finger depicted in graph 1910. The graph 1920 depicts the ML position of the projection 124 (black plot), the ML position of the target 110 (grey plot) and a 95% confidence interval range of the ML position of the projection 124 (dotted lines) for a group of young healthy subjects 190. In an example embodiment, the 95% confidence interval range is ±1.19 cm of the ML positions of the projection 124 depicted in graph 1920. The graph 1930 depicts the AP position of the projection 124 (black plot), the XYZ position of the target 110 (grey plot) and a 95% confidence interval range of the AP position of the projection 124 (dotted lines) for a group of young healthy subjects 190. In an example embodiment, the 95% confidence interval range is ±1.30 cm of the AP positions of the projection 124 depicted in graph 1930.

FIGS. 19E to 19F includes graphs 1950, 1960 that illustrate an example of a frequency spectrum of the body segment and a frequency spectrum of the moving target, according to an embodiment. FIGS. 19G to 19H includes graphs 1970, 1980 that illustrate an example of a frequency spectrum of the body center of mass and a frequency spectrum of the moving target, according to an embodiment.

The graphs 1950, 1960, 1970, 1980 of FIGS. 19E to 19H are similar to the graphs 450, 460, 470, 480 of FIGS. 4E to 4H except the amplitude of motion of the moving target 110 is based on 0.6563 AL. The graph 1950 depicts the amplitude of the frequency spectrum of the finger in the ML direction (black) and the amplitude of the frequency spectrum of the moving target in the ML direction (grey) for each discrete frequency $f_i$ of the moving target 110 expressed in equation 1. The graph 1960 depicts the amplitude of the frequency spectrum of the finger in the SI direction (black) and the amplitude of the frequency spectrum of the moving target in the SI direction (grey) for each discrete frequency $f_i$ of the moving target 110 expressed in equation 1. The graph 1970 depicts the amplitude of the frequency spectrum of the projection 124 in the ML direction (black) and the amplitude of the frequency spectrum of the moving target in the ML direction (grey) for each discrete frequency $f_i$ of the moving target 110 expressed in equation 1. The graph 1980 depicts the amplitude of the frequency spectrum of the projection 124 in the AP direction (black) and the amplitude of the frequency spectrum of the moving target in the XYZ direction (grey) for each discrete frequency $f_i$ of the moving target 110 expressed in equation 1.

In an example embodiment, the graphs 1950, 1960, 1970, 1980 of FIGS. 19E to 19H depict frequency spectrums of the tracking body segment position, the center of mass position and the moving target 110 position, where the amplitude of motion of the moving target 110 is based on 0.6563 AL. Table 7 below provides amplitudes of the frequency spectrums of FIGS. 19E to 19H for each discrete frequency component fi of the moving target 110, where the amplitude of motion of the moving target 110 is based on 0.6563 AL. In an example embodiment, in step 206, the ratio of the amplitude of the frequency spectrum of the tracking body segment to the amplitude of the frequency spectrum of the moving target and the ratio of the amplitude of the frequency spectrum of the body center of mass to the amplitude of the frequency spectrum of the moving target are computed using the amplitude values in Table 7.

TABLE 7

| Frequency (Hz) | | Disk Amplitude (cm) | | | Tracking Finger Amplitude (cm) | |
|---|---|---|---|---|---|---|
| i | f (i) | ML (x) | SI (y) | xyz | ML (x) | SI (y) |
| 1 | 0.024 | $2.70 \times 10^{+1}$ | $2.26 \times 10^{+1}$ | $1.88 \times 10^{+1}$ | $2.55 \times 10^{+1} \pm 1.16 \times 10^{+0}$ | $2.09 \times 10^{+1} \pm 9.28 \times 10^{-1}$ |
| 2 | 0.048 | $1.35 \times 10^{+1}$ | $1.13 \times 10^{+1}$ | $9.99 \times 10^{+0}$ | $1.26 \times 10^{+1} \pm 6.11 \times 10^{-1}$ | $1.08 \times 10^{+1} \pm 4.80 \times 10^{-1}$ |
| 3 | 0.096 | $6.74 \times 10^{+0}$ | $5.64 \times 10^{+0}$ | $4.45 \times 10^{+0}$ | $6.57 \times 10^{+0} \pm 3.05 \times 10^{-1}$ | $5.29 \times 10^{+0} \pm 2.39 \times 10^{-1}$ |
| 4 | 0.192 | $3.37 \times 10^{+0}$ | $2.82 \times 10^{+0}$ | $2.25 \times 10^{+0}$ | $3.13 \times 10^{+0} \pm 1.23 \times 10^{-1}$ | $2.76 \times 10^{+0} \pm 1.38 \times 10^{-1}$ |
| 5 | 0.288 | $2.25 \times 10^{+0}$ | $1.88 \times 10^{+0}$ | $1.52 \times 10^{+0}$ | $2.11 \times 10^{+0} \pm 1.12 \times 10^{-1}$ | $1.55 \times 10^{+0} \pm 8.20 \times 10^{-2}$ |
| 6 | 0.336 | $1.93 \times 10^{+0}$ | $1.61 \times 10^{+0}$ | $1.24 \times 10^{+0}$ | $1.95 \times 10^{+0} \pm 7.12 \times 10^{-2}$ | $1.59 \times 10^{+0} \pm 6.30 \times 10^{-2}$ |
| 7 | 0.480 | $1.35 \times 10^{+0}$ | $1.13 \times 10^{+0}$ | $9.06 \times 10^{-1}$ | $1.20 \times 10^{+0} \pm 1.13 \times 10^{-2}$ | $1.02 \times 10^{+0} \pm 6.86 \times 10^{-3}$ |
| 8 | 0.576 | $1.12 \times 10^{+0}$ | $9.40 \times 10^{-1}$ | $7.78 \times 10^{-1}$ | $1.10 \times 10^{+0} \pm 1.61 \times 10^{-2}$ | $1.00 \times 10^{+0} \pm 3.28 \times 10^{-2}$ |
| 9 | 0.720 | $8.99 \times 10^{-1}$ | $7.52 \times 10^{-1}$ | $5.88 \times 10^{-1}$ | $8.69 \times 10^{-1} \pm 7.06 \times 10^{-2}$ | $8.51 \times 10^{-1} \pm 6.05 \times 10^{-2}$ |
| 10 | 0.816 | $7.93 \times 10^{-1}$ | $6.64 \times 10^{-1}$ | $5.39 \times 10^{-1}$ | $6.00 \times 10^{-1} \pm 9.29 \times 10^{-2}$ | $6.04 \times 10^{-1} \pm 7.10 \times 10^{-2}$ |
| 11 | 0.912 | $7.09 \times 10^{-1}$ | $5.94 \times 10^{-1}$ | $4.41 \times 10^{-1}$ | $4.32 \times 10^{-1} \pm 9.02 \times 10^{-2}$ | $6.33 \times 10^{-1} \pm 9.89 \times 10^{-2}$ |
| 12 | 1.416 | $4.57 \times 10^{-1}$ | $3.82 \times 10^{-1}$ | $3.04 \times 10^{-1}$ | $3.08 \times 10^{-1} \pm 3.87 \times 10^{-2}$ | $2.98 \times 10^{-1} \pm 8.34 \times 10^{-3}$ |
| 13 | 2.184 | $2.96 \times 10^{-1}$ | $2.48 \times 10^{-1}$ | $1.97 \times 10^{-1}$ | $1.80 \times 10^{-1} \pm 3.91 \times 10^{-2}$ | $2.00 \times 10^{-1} \pm 7.62 \times 10^{-4}$ |
| 14 | 2.928 | $2.21 \times 10^{-1}$ | $1.85 \times 10^{-1}$ | $1.47 \times 10^{-1}$ | $5.37 \times 10^{-2} \pm 2.41 \times 10^{-1}$ | $6.00 \times 10^{-2} \pm 2.85 \times 10^{-2}$ |

| Frequency (Hz) | | CoM-BoS Amplitude (cm) | |
|---|---|---|---|
| i | f (i) | ML (x) | AP (z) |
| 1 | 0.024 | $6.18 \times 10^{+0} \pm 9.31 \times 10^{-1}$ | $5.55 \times 10^{-2} \pm 5.28 \times 10^{-2}$ |
| 2 | 0.048 | $3.31 \times 10^{+0} \pm 6.16 \times 10^{-1}$ | $9.81 \times 10^{-2} \pm 9.66 \times 10^{-2}$ |
| 3 | 0.096 | $1.85 \times 10^{+0} \pm 3.27 \times 10^{-1}$ | $4.37 \times 10^{-2} \pm 3.94 \times 10^{-2}$ |
| 4 | 0.192 | $6.81 \times 10^{-1} \pm 8.04 \times 10^{-2}$ | $4.88 \times 10^{-2} \pm 3.29 \times 10^{-2}$ |
| 5 | 0.288 | $3.38 \times 10^{-1} \pm 1.36 \times 10^{-2}$ | $3.25 \times 10^{-2} \pm 5.11 \times 10^{-3}$ |
| 6 | 0.336 | $3.79 \times 10^{-1} \pm 2.32 \times 10^{-2}$ | $4.07 \times 10^{-2} \pm 3.86 \times 10^{-2}$ |
| 7 | 0.480 | $2.32 \times 10^{-1} \pm 1.05 \times 10^{-1}$ | $3.67 \times 10^{-2} \pm 6.44 \times 10^{-3}$ |

TABLE 7-continued

| | | | |
|---|---|---|---|
| 8 | 0.576 | $1.29 \times 10^{-1} \pm 4.62 \times 10^{-2}$ | $4.01 \times 10^{-2} \pm 8.03 \times 10^{-4}$ |
| 9 | 0.720 | $9.67 \times 10^{-2} \pm 2.58 \times 10^{-2}$ | $2.96 \times 10^{-2} \pm 1.03 \times 10^{-2}$ |
| 10 | 0.816 | $5.08 \times 10^{-2} \pm 2.90 \times 10^{-3}$ | $3.22 \times 10^{-2} \pm 2.12 \times 10^{-2}$ |
| 11 | 0.912 | $4.50 \times 10^{-2} \pm 1.37 \times 10^{-2}$ | $1.55 \times 10^{-2} \pm 9.44 \times 10^{-3}$ |
| 12 | 1.416 | $2.59 \times 10^{-2} \pm 8.78 \times 10^{-3}$ | $2.66 \times 10^{-3} \pm 1.46 \times 10^{-3}$ |
| 13 | 2.184 | $4.82 \times 10^{-3} \pm 4.32 \times 10^{-3}$ | $1.71 \times 10^{-3} \pm 5.71 \times 10^{-4}$ |
| 14 | 2.928 | $6.18 \times 10^{-3} \pm 3.33 \times 10^{-3}$ | $1.64 \times 10^{-3} \pm 5.80 \times 10^{-4}$ |

FIGS. 20A to 20B includes graphs 2000, 2010 that illustrate an example of a position of the body segment and the moving target, according to an embodiment. FIGS. 20C to 20D includes graphs 2020, 2030 that illustrate an example of a position of a body center of mass and the moving target, according to an embodiment. The graphs 2000, 2010, 2020, 2030 of FIGS. 20A to 20D are similar to the graphs 400, 410, 420, 430 of FIGS. 4A to 4D except the amplitude of motion of the moving target 110 is based on 0.8125 AL. The graph 2000 depicts the ML position of the finger (black plot), the ML position of the target 110 (grey plot) and a 95% confidence interval range of the ML position of the finger (dotted lines) for a group of young healthy subjects 190. In an example embodiment, the 95% confidence interval range is ±10.26 cm of the ML positions of the finger depicted in graph 2000. The graph 2010 depicts the SI position of the finger (black plot), the SI position of the target 110 (grey plot) and a 95% confidence interval range of the SI position of the finger (dotted lines) for a group of young healthy subjects 190. In an example embodiment, the 95% confidence interval range is ±1.21 cm of the SI positions of the finger depicted in graph 2010. The graph 2020 depicts the ML position of the projection 124 (black plot), the ML position of the target 110 (grey plot) and a 95% confidence interval range of the ML position of the projection 124 (dotted lines) for a group of young healthy subjects 190. In an example embodiment, the 95% confidence interval range is ±12.59 cm of the ML positions of the projection 124 depicted in graph 2020. The graph 2030 depicts the AP position of the projection 124 (black plot), the XYZ position of the target 110 (grey plot) and a 95% confidence interval range of the AP position of the projection 124 (dotted lines) for a group of young healthy subjects 190. In an example embodiment, the 95% confidence interval range is ±0.77 cm of the AP positions of the projection 124 depicted in graph 2030.

FIGS. 20E to 20F includes graphs 2050, 2060 that illustrate an example of a frequency spectrum of the body segment and a frequency spectrum of the moving target, according to an embodiment. FIGS. 20G to 20H includes graphs 2070, 2080 that illustrate an example of a frequency spectrum of the body center of mass and a frequency spectrum of the moving target, according to an embodiment. The graphs 2050, 2060, 2070, 2080 of FIGS. 20E to 20H are similar to the graphs 450, 460, 470, 480 of FIGS. 4E to 4H except the amplitude of motion of the moving target 110 is based on 0.8125 AL. The graph 2050 depicts the amplitude of the frequency spectrum of the finger in the ML direction (black) and the amplitude of the frequency spectrum of the moving target in the ML direction (grey) for each discrete frequency $f_i$ of the moving target 110 expressed in equation 1. The graph 2060 depicts the amplitude of the frequency spectrum of the finger in the SI direction (black) and the amplitude of the frequency spectrum of the moving target in the SI direction (grey) for each discrete frequency fi of the moving target 110 expressed in equation 1. The graph 2070 depicts the amplitude of the frequency spectrum of the projection 124 in the ML direction (black) and the amplitude of the frequency spectrum of the moving target in the ML direction (grey) for each discrete frequency $f_i$ of the moving target 110 expressed in equation 1. The graph 2080 depicts the amplitude of the frequency spectrum of the projection 124 in the AP direction (black) and the amplitude of the frequency spectrum of the moving target in the XYZ direction (grey) for each discrete frequency $f_i$ of the moving target 110 expressed in equation 1.

In an example embodiment, the graphs 2050, 2060, 2070, 2080 of FIGS. 20E to 20H depict frequency spectrums of the tracking body segment position, the center of mass position and the moving target 110 position, where the amplitude of motion of the moving target 110 is based on 0.8125 AL. Table 8 below provides amplitudes of the frequency spectrums of FIGS. 20E to 20H for each discrete frequency component fi of the moving target 110, where the amplitude of motion of the moving target 110 is based on 0.8125 AL. In an example embodiment, in step 206, the ratio of the amplitude of the frequency spectrum of the tracking body segment to the amplitude of the frequency spectrum of the moving target and the ratio of the amplitude of the frequency spectrum of the body center of mass to the amplitude of the frequency spectrum of the moving target are computed using the amplitude values in Table 8.

TABLE 8

| Frequency (Hz) | | Disk Amplitude (cm) | | | Tracking Finger Amplitude (cm) | |
|---|---|---|---|---|---|---|
| i | f (i) | ML (x) | SI (y) | xyz | ML (x) | SI (y) |
| 1 | 0.024 | $3.34 \times 10^{+1}$ | $2.79 \times 10^{+1}$ | $2.33 \times 10^{+1}$ | $3.10 \times 10^{+1} \pm 1.47 \times 10^{+0}$ | $2.55 \times 10^{+1} \pm 1.19 \times 10^{+0}$ |
| 2 | 0.048 | $1.67 \times 10^{+1}$ | $1.40 \times 10^{+1}$ | $1.26 \times 10^{+1}$ | $1.54 \times 10^{+1} \pm 7.55 \times 10^{-1}$ | $1.31 \times 10^{+1} \pm 6.45 \times 10^{-1}$ |
| 3 | 0.096 | $8.34 \times 10^{+0}$ | $6.98 \times 10^{+0}$ | $5.46 \times 10^{+0}$ | $7.85 \times 10^{+0} \pm 3.68 \times 10^{-1}$ | $6.41 \times 10^{+0} \pm 3.07 \times 10^{-1}$ |
| 4 | 0.192 | $4.17 \times 10^{+0}$ | $3.49 \times 10^{+0}$ | $2.76 \times 10^{+0}$ | $3.86 \times 10^{+0} \pm 1.66 \times 10^{-1}$ | $3.31 \times 10^{+0} \pm 1.49 \times 10^{-1}$ |
| 5 | 0.288 | $2.78 \times 10^{+0}$ | $2.33 \times 10^{+0}$ | $1.86 \times 10^{+0}$ | $2.54 \times 10^{+0} \pm 1.30 \times 10^{-1}$ | $2.05 \times 10^{+0} \pm 1.10 \times 10^{-1}$ |
| 6 | 0.336 | $2.38 \times 10^{+0}$ | $2.00 \times 10^{+0}$ | $1.50 \times 10^{+0}$ | $2.38 \times 10^{+0} \pm 8.19 \times 10^{-2}$ | $1.92 \times 10^{+0} \pm 6.78 \times 10^{-2}$ |
| 7 | 0.480 | $1.67 \times 10^{+0}$ | $1.40 \times 10^{+0}$ | $1.11 \times 10^{+0}$ | $1.51 \times 10^{+0} \pm 2.05 \times 10^{-2}$ | $1.34 \times 10^{+0} \pm 4.67 \times 10^{-3}$ |
| 8 | 0.576 | $1.39 \times 10^{+0}$ | $1.16 \times 10^{+0}$ | $9.62 \times 10^{-1}$ | $1.35 \times 10^{+0} \pm 2.14 \times 10^{-2}$ | $1.22 \times 10^{+0} \pm 3.28 \times 10^{-2}$ |
| 9 | 0.720 | $1.11 \times 10^{+0}$ | $9.31 \times 10^{-1}$ | $7.16 \times 10^{-1}$ | $1.05 \times 10^{+0} \pm 7.39 \times 10^{-2}$ | $1.04 \times 10^{+0} \pm 8.78 \times 10^{-2}$ |
| 10 | 0.816 | $9.82 \times 10^{-1}$ | $8.22 \times 10^{-1}$ | $6.66 \times 10^{-1}$ | $8.00 \times 10^{-1} \pm 1.04 \times 10^{-1}$ | $8.57 \times 10^{-1} \pm 9.30 \times 10^{-2}$ |
| 11 | 0.912 | $8.78 \times 10^{-1}$ | $7.35 \times 10^{-1}$ | $5.33 \times 10^{-1}$ | $6.51 \times 10^{-1} \pm 1.12 \times 10^{-1}$ | $8.24 \times 10^{-1} \pm 1.05 \times 10^{-1}$ |

TABLE 8-continued

| 12 | 1.416 | $5.66 \times 10^{-1}$ | $4.73 \times 10^{-1}$ | $3.74 \times 10^{-1}$ | $4.23 \times 10^{-1} \pm 3.43 \times 10^{-2}$ | $4.30 \times 10^{-1} \pm 1.41 \times 10^{-2}$ |
| 13 | 2.184 | $3.67 \times 10^{-1}$ | $3.07 \times 10^{-1}$ | $2.41 \times 10^{-1}$ | $2.56 \times 10^{-1} \pm 4.19 \times 10^{-2}$ | $2.51 \times 10^{-1} \pm 1.05 \times 10^{-2}$ |
| 14 | 2.928 | $2.74 \times 10^{-1}$ | $2.29 \times 10^{-1}$ | $1.81 \times 10^{-1}$ | $8.89 \times 10^{-2} \pm 3.26 \times 10^{-2}$ | $8.30 \times 10^{-2} \pm 3.17 \times 10^{-2}$ |

| | Frequency (Hz) | CoM-BoS Amplitude (cm) | |
|---|---|---|---|
| i | f (i) | ML (x) | AP (z) |
| 1 | 0.024 | $6.98 \times 10^{+0} \pm 9.79 \times 10^{-1}$ | $1.40 \times 10^{-1} \pm 1.32 \times 10^{-1}$ |
| 2 | 0.048 | $3.46 \times 10^{+0} \pm 4.92 \times 10^{-1}$ | $2.94 \times 10^{-1} \pm 1.63 \times 10^{-1}$ |
| 3 | 0.096 | $2.01 \times 10^{+0} \pm 3.27 \times 10^{-1}$ | $8.17 \times 10^{-2} \pm 7.00 \times 10^{-2}$ |
| 4 | 0.192 | $8.25 \times 10^{-1} \pm 9.13 \times 10^{-2}$ | $9.54 \times 10^{-2} \pm 3.96 \times 10^{-2}$ |
| 5 | 0.288 | $5.78 \times 10^{-1} \pm 1.42 \times 10^{-2}$ | $1.48 \times 10^{-2} \pm 8.29 \times 10^{-3}$ |
| 6 | 0.336 | $4.14 \times 10^{-1} \pm 1.64 \times 10^{-2}$ | $5.62 \times 10^{-2} \pm 3.29 \times 10^{-2}$ |
| 7 | 0.480 | $2.40 \times 10^{-1} \pm 7.14 \times 10^{-2}$ | $4.77 \times 10^{-2} \pm 1.18 \times 10^{-2}$ |
| 8 | 0.576 | $1.54 \times 10^{-1} \pm 4.36 \times 10^{-2}$ | $5.49 \times 10^{-2} \pm 2.90 \times 10^{-3}$ |
| 9 | 0.720 | $1.42 \times 10^{-1} \pm 4.43 \times 10^{-2}$ | $2.33 \times 10^{-2} \pm 1.74 \times 10^{-3}$ |
| 10 | 0.816 | $8.49 \times 10^{-2} \pm 1.32 \times 10^{-2}$ | $1.67 \times 10^{-2} \pm 5.63 \times 10^{-3}$ |
| 11 | 0.912 | $6.17 \times 10^{-2} \pm 7.99 \times 10^{-3}$ | $2.33 \times 10^{-2} \pm 1.25 \times 10^{-2}$ |
| 12 | 1.416 | $3.54 \times 10^{-2} \pm 7.24 \times 10^{-3}$ | $1.16 \times 10^{-2} \pm 7.56 \times 10^{-3}$ |
| 13 | 2.184 | $6.79 \times 10^{-3} \pm 1.42 \times 10^{-3}$ | $1.62 \times 10^{-3} \pm 1.41 \times 10^{-3}$ |
| 14 | 2.928 | $5.29 \times 10^{-3} \pm 3.80 \times 10^{-3}$ | $1.90 \times 10^{-3} \pm 7.18 \times 10^{-4}$ |

FIGS. 21A to 21B includes graphs 2100, 2110 that illustrate an example of a position of the body segment and the moving target, according to an embodiment. FIGS. 21C to 21D includes graphs 2120, 2130 that illustrate an example of a position of a body center of mass and the moving target, according to an embodiment. The graphs 2100, 2110, 2120, 2130 of FIGS. 21A to 21D are similar to the graphs 400, 410, 420, 430 of FIGS. 4A to 4D except the amplitude of motion of the moving target 110 is based on 0.9688 AL. The graph 2100 depicts the ML position of the finger (black plot), the ML position of the target 110 (grey plot) and a 95% confidence interval range of the ML position of the finger (dotted lines) for a group of young healthy subjects 190. In an example embodiment, the 95% confidence interval range is ±6.91 cm of the ML positions of the finger depicted in graph 2100. The graph 2110 depicts the SI position of the finger (black plot), the SI position of the target 110 (grey plot) and a 95% confidence interval range of the SI position of the finger (dotted lines) for a group of young healthy subjects 190. In an example embodiment, the 95% confidence interval range is ±1.26 cm of the SI positions of the finger depicted in graph 2110. The graph 2120 depicts the ML position of the projection 124 (black plot), the ML position of the target 110 (grey plot) and a 95% confidence interval range of the ML position of the projection 124 (dotted lines) for a group of young healthy subjects 190. In an example embodiment, the 95% confidence interval range is ±7.62 cm of the ML positions of the projection 124 depicted in graph 2120. The graph 2130 depicts the AP position of the projection 124 (black plot), the XYZ position of the target 110 (grey plot) and a 95% confidence interval range of the AP position of the projection 124 (dotted lines) for a group of young healthy subjects 190. In an example embodiment, the 95% confidence interval range is ±0.71 cm of the AP positions of the projection 124 depicted in graph 2130.

FIGS. 21E to 21F includes graphs 2150, 2160 that illustrate an example of a frequency spectrum of the body segment and a frequency spectrum of the moving target, according to an embodiment. FIGS. 21G to 21H includes graphs 2170, 2180 that illustrate an example of a frequency spectrum of the body center of mass and a frequency spectrum of the moving target, according to an embodiment. The graphs 2150, 2160, 2170, 2180 of FIGS. 21E to 21H are similar to the graphs 450, 460, 470, 480 of FIGS. 4E to 4H except the amplitude of motion of the moving target 110 is based on 0.9688 AL. The graph 2150 depicts the amplitude of the frequency spectrum of the finger in the ML direction (black) and the amplitude of the frequency spectrum of the moving target in the ML direction (grey) for each discrete frequency $f_i$ of the moving target 110 expressed in equation 1. The graph 2160 depicts the amplitude of the frequency spectrum of the finger in the SI direction (black) and the amplitude of the frequency spectrum of the moving target in the SI direction (grey) for each discrete frequency fi of the moving target 110 expressed in equation 1. The graph 2170 depicts the amplitude of the frequency spectrum of the projection 124 in the ML direction (black) and the amplitude of the frequency spectrum of the moving target in the ML direction (grey) for each discrete frequency $f_i$ of the moving target 110 expressed in equation 1. The graph 2180 depicts the amplitude of the frequency spectrum of the projection 124 in the AP direction (black) and the amplitude of the frequency spectrum of the moving target in the XYZ direction (grey) for each discrete frequency $f_i$ of the moving target 110 expressed in equation 1.

In an example embodiment, the graphs 2150, 2160, 2170, 2180 of FIGS. 21E to 21H depict frequency spectrums of the tracking body segment position, the center of mass position and the moving target 110 position, where the amplitude of motion of the moving target 110 is based on 0.9688 AL. Table 9 below provides amplitudes of the frequency spectrums of FIGS. 21E to 21H for each discrete frequency component fi of the moving target 110, where the amplitude of motion of the moving target 110 is based on 0.9688 AL. In an example embodiment, in step 206, the ratio of the amplitude of the frequency spectrum of the tracking body segment to the amplitude of the frequency spectrum of the moving target and the ratio of the amplitude of the frequency spectrum of the body center of mass to the amplitude of the frequency spectrum of the moving target are computed using the amplitude values in Table 9.

TABLE 9

| Frequency (Hz) | | Disk Amplitude (cm) | | | Tracking Finger Amplitude (cm) | |
|---|---|---|---|---|---|---|
| i | f (i) | ML (x) | SI (y) | xyz | ML (x) | SI (y) |
| 1 | 0.024 | $3.98 \times 10^{+1}$ | $3.33 \times 10^{+1}$ | $2.78 \times 10^{+1}$ | $3.74 \times 10^{+1} \pm 1.78 \times 10^{+0}$ | $3.08 \times 10^{+1} \pm 1.33 \times 10^{+0}$ |
| 2 | 0.048 | $1.99 \times 10^{+1}$ | $1.67 \times 10^{+1}$ | $1.52 \times 10^{+1}$ | $1.85 \times 10^{+1} \pm 9.54 \times 10^{-1}$ | $1.57 \times 10^{+1} \pm 7.30 \times 10^{-1}$ |
| 3 | 0.096 | $9.95 \times 10^{+0}$ | $8.33 \times 10^{+0}$ | $6.43 \times 10^{+0}$ | $9.53 \times 10^{+0} \pm 4.60 \times 10^{-1}$ | $7.70 \times 10^{+0} \pm 3.41 \times 10^{-1}$ |
| 4 | 0.192 | $4.97 \times 10^{+0}$ | $4.16 \times 10^{+0}$ | $3.25 \times 10^{+0}$ | $4.58 \times 10^{+0} \pm 2.10 \times 10^{-1}$ | $3.95 \times 10^{+0} \pm 1.72 \times 10^{-1}$ |
| 5 | 0.288 | $3.32 \times 10^{+0}$ | $2.78 \times 10^{+0}$ | $2.20 \times 10^{+0}$ | $3.07 \times 10^{+0} \pm 1.67 \times 10^{-1}$ | $2.22 \times 10^{+0} \pm 1.29 \times 10^{-1}$ |
| 6 | 0.336 | $2.84 \times 10^{+0}$ | $2.38 \times 10^{+0}$ | $1.76 \times 10^{+0}$ | $2.83 \times 10^{+0} \pm 1.19 \times 10^{-1}$ | $2.22 \times 10^{+0} \pm 8.86 \times 10^{-2}$ |
| 7 | 0.480 | $.99 \times 10^{+0}$ | $1.67 \times 10^{+0}$ | $1.32 \times 10^{+0}$ | $1.74 \times 10^{+0} \pm 2.09 \times 10^{-2}$ | $1.51 \times 10^{+0} \pm 1.43 \times 10^{-2}$ |
| 8 | 0.576 | $.66 \times 10^{+0}$ | $1.39 \times 10^{+0}$ | $1.14 \times 10^{+0}$ | $1.56 \times 10^{+0} \pm 2.43 \times 10^{-2}$ | $1.38 \times 10^{+0} \pm 4.59 \times 10^{-2}$ |
| 9 | 0.720 | $.33 \times 10^{+0}$ | $1.11 \times 10^{+0}$ | $8.37 \times 10^{-1}$ | $1.17 \times 10^{+0} \pm 1.04 \times 10^{-1}$ | $1.16 \times 10^{+0} \pm 1.01 \times 10^{-1}$ |
| 10 | 0.816 | $.17 \times 10^{+0}$ | $9.80 \times 10^{-1}$ | $7.93 \times 10^{-1}$ | $8.54 \times 10^{-1} \pm 1.44 \times 10^{-1}$ | $8.99 \times 10^{-1} \pm 1.40 \times 10^{-1}$ |
| 11 | 0.912 | $.05 \times 10^{+0}$ | $8.77 \times 10^{-1}$ | $6.19 \times 10^{-1}$ | $5.93 \times 10^{-1} \pm 1.25 \times 10^{-1}$ | $9.56 \times 10^{-1} \pm 1.47 \times 10^{-1}$ |
| 12 | 1.416 | $6.74 \times 10^{-1}$ | $5.65 \times 10^{-1}$ | $4.42 \times 10^{-1}$ | $4.57 \times 10^{-1} \pm 5.27 \times 10^{-2}$ | $4.32 \times 10^{-1} \pm 2.39 \times 10^{-2}$ |
| 13 | 2.184 | $4.37 \times 10^{-1}$ | $3.66 \times 10^{-1}$ | $2.84 \times 10^{-1}$ | $2.55 \times 10^{-1} \pm 5.33 \times 10^{-2}$ | $2.60 \times 10^{-1} \pm 4.84 \times 10^{-3}$ |
| 14 | 2.928 | $3.26 \times 10^{-1}$ | $2.73 \times 10^{-1}$ | $2.14 \times 10^{-1}$ | $6.74 \times 10^{-2} \pm 3.62 \times 10^{-2}$ | $7.35 \times 10^{-2} \pm 3.44 \times 10^{-2}$ |

| Frequency (Hz) | | CoM-BoS Amplitude (cm) | |
|---|---|---|---|
| i | f (i) | ML (x) | AP (z) |
| 1 | 0.024 | $8.72 \times 10^{+0} \pm 9.67 \times 10^{-1}$ | $9.59 \times 10^{-2} \pm 2.52 \times 10^{-2}$ |
| 2 | 0.048 | $4.33 \times 10^{+0} \pm 5.98 \times 10^{-1}$ | $2.74 \times 10^{-1} \pm 1.95 \times 10^{-1}$ |
| 3 | 0.096 | $2.73 \times 10^{+0} \pm 4.30 \times 10^{-1}$ | $1.29 \times 10^{-1} \pm 1.10 \times 10^{-1}$ |
| 4 | 0.192 | $1.07 \times 10^{+0} \pm 1.06 \times 10^{-1}$ | $3.54 \times 10^{-2} \pm 3.53 \times 10^{-2}$ |
| 5 | 0.288 | $6.99 \times 10^{-1} \pm 1.98 \times 10^{-2}$ | $3.32 \times 10^{-2} \pm 1.84 \times 10^{-2}$ |
| 6 | 0.336 | $5.80 \times 10^{-1} \pm 1.36 \times 10^{-2}$ | $8.65 \times 10^{-2} \pm 3.42 \times 10^{-2}$ |
| 7 | 0.480 | $3.09 \times 10^{-1} \pm 9.71 \times 10^{-2}$ | $5.72 \times 10^{-2} \pm 1.60 \times 10^{-2}$ |
| 8 | 0.576 | $1.64 \times 10^{-1} \pm 5.70 \times 10^{-2}$ | $5.41 \times 10^{-2} \pm 6.71 \times 10^{-4}$ |
| 9 | 0.720 | $1.44 \times 10^{-1} \pm 4.72 \times 10^{-2}$ | $6.25 \times 10^{-2} \pm 7.09 \times 10^{-3}$ |
| 10 | 0.816 | $8.66 \times 10^{-2} \pm 7.97 \times 10^{-3}$ | $3.82 \times 10^{-2} \pm 2.76 \times 10^{-2}$ |
| 11 | 0.912 | $5.76 \times 10^{-2} \pm 1.35 \times 10^{-2}$ | $2.16 \times 10^{-2} \pm 1.52 \times 10^{-2}$ |
| 12 | 1.416 | $3.11 \times 10^{-2} \pm 9.16 \times 10^{-3}$ | $1.40 \times 10^{-2} \pm 9.68 \times 10^{-3}$ |
| 13 | 2.184 | $8.69 \times 10^{-3} \pm 4.45 \times 10^{-3}$ | $2.57 \times 10^{-3} \pm 2.47 \times 10^{-3}$ |
| 14 | 2.928 | $1.14 \times 10^{-2} \pm 4.94 \times 10^{-3}$ | $1.82 \times 10^{-3} \pm 1.79 \times 10^{-3}$ |

3. Hardware Overview

FIG. 22 is a block diagram that illustrates a computer system 2200 upon which an embodiment of the invention may be implemented. Computer system 2200 includes a communication mechanism such as a bus 2210 for passing information between other internal and external components of the computer system 2200. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit)). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 2200, or a portion thereof, constitutes a means for performing one or more steps of one or more methods described herein.

A sequence of binary digits constitutes digital data that is used to represent a number or code for a character. A bus 2210 includes many parallel conductors of information so that information is transferred quickly among devices coupled to the bus 2210. One or more processors 2202 for processing information are coupled with the bus 2210. A processor 2202 performs a set of operations on information. The set of operations include bringing information in from the bus 2210 and placing information on the bus 2210. The set of operations also typically include comparing two or more units of information, shifting positions of units of information, and combining two or more units of information, such as by addition or multiplication. A sequence of operations to be executed by the processor 2202 constitutes computer instructions.

Computer system 2200 also includes a memory 2204 coupled to bus 2210. The memory 2204, such as a random access memory (RAM) or other dynamic storage device, stores information including computer instructions. Dynamic memory allows information stored therein to be changed by the computer system 2200. RAM allows a unit of information stored at a location called a memory address to be stored and retrieved independently of information at neighboring addresses. The memory 2204 is also used by the processor 2202 to store temporary values during execution of computer instructions. The computer system 2200 also includes a read only memory (ROM) 2206 or other static storage device coupled to the bus 2210 for storing static information, including instructions, that is not changed by the computer system 2200. Also coupled to bus 2210 is a non-volatile (persistent) storage device 2208, such as a magnetic disk or optical disk, for storing information, including instructions, that persists even when the computer system 2200 is turned off or otherwise loses power.

Information, including instructions, is provided to the bus 2210 for use by the processor from an external input device 2212, such as a keyboard containing alphanumeric keys operated by a human user, or a sensor. A sensor detects conditions in its vicinity and transforms those detections into signals compatible with the signals used to represent information in computer system 2200. Other external devices coupled to bus 2210, used primarily for interacting with humans, include a display device 2214, such as a cathode ray tube (CRT) or a liquid crystal display (LCD), for presenting images, and a pointing device 2216, such as a mouse or a trackball or cursor direction keys, for controlling a position of a small cursor image presented on the display 2214 and issuing commands associated with graphical elements presented on the display 2214.

In the illustrated embodiment, special purpose hardware, such as an application specific integrated circuit (IC) 2220, is coupled to bus 2210. The special purpose hardware is configured to perform operations not performed by processor 2202 quickly enough for special purposes. Examples of application specific ICs include graphics accelerator cards for generating images for display 2214, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 2200 also includes one or more instances of a communications interface 2270 coupled to bus 2210. Communication interface 2270 provides a two-way communication coupling to a variety of external devices that operate with their own processors, such as printers, scanners and external disks. In general the coupling is with a network link 2278 that is connected to a local network 2280 to which a variety of external devices with their own processors are connected. For example, communication interface 2270 may be a parallel port or a serial port or a universal serial bus (USB) port on a personal computer. In some embodiments, communications interface 2270 is an integrated services digital network (ISDN) card or a digital subscriber line (DSL) card or a telephone modem that provides an information communication connection to a corresponding type of telephone line. In some embodiments, a communication interface 2270 is a cable modem that converts signals on bus 2210 into signals for a communication connection over a coaxial cable or into optical signals for a communication connection over a fiber optic cable. As another example, communications interface 2270 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 2270 sends and receives electrical, acoustic or electromagnetic signals, including infrared and optical signals, that carry information streams, such as digital data.

The term computer-readable medium is used herein to refer to any medium that participates in providing information to processor 2202, including instructions for execution. Such a medium may take many forms, including, but not limited to, non-volatile media, volatile media and transmission media. Non-volatile media include, for example, optical or magnetic disks, such as storage device 2208. Volatile media include, for example, dynamic memory 2204. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 2202, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 2202, except for carrier waves and other signals.

Logic encoded in one or more tangible media includes one or both of processor instructions on a computer-readable storage media and special purpose hardware, such as ASIC *2220.

Network link 2278 typically provides information communication through one or more networks to other devices that use or process the information. For example, network link 2278 may provide a connection through local network 2280 to a host computer 2282 or to equipment 2284 operated by an Internet Service Provider (ISP). ISP equipment 2284 in turn provides data communication services through the public, world-wide packet-switching communication network of networks now commonly referred to as the Internet 2290. A computer called a server 2292 connected to the Internet provides a service in response to information received over the Internet. For example, server 2292 provides information representing video data for presentation at display 2214.

The invention is related to the use of computer system 2200 for implementing the techniques described herein. According to one embodiment of the invention, those techniques are performed by computer system 2200 in response to processor 2202 executing one or more sequences of one or more instructions contained in memory 2204. Such instructions, also called software and program code, may be read into memory 2204 from another computer-readable medium such as storage device 2208. Execution of the sequences of instructions contained in memory 2204 causes processor 2202 to perform the method steps described herein. In alternative embodiments, hardware, such as application specific integrated circuit 2220, may be used in place of or in combination with software to implement the invention. Thus, embodiments of the invention are not limited to any specific combination of hardware and software.

The signals transmitted over network link 2278 and other networks through communications interface 2270, carry information to and from computer system 2200. Computer system 2200 can send and receive information, including program code, through the networks 2280, 2290 among others, through network link 2278 and communications interface 2270. In an example using the Internet 2290, a server 2292 transmits program code for a particular application, requested by a message sent from computer 2200, through Internet 2290, ISP equipment 2284, local network 2280 and communications interface 2270. The received code may be executed by processor 2202 as it is received, or may be stored in storage device 2208 or other non-volatile storage for later execution, or both. In this manner, computer system 2200 may obtain application program code in the form of a signal on a carrier wave.

Various forms of computer readable media may be involved in carrying one or more sequence of instructions or data or both to processor 2202 for execution. For example, instructions and data may initially be carried on a magnetic disk of a remote computer such as host 2282. The remote computer loads the instructions and data into its dynamic memory and sends the instructions and data over a telephone line using a modem. A modem local to the computer system 2200 receives the instructions and data on a telephone line and uses an infra-red transmitter to convert the instructions and data to a signal on an infra-red a carrier wave serving as the network link 2278. An infrared detector serving as communications interface 2270 receives the instructions and data carried in the infrared signal and places information representing the instructions and data onto bus 2210. Bus 2210 carries the information to memory 2204 from which processor 2202 retrieves and executes the instructions using some of the data sent with the instructions. The instructions and data received in memory 2204 may optionally be stored on storage device 2208, either before or after execution by the processor 2202.

FIG. 23 illustrates a chip set 2300 upon which an embodiment of the invention may be implemented. Chip set 2300 is programmed to perform one or more steps of a method described herein and includes, for instance, the processor and memory components described with respect to FIG. 22 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 2300, or a portion thereof, constitutes a means for performing one or more steps of a method described herein.

In one embodiment, the chip set 2300 includes a communication mechanism such as a bus 2301 for passing information among the components of the chip set 2300. A processor 2303 has connectivity to the bus 2301 to execute instructions and process information stored in, for example, a memory 2305. The processor 2303 may include one or more processing cores with each core configured to perform independently. A multi-core processor enables multiprocessing within a single physical package. Examples of a multi-core processor include two, four, eight, or greater numbers of processing cores. Alternatively or in addition, the processor 2303 may include one or more microprocessors configured in tandem via the bus 2301 to enable independent execution of instructions, pipelining, and multithreading. The processor 2303 may also be accompanied with one or more specialized components to perform certain processing functions and tasks such as one or more digital signal processors (DSP) 2307, or one or more application-specific integrated circuits (ASIC) 2309. A DSP 2307 typically is configured to process real-world signals (e.g., sound) in real time independently of the processor 2303. Similarly, an ASIC 2309 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 2303 and accompanying components have connectivity to the memory 2305 via the bus 2301. The memory 2305 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 2305 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

What is claimed is:

1. A method comprising:
   a) automatically obtaining on a processor movement data for a moving target including a position of the moving target at incremental time increments over a time period;
   b) automatically determining on a processor tracking data of a first subject to the moving target based on a first set of one or more sensors attached to a body of the first subject that measure a position of a body segment tracking the moving target and a position of a body center of mass at each time increment over the time period;
   c) automatically characterizing on a processor a response of the first subject to the moving target based on the movement data of the moving target and the tracking data of the first subject;
   d) automatically determining on a processor tracking data of a second subject to the moving target based on a second set of one or more sensors attached to a body of the second subject that measure a position of a body segment tracking the moving target and a position of a body center of mass at each time increment over the time period;
   e) automatically determining on a processor a risk of fall of the second subject based on a difference in the response of the first subject and the tracking data of the second subject;
   f) automatically presenting on a display device a result based on the risk of fall; and
   g) providing a treatment to the second subject based on the risk of fall.

2. A method as recited in claim 1, wherein the automatically obtaining the movement data for the target comprises automatically determining the movement data for the target and wherein the method further comprises automatically causing the target to move according to the movement data.

3. A method as recited in claim 1, wherein step c) comprises automatically determining a deviation between the position of the moving target and the position of the body segment measured by the first set of sensors at each time increment over the time period.

4. A method as recited in claim 3, wherein the deviation is a root mean square deviation.

5. A method as recited in claim 1, wherein step b) further comprises automatically determining an area between the feet of the first subject based on foot sensors of the first set of sensors at each time increment over the time period and wherein step c) comprises determining a deviation between the body center of mass projected within the area and a center of the area at each time increment over the time period.

6. A method as recited in claim 1, wherein the determining of the body center of mass in step b) comprises measuring a height of the first subject with the first set of sensors, measuring a position of a plurality of body segments with the first set of sensors and measuring a weight of the first subject with a platform and wherein the position of the body center of mass is based the height, the position of the plurality of body segments, and the weight of the first subject.

7. A method as recited in claim 1, wherein step c) comprises automatically determining a time delay between the position of the moving target and the position of the body segment and automatically determining a time delay between the position of the moving target and the position of the body center of mass at each time increment over the time period.

8. A method as recited in claim 1 wherein step b) is repeated for a plurality of first subjects, wherein step c) comprises characterizing a response for the plurality of first subjects and wherein step e) comprises determining the risk of fall based on the response for the plurality of first subjects and the tracking data of the second subject.

9. A method as recited in claim 2, wherein the determining of the movement data comprises determining at least one parameter of the moving target and wherein the position of the moving target is based on the at least one parameter of the moving target.

10. A method as recited in claim 9, wherein the determining at least one parameter of the moving target comprises determining an amplitude of the moving target based on an arm length of the first subject, wherein the arm length is measured by the first set of sensors.

11. A method as recited in claim 10, wherein the determining the amplitude of the moving target is based on one of a plurality of multiples of the arm length of the first subject and wherein steps a), b) and c) are automatically repeated for each amplitude based on each multiple of the arm length of the first subject.

12. A method as recited in claim 11, wherein step d) is performed based on the amplitude of the moving target based on one of the plurality of multiples of an arm length of the second subject and wherein step d) is automatically repeated for each amplitude based on each multiple of the arm length of the second subject.

13. A method as recited in claim 9, wherein the determining at least one parameter of the moving target comprises determining a frequency spectrum of the moving target and wherein step c) comprises:

automatically obtaining a Fourier transform of the position of the body segment to obtain a frequency spectrum of the body segment;

automatically obtaining a Fourier transform of the position of the body center of mass to obtain a frequency spectrum of the body center of mass;

automatically determining a ratio of a coefficient of the frequency spectrum of the body segment to a coefficient of the frequency spectrum of the moving target for at least one target frequency of the frequency spectrum of the moving target; and automatically determining a ratio of a coefficient of the frequency spectrum of the body center of mass to a coefficient of the frequency spectrum of the moving target for the at least one target frequency.

14. A method as recited in claim 13, wherein the position of the moving target is a sum of sine functions and wherein the frequency spectrum of the moving target comprises discrete target frequencies of each sine function.

15. A method as recited in claim 13, wherein the frequency spectrum of the moving target comprises target frequencies with non-zero amplitude coefficients, and wherein the target frequencies are integer multiples of each other.

16. A method as recited in claim 13, wherein step c) further comprises automatically determining a deviation between the position of the moving target and the position of the body segment as a function of the at least one target frequency, wherein the deviation is based on the ratio of the coefficient of the frequency spectrum of the body segment to the coefficient of the frequency spectrum of the moving target for the at least one target frequency.

17. A method as recited in claim 16, wherein the deviation is a root mean square deviation.

18. A system comprising:

a set of one or more sensors configured to be attached to a body of a subject to measure a position of a body segment and a position of a body center of mass;

a display device;

at least one processor; and at least one memory including one or more sequence of instructions;

the at least one memory and the one or more sequence of instructions configured to, with the at least one processor, cause the at least one processor to;

obtain movement data for a moving target including a position of the moving target at incremental time increments over a time period;

determine tracking data of a first subject to the moving target based on the set of sensors that measure a position of a body segment tracking the moving target and a position of a body center of mass at each time increment over the time period;

characterize a response of the first subject to the moving target based on the movement data of the moving target and the tracking data of the first subject;

determine tracking data of a second subject to the moving target based on the set of sensors that measure a position of a body segment tracking the moving target and a position of a body center of mass at each time increment over the time period;

determine a risk of fall of the second subject based on a difference in the response of the first subject and the tracking data of the second subject;

present on the display device a result based on the risk of fall; and cause a treatment to be provided to the second subject based on the risk of fall.

19. A non-transitory computer-readable medium carrying one or more sequences of instructions, wherein execution of the one or more sequences of instructions by one or more processors causes the one or more processors to perform the steps of:

obtaining movement data for a moving target including a position of the moving target at incremental time increments over a time period;

determining tracking data of a first subject to the moving target based on a first set of one or more sensors attached to a body of the first subject that measure a position of a body segment tracking the moving target and a position of a body center of mass at each time increment over the time period;

characterizing a response of the first subject to the moving target based on the movement data of the moving target and the tracking data of the first subject;

determining tracking data of a second subject to the moving target based on a second set of one or more sensors attached to a body of the second subject that measure a position of a body segment tracking the moving target and a position of a body center of mass at each time increment over the time period;

determining a risk of fall of the second subject based on a difference in the response of the first subject and the tracking data of the second subject;

presenting on a display device a result based on the risk of fall; and cause a treatment to be provided to the second subject based on the risk of fall.

* * * * *